(12) United States Patent
Melikian et al.

(10) Patent No.: US 7,557,213 B2
(45) Date of Patent: Jul. 7, 2009

(54) SUBSTITUTED QUINOLONES AND METHODS OF USE

(75) Inventors: Anita Melikian, San Francisco, CA (US); John Jessen Wright, Redwood City, CA (US); Antoni Krasinski, Mountain View, CA (US); Cheng Hu, Menlo Park, CA (US); Aaron Novack, San Jose, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 11/599,183

(22) Filed: Nov. 13, 2006

(65) Prior Publication Data

US 2007/0167443 A1  Jul. 19, 2007

Related U.S. Application Data

(60) Provisional application No. 60/735,692, filed on Nov. 10, 2005.

(51) Int. Cl.
*C07D 215/233* (2006.01)
*A61K 31/4709* (2006.01)

(52) U.S. Cl. .................................. 546/156; 514/312

(58) Field of Classification Search ................ 546/156; 514/312
See application file for complete search history.

(56) References Cited

U.S. PATENT DOCUMENTS

| 5,126,352 | A | 6/1992 | Ganguly et al. |
| 5,753,666 | A | 5/1998 | Beasley et al. |
| 6,677,351 | B2 | 1/2004 | Li et al. |
| 2003/0232818 | A1 | 12/2003 | Anderson et al. |
| 2004/0170634 | A1 | 9/2004 | Burns et al. |

FOREIGN PATENT DOCUMENTS

| WO | WO 2004/014859 A2 | 2/2004 |
| WO | WO 2004/014859 A3 | 2/2004 |
| WO | WO 2004/083207 A1 | 9/2004 |
| WO | WO 2005/000333 A1 | 1/2005 |
| WO | WO 2007/059108 A2 | 5/2007 |
| WO | WO 2007/059108 A3 | 5/2007 |

OTHER PUBLICATIONS

Balabanian, K. et al., "The Chemokine SDF-1/CXCL12 Binds to and Signals Through the Orphan Receptor RDC1 in T Lymphocytes," *JBC Papers in Press*, Aug. 17, 2005, pp. 1-9, two pages of figures.
Hattori, K. et al., "Plasma Elevation of Stromal Cell-Derived Factor-1 Induces Mobilization of Mature and Immature Hematopoietic Progenitor and Stem Cells," *Blood*, Jun. 1, 2001, vol. 97, No. 11, pp. 3354-3360, also located at <http://www.bloodjounral.org/cgi/content/abstract/97/11/3354>, last visited on Aug. 29, 2005, 3 pages.
IFE, R.J. et al., "Reversible Inhibitors of the Gastric ($H^+/K^+$)-ATPase. 3. 3-Substituted-4-(phenylamino)quinolines," *Journal of Medicinal Chemistry*, 1992, vol. 35, No. 18, pp. 3413-3422.
International Search Report mailed on Oct. 10, 2007, for PCT Application No. PCT/US06/44149, filed on Nov. 13, 2006, one page.
Silin, O.V. et al., "Synthesis of 5H-Pyrazolo[4,3-c]Quinolines," *Heterocycles*, 2004, vol. 63, No. 8, pp. 1883-1890.
Paine, J.B., "A Convenient Synthesis of Nicotinate Esters From 3-Cyanopyridones," *J. Heterocyclic Chem.*, Mar.-Apr. 1987, vol. 24, pp. 351-355.
Database Chemcats, Accession No. 2043176944, Catalog Name: Ryan Scientific Screening Library, RN: 866727-30-2, Jan. 25, 2008, 1 page.
Database Chemcats, RN: 866727-30-2, entered Nov. 4, 2005, 1 page.
Oliphant, C.M. et al., "Quinolones: A Comprehensive Review," *Clinical Pharmacology*, Feb. 1, 2002, vol. 65, No. 3, pp. 455-464.
Sandison, A.A. et al., "A New Heterocyclisation Reaction Leading to Cinnolin-4(1H)-one Derivatives," *J.C.S. Chem. Comm.*, 1974, pp. 752-752.
Supplementary European Search Report mailed on Dec. 4, 2008, for European Patent Application No. 06844355.5 filed on Nov. 13, 2006, 4 pages.
Valès, M. et al., "Enaminones Acylation: Competitive Formation of Quinolin-4-one and Isoquinolin-2-one Derivaties," *Synthesis*, 2001, No. 16, pp. 2419-2426.

*Primary Examiner*—Rita J Desai
*Assistant Examiner*—David K O'Dell
(74) *Attorney, Agent, or Firm*—Townsend and Townsend and Crew LLP

(57) ABSTRACT

Substituted quinolone compounds and compositions are provided along with methods for the use of those compounds in the treatment of diseases and disorders such as cancer.

15 Claims, No Drawings

SEQUENCE LISTING

<160> NUMBER OF SEQ ID NOS: 12

<210> SEQ ID NO 1
<211> LENGTH: 1089
<212> TYPE: DNA
<213> ORGANISM: Homo sapiens
<220> FEATURE:
<223> OTHER INFORMATION: CCXCKR2 coding sequence, RDC1, CXCR7 G-protein coupled receptor (GPCR)
<220> FEATURE:
<221> NAME/KEY: CDS
<222> LOCATION: (1)..(1089)
<223> OTHER INFORMATION: CCXCKR2

<400> SEQUENCE: 1

```
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacacccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacgggctc    1020
accaagctca tcgatgcctc cagagtctca gagacggagt actctgcctt ggagcagagc    1080
accaaatga                                                            1089
```

<210> SEQ ID NO 2
<211> LENGTH: 362
<212> TYPE: PRT
<213> ORGANISM: Homo sapiens
<220> FEATURE:
<223> OTHER INFORMATION: CCXCKR2, RDC1, CXCR7 G-protein coupled receptor (GPCR)

<400> SEQUENCE: 2

```
Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60
```

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 3
<211> LENGTH: 1089
<212> TYPE: DNA
<213> ORGANISM: Homo sapiens
<220> FEATURE:
<223> OTHER INFORMATION: CCXCKR2.2 coding sequence, RDC1, CXCR7
      G-proteincoupled receptor (GPCR)
<220> FEATURE:
<221> NAME/KEY: CDS
<222> LOCATION: (1)..(1089)
<223> OTHER INFORMATION: CCXCKR2.2

<400> SEQUENCE: 3
atggatctgc acctcttcga ctacgccgag ccaggcaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180

-continued

```
gccaactccg tggtggtctg ggtgaatatc caggccaaga ccacaggcta tgacacgcac      240
tgctacatct tgaacctggc cattgccgac ctgtgggttg tcctcaccat cccagtctgg      300
gtggtcagtc tcgtgcagca caaccagtgg cccatgggcg agctcacgtg caaagtcaca      360
cacctcatct tctccatcaa cctcttcagc ggcattttct tcctcacgtg catgagcgtg      420
gaccgctacc tctccatcac ctacttcacc aacaccccca gcagcaggaa gaagatggta      480
cgccgtgtcg tctgcatcct ggtgtggctg ctggccttct gcgtgtctct gcctgacacc      540
tactacctga agaccgtcac gtctgcgtcc aacaatgaga cctactgccg gtccttctac      600
cccgagcaca gcatcaagga gtggctgatc ggcatgagc tggtctccgt tgtcttgggc       660
tttgccgttc ccttctccat tatcgctgtc ttctacttcc tgctggccag agccatctcg      720
gcgtccagtg accaggagaa gcacagcagc cggaagatca tcttctccta cgtggtggtc      780
ttccttgtct gctggctgcc ctaccacgtg gcggtgctgc tggacatctt ctccatcctg      840
cactacatcc ctttcacctg ccggctggag cacgccctct tcacggccct gcatgtcaca      900
cagtgcctgt cgctggtgca ctgctgcgtc aaccctgtcc tctacagctt catcaatcgc      960
aactacaggt acgagctgat gaaggccttc atcttcaagt actcggccaa aacagggctc     1020
accaagctca tcgatgcctc cagagtgtcg gagacggagt actccgcctt ggagcaaaac     1080
gccaagtga                                                             1089
```

<210> SEQ ID NO 4
<211> LENGTH: 362
<212> TYPE: PRT
<213> ORGANISM: Homo sapiens
<220> FEATURE:
<223> OTHER INFORMATION: CCXCKR2.2, RDC1, CXCR7 G-protein coupled
      receptor (GPCR)

<400> SEQUENCE: 4

Met Asp Leu His Leu Phe Asp Tyr Ala Glu Pro Gly Asn Phe Ser Asp
 1               5                  10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Ser Gly Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

```
Glu Thr Tyr Cys Arg Ser Phe Tyr Pro Glu His Ser Ile Lys Glu Trp
            195                 200                 205

Leu Ile Gly Met Glu Leu Val Ser Val Val Leu Gly Phe Ala Val Pro
        210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
            290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Asn Ala Lys
        355                 360
```

<210> SEQ ID NO 5
<211> LENGTH: 1089
<212> TYPE: DNA
<213> ORGANISM: Homo sapiens
<220> FEATURE:
<223> OTHER INFORMATION: CCXCKR2.3 coding sequence, RDC1, CXCR7
      G-proteincoupled receptor (GPCR)
<220> FEATURE:
<221> NAME/KEY: CDS
<222> LOCATION: (1)..(1089)
<223> OTHER INFORMATION: CCXCKR2.3

<400> SEQUENCE: 5

```
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacacccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tgtcgctgtc ttctacttcc tgctggccag agccatctcg     720
gcgtccagtg accaggagaa gcacagcagc cggaagatca tcttctccta cgtggtggtc     780
ttccttgtct gctggttgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
```

```
aactacaggt acgagctgat gaaggccttc atcttcaagt actcggccaa aacagggctc    1020
accaagctca tcgatgcctc cagagtctca gagacggagt actctgcctt ggagcagagc    1080
accaaatga                                                            1089
```

<210> SEQ ID NO 6
<211> LENGTH: 362
<212> TYPE: PRT
<213> ORGANISM: Homo sapiens
<220> FEATURE:
<223> OTHER INFORMATION: CCXCKR2.3, RDC1, CXCR7 G-protein coupled
      receptor (GPCR)

<400> SEQUENCE: 6

```
Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Val Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
```

```
                325                 330                 335
Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 7
<211> LENGTH: 1089
<212> TYPE: DNA
<213> ORGANISM: Homo sapiens
<220> FEATURE:
<223> OTHER INFORMATION: CCXCKR2.4 coding sequence, RDC1, CXCR7
      G-proteincoupled receptor (GPCR)
<220> FEATURE:
<221> NAME/KEY: CDS
<222> LOCATION: (1)..(1089)
<223> OTHER INFORMATION: CCXCKR2.4

<400> SEQUENCE: 7
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacacccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacagggctc    1020
accaagctca tcgatgcctc cagagtctca gagacggagt actctgcctt ggagcagagc    1080
accaaatga                                                           1089

<210> SEQ ID NO 8
<211> LENGTH: 362
<212> TYPE: PRT
<213> ORGANISM: Homo sapiens
<220> FEATURE:
<223> OTHER INFORMATION: CCXCKR2.4, RDC1, CXCR7 G-protein coupled
      receptor (GPCR)

<400> SEQUENCE: 8

Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
```

```
                35                  40                  45
Phe Ile Tyr Ile Phe Ile Phe Val Ile Gly Met Ile Ala Asn Ser Val
    50                  55                  60
Val Val Trp Val Asn Ile Gln Ala Lys Thr Thr Gly Tyr Asp Thr His
 65                  70                  75                  80
Cys Tyr Ile Leu Asn Leu Ala Ile Ala Asp Leu Trp Val Val Leu Thr
                 85                  90                  95
Ile Pro Val Trp Val Val Ser Leu Val Gln His Asn Gln Trp Pro Met
            100                 105                 110
Gly Glu Leu Thr Cys Lys Val Thr His Leu Ile Phe Ser Ile Asn Leu
        115                 120                 125
Phe Gly Ser Ile Phe Phe Leu Thr Cys Met Ser Val Asp Arg Tyr Leu
    130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
                165                 170                 175
Leu Pro Asp Thr Tyr Tyr Leu Lys Thr Val Thr Ser Ala Ser Asn Asn
            180                 185                 190
Glu Thr Tyr Cys Arg Ser Phe Tyr Pro Glu His Ser Ile Lys Glu Trp
        195                 200                 205
Leu Ile Gly Met Glu Leu Val Ser Val Val Leu Gly Phe Ala Val Pro
    210                 215                 220
Phe Ser Ile Ile Ala Val Phe Tyr Phe Leu Leu Ala Arg Ala Ile Ser
225                 230                 235                 240
Ala Ser Ser Asp Gln Glu Lys His Ser Ser Arg Lys Ile Ile Phe Ser
                245                 250                 255
Tyr Val Val Val Phe Leu Val Cys Trp Leu Pro Tyr His Val Ala Val
            260                 265                 270
Leu Leu Asp Ile Phe Ser Ile Leu His Tyr Ile Pro Phe Thr Cys Arg
        275                 280                 285
Leu Glu His Ala Leu Phe Thr Ala Leu His Val Thr Gln Cys Leu Ser
    290                 295                 300
Leu Val His Cys Cys Val Asn Pro Val Leu Tyr Ser Phe Ile Asn Arg
305                 310                 315                 320
Asn Tyr Arg Tyr Glu Leu Met Lys Ala Phe Ile Phe Lys Tyr Ser Ala
                325                 330                 335
Lys Thr Gly Leu Thr Lys Leu Ile Asp Ala Ser Arg Val Ser Glu Thr
            340                 345                 350
Glu Tyr Ser Ala Leu Glu Gln Ser Thr Lys
        355                 360

<210> SEQ ID NO 9
<211> LENGTH: 1089
<212> TYPE: DNA
<213> ORGANISM: Homo sapiens
<220> FEATURE:
<223> OTHER INFORMATION: CCXCKR2.5 coding sequence, RDC1, CXCR7
      G-proteincoupled receptor (GPCR)
<220> FEATURE:
<221> NAME/KEY: CDS
<222> LOCATION: (1)..(1089)
<223> OTHER INFORMATION: CCXCKR2.5

<400> SEQUENCE: 9
atggatctgc atctcttcga ctactcagag ccagggaact tctcggacat cagctggccg     60
```

-continued

```
tgcaacagca gcgactgcat cgtggtggac acggtgatgt gtcccaacat gcccaacaaa    120
agcgtcctgc tctacacgct ctccttcatt tacattttca tcttcgtcat cggcatgatt    180
gccaactccg tggtggtctg ggtgaatatc caggccaaga ccacaggcta tgacacgcac    240
tgctacatct tgaacctggc cattgccgac ctgtgggttg tcctcaccat cccagtctgg    300
gtggtcagtc tcgtgcagca caaccagtgg cccatgggcg agctcacgtg caaagtcaca    360
cacctcatct tctccatcaa cctcttcagc agcatttcct tcctcacgtg catgagcgtg    420
gaccgctacc tctccatcac ctacttcacc aacaccccca gcagcaggaa gaagatggta    480
cgccgtgtcg tctgcatcct ggtgtggctg ctggccttct gcgtgtctct gcctgacacc    540
tactacctga agaccgtcac gtctgcgtcc aacaatgaga cctactgccg gtccttctac    600
cccgagcaca gcatcaagga gtggctgatc ggcatggagc tggtctccgt tgtcttgggc    660
tttgccgttc ccttctccat tatcgctgtc ttctacttcc tgctggccag agccatctcg    720
gcgtccagtg accaggagaa gcacagcagc cggaagatca tcttctccta cgtggtggtc    780
ttccttgtct gctggttgcc ctaccacgtg gcggtgctgc tggacatctt ctccatcctg    840
cactacatcc ctttcacctg ccggctggag cacgccctct tcacggccct gcatgtcaca    900
cagtgcctgt cgctggtgca ctgctgcgtc aaccctgtcc tctacagctt catcaatcgc    960
aactacaggt acgagctgat gaaggccttc atcttcaagt actcggccaa aacagggctc    1020
accaagctca tcgatgcctc cagagtctca gagacggagt actccgcctt ggagcagagc    1080
accaaatga                                                            1089
```

<210> SEQ ID NO 10
<211> LENGTH: 362
<212> TYPE: PRT
<213> ORGANISM: Homo sapiens
<220> FEATURE:
<223> OTHER INFORMATION: CCXCKR2.5, RDC1, CXCR7 G-protein coupled receptor (GPCR)

<400> SEQUENCE: 10

```
Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Ser Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175
```

```
Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
            245                 250                 255

Tyr Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:hRDC1 PCR
      primer hRDC1F

<400> SEQUENCE: 11
gaatgcggcc gctatggatc tgcatctctt cgact                              35

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:hRDC1 PCR
      primer hRDC1R

<400> SEQUENCE: 12
gaatgcggcc gctcatttgg tgctctgctc caag                               34
```

SUBSTITUTED QUINOLONES AND METHODS OF USE

CROSS-REFERENCES TO RELATED APPLICATIONS

This application claims the benefit of U.S. Provisional Application Ser. No. 60/735,692, filed Nov. 10, 2005, the contents of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Attached below.

BACKGROUND OF THE INVENTION

The present invention is directed to novel compounds and pharmaceutical compositions that inhibit the binding of the SDF-1 chemokine (also known as the CXCL12 chemokine) or I-TAC (also known as CXCL11) to the chemokine receptor CCXCKR2. These compounds are useful in preventing tumor cell proliferation, tumor formation, metastasis, inflammatory diseases, treatment of HIV infectivity, and treatment of stem cell differentiation and mobilization disorders (see also, co-pending U.S. Ser. Nos. 10/912,638 and 11/050,345).

Chemokines are a superfamily of small, cytokine-like proteins that induce cytoskeletal rearrangement, firm adhesion to endothelial cells, and directional migration and may also effect cell activation and proliferation. Chemokines act in a coordinated fashion with cell surface proteins to direct the specific homing of various subsets of cells to specific anatomical sites.

Early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

More recent studies suggest that another chemokine receptor, CCXCKR2, may also be a potential candidate in the treatment of cancer. CCXCKR2 is preferentially expressed in transformed cells over normal cells, with detectable expression in a number of human cancers. In vitro studies indicate that proliferation of CCXCKR2 expressing cells can be inhibited by an antagonist of CCXCKR2. In vivo studies in mice indicate that CCXCKR2 antagonists can inhibit tumor formation and tumor growth.

The potential importance of CCXCKR2 is illustrated by an alternative interpretation of the reduction in tumor volume seen by Bertolini and colleagues. This reduction could clearly be the result of an antibody-mediated clearance, and not the result of the anti-CXCR4 antibody as originally believed. In an antibody-mediated clearance, any antibody that recognized a protein on the cell surface of the lymphoma cells would have had the same effect as that attributed to the anti-CXCR4 antibody. Unfortunately, Bertolini and colleagues studies are inconclusive as to whether the observed tumor response was due to antibody-mediated clearance or interaction with CXCR4.

However it is now known that the lymphoma cells used by Bertolini and colleagues express both CXCR4 and CCX-CKR2. SDF-1 is the only ligand for CXCR4. SDF-1 and I-TAC both bind CCXCKR2. Using anti-SDF-1 antibody, it has now been shown that antagonists of CCXCKR2 are responsible for the reduction in tumor load and increased survival rate. Because SDF-1 is the only ligand for CXCR4, one would expect neutralization of SDF-1 with anti-SDF-1 antibody would be equivalent to the neutralization of CXCR4 with anti-CXCR4 antibody. However, experiments using an anti-SDF-1 antibody demonstrated only a partial reduction in tumor load and an increased survival rate. As a result, CCX-CKR2 is the likely target, as the continued activity appears due to the interactions of the second ligand, I-TAC, with CCXCKR2.

Until recently, the possible importance of CCXCKR2 in tumor cell proliferation, tumor growth, and metastasis was unknown. Now, with recent evidence pointing to the ability of certain CCXCKR2 antagonists to prevent the growth and spread of cancer, and expression patterns indicating a limited tissue distribution for the CCXCKR2 receptor.

Moreover, recently it has been discovered that CCXCKR2 can serve as a co-receptor for certain genetically divergent human immunodeficiency virus (HIV) and simian immunodeficiency virus (SIV), in particular for the HIV-2-ROD, an X4-tropic isolate (Shimizu, N. et al., J. Virol., (2000) 74: 619-626; Balabanian, K., et al., J. Biol. Chem., in press; published on Aug. 17, 2005 as Manuscript M508234200).

Still further, SDF-1, has been described to have a role in the mobilization of hematopoietic progenitor cells and stem cells, and in particular of those cells bearing the CXCR4 receptor, to specific hematopoietic tissues including bone marrow has been described (Hattori, K., et al., Blood, (2000) 97:3354-3360; WO 2005/000333, the disclosure of which are incorporated herein by reference). For example, it is known that CD34+ progenitor cells express CXCR4 and require SDF-1 produced by bone marrow stromal cells for chemoattraction and engraftment, and that in vitro, SDF-1 is chemotactic for both CD34+ cells and for progenitor/stem cells. SDF-1 is also an important chemoattractant, signaling via the CXCR4 receptor, for several other more committed progenitors and mature blood cells including T-lymphocytes, monocytes, pro- and pre-B lymphocytes, and megakaryocytes. As mentioned above, SDF-1 is the only ligand for the CXCR4 receptor. SDF-1 and I-TAC are both ligands for CCXCKR2 receptor. More recent studies suggest that the CCXCKR2 receptor may also play a part in stem cell mobilization processes.

In view of the above, it is apparent that compounds that are able to bind specifically to CCXCKR2 receptors may be useful to treating diseases and other biological conditions that may benefit from such interactions. The present invention provides such compounds along with pharmaceutical compositions and related methods for treatment.

BRIEF SUMMARY OF THE INVENTION

The present invention provides, in one aspect, compounds having formula I,

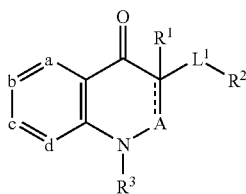

(I)

or pharmaceutically acceptable salts and N-oxides thereof. The various groups (e.g., $R^1$, $R^2$, $R^3$, $L^1$, A, a, b, c and d) are described in the Detailed Description of the Invention.

The compounds provided herein are useful for binding to CCXCKR2 (also referred to as CXCR7), and treating diseases that are dependent, at least in part, on CCXCKR2 activity. Accordingly, the present invention provides in further aspects, compositions containing one or more of the above-noted compounds in admixture with a pharmaceutically acceptable excipient.

In still another aspect, the present invention provides methods for treating various diseases, discussed further herein, comprising administering to a subject in need to such treatment a therapeutically effective amount of a compound of the above formula for a period of time sufficient to treat the disease.

BRIEF DESCRIPTION OF THE DRAWINGS

None

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For brevity, the term alkyl also includes haloalkyl group. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, piperidiny, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "arylene" by itself or as part of another substituent means a divalent radical derived from an aryl group, as exemplified by

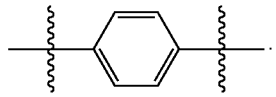

Typically, an arylene group is derived from a 6-12 membered aryl group (can be monocyclic, fused bicyclic or a covalently linked bicyclic such as a biphenyl group, for example). Similarly, heteroarylene refers to a divalent radical derived from a heteroaryl group, e.g.,

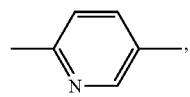

and the like.

As used herein, a wavy line, "〜", that intersects a single, double or triple bond in any chemical structure depicted herein, represent the point attachment of the single, double, or triple bond to the remainder of the molecule.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3)_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3)_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —CN and —$NO_2$ in a number ranging from zero to (2m'+1), where m' is the total number of carbon atoms in such radical. R', R" and R"' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substituent =O (e.g., —C(O)$CH_3$, —C(O)$CH_2CH_2$OR' and the like).

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R"', —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)2NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

As used herein, the term "progenitor cells" refers to cells that, in response to certain stimuli, can form differentiated heamtopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols.

As used herein, the term "stem cells" refer to cells that are less differentiated forms of progenitor cells. Typically, such cells are often positive for CD34. Some stem cells do not contain this marker, however. These CD34+ cells can be assayed using fluorescence activated cell sorting (FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"CCXCKR2" also referred to as "RDC1" or "CXCR7" refers to a seven-transmembrane domain presumed G-protein coupled receptor (GPCR). The CCXCKR2 dog ortholog was originally identified in 1991. See, Libert et al. *Science* 244: 569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad. Sci. USA* 88:4986-4990 (1991), which mistakenly described the protein as a receptor of vasoactive intestinal peptide. "CCXCKR2" includes sequences that are substantially similar to or conservatively modified variants of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

II. General

Compounds of the present invention can inhibit the binding of ligands to the CCXCKR2 receptor and are useful in the treatment of various diseases, including cancer, particularly solid tumor cancers and lymphomas. More recently, the inhibition of ligand binding to CCXCKR2 was noted to reduce the severity of rheumatoid arthritis in an animal model.

III. Embodiments of the Invention

A. Compounds

The present invention provides, in one aspect, compounds having formula I,

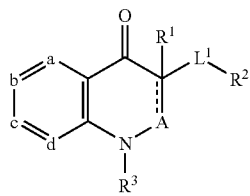

(I)

or pharmaceutically acceptable salts and N-oxides thereof; wherein ═══ represents a single or double bond.

In formula I, the symbol A is —N(H)—, —N($R^a$)—, —$CH_2$—, —CH($R^a$)—, or —C($R^a$)$_2$—, wherein $R^a$ is absent or is $C_{1-4}$ alkyl.

In formula I, the substituent $R^1$ is absent; or alternatively is hydrogen or $C_{1-6}$ alkyl. The linker $L^1$ is —C(O)—. The substituent $R^2$ is —$R^e$, and the substituent $R^3$ is selected from —$X^1$—$R^e$ and —$R^e$, wherein the linker $X^1$ is a $C_{1-2}$ alkylene.

For the substituents $R^2$ and $R^3$, the symbol $R^e$ represents a 5- or 6-membered aryl or heteroaryl group that is optionally substituted with 1-5 substituents selected from the group consisting of halogen, —CN, —$NO_2$, —$CO_2R^r$, —OC(O)$R^r$, —C(O)N$R^r R^s$, —C(O)$R^r$, —S(O)$R^t$, —S(O)$_2R^t$, —$R^t$, —C(NO$R^r$)$R^s$, —N$R^r$—C(O)N$R^r R^s$, —NH—C(N$H_2$)═NH, —N$R^r$C(N$H_2$)═NH, —NH—C(N$H_2$)═N$R^t$, —NH—C(NH$R^r$)═NH, —N$R^r$S(O)$_2R^t$, —N$R^r$S(O)$_2R^t$, —N$R^r$S(O)$_2$N$R^r R^s$, —$N_3$, —C(N$R^r$V)═NV, —N(V)C($R^r$)═NV, —$X^2$C(NO$R^r$)$R^s$, —$X^2$C(N$R^r$V)═NV, —$X^2$N(V)C($R^r$)═NV, —$X^2$N$R^r R^s$, —$X^2$S$R^r$, —$X^2$CN, —$X^2NO_2$, —$X^2CO_2R^r$, $X^2$OC(O)$R^r$, —$X^2$CON$R^r R^s$, —$X^2$C(O)$R^r$, —$X^2$OC(O)N$R^r R^s$, —$X^2$N$R^r$C(O)$R^r$, —$X^2$N$R^r$C(O)$_2R^t$, —$X^2$N$R^r$C(O)N$R^r R^s$, —$X^2$NH—C$_{(2)}$═NH, —$X^2$N$R^r$C(N$H_2$)═NH, —$X^2$NH—C(N$H_2$)═N$R^t$, —$X^2$NH—C(NH$R^r$)═NH, —$X^2$S(O)$R^t$, —$X^2$S(O)$_2R^t$, —$X^2$N$R^r$S(O)$_2R^t$, —$X^2$S(O)$_2$N$R^r R^s$, —$X^2N_3$, O$R^r$, —S$R^r$, N$R^r R^s$, —N$R^s$C(O)$R^r$, —N$R^s$C(O)$_2R^r$, —S(O)$_2R^t$, —S(O)$_2$N$R^r R^s$, —$X^2$O$R^r$, —O—$X^2$O$R^r$, —$X^2$N$R^r R^s$, —O—$X^2$N$R^r R^s$ and —N$R^s$—$X^2CO_2R^r$, wherein any two substituents located on adjacent atoms in $R^e$ can be combined to form a 5- to 7-membered ring having optionally having from 1-3 heteroatoms selected from N, O or S. The linker $X^2$ is $C_{1-8}$ alkylene, $C_{1-8}$ heteroalkylene, $C_{2-8}$ alkenylene, $C_{2-8}$ alkynylene, arylene or heteroarylene; and each $R^r$ and $R^s$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl. Optionally, $R^r$ and $R^s$ when attached to the same nitrogen atom can be combined with the nitrogen atom to form a five or six-membered ring having from 0 to 2 additional heteroatoms as ring members selected from N, O or S. Each $R^t$ substituent is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl. The symbol V is independently selected from the group consisting of —$R^t$, —CN, —$CO_2R^r$ and —$NO_2$, and each of $X^2$, $R^r$, $R^s$ and $R^t$ is optionally further substituted with from one to three members selected from the group consisting of —OH, —O$R^u$, —OC(O)NH$R^u$, —OC(O)N($R^u$)$_2$, —SH, —S$R^u$, —S(O)$R^u$, —S(O)$_2R^u$, —$SO_2NH_2$, —S(O)$_2$NH$R^u$, —S(O)$_2$N($R^u$)$_2$, —NHS(O)$_2R^u$, —N$R^u$S(O)$_2R^u$, —C(O)$NH_2$, —C(O)NH$R^u$, —C(O)N($R^u$)$_2$, —C(O)$R^u$, —NHC(O)$R^u$, —N$R^u$C(O)$R^u$, —NHC(O)$NH_2$, —N$R^u$C(O)$NH_2$, —N$R^u$C(O)NH$R^u$, —NHC(O)NH$R^u$, —N$R^u$C(O)N($R^u$)$_2$, —NHC(O)N($R^u$)$_2$, —$CO_2H$, —$CO_2R^u$, —NHCO$_2R^u$, —N$R^u$CO$_2R^u$, —CN, —$NO_2$, —$NH_2$, —NH$R^u$, —N($R^u$)$_2$, —N$R^u$S(O)$NH_2$ and —N$R^u$S(O)$_2$NH$R^u$, wherein each $R^u$ is independently an unsubstituted $C_{1-6}$ alkyl.

Returning to formula I, each of the ring vertices a, b, c and d is N, N—O, C(H) or C($R^4$), wherein the $R^4$ substituent, at each occurrence, is independently is selected from the group consisting of halogen, $C_{1-8}$ alkyl, $C_{1-8}$ haloalkyl, $C_{1-8}$ alkoxy and $C_{1-8}$ haloalkoxy. Optionally, any two $R^4$ substituents located on adjacent ring vertices are combined to form a 5- to 6-membered ring having from 0- to 2-heteroatoms selected from the group consisting of N, O and S.

Excluded from the compounds of the present invention are those provided in paragraph [0068].

Preferred Embodiments

In certain embodiment of formula I, the compounds of the invention have subformula Ia:

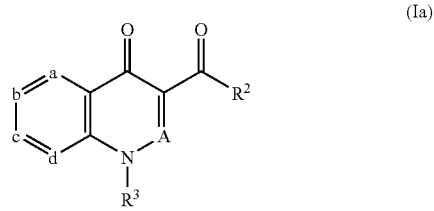

(Ia)

wherein A is N or CH. The substituent $R^2$ is —$R^e$; the substituent $R^3$ is selected from —$X^1$—$R^e$ and —$R^e$, wherein the linker $X^1$ is $C_{1-2}$ alkylene. The $R^e$ substituent at each occurrence in formula Ia is each independently a 5- to 6-membered aryl or heteroaryl group that is optionally substituted with 1-5 substituents selected from the group consisting of halogen, —CN, —$NO_2$, —$R^t$, —$CO_2R^r$, —CON$R^r R^s$, —$N_3$, —$X^2$N$R^r R^s$, —$X^2$S$R^r$, —$X^2$CN, —$X^2NO_2$, —$X^2CO_2R^r$, —$X^2$CON$R^r R^s$, —$X^2$C(O)$R^r$, —$X^2$N$R^s$C(O)$R^r$, —$X^2$N$R^s$C(O)$_2R^r$, —$X^2N_3$, —O$R^r$, —S$R^r$, —N$R^r R^s$, —N$R^s$C(O)$R^r$, —N$R^s$C(O)$_2R^t$, —$X^2$O$R^r$ and —N$R^s$—$X^2CO_2R^r$, wherein any two substituents located on adjacent atoms in $R^e$ can be combined to form a 5- to 7-membered ring having optionally having from 1-3 heteroatoms selected from N, O or S. Within this embodiment, the $R^e$ substituent is preferably substituted with from 1 to 2 substituents. The linker $X^2$ is $C_{1-4}$ alkylene or $C_{1-4}$ heteroalkylene. For brevity, in certain instances, the description of the possible $R^e$ groups for the $R^2$ and $R^3$ substituents is recited only once. It should be understood that the $R^e$ group for the $R^2$ substituent and for the $R^3$ substituent in formula Ia (and formula I) need not be the same and are to be independently selected from the groups presented. Each $R^r$ and $R^s$ substituent is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl, or optionally, $R^r$ and $R^s$ when attached to the same nitrogen atom can be combined with the nitrogen atom to form a five or six-membered ring having from 0 to 2 additional heteroatoms as ring members selected from N, O or S. The substituent $R^t$ is independently selected from the group consisting of $C_{1-8}$ alkyl, $C_{1-8}$ haloalkyl, aryl and heteroaryl and each of $X^2$, $R^r$, $R^s$ and $R^t$ is optionally further substituted with from one to three members selected from the group consisting of —OH, —$OR^u$, —$OC(O)NHR^u$, —$OC(O)N(R^u)_2$, —SH, —$SR^u$, —$S(O)R^u$, —$S(O)_2R^u$, —$SO_2NH_2$, —$S(O)_2NHR^u$, —$S(O)_2N(R^u)_2$, —$NHS(O)_2R^u$, —$NR^uS(O)_2R^u$, —$C(O)NH_2$, —$C(O)NHR^u$, —$C(O)N(R^u)_2$, —$C(O)R^u$, —$NHC(O)R^u$, —$NR^uC(O)R^u$, —$NHC(O)NH_2$, —$NR^uC(O)NH_2$, —$NR^uC(O)NHR^u$, —$NHC(O)NHR^u$, —$NR^uC(O)N(R^u)_2$, —$NHC(O)N(R^u)_2$, —$CO_2H$, —$CO_2R^u$, —$NHCO_2R^u$, —$NR^uCO_2R^u$, —CN, —$NO_2$, —$NH_2$, —$NHR^u$, —$N(R^u)_2$, —$NR^uS(O)NH_2$ and —$NR^uS(O)_2NHR^u$, wherein each $R^u$ is independently an unsubstituted $C_{1-6}$ alkyl.

The $R^2$ Substituent:

In one embodiment, in compounds having formula I or Ia, the substituent $R^2$ which is —$R^e$ is an optionally substituted heteroaryl group. In another embodiment of the invention, $R^2$ substitutent is an optionally substituted pyridyl group. Within certain embodiments of the invention, the $R^2$ that is —$R^e$ is selected from the group consisting of:

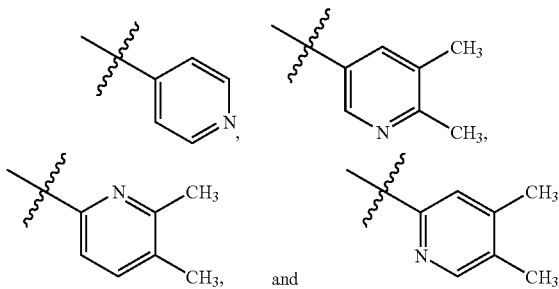

In still other embodiments, the $R^2$ that is —$R^e$ is selected from the group consisting of:

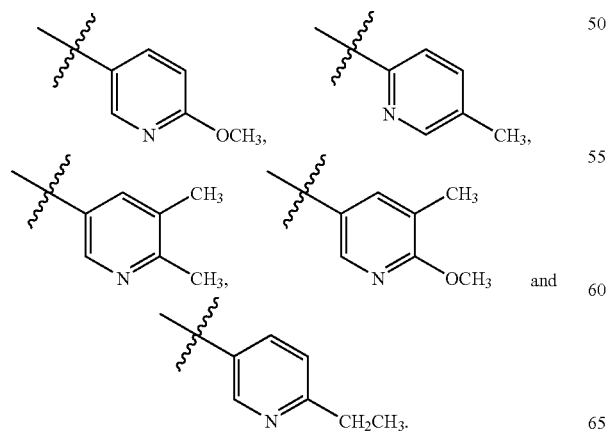

In yet another embodiment of the invention, in compounds having formula I or Ia, the $R^2$ substituent is —$R^e$ that is an optionally substituted phenyl ring. Within certain embodiments of the invention, the $R^2$ substituent is —$R^e$ that is a phenyl ring having the formula:

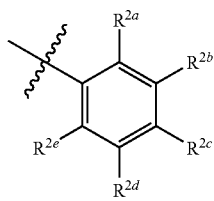

wherein $R^{2a}$, $R^{2b}$, $R^{2c}$, $R^{2d}$ and $R^{2e}$ are each independently selected from the group consisting of hydrogen, halogen, —CN, —$NO_2$, —$OR^r$, —$SR^r$, —$NR^rR^s$, —$CO_2R^r$, —$C(O)NR^rR^s$, optionally substituted $C_{1-8}$ alkyl, optionally substituted $C_{1-8}$ haloalkyl and optionally substituted $C_{3-6}$ cycloalkyl. In another embodiment, $R^{2a}$, $R^{2d}$ and $R^{2e}$ are each hydrogen, and $R^{2b}$ and $R^{2c}$ are each independently selected from the group consisting of halogen, —$OR^r$, —$SR^r$, —$NR^rR^s$, optionally substituted $C_{1-8}$ alkyl, optionally substituted $C_{1-8}$ haloalkyl and optionally substituted $C_{3-6}$ cycloalkyl. In yet another embodiment, $R^{2a}$, $R^{2b}$, $R^{2d}$ and $R^{2e}$ are each hydrogen, and $R^{2c}$ is selected from the group consisting of halogen, —$OR^r$, —$SR^r$, —$NR^rR^s$, optionally substituted $C_{1-8}$ alkyl, optionally substituted $C_{1-8}$ haloalkyl and optionally substituted $C_{3-6}$ cycloalkyl.

In yet another embodiment, the $R^2$ substituent is —$R^e$ that is selected from the group consisting of

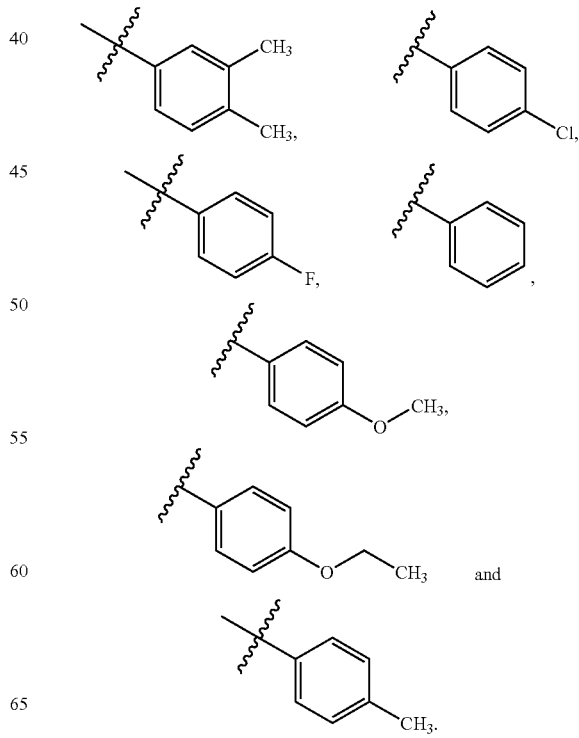

In still another embodiment, the R² substituent is —Rᵉ that is selected from the group consisting of:

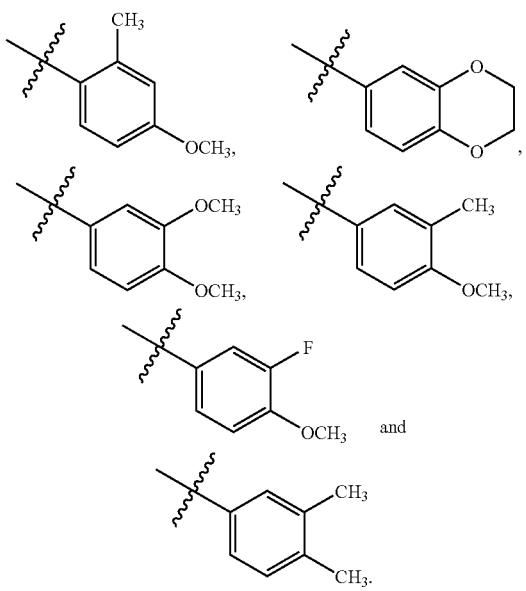

The R³ Substituent:

As noted above, in compounds having formula I and Ia, the substituent R³ is selected from —X¹—Rᵉ, and —Re. Within certain embodiments of the invention, the symbol $R^e$ for the R³ substituent in formula I and Ia is an optionally substituted heteroaryl group. In other embodiments, it is an optionally substituted pyridyl group.

In another embodiment of the invention, in compounds having formula I (or Ia), the symbol $R^e$ for a R³ substituent is a pyridyl group having the formula

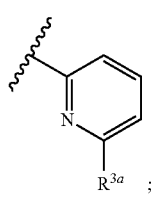

wherein $R^{3a}$ is substituent selected from the group consisting of halogen, —CN, —NO₂, —CO₂Rʳ, —OC(O)Rʳ, —C(O)NR'Rˢ, —C(O)Rʳ, —S(O)Rᵗ, —S(O)₂Rᵗ, —Rᵗ, —C(NORʳ)Rˢ, —NRʳ—C(O)NR'Rˢ, —NH—C(NH₂)=NH, —NR'C(NH₂)=NH, —NH—C(NH₂)=NRᵗ, —NH—C(NHRʳ)=NH, —NR'S(O)₂Rᵗ, —NR'S(O)₂Rᵗ, —NR'S(O)₂NR'Rˢ, —N₃, —C(NR'V)=NV, —N(V)C(R')=NV, —X²C(NORʳ)Rˢ, —X²C(NR'V)=NV, —X²N(V)C(R')=NV, —X²NR'Rˢ, —X²SRʳ, —X²CN, —X²NO₂, —X²CO₂Rʳ, —X²OC(O)Rʳ, —X²CONR'Rˢ, —X²C(O)Rʳ, —X²OC(O)NR'Rˢ, —X²NRˢC(O)Rʳ, —X²NRˢC(O)₂Rᵗ, —X²NRʳC(O)NR'Rˢ, —X²NH—C(NH₂)=NH, —X²NR'C(NH₂)=NH, —X²NH—C(NH₂)=NRᵗ, —X²NH—C(NHRʳ)=NH, —X²S(O)Rᵗ, —X²S(O)₂Rᵗ, —X²NR'S(O)₂Rᵗ, —X²S(O)₂NR'Rˢ, —X²N₃, —ORʳ, —SRʳ, —NR'Rˢ, —NRˢC(O)Rʳ, —NRˢC(O)₂Rᵗ, —S(O)₂Rᵗ, —S(O)₂NR'Rˢ, —X²ORʳ, —O—X²ORʳ, —X²NR'Rˢ, —O—X²NR'Rˢ and —NRˢ—X²CO₂Rʳ. In another embodiment, in compounds of formula I or Ia, the $R^{3a}$ substituent is selected from the group consisting of halogen, —CN, —NO₂, —Rᵗ, —CO₂Rʳ, —CONR'Rˢ, —N₃, —X²R'Rˢ, —X²SRʳ, —X²CN, —X²NO₂, —X²CO₂Rʳ, —X²CONR'Rˢ, —X²C(O)Rʳ, —X²NRˢC(O)Rʳ, —X²NRˢC(O)₂Rᵗ, —X²N₃, —ORʳ, —SRʳ, —NR'Rˢ, —NRˢC(O)Rʳ, —NRˢC(O)₂Rᵗ, —X²ORʳ and —NRˢ—X²CO₂Rʳ.

In another embodiment, the symbol $R^e$ for a R³ substituent is selected from the group consisting of:

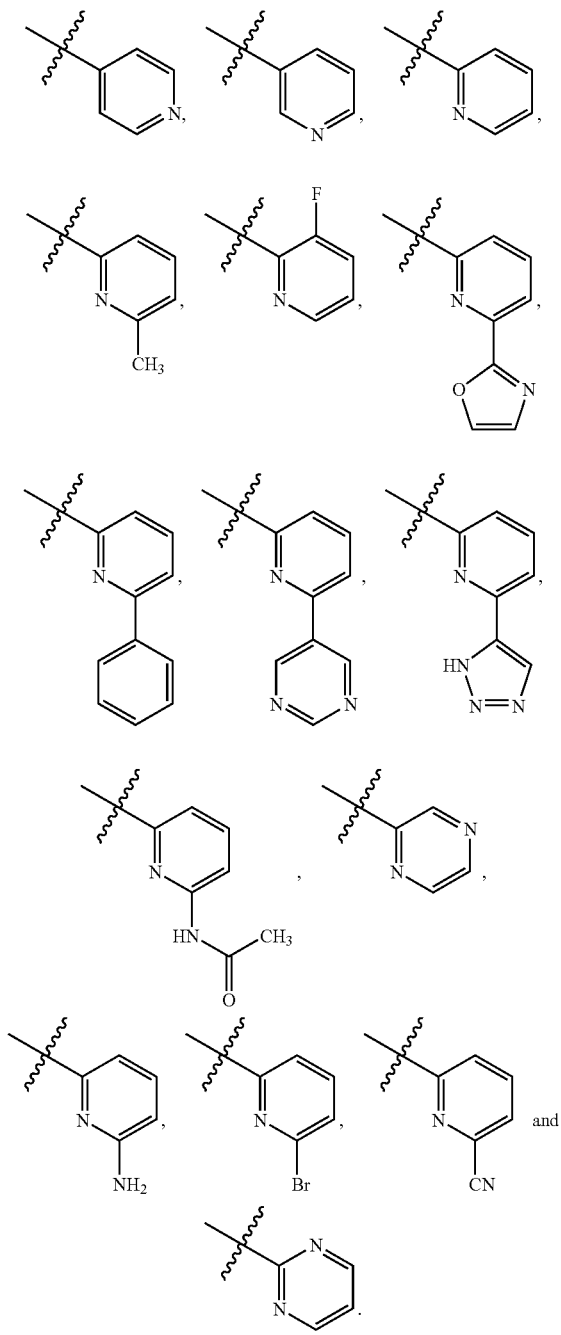

In each of the groups of embodiments above, more preferably R³ is —X¹—Rᵉ wherein X¹ is CH₂ and $R^e$ is selected from the indicated pyridyl, pyrimidine or pyrazine groups.

In yet another embodiment of the invention, the symbol $R^e$ for a $R^3$ substituent is a phenyl ring having the formula

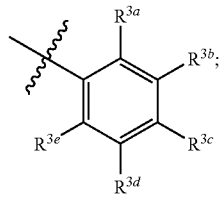

wherein $R^{3a}$, $R^{3b}$, $R^{3c}$, $R^{3d}$ and $R^{3e}$ are each independently selected from the group consisting of hydrogen, halogen, —CN, —NO$_2$, OR$^r$, —SR$^r$, —NR$^r$R$^s$, —CO$_2$R$^r$, —C(O)NR$^r$R$^s$, optionally substituted $C_{1-8}$ alkyl, optionally substituted $C_{1-8}$ haloalkyl and optionally substituted $C_{3-6}$ cycloalkyl.

Within certain embodiments, the symbol $R^e$ for a $R^3$ substituent is selected from the group consisting of

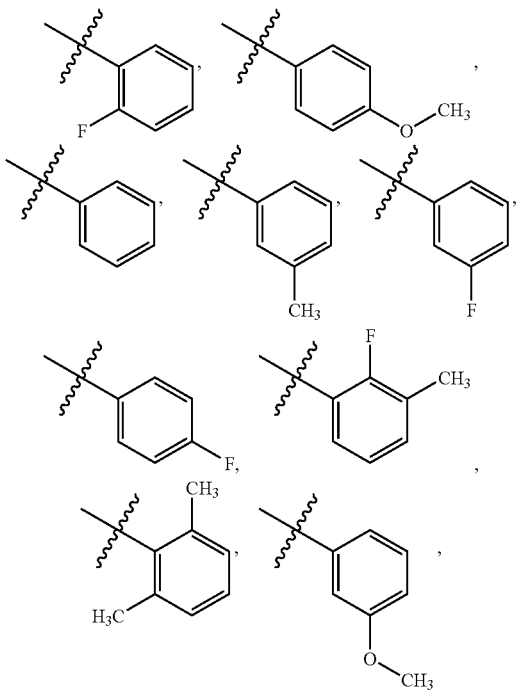

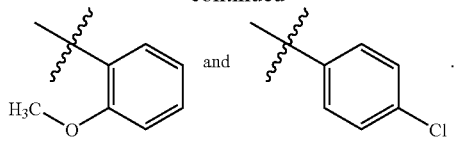

In each of the groups of embodiments above, more preferably $R^3$ is —$X^1$—$R^e$ wherein $X^1$ is CH$_2$ and $R^e$ is selected from the indicated phenyl groups.

The Ring Vertices a, b, c and d:

In one embodiment of the invention, compounds having formula I or Ia the ring vertices a, b, c and d are each CH. In another embodiment, in compounds having formula I or Ia, the ring vertices a, b, c and d are each independently selected from the group consisting of CH or C(R$^4$), wherein each R$^4$ is independently selected from the group consisting of halogen, $C_{1-8}$ alkyl, $C_{1-8}$ haloalkyl and $C_{1-8}$ alkoxy; or alternatively any two R$^4$ substituents located on adjacent ring vertices are combined to form a 5- to 7-membered ring having 1 to 2 heteroatoms selected from the group consisting of N and O. Within this aspect of the invention, in certain embodiments, the ring vertices a, c and d are each CH, and the ring vertex b is CR$^4$, wherein the R$^4$ substituent is a $C_{1-4}$ haloalkyl. In certain other embodiments, the ring vertices a and d are each CH and the ring vertices b and c are each C(R$^4$) wherein the R$^4$ substitutent are combined to form a 5- or 6-membered ring having two oxygen atoms.

In yet another embodiment of the invention, in compounds having formula I and Ia, at least one ring vertex is N or N—O.

In yet another embodiment of the invention, in a compound having formula I or Ia, the ring vertices a, c and d are each C(H) or C(R$^4$) and the ring vertex b is N or N—O. Within certain other embodiments, the ring vertices a, b and d are each C(H) or C(R$^4$) and the ring vertex c is N or N—O. In yet another embodiment of the invention, the ring vertices a, b and c in compounds having formula I are each C(H) or C(R$^4$) and the ring vertex d is N or N—O. In yet another embodiment of the invention, in formula I, the ring vertices b, c and d are each C(H) or C(R$^4$) and the ring vertex a is N or N—O. In yet another embodiment, in the compounds of formula I, two ring vertices are N or N—O.

A family of specific compound of particular interest having formula I or Ia consists of compounds, pharmaceutically acceptable salts, hydrates or N-oxides thereof, as set forth in Table 1.

TABLE I 1. 1-(3-Methyl-benzyl)-3-(pyridine-4-carbonyl)-1H-quinolin-4-one
2. 3-(Pyridine-4-carbonyl)-1-pyridin-2-ylmethyl-1H-quinolin-4-one
3. 3-(3,4-Dimethyl-benzoyl)-1-(2-fluoro-benzyl)-6-trifluoromethyl-1H-quinolin-4-one
4. 3-(3,4-Dimethyl-benzoyl)-1-pyridin-2-ylmethyl-6-trifluoromethyl-1H-quinolin-4-one
5. 8-(3,4-Dimethyl-benzoyl)-6-pyridin-4-ylmethyl-2,3-dihydro-6H-[1,4]dioxino[2,3-g]quinolin-9-one
6. 8-(3,4-Dimethyl-benzoyl)-6-pyridin-3-ylmethyl-2,3-dihydro-6H-[1,4]dioxino[2,3-g]quinolin-9-one
7. 8-(3,4-Dimethyl-benzoyl)-6-pyridin-2-ylmethyl-2,3-dihydro-6H-[1,4]dioxino[2,3-g]quinolin-9-one
8. 3-(3,4-Dimethyl-benzoyl)-1-pyridin-4-ylmethyl-1H-quinolin-4-one
9. 3-(3,4-Dimethyl-benzoyl)-1-pyridin-3-ylmethyl-1H-quinolin-4-one
10. 3-(3,4-Dimethyl-benzoyl)-1-(3-methyl-benzyl)-1H-quinolin-4-one
11. 6-Cyclopropylmethyl-8-(3,4-dimethyl-benzoyl)-2,3-dihydro-6H-[1,4]dioxino[2,3-g]quinolin-9-one TABLE I-continued 12. 3-(3,4-Dimethyl-benzoyl)-1-pyridin-2-ylmethyl-1H-quinolin-4-one
13. 8-(3,4-Dimethyl-benzoyl)-6-(2-fluoro-benzyl)-2,3-dihydro-6H-[1,4]dioxino[2,3-g]quinolin-9-one
14. 8-(3,4-Dimethyl-benzoyl)-6-(2-methyl-benzyl)-2,3-dihydro-6H-[1,4]dioxino[2,3-g]quinolin-9-one
15. 8-(3,4-Dimethyl-benzoyl)-6-(3-methyl-benzyl)-2,3-dihydro-6H-[1,4]dioxino[2,3-g]quinolin-9-one
16. 3-(3,4-Dimethyl-benzoyl)-1-(2-fluoro-benzyl)-1H-quinolin-4-one
17. 7-(3,4-Dimethyl-benzoyl)-5-pyridin-4-ylmethyl-5H-[1,3]dioxolo[4,5-g]quinolin-8-one
18. 7-(3,4-Dimethyl-benzoyl)-5-pyridin-3-ylmethyl-5H-[1,3]dioxolo[4,5-g]quinolin-8-one
19. 7-(3,4-Dimethyl-benzoyl)-5-pyridin-2-ylmethyl-5H-[1,3]dioxolo[4,5-g]quinolin-8-one
20. 3-Benzoyl-1-(3-methyl-benzyl)-1H-quinolin-4-one
21. 7-(3,4-Dimethyl-benzoyl)-2,2-difluoro-5-(2-fluoro-benzyl)-5H-[1,3]dioxolo[4,5-g]quinolin-8-one
22. 3-(3-Methyl-benzoyl)-1-(3-methyl-benzyl)-1H-quinolin-4-one
23. 1-(2-Fluoro-benzyl)-3-(3-methyl-benzoyl)-1H-quinolin-4-one
24. 3-(3-Methyl-benzoyl)-1-pyridin-2-ylmethyl-1H-quinolin-4-one
25. 3-(3,4-Dimethyl-benzoyl)-1-(6-methyl-pyridin-2-ylmethyl)-1H-quinolin-4-one
26. 1-(2-Fluoro-benzyl)-3-(2-methyl-pyridine-4-carbonyl)-1H-quinolin-4-one
27. 3-(2-Methyl-pyridine-4-carbonyl)-1-(6-methyl-pyridin-2-ylmethyl)-1H-quinolin-4-one
28. 1-(3-Methyl-benzyl)-3-(2-methyl-pyridine-4-carbonyl)-1H-quinolin-4-one
29. 3-(3,4-Dimethyl-benzoyl)-1-phenethyl-1H-quinolin-4-one
30. 1-(5-Chloro-[1,2,3]thiadiazol-4-ylmethyl)-3-(3,4-dimethyl-benzoyl)-1H-quinolin-4-one
31. 3-(3,4-Dimethyl-benzoyl)-1-(5-methyl-isoxazol-3-ylmethyl)-1H-quinolin-4-one
32. 3-(3,4-Dimethyl-benzoyl)-1-thiazol-4-ylmethyl-1H-quinolin-4-one
33. 1-(6-Bromo-pyridin-2-ylmethyl)-3-(3,4-dimethyl-benzoyl)-1H-quinolin-4-one
34. 1-(2-Fluoro-benzyl)-3-(pyridine-3-carbonyl)-1H-quinolin-4-one
35. 3-(3,4-Dimethyl-benzoyl)-1-[1,2,3,5]oxatriazol-4-ylmethyl-1H-quinolin-4-one
36. 1-(3-Methyl-benzyl)-3-(pyridine-3-carbonyl)-1H-quinolin-4-one
37. 1-(6-Methyl-pyridin-2-ylmethyl)-3-(pyridine-3-carbonyl)-1H-quinolin-4-one
38. 3-(3,4-Dimethyl-benzoyl)-1-(2-trifluoromethyl-benzyl)-1H-quinolin-4-one
39. 3-(3,4-Dimethyl-benzoyl)-1-(3-fluoro-pyridin-2-ylmethyl)-1H-quinolin-4-one
40. 3-(3,4-Dimethyl-benzoyl)-1-phenyl-1H-quinolin-4-one
41. 1-Cyclohexylmethyl-3-(3,4-dimethyl-benzoyl)-1H-quinolin-4-one
42. 3-(5,6-Dimethyl-pyridine-3-carbonyl)-1-(3-fluoro-pyridin-2-ylmethyl)-1H-quinolin-4-one
43. 3-(5,6-Dimethyl-pyridine-3-carbonyl)-1-(6-oxazol-2-yl-pyridin-2-ylmethyl)-1H-quinolin-4-one
44. 3-(3,4-Dimethyl-benzoyl)-1-(6-phenyl-pyridin-2-ylmethyl)-1H-quinolin-4-one
45. 3-(3,4-Dimethyl-benzoyl)-1-(6-methyl-pyridin-2-ylmethyl)-1H-cinnolin-4-one
46. 3-(3,4-Dimethyl-benzoyl)-1-(2-fluoro-3-methyl-benzyl)-1H-quinolin-4-one
47. 3-(3,4-Dimethyl-benzoyl)-1-(2-fluoro-benzyl)-1H-[1,6]naphthyridin-4-one
48. 3-(3,4-Dimethyl-benzoyl)-1-(3-methyl-benzyl)-1H-[1,6]naphthyridin-4-one
49. 3-(3,4-Dimethyl-benzoyl)-1-(3H-[1,2,3]triazol-4-ylmethyl)-1H-quinolin-4-one
50. 3-(5,6-Dimethyl-pyridine-2-carbonyl)-1-(2-fluoro-benzyl)-1H-quinolin-4-one
51. 3-(5,6-Dimethyl-pyridine-3-carbonyl)-1-(6-methyl-pyridin-2-ylmethyl)-1H-quinolin-4-one
52. 1-(6-Amino-pyridin-2-ylmethyl)-3-(3,4-dimethyl-benzoyl)-1H-quinolin-4-one
53. N-{6-[3-(3,4-Dimethyl-benzoyl)-4-oxo-4H-quinolin-1-ylmethyl]-pyridin-2-yl}-acetamide
54. 1-(6-Bromo-pyridin-2-ylmethyl)-3-(3,4-dimethyl-benzoyl)-6-fluoro-1H-quinolin-4-one
55. 1-(6-Bromo-pyridin-2-ylmethyl)-3-(5,6-dimethyl-pyridine-3-carbonyl)-1H-quinolin-4-one
56. 3-(3,4-Dimethyl-benzoyl)-6-fluoro-1-(3-methyl-benzyl)-1H-quinolin-4-one
57. 3-(3,4-Dimethyl-benzoyl)-1-pyrimidin-2-ylmethyl-1H-quinolin-4-one
58. 3-(3,4-Dimethyl-benzoyl)-1-pyrazin-2-ylmethyl-1H-quinolin-4-one
59. 3-(3,4-Dimethyl-benzoyl)-1-(2,6-dimethyl-benzyl)-1H-quinolin-4-one
60. 1-(6-Bromo-pyridin-2-ylmethyl)-3-(3,4-dimethyl-benzoyl)-1H-quinolin-4-one
61. 6-[3-(3,4-Dimethyl-benzoyl)-4-oxo-4H-quinolin-1-ylmethyl]-pyridine-2-carbonitrile Excluded from the above generic formula are those compounds that are either commercially available or known in the literature, including: 5-Benzyl-7-(4-methyl-benzoyl)-5H-[1,3]dioxolo[4,5-g]quinolin-8-one; 5-Benzyl-7-(4-ethyl-benzoyl)-5H-[1,3]dioxolo[4,5-g]quinolin-8-one; 5-Benzyl-7-(3,4-dimethyl-benzoyl)-5H-[1,3]dioxolo[4,5-g]quinolin-8-one; 5-Benzyl-7-(4-chloro-benzoyl)-5H-[1,3]dioxolo[4,5-g]quinolin-8-one; 7-Benzoyl-5-(4-chloro-benzyl)-5H-[1,3]dioxolo[4,5-g]quinolin-8-one; 5-(4-Chloro-benzyl)-7-(4-methyl-benzoyl)-5H-[1,3]dioxolo[4,5-g]quinolin-8-one; 5-(4-Chloro-benzyl)-7-(4-methoxy-benzoyl)-5H-[1,3]dioxolo[4,5-g]quinolin-8-one; 5-(4-Chloro-benzyl)-7-(4-ethoxy-benzoyl)-5H-[1,3]dioxolo[4,5-g]quinolin-8-one; 5-(4-Chloro-benzyl)-7-(4-fluoro-benzoyl)-5H-[1,3]dioxolo[4,5-g]quinolin-8-one; 5-(2-Fluoro-benzyl)-7-(4-methyl-benzoyl)-5H-[1,3]dioxolo[4,5-g]quinolin-8-one; 7-(3,4-Dimethyl-benzoyl)-5-(2-fluoro-benzyl)-5H-[1,3]dioxolo[4,5-g]quinolin-8-one; 7-(4-Ethoxy-benzoyl)-5-(2-fluorobenzyl)-5H-[1,3]dioxolo[4,5-g]quinolin-8-one; 7-(4-Chloro-benzoyl)-5-(2-fluoro-benzyl)-5H-[1,3]dioxolo[4,5-g]quinolin-8-one; 5-(3-Fluoro-benzyl)-7-(4-methyl-benzoyl)-5H-[1,3]dioxolo[4,5-g]quinolin-8-one; 7-(3,4-Dimethyl-benzoyl)-5-(3-fluoro-benzyl)-5H-[1,3]dioxolo[4,5-g]quinolin-8-one; 5-(3-Fluoro-benzyl)-7-(4-methoxy-benzoyl)-5H-[1,3]dioxolo[4,5-g]quinolin-8-one; 7-Benzoyl-5-(4-methyl-benzyl)-5H-[1,3]dioxolo[4,5-g]quinolin-8-one; 7-(4-Methyl-benzoyl)-5-(4-methyl-benzyl)-5H-[1,3]dioxolo[4,5-g]quinolin-8-one; 7-(3,4-Dimethyl-benzoyl)-5-(4-methyl-benzyl)-5H-[1,3]dioxolo[4,5-g]quinolin-8-one; 7-(4-Ethoxy-benzoyl)-5-(4-methyl-benzyl)-5H-[1,3]dioxolo[4,5-g]quinolin-8-one; 7-(4-Fluoro-benzoyl)-5-(4-methyl-benzyl)-5H-[1,3]dioxolo[4,5-g]quinolin-8-one; 7-(4-Chloro-benzoyl)-5-(4-methyl-benzyl)-5H-[1,3]dioxolo[4,5-g]quinolin-8-one; 5-(4-Fluoro-benzyl)-7-(4-methyl-benzoyl)-5H-[1,3]dioxolo[4,5-g]quinolin-8-one; 7-(4-Ethyl-benzoyl)-5-(4-fluoro-benzyl)-5H-[1,3]dioxolo[4,5-g]quinolin-8-one; 7-(3,4-Dimethyl-benzoyl)-5-(4-fluoro-benzyl)-5H-[1,3]dioxolo[4,5-g]quinolin-8-one; 7-(4-Ethoxy-benzoyl)-5-(4-fluoro-benzyl)-5H-[1,3]dioxolo[4,5-g]quinolin-8-one; 7-(4-Chloro-benzoyl)-5-(4-fluoro-benzyl)-5H-[1,3]dioxolo[4,5-g]quinolin-8-one; 7-Benzoyl-5-(3-methyl-benzyl)-5H-[1,3]dioxolo[4,5-g]quinolin-8-one; 7-(4-Methyl-benzoyl)-5-(3-methyl-benzyl)-5H-[1,3]dioxolo[4,5-g]quinolin-8-one; 7-(3,4-Dimethyl-benzoyl)-5-(3-methyl-benzyl)-5H-[1,3]dioxolo[4,5-g]quinolin-8-one; 7-(4-Methoxy-benzoyl)-5-(3-methyl-benzyl)-5H-[1,3]dioxolo[4,5-g]quinolin-8-one; 7-(4-Ethoxy-benzoyl)-5-(3-methyl-benzyl)-5H-[1,3]dioxolo[4,5-g]quinolin-8-one; 7-(4-Fluoro-benzoyl)-5-(3-methyl-benzyl)-5H-[1,3]dioxolo[4,5-g]quinolin-8-one; 7-(4-Chloro-benzoyl)-5-(3-methyl-benzyl)-5H-[1,3]dioxolo[4,5-g]quinolin-8-one; 7-(4-Ethyl-benzoyl)-5-(2-methoxy-benzyl)-5H-[1,3]dioxolo[4,5-g]quinolin-8-one; 7-(3,4-Dimethyl-benzoyl)-5-(2-methoxy-benzyl)-5H-[1,3]dioxolo[4,5-g]quinolin-8-one; 7-(4-Ethoxy-benzoyl)-5-(2-methoxy-benzyl)-5H-[1,3]dioxolo[4,5-g]quinolin-8-one; 5-(3-Methoxy-benzyl)-7-(4-methyl-benzoyl)-5H-[1,3]dioxolo[4,5-g]quinolin-8-one; 7-(4-Ethyl-benzoyl)-5-(3-methoxy-benzyl)-5H-[1,3]dioxolo[4,5-g]quinolin-8-one; 7-(3,4-Dimethyl-benzoyl)-5-(3-methoxy-benzyl)-5H-[1,3]dioxolo[4,5-g]quinolin-8-one; 7-(4-Ethoxy-benzoyl)-5-(3-methoxy-benzyl)-5H-[1,3]dioxolo[4,5-g]quinolin-8-one; 7-(4-Chloro-benzoyl)-5-(3-methoxy-benzyl)-5H-[1,3]dioxolo[4,5-g]quinolin-8-one; 7-(3,4-Dimethyl-benzoyl)-5-(4-methoxy-benzyl)-5H-[1,3]dioxolo[4,5-g]quinolin-8-one; 7-(4-Chloro-benzoyl)-5-(4-methoxy-benzyl)-5H-[1,3]dioxolo[4,5-g]quinolin-8-one; N-(2,3-Dihydro-benzo[1,4]dioxin-6-yl)-2-[7-(4-ethyl-benzoyl)-8-oxo-8H-[1,3]dioxolo[4,5-g]quinolin-5-yl]-acetamide; N-(2,3-Dihydro-benzo[1,4]dioxin-6-yl)-2-[7-(3,4-dimethyl-benzoyl)-8-oxo-8H-[1,3]dioxolo[4,5-g]quinolin-5-yl]-acetamide; N-(2,3-Dihydro-benzo[1,4]dioxin-6-yl)-2-[7-(4-methoxy-benzoyl)-8-oxo-8H-[1,3]dioxolo[4,5-g]quinolin-5-yl]-acetamide; N-(2,3-Dihydro-benzo[1,4]dioxin-6-yl)-2-[7-(4-ethoxy-benzoyl)-8-oxo-8H-[1,3]dioxolo[4,5-g]quinolin-5-yl]-acetamide; N-(2,3-Dihydro-benzo[1,4]dioxin-6-yl)-2-[7-(4-fluoro-benzoyl)-8-oxo-8H-[1,3]dioxolo[4,5-g]quinolin-5-yl]-acetamide; 2-[7-(4-Chloro-benzoyl)-8-oxo-8H-[1,3]dioxolo[4,5-g]quinolin-5-yl]-N-(2,3-dihydro-benzo[1,4]dioxin-6-yl)-acetamide; N-Benzo[1,3]dioxol-5-yl-2-[7-(4-chloro-benzoyl)-8-oxo-8H-[1,3]dioxolo[4,5-g]quinolin-5-yl]-acetamide; N-Benzo[1,3]dioxol-5-yl-2-[7-(4-methyl-benzoyl)-8-oxo-8H-[1,3]dioxolo[4,5-g]quinolin-5-yl]-acetamide; N-Benzo[1,3]dioxol-5-yl-2-[7-(4-ethyl-benzoyl)-8-oxo-8H-[1,3]dioxolo[4,5-g]quinolin-5-yl]-acetamide; N-Benzo[1,3]dioxol-5-yl-2-[7-(3,4-dimethyl-benzoyl)-8-oxo-8H-[1,3]dioxolo[4,5-g]quinolin-5-yl]-acetamide; N-Benzo[1,3]dioxol-5-yl-2-[7-(4-methoxy-benzoyl)-8-oxo-8H-[1,3]dioxolo[4,5-g]quinolin-5-yl]-acetamide; N-Benzo[1,3]dioxol-5-yl-2-[7-(4-ethoxy-benzoyl)-8-oxo-8H-[1,3]dioxolo[4,5-g]quinolin-5-yl]-acetamide; N-Benzo[1,3]dioxol-5-yl-2-[7-(4-fluoro-benzoyl)-8-oxo-8H-[1,3]dioxolo[4,5-g]quinolin-5-yl]-acetamide; N-Benzo[1,3]dioxol-5-yl-2-[7-(4-chloro-benzoyl)-8-oxo-8H-[1,3]dioxolo[4,5-g]quinolin-5-yl]-acetamide; 2-(7-Benzoyl-8-oxo-8H-[1,3]dioxolo[4,5-g]quinolin-5-yl)-N-(4-methoxy-phenyl)-acetamide; N-(4-Methoxy-phenyl)-2-[7-(4-methyl-benzoyl)-8-oxo-8H-[1,3]dioxolo[4,5-g]quinolin-5-yl]-acetamide; 2-[7-(4-Ethyl-benzoyl)-8-oxo-8H-[1,3]dioxolo[4,5-g]quinolin-5-yl]-N-(4-methoxy-phenyl)-acetamide; 2-[7-(3,4-Dimethyl-benzoyl)-8-oxo-8H-[1,3]dioxolo[4,5-g]quinolin-5-yl]-N-(4-methoxy-phenyl)-acetamide; 2-[7-(4-Ethoxy-benzoyl)-8-oxo-8H-[1,3]dioxolo[4,5-g]quinolin-5-yl]-N-(4-methoxy-phenyl)-acetamide; 2-[7-(4-Fluoro-benzoyl)-8-oxo-8H-[1,3]dioxolo[4,5-g]quinolin-5-yl]-N-(4-methoxy-phenyl)-acetamide; 2-[7-(4-Chloro-benzoyl)-8-oxo-8H-[1,3]dioxolo[4,5-g]quinolin-5-yl]-N-(4-methoxy-phenyl)-acetamide; 2-(7-Benzoyl-8-oxo-8H-[1,3]dioxolo[4,5-g]quinolin-5-yl)-N-(3,4-dimethoxy-phenyl)-acetamide; N-(3,4-Dimethoxy-phenyl)-2-[7-(4-ethyl-benzoyl)-8-oxo-8H-[1,3]dioxolo[4,5-g]quinolin-5-yl]-acetamide; 2-(7-Benzoyl-8-oxo-8H-[1,3]dioxolo[4,5-g]quinolin-5-yl)-N-(4-ethoxy-phenyl)-acetamide; N-(4-Ethoxy-phenyl)-2-[7-(4-methyl-benzoyl)-8-oxo-8H-[1,3]dioxolo[4,5-g]quinolin-5-yl]-acetamide; N-(4-Ethoxy-phenyl)-2-[7-(4-ethyl-benzoyl)-8-oxo-8H-[1,3]dioxolo[4,5-g]quinolin-5-yl]-acetamide; N-(4-Ethoxy-phenyl)-2-[7-(4-methoxy-benzoyl)-8-oxo-8H-[1,3]dioxolo[4,5-g]quinolin-5-yl]-acetamide; N-(4-Ethoxy-phenyl)-2-[7-(4-fluoro-benzoyl)-8-oxo-8H-[1,3]dioxolo[4,5-g]quinolin-5-yl]-acetamide; 2-[7-(4-Chloro-benzoyl)-8-oxo-8H-[1,3]dioxolo[4,5-g]quinolin-5-yl]-N-(4-ethoxy-phenyl)-acetamide; 2-(7-Benzoyl-8-oxo-8H-[1,3]dioxolo[4,5-g]quinolin-5-yl)-N-(3-methoxy-phenyl)-acetamide; N-(3-Methoxy-phenyl)-2-[7-(4-methyl-benzoyl)-8-oxo-8H-[1,3]dioxolo[4,5-g]quinolin-5-yl]-acetamide; 2-[7-(4-Ethyl-benzoyl)-8-oxo-8H-[1,3]dioxolo[4,5-g]quinolin-5-yl]-N-(3-methoxy-phenyl)-acetamide; 2-[7-(3,4-Dimethyl-benzoyl)-8-oxo-8H-[1,3]dioxolo[4,5-g]quinolin-5-yl]-N-(3-methoxy-phenyl)-acetamide; 2-[7-(4-Methoxy-benzoyl)-8-oxo-8H-[1,3]dioxolo[4,5-g]quinolin-5-yl]-N-(3-methoxy-phenyl)-acetamide; 2-[7-(4-Ethoxy-benzoyl)-8-oxo-8H-[1,3]dioxolo[4,5-g]quinolin-5-yl]-N-(3-methoxy-phenyl)-acetamide; 2-[7-(4-Fluoro-benzoyl)-8-oxo-8H-[1,3]dioxolo[4,5-g]quinolin-5-yl]-N-(3-methoxy-phenyl)-acetamide; 2-[7-(4-Chloro-benzoyl)-8-oxo-8H-[1,3]dioxolo[4,5-g]quinolin-5-yl]-N-(3-methoxy-phenyl)-acetamide; 2-(7-Benzoyl-8-oxo-8H-[1,3]dioxolo[4,5-g]quinolin-5-yl)-N-(3,5-dimethoxy-phenyl)-acetamide; N-(3,5-Dimethoxy-phenyl)-2-[7-(4-methyl-benzoyl)-8-oxo-8H-[1,3]dioxolo[4,5-g]quinolin-5-yl]-acetamide; N-(3,5-Dimethoxy-phenyl)-2-[7-(4-ethyl-benzoyl)-8-oxo-8H-[1,3]dioxolo[4,5-g]quinolin-5-yl]-acetamide; N-(3,5-Dimethoxy-phenyl)-2-[7-(3,4-dimethyl-benzoyl)-8-oxo-8H-[1,3]dioxolo[4,5-g]quinolin-5-yl]-acetamide; N-(3,5-Dimethoxy-phenyl)-2-[7-(4-methoxy-benzoyl)-8-oxo-8H-[1,3]dioxolo[4,5-g]quinolin-5-yl]-acetamide; N-(3,5-Dimethoxy-phenyl)-2-[7-(4-ethoxy-benzoyl)-8-oxo-8H-[1,3]dioxolo[4,5-g]quinolin-5-yl]-acetamide; N-(3,5-Dimethoxy-phenyl)-2-[7-(4-fluoro-benzoyl)-8-oxo-8H-[1,3]dioxolo[4,5-g]quinolin-5-yl]-acetamide; 2-[7-(4-Chloro-benzoyl)-8-oxo-8H-[1,3]dioxolo[4,5-g]quinolin-5-yl]-N-(3,5-dimethoxy-phenyl)-acetamide; N-(2,5-Dimethoxy-phenyl)-2-[7-(4-ethyl-benzoyl)-8-oxo-8H-[1,3]dioxolo[4,5-g]quinolin-5-yl]-acetamide; 2-(7-Benzoyl-8-oxo-8H-[1,3]dioxolo[4,5-g]quinolin-5-yl)-N-(2,4-dimethoxy-phenyl)-acetamide; N-(2,4-Dimethoxy-phenyl)-2-[7-(4-methyl-benzoyl)-8-oxo-8H-[1,3]dioxolo[4,5-g]quinolin-5-yl]-acetamide; N-(2,4-Dimethoxy-phenyl)-2-[7-(4-ethyl-benzoyl)-8-oxo-8H-[1,3]dioxolo[4,5-g]quinolin-5-yl]-acetamide; N-(2,4-Dimethoxy-phenyl)-2-[7-(4-methoxy-benzoyl)-8-oxo-8H-[1,3]dioxolo[4,5-g]quinolin-5-yl]-acetamide; N-(2,4-Dimethoxy-phenyl)-2-[7-(4-ethoxy-benzoyl)-8-oxo-8H-[1,3]dioxolo[4,5-g]quinolin-5-yl]-acetamide; N-(2,4-Dimethoxy-phenyl)-2-[7-(4-fluoro-benzoyl)-8-oxo-8H-[1,3]dioxolo[4,5-g]quinolin-5-yl]-acetamide; 2-[7-(4-Chloro-benzoyl)-8-oxo-8H-[1,3]dioxolo[4,5-g]quinolin-5-yl]-N-(2,4-dimethoxy-phenyl)-acetamide; 2-(7-Benzoyl-8-oxo-8H-[1,3]dioxolo[4,5-g]quinolin-5-yl)-N-(4-fluoro-phenyl)-acetamide; N-(4-Fluoro-phenyl)-2-[7-(4-methyl-benzoyl)-8-oxo-8H-[1,3]dioxolo[4,5-g]quinolin-5-yl]-acetamide; 2-[7-(4-Ethyl-benzoyl)-8-oxo-8H-[1,3]dioxolo[4,5-g]quinolin-5-yl]-N-(4-fluoro-phenyl)-acetamide; 2-[7-(3,4-Dimethyl-benzoyl)-8-oxo-8H-[1,3]dioxolo[4,5-g]quinolin-5-yl]-N-(4-fluoro-phenyl)-acetamide; N-(4-Fluoro-phenyl)-2-[7-(4-methoxy-benzoyl)-8-oxo-8H-[1,3]dioxolo[4,5-g]quinolin-5-yl]-acetamide; 2-[7-(4-Ethoxy-benzoyl)-8-oxo-8H-[1,3]dioxolo[4,5-g]quinolin-5-yl]-N-(4-fluoro-phenyl)-acetamide; 2-[7-(4-Chloro-benzoyl)-8-oxo-8H-[1,3]dioxolo[4,5-g]quinolin-5-yl]-N-(4-fluoro-phenyl)-acetamide; N-(3,4-Difluoro-phenyl)-2-[7-(4-methyl-benzoyl)-8-oxo-8H-[1,3]dioxolo[4,5-g]quinolin-5-yl]-acetamide; N-(3,4-Difluoro-phenyl)-2-[7-(4-ethyl-benzoyl)-8-oxo-8H-[1,3]dioxolo[4,5-g]quinolin-5-yl]-acetamide; N-(3,4-Difluoro-phenyl)-2-[7-(4-methoxy-benzoyl)-8-oxo-8H-[1,3]dioxolo[4,5-g]quinolin-5-yl]-acetamide; N-(3,4-Difluoro-phenyl)-2-[7-(4-ethoxy-benzoyl)-8-oxo-8H-[1,3]dioxolo[4,5-g]quinolin-5-yl]-acetamide; 2-(7-Benzoyl-8-oxo-8H-[1,3]dioxolo[4,5-g]quinolin-5-yl)-N-(4-chloro-phenyl)-acetamide; N-(4-Chloro-phenyl)-2-[7-(4-methyl-benzoyl)-8-oxo-8H-[1,3]dioxolo[4,5-g]quinolin-5-yl]-acetamide; N-(4-Chloro-phenyl)-2-[7-(4-ethyl-benzoyl)-8-oxo-8H-[1,3]dioxolo[4,5-g]quinolin-5-yl]-acetamide; N-(4-Chloro-phenyl)-2-[7-(3,4-dimethyl-benzoyl)-8-oxo-8H-[1,3]dioxolo[4,5-g]quinolin-5-yl]-acetamide; N-(4-Chloro-phenyl)-2-[7-(4-ethoxy-benzoyl)-8-oxo-8H-[1,3]dioxolo[4,5-g]quinolin-5-yl]-acetamide; N-(4-Chloro-phenyl)-2-[7-(4-fluoro-benzoyl)-8-oxo-8H-[1,3]dioxolo[4,5-g]quinolin-5-yl]-acetamide; 2-[7-(4-Chloro-benzoyl)-8-oxo-8H-[1,3]dioxolo[4,5-g]quinolin-5-yl]-N-(4-chloro-phenyl)-acetamide; 2-[8-Oxo-7-(toluene-4-sulfonyl)-8H-[1,3]dioxolo[4,5-g]quinolin-5-yl]-N-phenyl-acetamide; 2-[7-(4-Fluoro-benzenesulfonyl)-8-oxo-8H-[1,3]dioxolo[4,5-g]quinolin-5-yl]-N-phenyl-acetamide; 2-[7-(4-Chloro-benzenesulfonyl)-8-oxo-8H-[1,3]dioxolo[4,5-g]quinolin-5-yl]-N-phenyl-acetamide; 2-(7-Benzenesulfonyl-8-oxo-8H-[1,3]dioxolo[4,5-g]quinolin-5-yl)-N-(4-chloro-phenyl)-acetamide; 2-(7-Benzenesulfonyl-8-oxo-8H-[1,3]dioxolo[4,5-g]quinolin-5-yl)-N-(4-fluoro-phenyl)-acetamide; N-(4-Fluoro-phenyl)-2-[8-oxo-7-(toluene-4-sulfonyl)-8H-[1,3]dioxolo[4,5-g]quinolin-5-yl]-acetamide; 2-[7-(4-Fluoro-benzenesulfonyl)-8-oxo-8H-[1,3]dioxolo[4,5-g]quinolin-5-yl]-N-(4-fluoro-phenyl)-acetamide; 2-(7-Benzenesulfonyl-8-oxo-8H-[1,3]dioxolo[4,5-g]quinolin-5-yl)-N-p-tolyl-acetamide; 2-[8-Oxo-7-(toluene-4-sulfonyl)-8H-[1,3]dioxolo[4,5-g]quinolin-5-yl]-N-p-tolyl-acetamide; 2-[7-(4-Fluoro-benzenesulfonyl)-8-oxo-8H-[1,3]dioxolo[4,5-g]quinolin-5-yl]-N-p-tolyl-acetamide; 2-(7-Benzenesulfonyl-8-oxo-8H-[1,3]dioxolo[4,5-g]quinolin-5-yl)-N-(4-methoxy-phenyl)-acetamide; 2-(7-Benzenesulfonyl-8-oxo-8H-[1,3]dioxolo[4,5-g]quinolin-5-yl)-N-(4-ethyl-phenyl)-acetamide; 2-[8-Oxo-7-(toluene-4-sulfonyl)-8H-[1,3]dioxolo[4,5-g]quinolin-5-yl]-N-m-tolyl-acetamide; 2-[7-(4-Fluoro-benzenesulfonyl)-8-oxo-8H-[1,3]dioxolo[4,5-g]quinolin-5-yl]-N-m-tolyl-acetamide; 2-[8-Oxo-7-(toluene-4-sulfonyl)-8H-[1,3]dioxolo[4,5-g]quinolin-5-yl]-N-o-tolyl-acetamide; 2-[7-(4-Fluoro-benzenesulfonyl)-8-oxo-8H-[1,3]dioxolo[4,5-g]quinolin-5-yl]-N-o-tolyl-acetamide; 5-Benzyl-7-(4-fluoro-benzenesulfonyl)-5H-[1,3]dioxolo[4,5-g]quinolin-8-one; 5-Benzyl-7-(4-chloro-benzenesulfonyl)-5H-[1,3]dioxolo[4,5-g]quinolin-8-one; 7-(4-Fluoro-benzenesulfonyl)-5-(2-methyl-benzyl)-5H-[1,3]dioxolo[4,5-g]quinolin-8-one; 7-(4-Isopropyl-benzenesulfonyl)-5-(2-methyl-benzyl)-5H-[1,3]dioxolo[4,5-g]quinolin-8-one; 7-(4-Chloro-benzenesulfonyl)-5-(2-methyl-benzyl)-5H-[1,3]dioxolo[4,5-g]quinolin-8-one; 5-(3-Methyl-benzyl)-7-(toluene-4-sulfonyl)-5H-[1,3]dioxolo[4,5-g]quinolin-8-one; 7-(4-Chloro-benzenesulfonyl)-5-(3-methyl-benzyl)-5H-[1,3]dioxolo[4,5-g]quinolin-8-one; 7-(4-Isopropyl-benzenesulfonyl)-5-(4-methyl-benzyl)-5H-[1,3]dioxolo[4,5-g]quinolin-8-one; 7-(4-Chloro-benzenesulfonyl)-5-(4-methyl-benzyl)-5H-[1,3]dioxolo[4,5-g]quinolin-8-one; 5-(2-Chloro-benzyl)-7-(toluene-4-sulfonyl)-5H-[1,3]dioxolo[4,5-g]quinolin-8-one; 5-(3-Chloro-benzyl)-7-(toluene-4-sulfonyl)-5H-[1,3]dioxolo[4,5-g]quinolin-8-one; 5-(4-Chloro-benzyl)-7-(toluene-4-sulfonyl)-5H-[1,3]dioxolo[4,5-g]quinolin-8-one; 5-(2-Fluoro-benzyl)-7-(toluene-4-sulfonyl)-5H-[1,3]dioxolo[4,5-g]quinolin-8-one; 7-(4-Chloro-benzenesulfonyl)-5-(2-fluoro-benzyl)-5H-[1,3]dioxolo[4,5-g]quinolin-8-one; 5-(3-Fluoro-benzyl)-7-(toluene-4-sulfonyl)-5H-[1,3]dioxolo[4,5-g]quinolin-8-one; 5-(4-Fluoro-benzyl)-7-(4-isopropyl-benzenesulfonyl)-5H-[1,3]dioxolo[4,5-g]quinolin-8-one; 5-(3-Methoxy-benzyl)-7-(toluene-4-sulfonyl)-5H-[1,3]dioxolo[4,5-g]quinolin-8-one; 7-(4-Chloro-benzenesulfonyl)-5-(4-methoxy-benzyl)-5H-[1,3]dioxolo[4,5-g]quinolin-8-one; 3-Benzoyl-1-benzyl-6-methyl-1H-quinolin-4-one; 3-Benzoyl-1-benzyl-5,7-dimethoxy-1H-quinolin-4-one; 1-Benzyl-6-methoxy-3-(4-methoxy-benzoyl)-1H-quinolin-4-one; 1-Benzyl-6-methyl-3-(4-methoxy-benzoyl)-1H-quinolin-4-one; 3-(Benzo[1,3]dioxole-5-carbonyl)-1-benzyl-1H-quinolin-4-one; 3-Benzoyl-1-methyl-1H-quinolin-4-one; 7-Methyl-3-(4-methylbenzoyl)-1-(3-trifluoromethylbenzyl)-1H-[1,8]naphthyridin-4-one; 1-(3-Fluorobenzyl)-7-methyl-3-(4-methylbenzoyl)-1H-[1,8]naphthyridin-4-one; 7-Methyl-3-(4-methylbenzoyl)-1-(3-methylbenzyl)-1H-[1,8]naphthyridin-4-one; 1-(3-Methoxybenzyl)-7-methyl-3-(4-methylbenzoyl)-1H-[1,8]naphthyridin-4-one; 7-Methyl-3-(4-methylbenzoyl)-1-(4-methylbenzyl)-1H-[1,8]naphthyridin-4-one; 1-(2,5-Dimethylbenzyl)-7-methyl-3-(4-methylbenzoyl)-1H-[1,8]naphthyridin-4-one; 1-(3-Chlorobenzyl)-7-methyl-3-(4-methylbenzoyl)-1H-[1,8]naphthyridin-4-one; 1-(2-Chloro-6-fluorobenzyl)-7-methyl-3-(4-methylbenzoyl)-1H-[1,8]naphthyridin-4-one; 1-(4-Fluorobenzyl)-7-methyl-3-(4-methylbenzoyl)-1H-[1,8]naphthyridin-4-one; 7-Methyl-3-(4-methylbenzoyl)-1-(2-methylbenzyl)-1H-[1,8]naphthyridin-4-one; 1-(4-Chlorobenzyl)-7-methyl-3-(4-methylbenzoyl)-1H-[1,8]naphthyridin-4-one; 1-(2-Fluorobenzyl)-7-methyl-3-(4-methylbenzoyl)-1H-[1,8]naphthyridin-4-one; 1-Benzyl-7-methyl-3-(4-methylbenzoyl)-1H-[1,8]naphthyridin-4-one; 7-(3-Aminopyrrolidin-1-yl)-3-benzoyl-1-(2,4-dimethoxybenzyl)-6-fluoro-1H-[1,8]naphthyridin-4-one; 3-Benzoyl-7-chloro-1,2-dibenzyl-6-fluoro-1H-[1,8]naphthyridin-4-one; 3-Benzoyl-2-benzyl-1-(4-methoxybenzyl)-1H-[1,8]naphthyridin-4-one; 3-Benzoyl-1,2-dibenzyl-1H-[1,8]naphthyridin-4-one; 3-Benzoyl-4-hydroxy-1-(4-nitrobenzyl)-1H-[1,8]naphthyridin-2-one; 1,3-Dibenzoyl-4-hydroxy-1H-[1,8]naphthyridin-2-one.

Preparation of Compounds

Certain compounds of the invention can be prepared following methodology as described in Silin, Olexiy V., et al., *Heterocycles* (2004) 63(8): 1883-1890. Compounds can also be prepared as shown in the synthetic procedures outlined in the Examples section of this document. In addition the syntheses of certain intermediate compounds that are useful in the preparation of compounds of the invention are described below.

SCHEME 1

Preparation of tert-butyl-carbamic acid azidomethyl ester (iii)

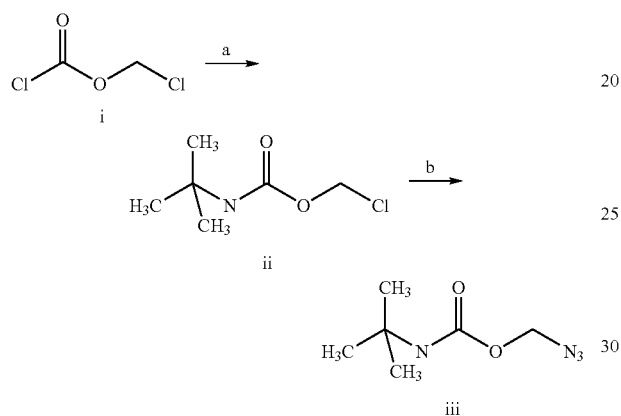

As shown in Scheme 1, Chloroformate i can be combined with tert-butyl amine in dichloromethane at lower temperature (e.g., −20° C. to RT) for approximately 1 h to provide carbamate ii (see, Step a). Carbamate ii when combined with sodium azide in aqueous solution for about 1 day will provide compound iii (see, Step b).

SCHEME 2

Preparation of 5,6-dimethyl-nicotinoyl chloride hydrochloride (x)

As shown in Step a of Scheme 2, 2-butanone iv is combined with ethyl formate and sodium methoxide in a mixture of diethyl ether and ethanol at low temperatures (e.g., 10° C. to RT) for 16 h to prepare sodium enolate v. Step b shows that pyridinone vi can be prepared by combining v with cyanoacetamide piperidinium acetate in water and heating the resultant solution at reflux for 4 h. As shown in Step c, pyridinone vi can be converted to bromopyridine vii upon heating with phosphorus tribromide at 190° C. for 1 h. Dehalogenation of vii can be achieved by heating vii in a mixture of acetic acid and ethanol in the presence of Zinc metal (e.g., zinc dust) for 1 h to provide the dehalogenated cyano compound viii. Hydrolysis of cyanopyridine viii can be achieved by heating viii in an aqueous solution of concentrated HCl at reflux for 5 h followed by neutralization of the reaction mixture with a solution of aqueous NaOH to provide carboxylic acid ix. The acid ix can be further coverted to the acid chloride x by heating with thionyl chloride in the presence of catalytic amount of DMF at 60° C. for 1 h.

SCHEME 3

Preparation of 2-bromomethyl-6-methyl-pyridine (xii)

Bromomethylpyridine xii can be prepared following a literature procedure (see, John B. Paine III *J. Het. Chem.* 1987, 351).

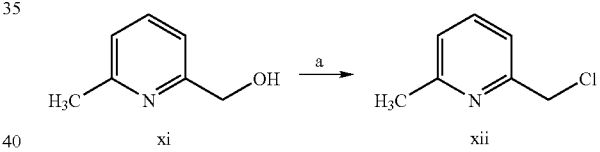

As shown in Scheme 3, hydroxymethylpyridine xi can be combined with PBr$_3$ in a dichloromethane solution and stirred at RT for 30 min to provide bromomethylpyridine xii.

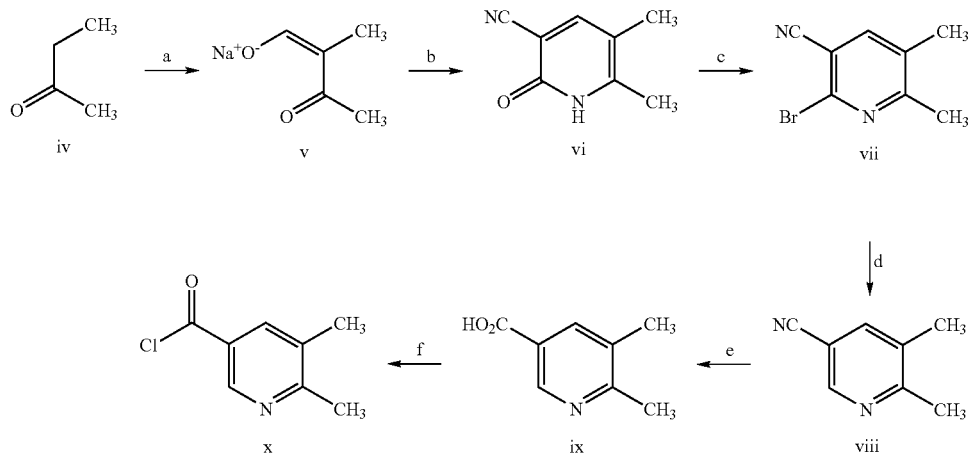

SCHEME 4

Preparation of 5,6-dimethyl-pyridine-2-carbonyl chloride hydrochloride (xviii)

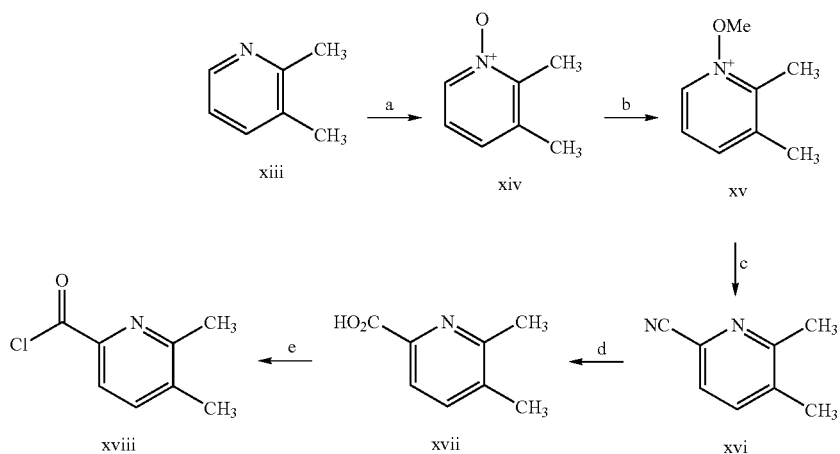

As shown in Step a of Scheme 4, pyridine-N-oxide xiv can be prepared by stirring pyridine xiii with m-chloroperbenzoic acid in a dichloromethane solution at RT for approximately 10 h. The N-oxide xiv oxygen atom can be methylated by using dimethylsulfate as the alkylating reagent and stirring with xiv in a dichloromethane/triethylamine solution for 24 h at RT can provide the methylated compound xv. As shown in Step c, the reaction between compound xv with KCN in water at elevated temperature (e.g. 60° C.) for 3 hours provided compound cyano product xvi. Cyano xvi can be hydrolyzed by dissolving the compound in a concentrated HCl solution and heating the resultant solution at reflux for approximately 1 day, and then neutralizing the solution with an aqueous solution of NaOH to provide acid xvii. The acid xvii can be converted to the acid chloride xviii upon heating xvii in a solution of thionyl chloride in the presence of a catalytic amount of DMF at 50° C. for 2 hours.

SCHEME 5

Preparation of 2-chloromethyl pyrimidine (xx)

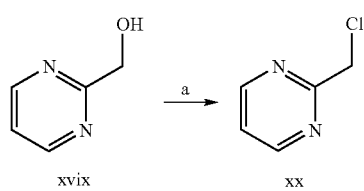

Pyrimidine xx can be prepared by stirring hydroxymethyl pyrimidine xvix with SOCl$_2$ at room temperature for 2 h.

Scheme 6

Preparation of N-(6-bromomethyl-pyridin-2-yl)-2,2,2-trifluoro-acetamide (xxiii)

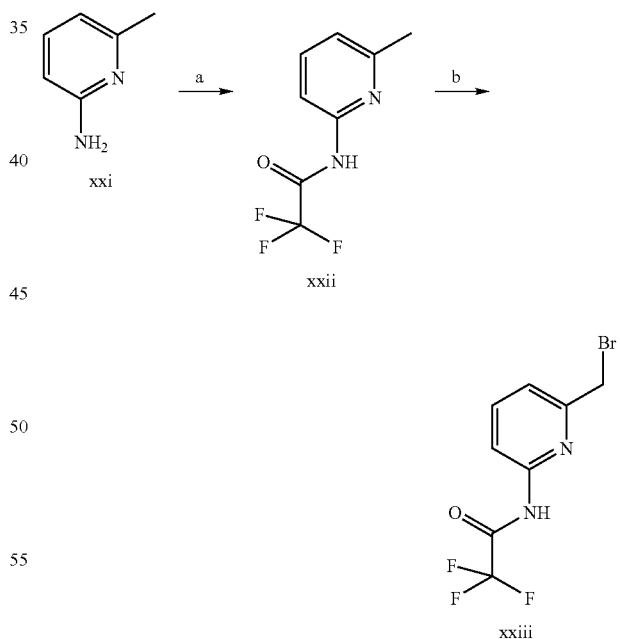

2,2,2-trifluoro-N-(6-methyl-pyridin-2-yl)-acetamide xxii can be prepared from 6-methyl-pyridin-2-ylamine and trifluoroacetic anhydride in DCM. Radical bromination of xxii with N-bromosuccinimide and benzoyl peroxide in refluxing carbon tetrachloride affords N-(6-bromomethyl-pyridin-2-yl)-2,2,2-trifluoro-acetamide xxiii.

SCHEME 7

Preparation of 2-iodo-5,6,7,8-tetrahydro-quinoline (xxvii)

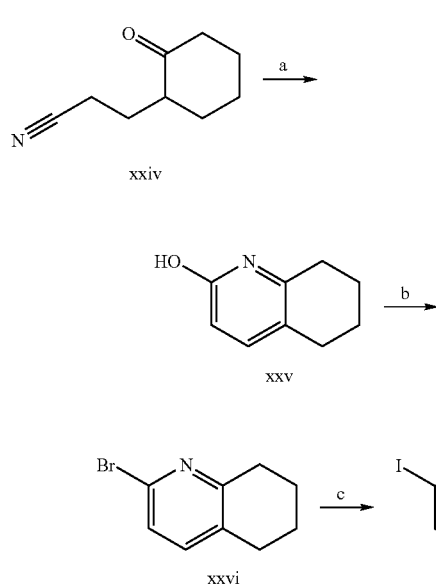

5,6,7,8-tetrahydro-quinolin-2-ol xxv can be prepared according to the procedure described by A. I. Meyers and G. Garcia-Munoz in *J. Org. Chem.* 1964 p. 1435-38 from 3-(2-oxo-cyclohexyl)-propionitrile xxiv and 96% sulfuric acid. Treatment of xxv with phosphorus tribromide at 180° C. gives 2-bromo-5,6,7,8-tetrahydro-quinoline xxvi, which is converted to 2-iodo-5,6,7,8-tetrahydro-quinoline xxvii by the action of sodium iodide and trimethylsilyl chloride in acetonitrile in a sealed tube at 130° C.

SCHEME 8

Preparation of 2-iodo-4,5-dimethyl-pyridine (xxix)

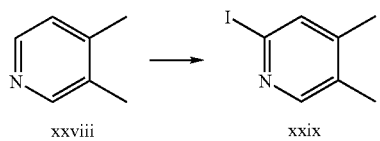

2-iodo-4,5-dimethyl-pyridine xxix can be prepared according to the procedure described by T. Kaminski et al in *Eur. J. Org. Chem.* 2003 p. 3855-60 from 3,4-lutidine xxviii, N,N-dimethylaminoethanol, n-butyllithium in hexanes followed by quenching with iodine in THF.

SCHEME 9

Preparation of 2-bromo-6-(1-bromo-ethyl)-pyridine (xxxii)

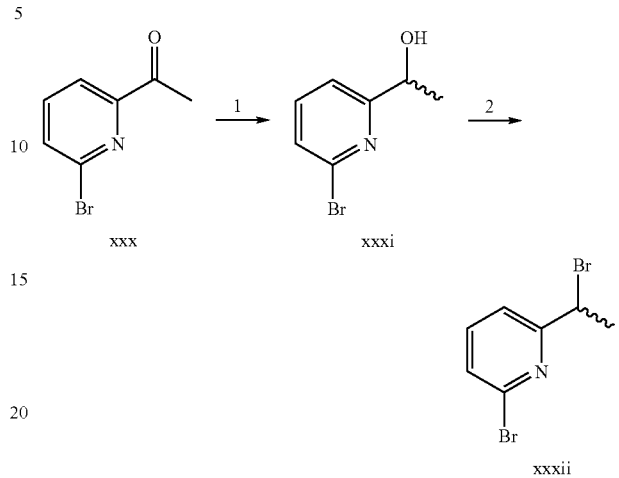

1-(6-Bromo-pyridin-2-yl)-ethanol xxxi can be prepared from 1-(6-bromo-pyridin-2-yl)-ethanone xxx by reduction with sodium borohydride in methanol. The intermediate xxxi is converted to the product xxxii by heating to 80° C. in phosphorus tribromide.

B. Compositions

In addition to the compounds provided above, compositions for modulating CCXCKR2 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

In one embodiment, pharmaceutical compositions comprising compounds, pharmaceutically acceptable salts, hydrates or N-oxides thereof having formula I or Ia, as set forth in Table 1 (vide supra) are of particular interest for the present invention. In another embodiment, pharmaceutical compositions comprising compounds as set forth in Table 2 (vide infra) are also of particular interest for the present invention.

TABLE 2

1. 7-(4-Chloro-benzoyl)-5-(3-methyl-benzyl)-5H-[1,3]dioxolo[4,5-g]quinolin-8-one
2. 7-(4-Fluoro-benzoyl)-5-(3-methyl-benzyl)-5H-[1,3]dioxolo[4,5-g]quinolin-8-one
3. 7-(4-Methyl-benzoyl)-5-(3-methyl-benzyl)-5H-[1,3]dioxolo[4,5-g]quinolin-8-one
4. 5-(3-Fluoro-benzyl)-7-(4-methyl-benzoyl)-5H-[1,3]dioxolo[4,5-g]quinolin-8-one
5. 7-(4-Chloro-benzoyl)-5-(2-fluoro-benzyl)-5H-[1,3]dioxolo[4,5-g]quinolin-8-one
6. 7-Benzoyl-5-(3-methyl-benzyl)-5H-[1,3]dioxolo[4,5-g]quinolin-8-one
7. 7-(3,4-Dimethyl-benzoyl)-5-(3-methyl-benzyl)-5H-[1,3]dioxolo[4,5-g]quinolin-8-one
8. 7-(3,4-Dimethyl-benzoyl)-5-(4-fluoro-benzyl)-5H-[1,3]dioxolo[4,5-g]quinolin-8-one
9. 7-(3,4-Dimethyl-benzoyl)-5-(4-methyl-benzyl)-5H-[1,3]dioxolo[4,5-g]quinolin-8-one
10. 7-(3,4-Dimethyl-benzoyl)-5-(3-fluoro-benzyl)-5H-[1,3]dioxolo[4,5-g]quinolin-8-one
11. 7-(3,4-Dimethyl-benzoyl)-5-(2-fluoro-benzyl)-5H-[1,3]dioxolo[4,5-g]quinolin-8-one
12. 5-(4-Methoxy-benzyl)-7-(4-methyl-benzoyl)-5H-[1,3]dioxolo[4,5-g]quinolin-8-one
13. 7-(3,4-Dimethyl-benzoyl)-5-(3-methoxy-benzyl)-5H-[1,3]dioxolo[4,5-g]quinolin-8-one
14. 7-(3,4-Dimethyl-benzoyl)-5-(2-methoxy-benzyl)-5H-[1,3]dioxolo[4,5-g]quinolin-8-one
15. 7-(4-Ethoxy-benzoyl)-5-(3-methyl-benzyl)-5H-[1,3]dioxolo[4,5-g]quinolin-8-one
16. 7-(4-Methoxy-benzoyl)-5-(3-methyl-benzyl)-5H-[1,3]dioxolo[4,5-g]quinolin-8-one
17. 7-(4-Ethoxy-benzoyl)-5-(3-fluoro-benzyl)-5H-[1,3]dioxolo[4,5-g]quinolin-8-one
18. 5-(4-Chloro-benzyl)-7-(4-ethoxy-benzoyl)-5H-[1,3]dioxolo[4,5-g]quinolin-8-one
19. 5-(4-Chloro-benzyl)-7-(4-methoxy-benzoyl)-5H-[1,3]dioxolo[4,5-g]quinolin-8-one
20. 5-Benzyl-7-(3,4-dimethyl-benzoyl)-5H-[1,3]dioxolo[4,5-g]quinolin-8-one
21. 5-Benzyl-7-(4-methyl-benzoyl)-5H-[1,3]dioxolo[4,5-g]quinolin-8-one

C. Methods of Use

While not wishing to be bound by any particular theory, the compounds and compositions of the present invention are considered to provide a therapeutic effect by inhibiting the binding of SDF-1 and/or I-TAC to the CCXCKR2 receptor. Therefore, the compounds and compositions of the present invention can be used in the treatment or prevention of diseases or disorders in a mammal in which the inhibition of binding of SDF-1 and/or I-TAC to the CCKCR2 receptor would provide a therapeutic effect. Diseases and disorders that can be treated by the compounds or compositions of the present invention include cancer, inflammation, HIV infectivity, progenitor/stem cell disorders, among others. In particular, SDF-1 is known to provide a target for interfering with the development or spread of cancer cells in a mammal, such as a human. Inhibition of the binding of I-TAC to the CCX-CKR2 receptor prevents the formation of vascularized tumors. By contacting the compositions described above with a cancer cell that expresses the CCXCKR2 receptor, the response that would otherwise trigger in the cancer cell can be reduced. Accordingly, the present invention is also directed to methods that are useful in the prevention and/or treatment of various disease, including cancer, particularly solid tumor cancers, more particularly breast cancer.

As determined by radiolabeled SDF-1 binding and I-TAC displacement, CCXCKR2 was preferentially expressed in human transformed cells. Included in Table 3 are those tissue types in which CCXCKR2 was expressed (CCXCKR2$^+$) as well as those tissue types in which CCXCKR2 was not expressed (CCXCKR2$^-$).

TABLE 3

| CCXCKR2$^+$ | CCXCKR2$^-$ |
| --- | --- |
| Human Cervical Adenocarcinoma | Normal Mouse Adult Progenitors (c-kit+ & CD34+ BM derived) |
| Human Adenocarcinoma, Mammary Gland | Human Acute Lymphoblastic Leukemia, T Cell |
| Human Burkitt's Lymphoma, B Lymphocyte | Normal Murine Bone Marrow |
| Human Glioblastoma Multiforme, Brain | Normal Murine Thymus |
| Human Carcinoma, Prostate | Normal Murine Lung |

TABLE 3-continued

| CCXCKR2$^+$ | CCXCKR2$^-$ |
| --- | --- |
| Murine Lymphoblastic Leukemia, B Lymphocyte | Normal Murine Spleen |
| Murine Mammary Gland Tumor | Normal Murine Liver |
| Normal Murine Fetal Liver | Normal Murine PBL |
| Normal Mouse Brain | Normal Human PBL |
| Normal Mouse Kidney | Normal Murine Heart |
| | Normal Murine Pancreas |

In one embodiment, a preferred method of inhibiting the binding of the chemokines SDF-1 and/or I-TAC to a CCX-CKR2 receptor includes contacting one or more of the previously mentioned compounds with a cell that expresses the CCXCKR2 receptor for a time sufficient to inhibit the binding of these chemokines to the CCXCKR2 receptor.

Methods of Treating Cancer

More specifically, the present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions of the present invention are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma.* Blood, No. 1, Vol. 96, pp. 282-87 (1 Jul. 2000); Pengnian, L., *Antiangiogenic gene therapy targeting the endothelium-specific receptor tyrosine kinase Tie2.* Proc. Natl. Acad. Sci. USA, Vol. 95, pp. 8829-34 (July 1998); and Pulaski, B. *Cooperativity of Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model.* Cancer Research, Vol. 60, pp. 2710-15 (May 15, 2000).

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with CCXCKR2 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (1) other antagonists of the chemokine receptors, especially CCR5, CXCR2, CXCR3, CCR2, CCR3, CCR4, CCR7, CX$_3$CR1 and CXCR6; (m) lubricants or emollients such as petrolatum and lanolin, (n) keratolytic agents (e.g., tazarotene), (o) vitamin D$_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Method of Treating HIV Infectivity

Still further, the compounds and compositions of the present invention are useful for the (prophylactic, curative or palliative) treatment of HIV infectivity, and can be combined with other compounds and compositions having therapeutic utilities that may require treatment either before, after or simultaneously with the treatment of HIV infectivity with the present compounds.

In certain aspects, in the treatment of HIV infectivity, an appropriate dosage level will generally be about 0.001 to 100 mg per kg patient body weight per day which can be administered in single or multiple doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Included within the scope of the invention are embodiments comprising the co-administration of a compound of the invention with one or more additional therapeutic agents, and compositions containing a compound of the invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the invention. For example, in the treatment of an HIV or related retroviral infection, it may be desirable to additionally treat opportunistic infections, neoplasms and other conditions which occur as a result of the immuno-compromised state of the patient being treated.

Preferred combinations of the invention include simultaneous or sequential treatment with a compound of the invention and one or more: (a) reverse transcriptase inhibitors such as abacavir, adefovir, didanosine, lamivudine, stavudine, zalcitabine and zidovudine; (b) non-nucleoside reverse transcriptase inhibitors such as capavirine, delavirdine, efavirenz, and nevirapine; (c) HIV protease inhibitors such as indinivir, nelfinavir, ritonavir, and saquinavir; (d) CCR5 antagonists such as TAK-779 or UK-427,857; (e) CXCR4 antagonists such as AMD-3100; (f) integrase inhibitors, such as L-870, 810 or S-1360; (g) inhibitors of viral fusion such as T-20; (h) investigational drugs such as trizivir, KNI-272, amprenavir, GW-33908, FTC, PMPA, MKC-442, MSC-204, MSH-372, DMP450, PNU-140690, ABT-378, KNI-764, DPC-083, TMC-120 or TMC-125; (i) antifungal agents, such as fluconazole, itraconazole or voriconazole; or (j) antibacterial agents, such as azithromycin.

Method of Treating Progenitor/Stem Cell Mobilization Disorders

Still further, the compounds and compositions of the present invention can be useful for the treatment of progenitor/stem cell differentiation and mobilization disorders using procedures and protocols as described in WO05/000333, incorporated herein by reference in its entirety for all purposes. Typical conditions which may be ameliorated or otherwise benefited include hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound healing and treatment of bacterial infections.

In the treatment or prevention of progenitor or stem cell mobilization disorders an appropriate dosage level will generally be about 0.001 to 100 mg per kg patient body weight per day which can be administered in single or multiple doses. The compounds may be administered as a single dose, a dose over time, as in i.v., or transdermal administration, or in multiple doses. The compounds of the invention can also be used in ex vivo treatment protocols to prepare cell cultures which are then used to replenish the blood cells of the subject. Ex vivo treatment can be conducted on autologous cells harvested from the peripheral blood or bone marrow or from allografts from matched donors.

The present compounds can be combined with other compounds and compositions having therapeutic utilities that may require treatment either before, after or simultaneously with the treatment of the progenitor/stem cell disorder with the present compounds. Accordingly, combination methods and compositions are also a component of the present invention to prevent and treat the condition or disease of interest.

In one embodiment, the compounds and pharmaceutical compositions comprising compounds as set forth in Tables 1 and 2 are of particular interest for use in the methods described for the present invention.

IV. EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; Pd$_2$dba$_3$, tris(dibenzylideneacetone)dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Preparation of 1-(6-bromo-pyridin-2-ylmethyl)-3-(3, 4-dimethyl-benzoyl)-1H-quinolin-4-one (4a)

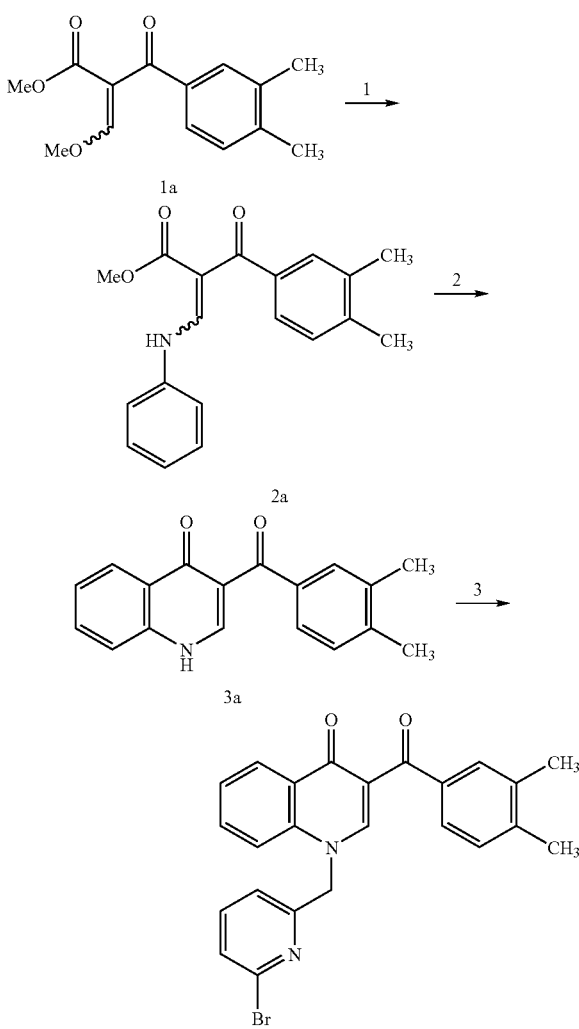

Step 1: Synthesis of 2-(3,4-Dimethyl-benzoyl)-3-phenylamino-acrylic acid methyl ester (2a)

Crude 2-(3,4-dimethyl-benzoyl)-3-methoxy-acrylic acid methyl ester 1a(13.7 g, 55.1 mmol) and of aniline (5.12 g, 55.1 mmol) were heated neat at 100° C. for 30 minutes, then cooled down to room temperature and recrystallized from dichloromethane/hexane to yield 7.94 g of 2-(3,4-Dimethyl-benzoyl)-3-phenylamino-acrylic acid methyl ester 2a as a yellow crystalline solid: LC-MSD, m/z for $C_{19}H_{19}NO_3$ [M+H]+=310.4; HPLC retention time: 2.8 min.

Step 2: Synthesis of 3-(3,4-Dimethyl-benzoyl)-1H-quinolin-4-one (3a)

2-(3,4-dimethyl-benzoyl)-3-phenylamino-acrylic acid methyl ester 2a(7.00 g, 22.6 mmol) (prepared as described by Silin, O. V.; et al. Heterocycles, 2004, 63, 1883-90) was heated at 260° C. in 150 mL of diphenyl ether for 6 h, then cooled down and 100 mL of hexane was added to the reaction solution. The mixture was filtered and the solid was washed with hexane to give 5.06 g of 3-(3,4-Dimethyl-benzoyl)-1H-quinolin-4-one 3a as off-white crystals: LC-MSD, m/z for $C_{18}H_{15}NO_2$ [M+H]+=278.4; HPLC retention time: 1.7 min.

Step 3: Synthesis of 1-(6-Bromo-pyridin-2-ylmethyl)-3-(3,4-dimethyl-benzoyl)-1H-quinolin-4-one (4a)

3-(3,4-dimethyl-benzoyl)-1H-quinolin-4-one (1.20 g, 4.32 mmol) 3a was suspended in 20 mL N,N-dimethylformamide followed by the addition of 60% sodium hydride (207 mg, 5.18 mmol). After approximately 5 minutes, 2-bromomethyl-6-methyl-pyridine (1.30 g, 5.18 mmol) was added and the mixture was stirred at rt for 12 hours. Then 100 mL of water was added to the reaction mixture and the precipitate was removed by filtration. Flash chromatography using 10-80% ethyl acetate in hexane yielded 1.82 g of the product 4a as white solid: LC-MSD, m/z for $C_{24}H_{19}BrN_2O_2$ [M+H]+=447.4, 449.4; HPLC retention time: 2.4 min; $^1$H NMR (400 MHz, CDCl$_3$): δ 2.3 (s, 3H), 2.35 (s, 3H), 5.5 (s, 2H), 6.9-7.0 (m, 1H), 7.1-7.2 (m, 1H), 7.3-7.4 (m, 1H), 7.4-7.55 (m, 3H), 7.55-7.7 (m, 3H), 8.3 (s, 1H), 8.4-8.5 (m, 1H).

Example 2

Preparation of 1-cyclohexylmethyl-3-(3,4-dimethyl-benzoyl)-1H-quinolin-4-one (4b)

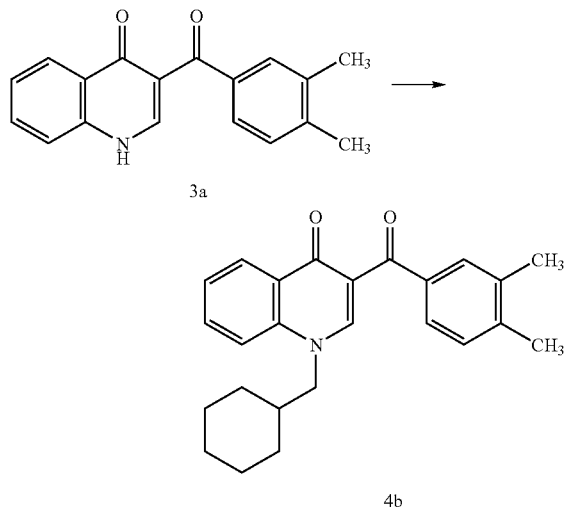

The titled compound was prepared following the procedure described in Step 3 of Example 1. 63 mg (0.23 mmol) of 3-(3,4-dimethyl-benzoyl)-1H-quinolin-4-one 3a, 12 mg (0.30 mmol) of 60% sodium hydride and 52 mg (0.30 mmol) of cyclohexylmethyl bromide and 0.9 mL N,N-dimethylformamide were combined at 90° C. for 5 h. Flash chromatography using 10-75% ethyl acetate in hexane yielded 50 mg of the product 4b as white solid: LC-MSD, m/z for $C_{25}H_{27}NO_2$ [M+H]+=374.6; HPLC retention time: 2.8 min; $^1$H NMR (400 MHz, CDCl$_3$): δ 1.0-1.3 (m, 6H), 1.7-1.85 (m, 4H), 1.9-2.0 (m, 1H), 2.3 (s, 3H), 2.35 (s, 3H), 4.0-4.05 (m, 2H), 7.15-7.2 (m, 1H), 7.4-7.5 (m, 2H), 7.5-7.6 (m, 1H), 7.6 (s, 1H), 7.65-7.75 (m, 1H), 8.05 (s, 1H), 8.45-8.5 (m, 1H).

Example 3

Preparation of 3-(3,4-dimethyl-benzoyl)-1-(1H-[1,2,3]triazol-4-ylmethyl)-1H-quinolin-4-one (4d)

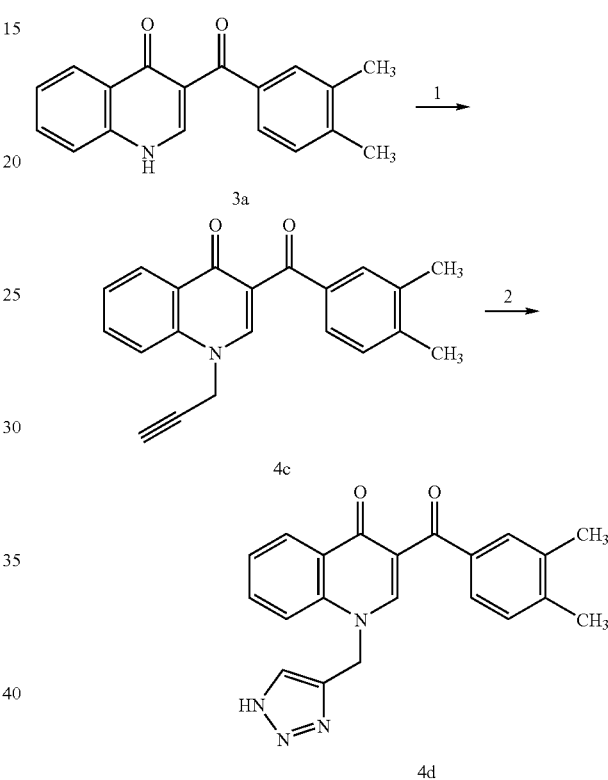

Step 1: Synthesis of 3-(3,4-Dimethyl-benzoyl)-1-prop-2-ynyl-1H-quinolin-4-one (4c)

Compound 4c was prepared following the procedure described in Step 3 of Example 1, briefly described here, 60 mg (0.22 mmol) of 3-(3,4-dimethyl-benzoyl)-1H-quinolin-4-one 3a, 10 mg (0.26 mmol) of 60% sodium hydride and 39 mg (0.26 mmol) of 80% propargyl bromide in toluene were combined in 0.5 mL N,N-dimethylformamide at and stirred at rt for 2 h. Flash chromatography using 30-100% ethyl acetate in hexane yielded 62 mg of the product 4d as white solid: LC-MSD, m/z for $C_{21}H_{17}NO_2$ [M+H]+=316.5; HPLC retention time: 2.1 min.

Step 2: Synthesis of 3-(3,4-Dimethyl-benzoyl)-1-(1H-[1,2,3] triazol-4-ylmethyl)-1H-quinolin-4-one (4d)

29 mg (0.092 mmol) of 3-(3,4-dimethyl-benzoyl)-1-prop-2-ynyl-1H-quinolin-4-one 4c (prepared as described by Paine, J. B.; J. Het. Chem. 1987, 351), 19 mg (0.11 mmol) of tert-butyl-carbamic acid azidomethyl ester, 5.0 mg (0.078 mmol) of copper powder, and 2.0 mg (0.008 mmol) of copper (II) sulfate pentahydrate were combined in a mixture of 0.5 mL tert-butanol and 0.2 mL water and stirred at 80° C. for 4 h. Then 70 mg (1.75 mmol) of sodium hydroxide in 1 mL water was added to that mixture and the resultant mixture was stirred at 80° C. for another hour. The mixture was filtered and purified using reverse phase HPLC (mobile phase with a gradient 15-80% acetonitrile in 50 min). Lyophilization of the HPLC fractions containing purified 4d provided 18 mg of a pale yellow product as the trifluoroacetate salt: LC-MSD, m/z for $C_{21}H_{18}N_4O_2$, [M+H]+=359.5, HPLC retention time: 1.5 min; $^1$H NMR (400 MHz, CDCl$_3$): δ 2.25 (s, 3H), 2.3 (s, 3H), 6.7 (s, 2H), 7.1-7.2 (m, 1H), 7.4-7.45 (m, 1H), 7.45-7.5 (m, 2H), 7.75-7.85 (m, 3H), 8.4-8.5 (m, 1H), 8.65 (s, 1H).

Example 4

Preparation of 3-(3,4-dimethyl-benzoyl)-1-phenyl-1H-quinolin-4-one (4e)

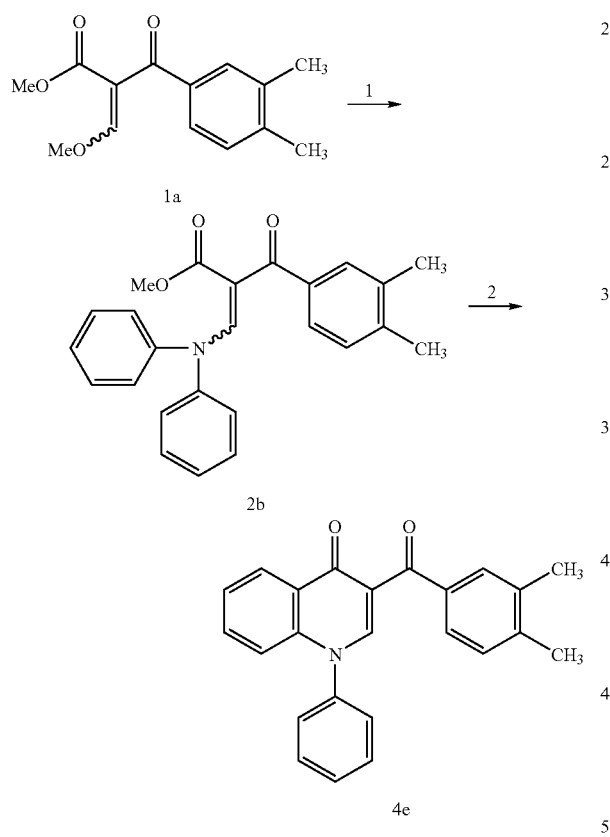

Step 1: Synthesis of 2-(3,4-Dimethyl-benzoyl)-3-diphenylamino-acrylic acid methyl ester (2b)

Compound 2b was prepared following the procedure described in Step 2 of Example 1 using 1.08 g (4.36 mmol) of the crude 2-(3,4-dimethyl-benzoyl)-3-methoxy-acrylic acid a methyl ester and 738 mg (4.36 mmol) of diphenylamine. The crude product was purified using flash chromatography (0-40% ethyl acetate in hexane) to yield 955 mg of 2-(3,4-dimethyl-benzoyl)-3-diphenylamino-acrylic acid methyl ester 2b as a yellow crystalline solid: LC-MSD, m/z for $C_{25}H_{24}NO_3$, [M+H]+=386.5, retention time: 2.9 min.

Step 2: 3-(3,4-Dimethyl-benzoyl)-1-phenyl-1H-quinolin-4-one (4e)

2-(3,4-dimethyl-benzoyl)-3-diphenylamino-acrylic acid methyl ester 2b (450 mg, 1.27 mmol) was heated in 2 mL of polyphosphoric acid at 90° C. for 1 h, then quenched using water/dichloromethane. The organic layer was dried and concentrated to provide the crude product which was purified using flash chromatography (30-100% ethyl acetate in hexane) to yield 26 mg of 3-(3,4-dimethyl-benzoyl)-1-phenyl-1H-quinolin-4-one 4e as a dark yellow crystalline solid: LC-MSD, m/z for $C_{24}H_{19}NO_2$, [M+H]+=354.1; HPLC retention time: 2.6 min; $^1$H NMR (400 MHz, CDCl$_3$): δ 2.3 (s, 3H), 2.35 (s, 3H), 7.0-7.1 (m, 1H), 7.1-7.2 (m, 1H), 7.4-7.5 (m, 3H), 7.5-7.7 (m, 4H), 7.7 (s, 1H), 8.2 (s, 1H), 8.4-8.5 (m, 1H).

Example 5

Preparation of 3-(3,4-dimethyl-benzoyl)-1-(2-fluoro-benzyl)-6-trifluoromethyl-1H-quinolin-4-one (4f)

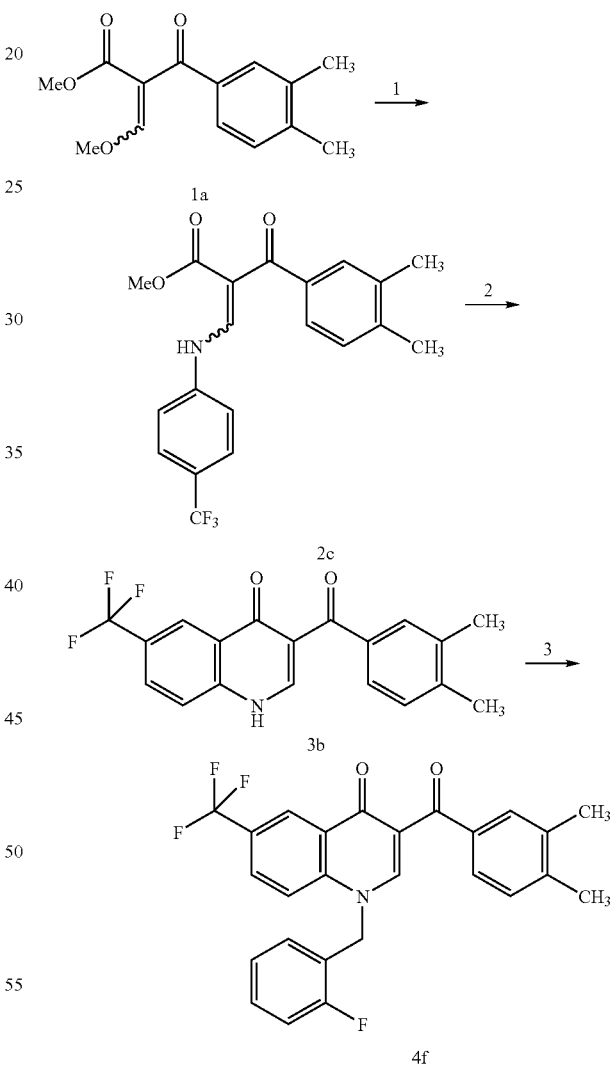

Step 1: Synthesis of 2-(3,4-Dimethyl-benzoyl)-3-(4-trifluoromethyl-phenylamino)-acrylic acid methyl ester (2c)

Compound 2c was prepared following the procedure described in Step 2 of Example 1 using 598 mg (2.41 mmol) of the crude 2-(3,4-dimethyl-benzoyl)-3-methoxy-acrylic acid methyl ester 1a and 427 mg (2.65 mmol) of 4-trifluoromethyl-phenylamine. The product 2c was purified by flash chromatography (0-40% ethyl acetate in hexane) to yield 151 mg of 2-(3,4-dimethyl-benzoyl)-3-(4-trifluoromethyl-phenylamino)-acrylic acid methyl ester as a yellow crystalline solid: LC-MSD, m/z for $C_{20}H_{18}F_3NO_3$ [M+H]+=378.5; HPLC retention time: 3.0 min.

Step 2: Synthesis of 3-(3,4-Dimethyl-benzoyl)-6-trifluoromethyl-1H-quinolin-4-one (3b)

2-(3,4-dimethyl-benzoyl)-3-(4-trifluoromethyl-phenylamino)-acrylic acid methyl ester 2c (151 mg, 0.40 mmol) was refluxed in 5 mL of nitrobenzene for 3 h, then cooled down and to it was added 10 mL of hexane. The crude product precipitated out of solution and was isolated by filtration. The crude product was washed with hexane to give 115 mg of 3-(3,4-dimethyl-benzoyl)-6-trifluoromethyl-1H-quinolin-4-one as off-white crystals 3b: LC-MSD, m/z for $C_{19}H_{14}F_3NO_2$, [M+H]+=346.4,; HPLC retention time: 2.3 min.

Step 3: Synthesis of 3-(3,4-Dimethyl-benzoyl)-1-(2-fluoro-benzyl)-6-trifluoromethyl-1H-quinolin-4-one (4f)

Compound 4f was prepared following the procedure described in Step 3 of Example 1. Briefly described here, 55 mg (0.16 mmol) of 3-(3,4-dimethyl-benzoyl)-6-trifluoromethyl-1H-quinolin-4-one 3b, 8 mg (0.21 mmol) of 60% sodium hydride and 40 mg (0.21 mmol) of 2-fluorobenzyl bromide were combined in 0.5 mL N,N-dimethylformamide at rt for 16 h. Flash chromatography of the crude product using 10-80% ethyl acetate in hexane yielded 58 mg of the product 4f as white solid: LC-MSD, m/z for $C_{26}H_{19}F_4NO_2$ [M+H]+=454.5, HPLC retention time: 2.9 min: $^1$H NMR (400 MHz, CDCl$_3$): δ 2.3 (s, 3H), 2.35 (s, 3H), 5.5 (s, 2H), 7.05-7.2 (m, 4H), 7.3-7.4 (m, 1H), 7.5-7.6 (m, 2H), 7.65 (s, 1H), 7.8-7.85 (m, 1H), 8.3 (s, 1H), 8.75-8.8 (m, 1H).

Example 6

Preparation of 3-(5,6-dimethyl-pyridine-3-carbonyl)-1-(2-fluoro-benzyl)-1H-quinolin-4-one (4g)

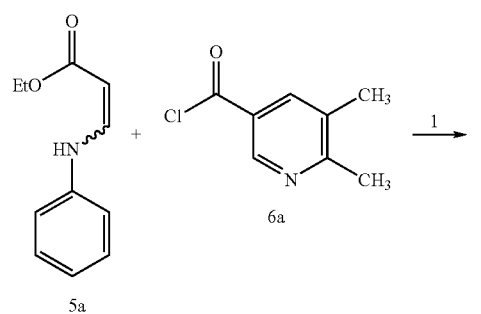

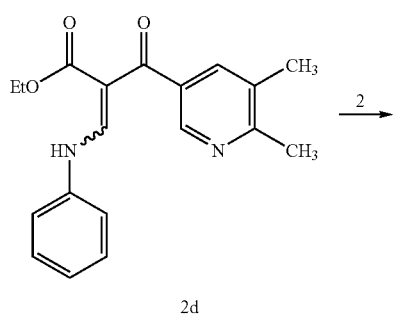

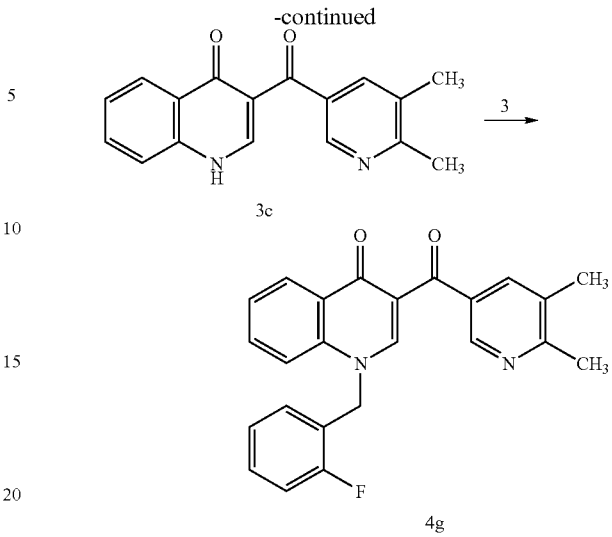

Step 1: Synthesis of 2-(5,6-Dimethyl-pyridine-3-carbonyl)-3-phenylamino-acrylic acid ethyl ester (2d)

3.31 g (16.0 mmol) of 5,6-dimethyl-nicotinoyl chloride hydrochloride 6a (prepared as described by Paine, J. B.; J. Het. Chem. 1987, 351) was dissolved in 35 mL of dry tetrahydrofuran and cooled down to −10° C. under nitrogen atmosphere. To the resultant solution was added 1.60 g (40.0 mmol) of 60% sodium hydride and the mixture was stirred for 15 minutes, followed by the addition of 3.06 g (16.0 mmol) of 3-phenylamino-acrylic acid ethyl ester 5a. The mixture was stirred at −10° C. for 2 hours, followed by the addition of 100 mL of water to the reaction mixture. The product was extracted twice with 100 mL dichloromethane. The combined organic extracts were dried with MgSO$_4$ and concentrated in vacuo. Purification of the crude product using flash chromatography (10-75% ethyl acetate in hexane) yielded 400 mg of 2-(5,6-dimethyl-pyridine-3-carbonyl)-3-phenylamino-acrylic acid ethyl ester 2d as a yellow solid.

Step 2: Synthesis of 3-(5,6-Dimethyl-pyridine-3-carbonyl)-1H-quinolin-4-one (3c)

Compound 3c was prepared following the procedure described in Step 2 of Example 1 using 400 mg (1.23 mmol) of 2-(5,6-dimethyl-pyridine-3-carbonyl)-3-phenylamino-acrylic acid ethyl ester 2d, and 50 mL of diphenyl ether. The reaction time was 1 h. Purification of the crude product by flash chromatography using 60-100% ethyl acetate in hexane followed by 0-25% methanol in ethyl acetate yielded 201 mg of the product 3c as off-white solid: LC-MSD, m/z for $C_{17}H_{14}N_2O_2$ [M+H]+=279.4, HPLC retention time: 0.25 min.

Step 3: Synthesis of 3-(5,6-Dimethyl-pyridine-3-carbonyl)-1-(2-fluoro-benzyl)-1H-quinolin-4-one (4g)

Compound 4g was prepared following the procedure described in Step 3 of Example 1. 63 mg (0.23 mmol) of 3-(5,6-dimethyl-pyridine-3-carbonyl)-1H-quinolin-4-one 3c, 11 mg (0.27 mmol) of 60% sodium hydride and 51 mg (0.27 mmol) of 2-fluorobenzyl bromide were combined in 1 mL N,N-dimethylformamide at rt for 1 h. The product was purified using reverse phase HPLC, mobile phase with a gradient 10-70% acetonitrile in 50 min. The HPLC fractions containing pure product were combined and the combined solutions was lyophilized with 1 mL of 1 M HCl to give 82 mg of a pale yellow solid 4g as its HCl salt: LC-MSD, m/z for $C_{24}H_{19}FN_2O_2$ [M+H]+=387.5, HPLC retention time: 1.2 min; $^1$H NMR (400 MHz, CDCl$_3$): δ 2.55 (s, 3H), 2.9 (s, 3H), 5.55 (s, 2H), 7.05-7.2 (m, 3H), 7.3-7.4 (m, 1H), 7.45-7.55 (m, 2H), 7.65-7.75 (m, 1H), 8.35-8.45 (m, 2H), 8.6 (s, 1H), 8.85 (s, 1H).

Example 7

Preparation of 3-(5,6-dimethyl-pyridine-3-carbonyl)-1-(6-methyl-pyridin-2-ylmethyl)-1H-quinolin-4-one (4h)

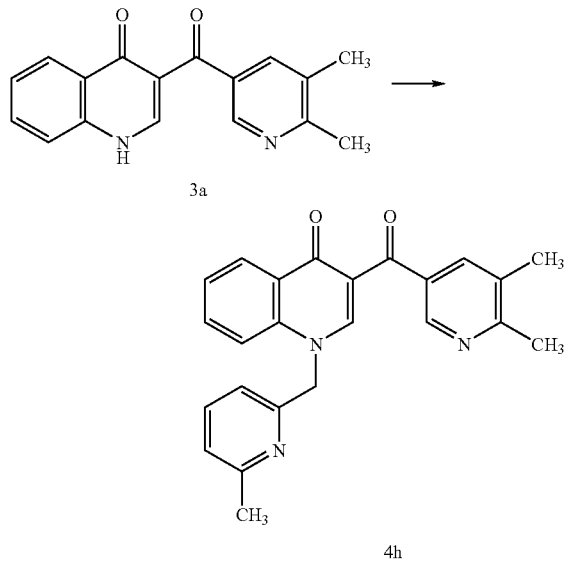

Compound 4h was prepared following the procedure described in Step 3 of Example 1. Briefly described here, 65 mg (0.23 mmol) of 3-(5,6-dimethyl-pyridine-3-carbonyl)-1H-quinolin-4-one 3c, 11 mg (0.28 mmol) of 60% sodium hydride and 52 mg (0.28 mmol) of 2-bromomethyl-6-methyl-pyridine (prepared as described by Paine, J. B.; *J. Het. Chem.* 1987, 351) in 0.7 mL N,N-dimethylformamide were stirred at rt for 2 h. The product was purified using reverse phase HPLC, mobile phase with a gradient 10-70% acetonitrile in 50 min. HPLC fractions containing pure product 4h were lyophilized to give 41 mg of a white solid as trifluoroacetate salt: LC-MSD, m/z for $C_{24}H_{21}N_3O_2$ [M+H]+=384.5, HPLC retention time: 0.4 min; $^1$H NMR (400 MHz, CDCl$_3$): δ 2.5 (s, 3H), 2.8 (s, 3H), 2.85 (s, 3H), 6.05 (s, 2H), 7.2-7.3 (m, 1H), 7.4-7.5 (m, 2H), 7.5-7.6 (m, 1H), 7.6-7.7 (m, 1H), 8.0-8.1 (m, 1H), 8.3-8.4 (m, 1H), 8.4 (s, 1H), 8.7 (s, 1H), 8.9 (s, 1H).

Example 8

Preparation of 3-(5,6-dimethyl-pyridine-2-carbonyl)-1-(2-fluoro-benzyl)-1H-quinolin-4-one (4i)

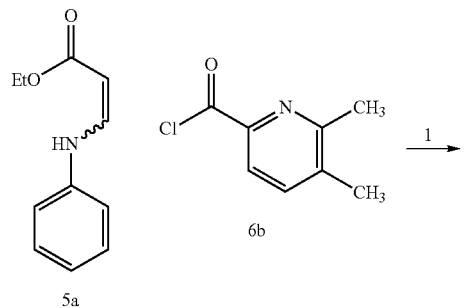

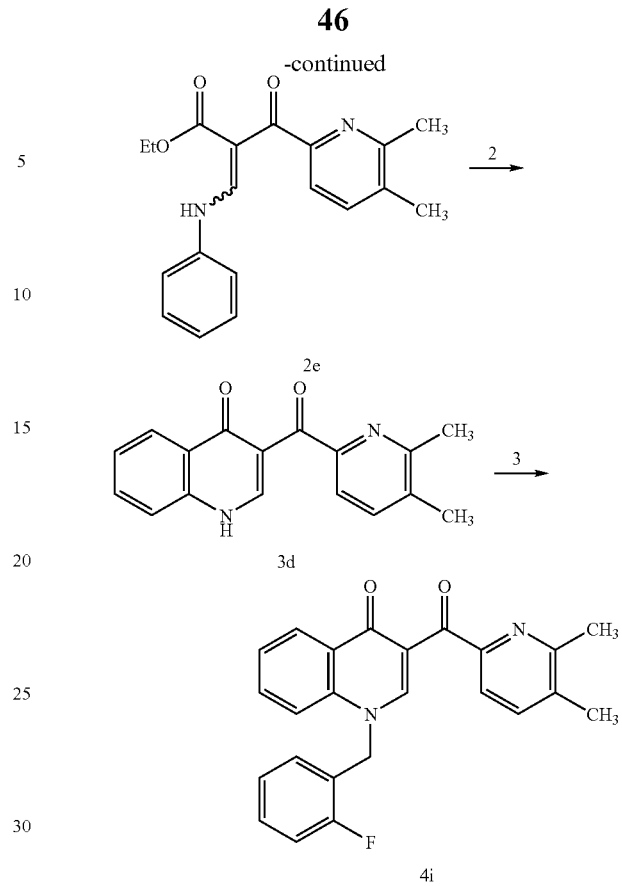

Step 1: 2-(5,6-Dimethyl-pyridine-2-carbonyl)-3-phenylamino-acrylic acid ethyl ester (2e)

Compound 2e was prepared following the procedure outlined in Step 1 of Example 6 using 2.28 g (11.0 mmol) of 5,6-dimethyl-pyridine-2-carbonyl chloride hydrochloride (prepared as described by Paine, J. B.; *J. Het. Chem.* 1987, 351), 1.91 g (10.0 mmol) of 3-phenylamino-acrylic acid ethyl ester, 1.08 g (27.0 mmol) of 60% sodium hydride and 25 mL tetrahydrofuran. Flash chromatography using 10-80% ethyl acetate in hexane yielded 575 mg of the product as yellow solid. LC-MSD, m/z for $C_{19}H_{20}N_2O_3$ [M+H]+=325.5, HPLC retention time: 1.9 min.

Step 2: 3-(5,6-Dimethyl-pyridine-2-carbonyl)-1H-quinolin-4-one (3d)

Compound 3d was prepared following the procedure outlined in Step 2 of Example 1 using 575 mg (1.77 mmol) of 2-(5,6-dimethyl-pyridine-3-carbonyl)-3-phenylamino-acrylic acid ethyl ester 2e, 30 mL of diphenyl ether. The reaction time was 2 h. Flash chromatography using 50-100% ethyl acetate in hexane followed by 0-30% methanol in ethyl acetate yielded 100 mg of the product 3d as off-white solid: LC-MSD, m/z for $C_{17}H_{14}N_2O_2$ [M+H]+: 279.4, HPLC retention time: 0.4 min.

Step 3: 3-(5,6-Dimethyl-pyridine-2-carbonyl)-1-(2-fluoro-benzyl)-1H-quinolin-4-one (4i)

Compound 4i was prepared following the procedure outlined in Step 3 of Example 1. Briefly described here, 32 mg (0.12 mmol) of 3-(5,6-dimethyl-pyridine-2-carbonyl)-1H-quinolin-4-one 3d, 6 mg (0.14 mmol) of 60% sodium hydride and 26 mg (0.14 mmol) of 2-fluorobenzyl bromide were combined in 0.5 mL N,N-dimethylformamide and stirred at rt for 2 h. The product was purified using reverse phase HPLC, mobile phase with a gradient 10-70% acetonitrile in 50 min.

The HPLC fractions containing pure product were lyophilized to give 43 mg of a pale yellow solid 4i as trifluoroacetate salt: LC-MSD, m/z for $C_{24}H_{19}FN_2O_2$ [M+H]+=387.5, HPLC retention time: 1.8 min; $^1H$ NMR (400 MHz, CDCl$_3$): δ 2.5 (s, 3H), 2.8 (s, 3H), 5.7 (s, 2H), 7.1-7.2 (m, 3H), 7.3-7.4 (m, 1H), 7.5-7.6 (m, 1H), 7.6-7.7 (m, 1H), 7.7-7.8 (m, 1H), 8.1-8.2 (m, 1H), 8.5-8.6 (m, 1H), 9.05 (s, 1H).

Example 9

Preparation of 3-(3,4-dimethyl-benzoyl)-1-(6-methyl-pyridin-2-ylmethyl)-1H-cinnolin-4-one (9a)

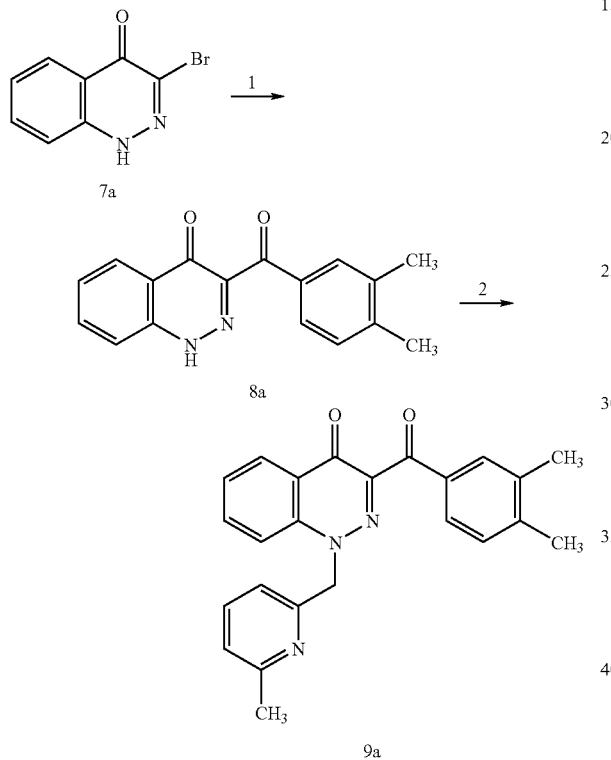

Step 1: 3-(3,4-Dimethyl-benzoyl)-1H-cinnolin-4-one(8a)

1.49 g (6.61 mmol) of 3-bromo-1H-cinnolin-4-one 7a (Prepared as described in U.S. Pat. No. 4,379,929), 2.48 g (16.5 mmol) of 3,4-dimethylphenylboronic acid, 4.57 g (33.1 mmol) of potassium carbonate and 464 mg (0.661 mmol) of bis(triphenylphosphine)palladium(II) dichloride were stirred in 50 mL of anisole at 150° C. under the atmosphere of carbon monoxide for 3 h. The mixture was cooled down, filtered and concentrated in vacuo. Flash chromatography of the crude product 8a using 10-80% ethyl acetate in hexane to give 78 mg of the product as off-white solid: LC-MSD, m/z for $C_{17}H_{14}N_2O_2$ [M+H]+=279.1, HPLC retention time: 1.9 min.

Step 2: 3-(3,4-Dimethyl-benzoyl)-1-(6-methyl-pyridin-2-ylmethyl)-1H-cinnolin-4-one (9a)

Compound 9a was prepared following the procedure outlined in Step 3 of Example 1. Briefly described here, 36 mg (0.13 mmol) of 3-(3,4-dimethyl-benzoyl)-1H-cinnolin-4-one 8a, 7 mg (0.17 mmol) of 60% sodium hydride and 33 mg (0.17 mmol) of 2-bromomethyl-6-methyl-pyridine in 0.7 mL N,N-dimethylformamide at rt for 3 h. The product was purified using reverse phase HPLC, mobile phase with a gradient 10-70% acetonitrile in 50 min. The HPLC fractions containing pure product were combined and lyophilized to give 34 mg of a pale yellow solid 9a as the trifluoroacetate salt: LC-MSD, m/z for $C_{24}H_{21}N_3O_2$ [M+H]+=384.5, HPLC retention time: 2.3 min; $^1H$ NMR (400 MHz, CDCl$_3$): δ 2.3 (s, 3H), 2.35 (s, 3H), 2.85 (s, 3H), 6.1 (s, 2H), 7.15-7.2 (m, 1H), 7.25-7.3 (m, 1H), 7.45-7.55 (m, 2H), 7.6-7.7 (m, 3H), 7.7-7.8 (m, 1H), 8.0-8.1 (m, 1H), 8.3-8.4 (m, 1H).

Example 10

Preparation of 3-(3,4-dimethyl-benzoyl)-1-thiazol-4-ylmethyl-1H-quinolin-4-one (4j)

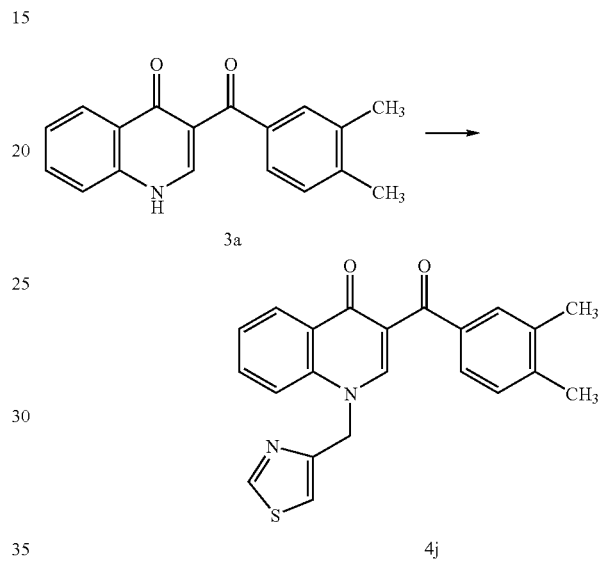

Compound 4j was prepared following the procedure outlined in Step 3 of Example 1. Briefly described here, 50 mg (0.18 mmol) of 3-(3,4-dimethyl-benzoyl)-1H-quinolin-4-one 3a, 19 mg (0.47 mmol) of 60% sodium hydride and 40 mg (0.25 mmol) of 4-chloromethyl thiazole hydrochloride were combined in 1 mL N,N-dimethylformamide and stirred at 70° C. for 2 h. The crude product was purified by flash chromatography using 20-100% ethyl acetate in hexane yielded 54 mg of the product as white solid: LC-MSD, m/z for $C_{22}H_{18}N_2O_2S$ [M+H]+=375.5; HPLC retention time: 2.1 min; $^1H$ NMR (400 MHz, CDCl$_3$): δ 2.3 (s, 3H), 2.35 (s, 3H), 5.6 (s, 2H), 7.1-7.2 (m, 2H), 7.4-7.5 (m, 1H), 7.5-7.6 (m, 2H), 7.6-7.7 (m, 2H), 8.3 (s, 1H), 8.45-8.5 (m, 1H), 8.8-8.85 (m, 1H).

Example 11

Preparation of 3-(3,4-dimethyl-benzoyl)-1-pyrimidin-2-ylmethyl-1H-quinolin-4-one (4k)

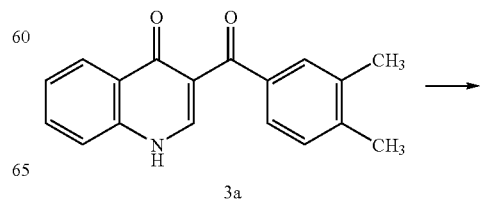

-continued

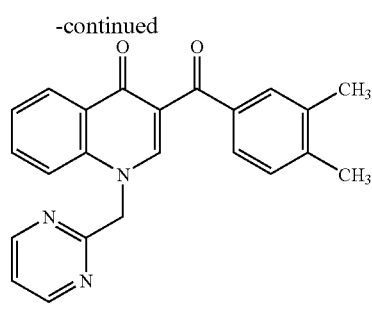

4k

Compound 4k was prepared following the procedure outlined in Step 3 of Example 1. Briefly described here, 97 mg (0.35 mmol) of 3-(3,4-dimethyl-benzoyl)-1H-quinolin-4-one, 18 mg (0.45 mmol) of 60% sodium hydride and 66 mg (0.51 mmol) of 2-chloromethyl pyrimidine (prepared as described by Paine, J. B.; *J. Het. Chem.* 1987, 351) were combined in 1 mL N,N-dimethylformamide and heated at 80° C. for 2 h. The product was purified using reverse phase HPLC (mobile phase with a gradient 10-50% acetonitrile in 50 min), to give 57 mg of a pale yellow solid 4k as trifluoroacetate salt: LC-MSD, m/z for $C_{23}H_{19}N_3O_2$ [M+H]+=370.5, HPLC retention time: 2.4 min; $^1$H NMR (400 MHz, CDCl$_3$): δ 2.3 (s, 3H), 2.35 (s, 3H), 5.6 (s, 2H), 7.15-7.2 (m, 1H), 7.25-7.3 (m, 1H), 7.4-7.5 (m, 1H), 7.5-7.55 (m, 1H), 7.6-7.7 (m, 3H), 8.4-8.5 (m, 2H), 8.7-8.75 (m, 2H).

Example 12

Preparation of 3-(3,4-dimethyl-benzoyl)-1-(2-fluoro-benzyl)-2,3-dihydro-1H-quinolin-4-one (4l)

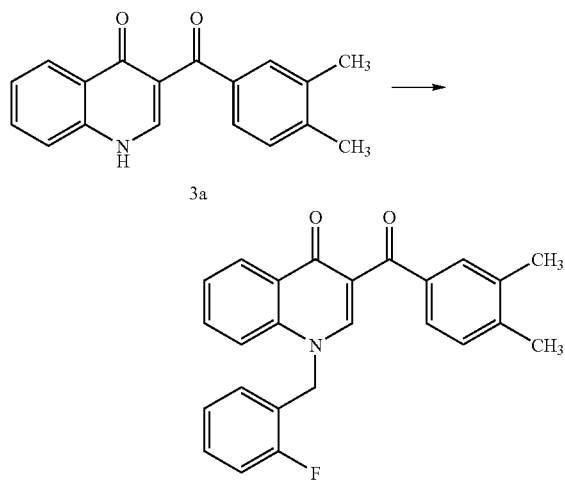

In 3 mL of anhydrous dimethylformamide was suspended 16 mg (0.4 mmol) of sodium hydride (60%), 86 mg (0.31 mmol) of 3-(3,4-dimethyl-benzoyl)-2,3-dihydro-1H-quinolin-4-one 3a was added and the mixture was stirred at rt. After 30 minutes, 75.6 mg (0.40 mmol) of 2-fluorobenzylbromide was added and the reaction was stirred at room temperature for 1 hour. The reaction mixture was quenched by the addition of 10 mL of water. The crude product precipitated out were isolated by filtration and purified by flash chromatography to yield 25 mg of colorless solid 4l: LC-MSD, m/z for $C_{25}H_{20}FNO_2$ [M+H]+=386.4, [M+2H]+=387.4; Reverse phase HPLC (gradient acetonitrile 0.1% TFA 20-95% in 4 min) retention time=2.526 min; $^1$H NMR (400 MHz, CDCl$_3$/HCl): δ 2.2-2.3 (d, 6H), 5.7 (s, 2H), 7.1-7.3 (m, 4H), 7.3-7.4 (m, 1H), 7.4-7.5 (m, 2H), 7.54 (s, 1H), 7.6-7.66 (d, 1H), 7.67-7.74 (t, 1H), 8.2 (d, 1H), 8.58 (s, 1H).

Example 13

Preparation of 3-(3,4-Dimethyl-benzoyl)-1-(3-methyl-benzyl)-2,3-dihydro-1H-quinolin-4-one (4m)

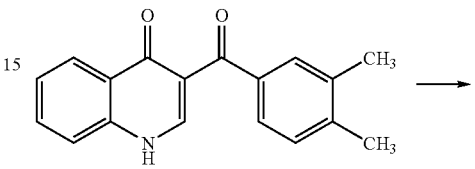

3a

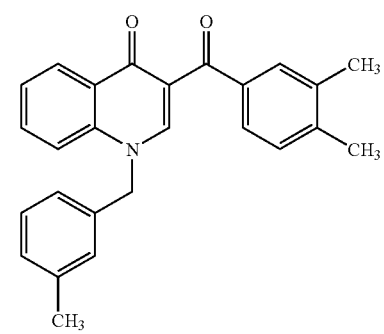

4m

Compound 4m was prepared following the procedure outlined in Step 3 of Example 1 using 16 mg (0.4 mmol) of sodium hydride (60%), 86 mg (0.31 mmol) of 3-(3,4-dimethyl-benzoyl)-2,3-dihydro-1H-quinolin-4-one 3a, 3 mL of anhydrous dimethylformamide, and 74.0 mg (0.40 mmol) of 3-methylbenzylbromide. The crude product 4m was purified by flash chromatograph to yield 55 mg of colorless solid: LC-MSD, m/z for $C_{26}H_{23}NO_2$, [M+H]+: 382.5, [M+H]+: 383.5; Reverse phase HPLC (gradient acetonitrile 0.1% TFA 20-95% in 4 min) retention time=2.628 min; $^1$H NMR (400 MHz, CDCl$_3$/HCl): δ 2.3-2.4 (t, 9H), 5.4 (s, 2H), 7.0 (d, 2H), 7.12 (d, 1H), 7.18 (d, 1H), 7.25 (d, 1H), 7.4 (t, 2H), 7.58 (m, 2H), 7.65 (s, 1H), 8.26 (s, 1H), 7.48 (s, 1H).

Example 14

Preparation of 3-(3,4-Dimethyl-benzoyl)-1-pyridin-2-ylmethyl-2,3-dihydro-1H-quinolin-4-one (4n)

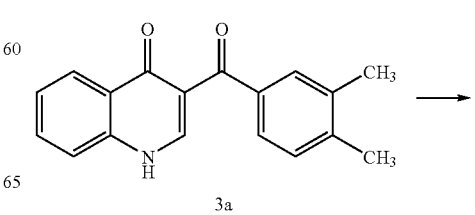

3a

-continued

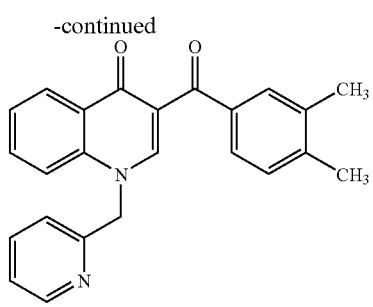

4n

Compound 4n was prepared following the procedure outlined in Step 3 of Example 1 using 32 mg (0.8 mmol) of sodium hydride (60%), 86 mg (0.31 mmol) of 3-(3,4-dimethyl-benzoyl)-2,3-dihydro-1H-quinolin-4-one 3 mL of anhydrous dimethylformamide, and 101.2 mg (0.40 mmol) of 2-bromomethylpyridine hydrobromide. The crude product 4n was purified by flash chromatography to yield 32 mg pale yellow solid (29%): LC-MSD, m/z for $C_{24}H_{20}N_2O_2$, [M+H]+=369.4, [M+2H]+=370.4; Reverse phase HPLC (gradient acetonitrile 0.1% TFA 20-95% in 4 min) retention time=2.084 min; $^1$H NMR (400 MHz, CDCl$_3$/HCl): δ 2.32 (d, 6H), 5.50 (s, 2H), 7.1 (d, 1H), 7.2 (d, 1H), 7.25-7.3 (m, 1H), 7.3-7.5 (m, 2H), 7.54-7.62 (m, 2H), 7.62-7.7 (m, 2H), 8.34 (s, 1H), 8.4-8.5 (m, 1H), 8.62 (d, 1H).

Example 15

Preparation of 3-(3,4-Dimethyl-benzoyl)-1-pyridin-3-ylmethyl-2,3-dihydro-1H-quinolin-4-one (4o)

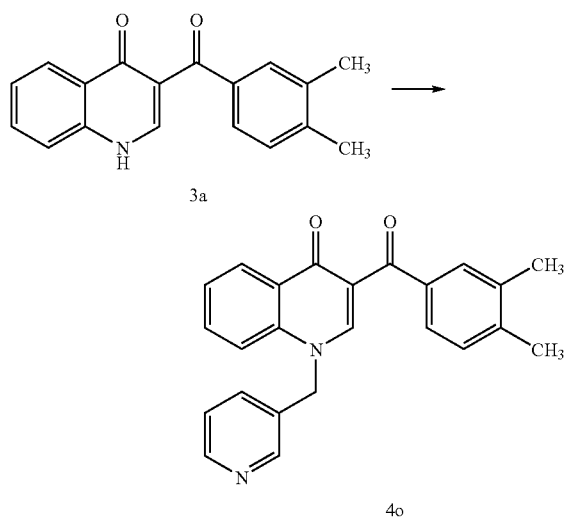

Compound 4o was prepared following the procedure outlined in Step 3 of Example 1 using 32 mg (0.8 mmol) of sodium hydride (60%), 86 mg (0.31 mmol) of 3-(3,4-dimethyl-benzoyl)-2,3-dihydro-1H-quinolin-4-one 3a, 3 mL of anhydrous dimethylformamide, and 101.2 mg (0.40 mmol) of 3-bromomethylpyridine hydrobromide. The crude product was purified by flash chromatography to yield 29 mg of pale yellow solid 4o: LC-MSD, m/z for $C_{24}H_{20}N_2O_2$, [M+H]+=369.4, [M+2H]+=370.4; Reverse phase HPLC (gradient acetonitrile 0.1% TFA 20-95% in 4 min) retention time=1.436 min; $^1$H NMR (400 MHz, CDCl$_3$/HCl): δ 2.30 (d, 6H), 5.4 (s, 2H), 7.17 (d, 1H), 7.26-7.32 (m, 2H), 7.40 (t, 1H), 7.52-7.64 (m, 3H), 8.27 (s, 1H), 8.46 (d, 1H), 8.58-8.64 (m, 2H).

Example 16

Preparation of 3-(3,4-Dimethyl-benzoyl)-1-pyridin-3-ylmethyl-2,3-dihydro-1H-quinolin-4-one (4p)

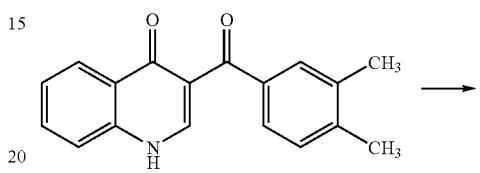

3a

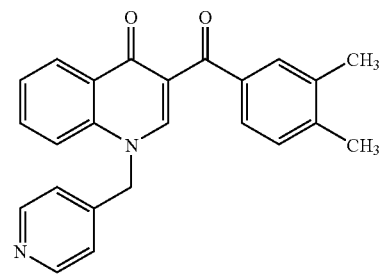

4p

Compound 4p was prepared following the procedure outlined in Step 3 of Example 1 using 32 mg (0.8 mmol) of sodium hydride (60%), 86 mg (0.31 mmol) of 3-(3,4-dimethyl-benzoyl)-2,3-dihydro-1H-quinolin-4-one 3a, 3 mL of anhydrous dimethylformamide, and 101.2 mg (0.40 mmol) of 4-bromomethylpyridine hydrobromide. The crude product was purified by flash chromatography to yield 27 mg of yellowish solid 4p: LC-MSD, m/z for $C_{24}H_{20}N_2O_2$, [M+H]+=369.4, [M+2H]+=370.4; Reverse phase HPLC (gradient acetonitrile 0.1% TFA 20-95% in 4 min) retention time=1.334 min; $^1$H NMR (400 MHz, CDCl$_3$/HCl): δ 2.30 (d, 6H), 5.4 (s, 2H), 7.10 (d, 1H), 7.16-7.22 (m, 2H), 7.42 (t, 1H), 7.52-7.66 (m, 3H), 8.26 (d, 1H), 8.48 (m, 1H), 8.58-8.64 (m, 2H).

Example 17

Preparation of 1-(2-Fluoro-benzyl)-3-(pyridine-4-carbonyl)-1H-quinolin-4-one (4q)

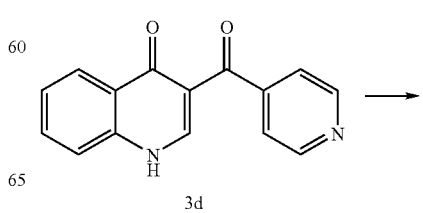

3d

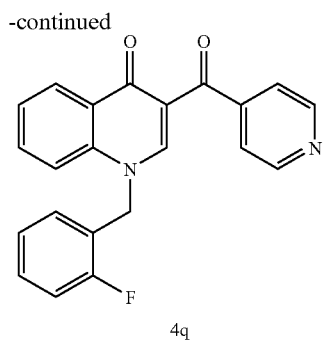

4q

Compound 4q was prepared following the procedure outlined in Step 3 of Example 1 using 15.6 mg (0.39 mmol) of sodium hydride (60%), 75 mg (0.30 mmol) of 3-(pyridine-4-carbonyl)-1H-quinolin-4-one 3d, 3 mL of anhydrous dimethylformamide, and 73.7 mg (0.39 mmol) of 2-fluorobenzylbromide. The crude product was purified by flash chromatograph to yield 27 mg of pale yellow solid 4q: LC-MSD, m/z for $C_{22}H_{15}FN_2O_2$ [M+H]+=359.4, [M+2H]+=360.4; Reverse phase HPLC (gradient acetonitrile 0.1% TFA 20-95% in 4 min) retention time=1.444 min; $^1$H NMR (400 MHz, CDCl$_3$/HCl): δ 5.50 (s, 2H), 7.06 (t, 1H), 7.12 (t, 1H), 7.17 (t, 1H), 7.35 (m, 1H), 7.4-7.5 (m, 2H), 7.54-7.68 (m, 2H), 7.62-7.68 (m, 1H), 8.40-8.46 (m, 1H), 8.48 (s, 1H), 8.70-8.78 (m, 2H).

Example 18

Preparation of 3-(Pyridine-4-carbonyl)-1-pyridin-2-ylmethyl-1H-quinolin-4-one (4r)

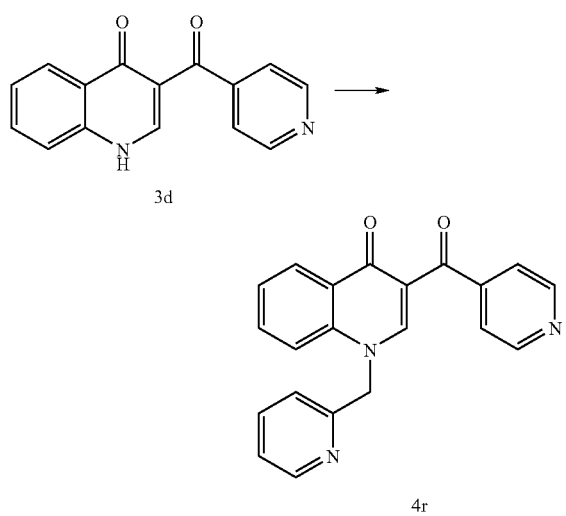

4r

Compound 4r was prepared following the procedure outlined in Step 3 of Example 1 using 21 mg (0.52 mmol) of sodium hydride (60%), 100 mg (0.40 mmol) of 3-(pyridine-4-carbonyl)-1H-quinolin-4-one 3d, 3 mL of anhydrous dimethylformamide, and 131 mg (0.52 mmol) of 2-bromomethylpyridine hydrobromide. The crude product was purified by preparative HPLC to yield 27 mg of pale yellow solid 4r: LC-MSD, m/z for $C_{21}H_{15}N_3O_2$, [M+H]+=342.5, [M+2H]+=343.5; Reverse phase HPLC (gradient acetonitrile 0.1% TFA 20-95% in 4 min) retention time=0.321 min; $^1$H NMR (400 MHz, CDCl$_3$/HCl): δ 5.55 (s, 2H), 7.16 (d, 1H), 7.26-7.3 (m, 1H), 7.40-7.48 (m, 2H), 7.57-7.62 (m, 3H), 7.68 (t, 1H), 8.42 (d, 1H), 8.54 (s, 1H), 8.61 (d, 2H), 8.72-8.76 (m, 2H).

Example 19

Preparation of 1-(3-Methyl-benzyl)-3-(pyridine-4-carbonyl)-1H-quinolin-4-one (4s)

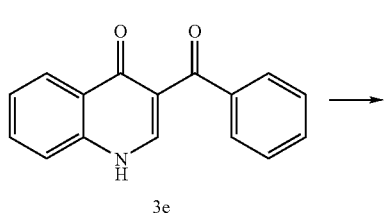

4s

Compound 4s was prepared following the procedure outlined in Step 3 of Example 1 using 21 mg (0.52 mmol) of sodium hydride (60%), 100 mg (0.40 mmol) of 3-(pyridine-4-carbonyl)-1H-quinolin-4-one 3d, 3 mL of anhydrous dimethylformamide, and 74.3 mg (0.52 mmol) of 3-methylbenzylbromide. The crude product was purified by flash chromatograph to yield 55 mg of pale yellow solid: LC-MSD, m/z for $C_{23}H_{18}N_2O_2$, [M+H]+=355.4, [M+2H]+=356.4; Reverse phase HPLC (gradient acetonitrile 0.1% TFA 20-95% in 4 min) retention time=1.770 min; $^1$H NMR (400 MHz, CDCl$_3$/HCl): δ 2.35 (s, 3H), 5.42 (s, 2H), 7.01 (d, 2H), 7.16 (d, 1H), 7.24-7.3 (m, 1H), 7.41-7.47 (t, 2H), 7.56-7.66 (m, 3H), 8.43-8.48 (m, 2H), 8.73-8.77 (m, 2H).

Example 20

Preparation of 3-Benzoyl-1-(3-methyl-benzyl)-1H-quinolin-4-one (4t)

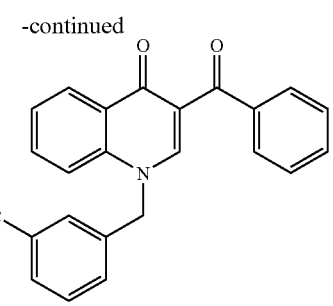

4t

Compound 4t was prepared following the procedure outlined in Step 3 of Example 1 using 16 mg (0.4 mmol) of sodium hydride (60%), 75 mg (0.31 mmol) of 3-benzoyl-2,3-dihydro-1H-quinolin-4-one 3e, 3 mL of anhydrous dimethylformamide, 75.6 mg (0.40 mmol) of 3-methylbenzylbromide. The crude product 4t was purified by flash chromatography to yield 45 mg of colorless solid: LC-MSD, m/z for $C_{24}H_{19}NO_2$, [M+H]+=354.4, [M+2H]+=355.4; Reverse phase HPLC (gradient acetonitrile 0.1% TFA 20-95% in 4 min) retention time=2.146 min; $^1$H NMR (400 MHz, CDCl$_3$/HCl): δ 2.35 (s, 3H), 5.38 (s, 2H), 7.00 (d, 2H), 7.33 (d, 1H), 7.22-7.26 (m, 1H), 7.36-7.45 (m, 4H), 7.50-7.60 (m, 2H), 7.82-7.86 (m, 2H), 8.31 (s, 1H), 8.44-8.48 (m, 1H).

Example 21

Preparation of 3-Benzoyl-1-(2-fluoro-benzyl)-1H-quinolin-4-one (4u)

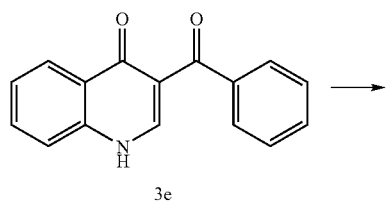

3e

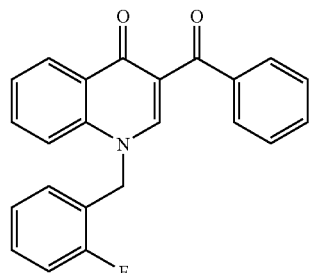

4u

Compound 4u was prepared following the procedure outlined in Step 3 of Example 1 using 16 mg (0.4 mmol) of sodium hydride (60%), 75 mg (0.31 mmol) of 3-benzoyl-2,3-dihydro-1H-quinolin-4-one, 3 mL of anhydrous dimethylformamide, and 74 mg (0.40 mmol) of 2-fluorobenzylbromide. The crude product was purified by flash chromatography to yield 42 mg of a colorless solid 4u: LC-MSD, m/z for $C_{23}H_{16}FNO_2$, [M+H]+=358.4, [M+2H]+=359.4; Reverse phase HPLC (gradient acetonitrile 0.1% TFA 20-95% in 4 min) retention time =2.291 min; $^1$H NMR (400 MHz, CDCl$_3$/HCl): δ 5.42 (s, 2H), 7.00-7.20 (m, 3H), 7.28-7.46 (m, 5H), 7.51 (t, 1H), 7.61 (t, 1H), 7.78-7.86 (m, 2H), 8.32 (d, 1H), 8.46 (m, 1H).

Example 22

Preparation of 7-(3,4-Dimethyl-benzoyl)-2,2-difluoro-5-(2-fluoro-benzyl)-5H-[1,3]dioxolo[4,5-g]quinolin-8-one (4v)

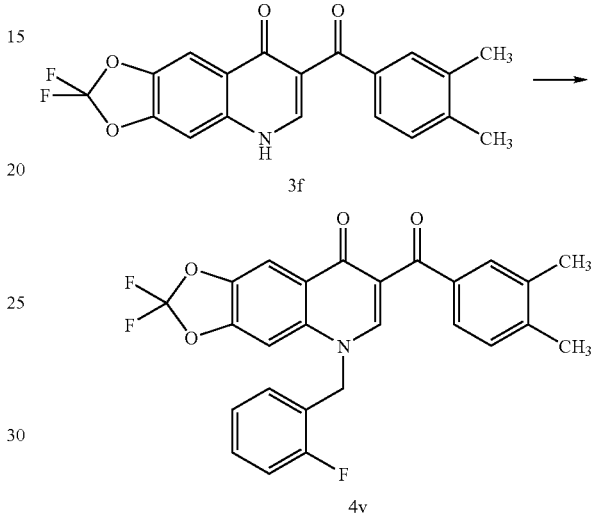

Compound 4v was prepared following the procedure outlined in Step 3 of Example 1 using 10.4 mg (0.26 mmol) of sodium hydride (60%), 71 mg (0.20 mmol) of 7-(3,4-dimethyl-benzoyl)-2,2-difluoro-5H-[1,3]dioxolo[4,5-g]quinolin-8-one, 3 mL of anhydrous dimethylformamide, and 49.1 mg (0.26 mmol) of 2-fluorobenzylbromide. The crude product was purified by flash chromatography to yield 29 mg of 4v as a colorless solid: Reverse phase HPLC (gradient acetonitrile 0.1% TFA 20-95% in 4 min) retention time=2.922 min; LC-MSD, m/z for $C_{24}H_{18}F_3NO_4$, [M+H]+=466.4, [M+2H]+=467.4; $^1$H NMR (400 MHz, CDCl$_3$/HCl): δ 2.2-2.4 (d, 6H), 5.40 (s, 2H), 7.02-7.10 (m, 2H), 7.12-7.22 (m, 3H), 7.34-7.42 (m, 1H), 7.52-7.57 (d, 1H), 7.62 (s, 1H), 8.10 (s, 1H), 8.24 (s, 1H).

Example 23

Preparation of 3-(3-Methyl-benzoyl)-1-pyridin-2-ylmethyl-1H-quinolin-4-one (4w)

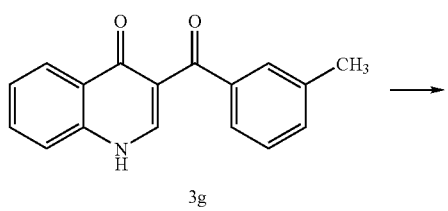

3g

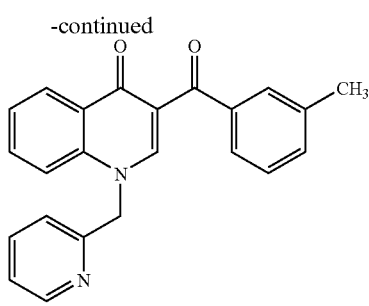

4w

Compound 4w was prepared following the procedure outlined in Step 3 of Example 1 using 52 mg (1.3 mmol) of sodium hydride (60%), 132 mg (0.5 mmol) of 3-(3-methyl-benzoyl)-2,3-dihydro-1H-quinolin-4-one 3g, 3 mL of anhydrous dimethylformamide, and 164 mg (0.65 mmol) of 2-bromomethylpyridine hydrobromide. The crude product was purified by flash chromatography to yield 55 mg of a pale yellow solid 4w: Reverse phase HPLC (gradient acetonitrile 0.1% TFA 20-95% in 4 min) retention time=1.913 min; LC-MSD, m/z for $C_{23}H_{18}N_2O_2$, [M+H]+=355.4, [M+2H]+=356.4; $^1$H NMR (400 MHz, CDCl$_3$/HCl): δ 2.40 (s, 3H), 5.50 (s, 2H), 7.12 (d, 1H), 7.22-7.35 (m, 3H), 7.38-7.46 (m, 2H), 7.56-7.68 (m, 4H), 8.56 (s, 1H), 8.46 (d, 1H), 8.62 (d, 1H).

Example 24

Preparation of 1-(2-Fluoro-benzyl)-3-(3-methyl-benzoyl)-1H-quinolin-4-one (4x)

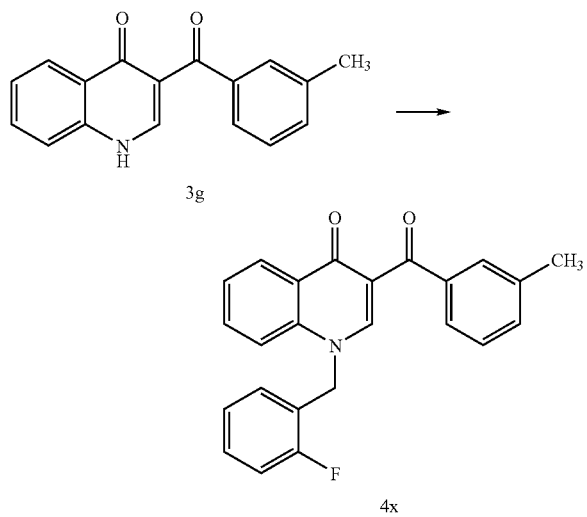

Compound 4x was prepared following the procedure outlined in Step 3 of Example 1 using 26 mg (0.65 mmol) of sodium hydride (60%), 132 mg (0.50 mmol) of 3-(3-methyl-benzoyl)-2,3-dihydro-1H-quinolin-4-one, 3 mL of anhydrous dimethylformamide, and 123 mg (0.65 mmol) of 2-fluorobenzylbromide. The crude product was purified by flash chromatography to yield 85 mg of a colorless solid 4x: LC-MSD, m/z for $C_{24}H_{18}FNO_2$, [M+H]+=372.4, [M+2H]+=373.4; Reverse phase HPLC (gradient acetonitrile 0.1% TFA 20-95% in 4 min) retention time=2.687 min; $^1$H NMR (400 MHz, CDCl$_3$/HCl): δ 2.40 (s, 3H), 5.42 (s, 2H), 7.02-7.18 (m, 3H), 7.28-7.36 (m, 3H), 7.36-7.42 (m, 2H), 7.58-7.66 (m, 3H), 8.31 (s, 1H), 8.43-8.47 (m, 1H).

Example 25

Preparation of 3-(3-Methyl-benzoyl)-1-(3-methyl-benzyl)-1H-quinolin-4-one (4y)

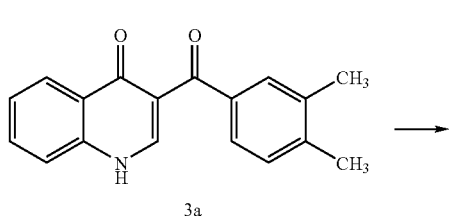

Compound 4y was prepared following the procedure outlined in Step 3 of Example 1 using 26 mg (0.65 mmol) of sodium hydride (60%), 132 mg (0.50 mmol) of 3-(3-methyl-benzoyl)-2,3-dihydro-1H-quinolin-4-one, 3 mL of anhydrous dimethylformamide, and 120 mg (0.65 mmol) of 3-methylbenzylbromide. The crude product was purified by flash chromatography to yield 92 mg of a colorless solid 4y: LC-MSD, m/z for $C_{25}H_{21}NO_2$, [M+H]+=368.5, [M+2H]+=369.5; Reverse phase HPLC (gradient acetonitrile 0.1% TFA 20-95% in 4 min) retention time=2.586 min; $^1$H NMR (400 MHz, CDCl$_3$/HCl): δ 2.37 (s, 3H), 2.42 (s, 3H), 5.39 (s, 2H), 7.01 (d, 2H), 7.15 (d, 1H), 7.22-7.44 (m, 5H), 7.55-7.58 (m, 3H), 8.29 (s, 1H), 8.47 (d, 1H).

Example 26

Preparation of 3-(3,4-Dimethyl-benzoyl)-1-(6-methyl-pyridin-2-ylmethyl)-1H-quinolin-4-one (4z)

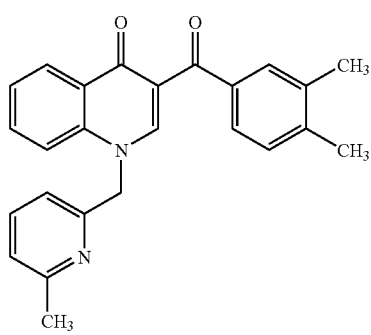

4z

Compound 4z was prepared following the procedure outlined in Step 3 of Example 1 using 15.6 mg (0.39 mmol) of sodium hydride (60%), 83.2 mg (0.30 mmol) of 3-(3,4-dimethyl-benzoyl)-2,3-dihydro-1H-quinolin-4-one, 3 mL of anhydrous dimethylformamide, and 73.0 mg (0.39 mmol) of 3-methylbenzylbromide. The crude product was purified by flash chromatography to yield 61 mg of a colorless solid 4z: LC-MSD, M/z for $C_{25}H_{22}N_2O_2$, [M+H]+=383.4, [M+2H]+=384.4; Reverse phase HPLC (gradient acetonitrile 0.1% TFA 20-95% in 4 min) retention time=2.484 min; $^1$H NMR (400 MHz, CDCl$_3$/HCl): δ 2.32 (d, 6H), 2.58 (s, 3H), 5.42 (s, 2H), 6.83 (d, 1H), 7.08 (d, 1H), 7.16 (d, 1H), 7.36-7.43 (m, 2H), 7.48-7.60 (m, 3H), 7.64 (s, 1H), 8.31 (s, 1H), 8.46 (d, 1H).

Example 27

Preparation of 3-(3,4-Dimethyl-benzoyl)-1-phenethyl-1H-quinolin-4-one (4aa)

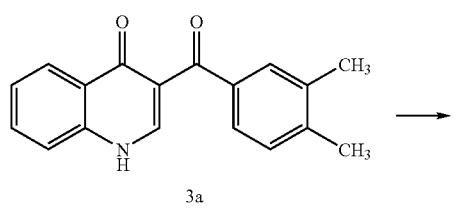

4aa

Compound 4aa was prepared following the procedure outlined in Step 3 of Example 1 using 26 mg (0.65 mmol) of sodium hydride (60%), 138.6 mg (0.50 mmol) of 3-(3,4-dimethyl-benzoyl)-2,3-dihydro-1H-quinolin-4-one 3a, 3 mL of anhydrous dimethylformamide, and 120.3 mg (0.65 mmol) of phenethylbromide. The crude product was purified by flash chromatograph to yield 44 mg of a colorless solid 4aa: LC-MSD, m/z for $C_{26}H_{23}NO_2$, [M+H]+=382.5, [M+2H]+=383.5; Reverse phase HPLC (gradient acetonitrile 0.1% TFA 20-95% in 4 min) retention time=2.551 min; $^1$H NMR (400 MHz, CDCl$_3$/HCl): δ 2.30 (d, 6H), 3.20 (t, 2H), 4.40 (t, 3H), 7.08 (d, 2H), 7.13 (d, 1H), 7.20-7.32 (m, 3H), 7.38-7.47 (m, 2H), 7.53-7.58 (d, 2H), 7.73 (t, 1H), 7.80 (s, 1H), 8.48 (d, 1H).

Example 28

Preparation of 1-(5-Chloro-[1,2,3]thiadiazol-4-ylmethyl)-3-(3,4-dimethyl-benzoyl)-1H-quinolin-4-one (4bb)

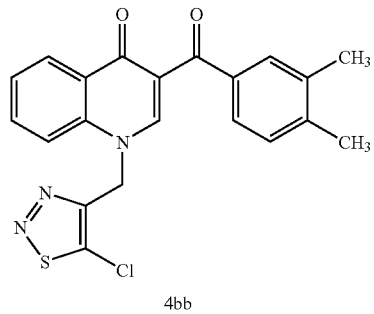

In 3 mL of anhydrous dimethylformamide was suspended 26 mg (0.65 mmol) of sodium hydride (60%), and to it was added 138.7 mg (0.50 mmol) of 3-(3,4-dimethyl-benzoyl)-2,3-dihydro-1H-quinolin-4-one 3a. The mixture was stirred at rt for 30 min. 110 mg (0.65 mmol) of 5-chloro-4-chloromethyl-1,2,3-thodiazole was added to the reaction mixture and the reaction solution was stirred at 80° C. for 3 hour. The reaction solution was quenched by the addition of 10 mL of water. The crude product 4bb precipitated out of solution and was isolated by filtration. Purification of the crude product by flash chromatograph provided 25 mg of the product 4bb as a colorless solid: LC-MSD, m/z for $C_{21}H_{16}ClN_3O_2S$, [M+H]+=410.4, [M+2H]+=411.4; Reverse phase HPLC (gradient acetonitrile 0.1% TFA 20-95% in 4 min) retention time=2.308 min; $^1$H NMR (400 MHz, CDCl$_3$/HCl): δ 2.32 (d, 6H), 5.72 (s, 2H), 7.17 (d, 1H), 7.42 (t, 1H), 7.55 (d, 1H), 7.62 (d, 1H), 7.67 (t, 1H), 7.77 (d, 1H), 8.42-8.48 (m, 2H).

Example 29

Preparation of 3-(3,4-Dimethyl-benzoyl)-1-(5-methyl-isoxazol-3-ylmethyl)-1H-quinolin-4-one (4cc)

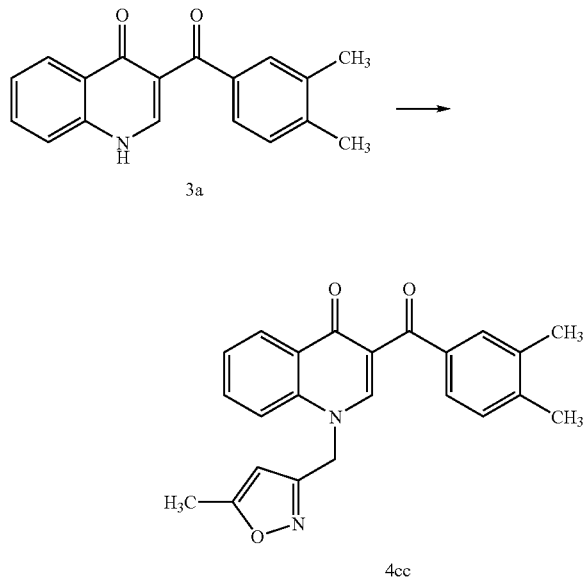

26 mg (0.65 mmol) of sodium hydride (60%) was suspended in 3 mL of anhydrous dimethylformamide and to it was added 138.7 mg (0.50 mmol) of 3-(3,4-dimethyl-benzoyl)-2,3-dihydro-1H-quinolin-4-one 3a and the resultant mixture was stirred at rt for 30 min. Then 77.4 mg (0.65 mmol) of 3-chloromethyl-1,2,4-oxadiazole was added to the reaction solution and the mixture was stirred at 80° C. for 1 h. The reaction solution was quenched by the addition of 10 mL of water. The crude product precipitated out of solution and was isolated by filtration. Purification of the crude product by flash chromatography provided 55 mg of 4cc as a colorless solid: LC-MSD, m/z for $C_{23}H_{20}N_2O_3$, [M+H]+=373.4, [M+2H]+=374.4; Reverse phase HPLC (gradient acetonitrile 0.1% TFA 20-95% in 4 min) retention time =2.639 min; $^1$H NMR (400 MHz, CDCl$_3$/HCl): δ 2.30 (d, 6H), 2.36 (s, 3H), 5.38 (s, 2H), 5.90 (s, 1H), 7.15 (d, 1H), 7.42 (t, 1H), 7.50-7.68 (m, 4H), 8.27 (s, 1H), 8.44 (d, 1H).

Example 30

Preparation of 3-(3,4-Dimethyl-benzoyl)-1-(5-methyl-isoxazol-3-ylmethyl)-1H-quinolin-4-one (4dd)

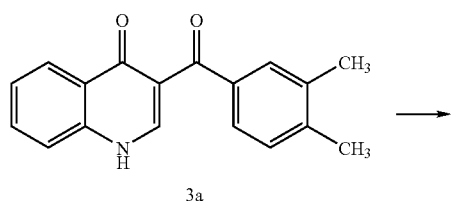

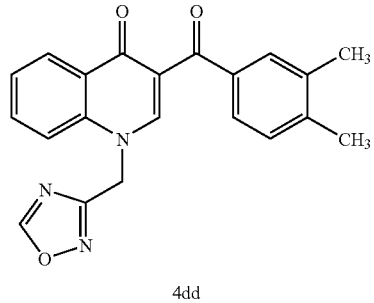

26 mg (0.65 mmol) of sodium hydride (60%) was suspended in 3 mL of anhydrous dimethylformamide and to it was added 138.7 mg (0.50 mmol) of 3-(3,4-dimethyl-benzoyl)-2,3-dihydro-1H-quinolin-4-one 3a and the mixture was stirred at rt for 30 min. Then 86 mg (0.65 mmol) of 3-chloromethyl-5-methylisoxazole was added and the reaction mixture was stirred at 80° C. for 3 hour. The reaction solution was quenched by the addition of 10 mL of water. The crude product precipitated out of solution and was isolated by filtration. Purification of the crude product by flash chromatography provided 52 mg of a colorless solid 4dd: LC-MSD, m/z for $C_{21}H_{17}N_3O_3$, [M+H]+=359.4, [M+2H]+=360.4; Reverse phase HPLC (gradient acetonitrile 0.1% TFA 20-95% in 4 min) retention time=2.002 min; $^1$H NMR (400 MHz, CDCl$_3$/HCl): δ 2.28 (d, 6H), 5.52 (s, 2H), 7.17 (d, 1H), 7.42 (t, 1H), 7.55-7.70 (m, 4H), 8.34 (s, 1H), 8.42 (d, 1H), 8.72 (s, 1H).

Example 31

Preparation of 1-(2-Fluoro-benzyl)-3-(2-methyl-pyridine-4-carbonyl)-1H-quinolin-4-one (4ee)

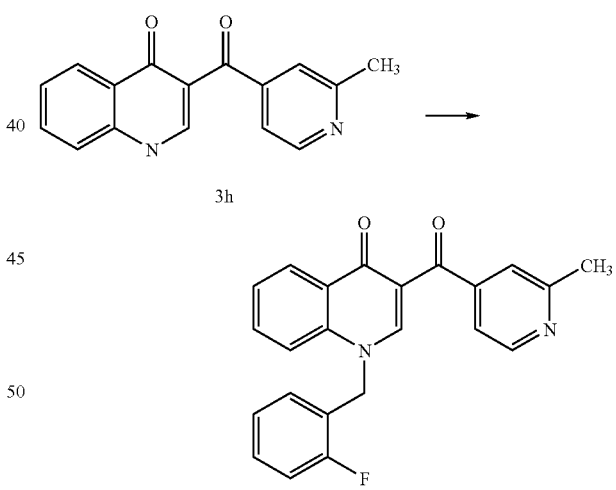

Compound 4ee was prepared following the procedure outlined in Step 3 of Example 1 using 10.4 mg (0.26 mmol) of sodium hydride (60%), 53 mg (0.20 mmol) of 3-(2-methyl-pyridine-4-carbonyl)-1H-quinolin-4-one 3h, 3 mL of anhydrous dimethylformamide, and 49 mg (0.26 mmol) of 2-fluorobenzylbromide. The crude product 4ee was purified by flash chromatography to yield 21 mg of a colorless solid 4ee: LC-MSD, m/z for $C_{23}H_{17}FN_2O_2$, [M+H]+=373.5, [M+2H]+=374.5; Reverse phase HPLC (gradient acetonitrile 0.1% TFA 20-95% in 4 min) retention time=1.296 min; $^1$H NMR (400 MHz, CDCl$_3$/HCl): δ 2.60 (s, 3H), 5.43 (s, 2H), 7.02-7.20 (m, 3H), 7.32-7.40 (m, 2H), 7.40-7.47 (m, 3H), 7.64 (t, 1H), 8.44 (m, 2H), 8.60 (d, 1H).

Example 32

Preparation of 3-(2-Methyl-pyridine-4-carbonyl)-1-(6-methyl-pyridin-2-ylmethyl)-1H-quinolin-4-one (4ff)

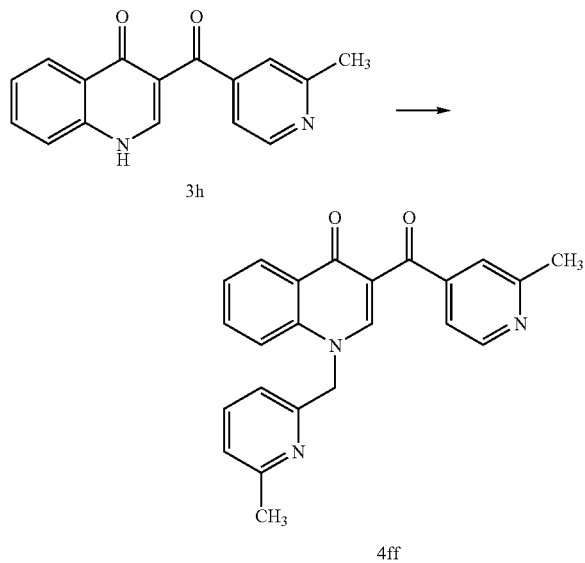

Compound 4ff was prepared following the procedure outlined in Step 3 of Example 1 using 10.4 mg (0.26 mmol) of sodium hydride (60%), 53 mg (0.20 mmol) of 3-(2-methyl-pyridine-4-carbonyl)-1H-quinolin-4-one 3h, 3 mL of anhydrous dimethylformamide, and 48.7 mg (0.26 mmol) of 2-bromomethyl-6-methyl-pyridine. The crude product was purified by preparative HPLC to yield 15 mg of colorless solid 4ff: LC-MSD, m/z for $C_{23}H_{19}N_3O_2$, [M+H]+=370.5, [M+2H]+=371.5; Reverse phase HPLC (gradient acetonitrile 0.1% TFA 20-95% in 4 min) retention time=1.976 min; $^1$H NMR (400 MHz, $CDCl_3$/HCl): δ 2.57 (s, 3H), 2.61 (s, 3H), 5.43 (s, 2H), 6.87 (d, 1H), 7.10 (d, 1H), 7.32-7.48 (m, 4H), 7.53 (t, 1H), 7.59 (t, 1H), 8.41 (d, 1H), 8.49 (d, 1H), 8.59 (d, 1H).

Example 33

Preparation of 1-(3-Methyl-benzyl)-3-(2-methyl-pyridine-4-carbonyl)-1H-quinolin-4-one (4gg)

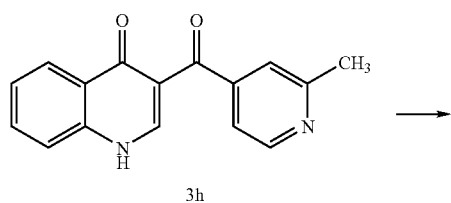

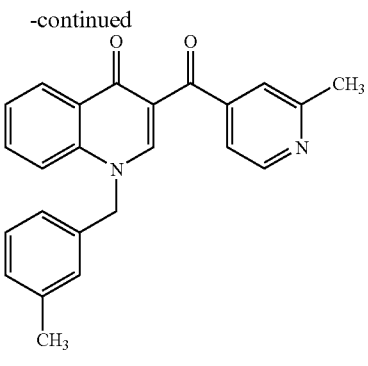

Compound 4gg was prepared following the procedure outlined in Step 3 of Example 1 using 10.4 mg (0.26 mmol) of sodium hydride (60%), 53 mg (0.20 mmol) of 3-(2-methyl-pyridine-4-carbonyl)-1H-quinolin-4-one 3h, 3 mL of anhydrous dimethylformamide, and 48 mg (0.26 mmol) of 3-methylbenzylbromide. The crude product was purified by preparative HPLC to yield 27 mg of a colorless solid 4gg: LC-MSD, m/z for $C_{24}H_{20}N_2O_2$, [M+H]+=369.5, [M+2H]+=370.5; Reverse phase HPLC (gradient acetonitrile 0.1% TFA 20-95% in 4 min) retention time=1.605 min; $^1$H NMR (400 MHz, $CDCl_3$/HCl): δ 2.35 (s, 3H), 2.61 (s, 3H), 5.40 (s, 2H), 7.00 (d, 2H), 7.15 (d, 1H), 7.25 (t, 1H), 7.35 (d, 1H), 7.39-7.46 (m, 3H), 7.60 (t, 1H), 8.40-8.46 (m, 2H), 8.60 (d, 1H).

Example 34

Preparation of 1-(3-Methyl-benzyl)-3-(pyridine-3-carbonyl)-1H-quinolin-4-one (4hh)

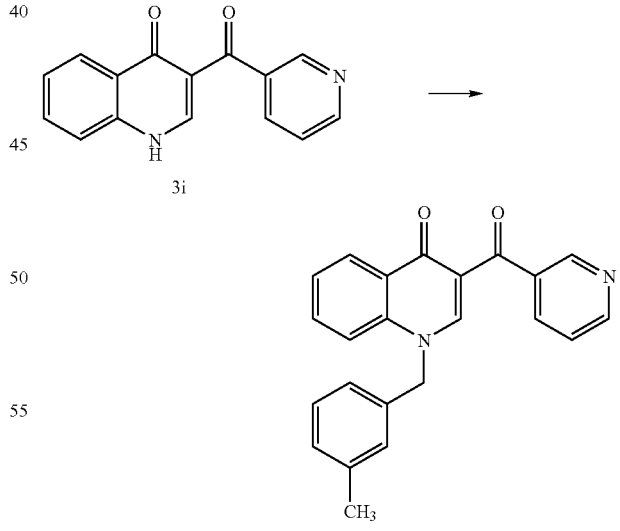

Compound 4hh was prepared following the procedure outlined in Step 3 of Example 1 using 16 mg (0.40 mmol) of sodium hydride (60%), 75 mg (0.30 mmol) of 3-(pyridine-3-carbonyl)-1H-quinolin-4-one, 3 mL of anhydrous dimethylformamide, and 74.0 mg (0.4 mmol) of 3-methylbenzylbromide. The crude product was purified by flash chromatography to yield 35 mg of 4hh as a colorless solid: LC-MSD, m/z for $C_{23}H_{18}N_2O_2$, [M+H]+=355.4, [M+2H]+=356.4; Reverse phase HPLC (gradient acetonitrile 0.1% TFA 20-95% in 4 min) retention time=1.710 min; $^1$H NMR (400 MHz, CDCl$_3$/HCl): δ 2.36 (s, 3H), 5.41 (s, 2H), 7.00 (d, 2H), 7.12-7.28 (m, 2H), 7.34-7.45 (m, 3H), 7.60 (m, 1H), 8.09 (m, 1H), 8.42-8.46 (m, 2H), 8.71 (m, 2H), 8.99 (s, 1H).

Example 35

Preparation of 1-(2-Fluoro-benzyl)-3-(pyridine-3-carbonyl)-1H-quinolin-4-one (4ii)

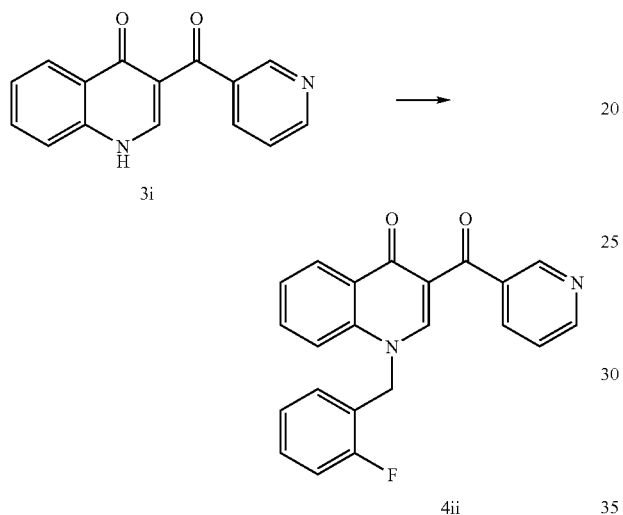

Compound 4ii was prepared following the procedure outlined in Step 3 of Example 1 using 16 mg (0.40 mmol) of sodium hydride (60%), 75 mg (0.30 mmol) of 3-(pyridine-3-carbonyl)-1H-quinolin-4-one, 3 mL of anhydrous dimethylformamide, and 75.6 mg (0.4 mmol) of 2-fluorobenzylbromide. The crude product was purified by flash chromatography to yield 35 mg of a colorless solid 4ii: LC-MSD, m/z for $C_{22}H_{15}FN_2O_2$, [M+H]+=359.4, [M+2H]+=360.4; Reverse phase HPLC (gradient acetonitrile 0.1% TFA 20-95% in 4 min) retention time=1.432 min; $^1$H NMR (400 MHz, CDCl$_3$HCl): δ 5.46 (s, 2H), 7.02-7.20 (m, 3H), 7.32-7.38 (m, 2H), 7.40-7.46 (m, 2H), 7.64 (t, 1H), 8.08 (d, 1H), 8.45 (d, 2H), 8.71 (d, 1H), 8.98 (s, 1H).

Example 36

Preparation of 1-(6-Methyl-pyridin-2-ylmethyl)-3-(pyridine-3-carbonyl)-1H-quinolin-4-one (4jj)

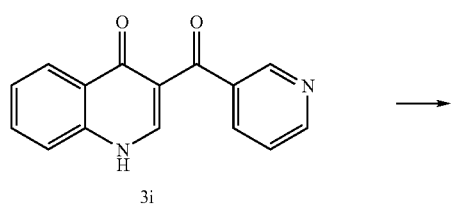

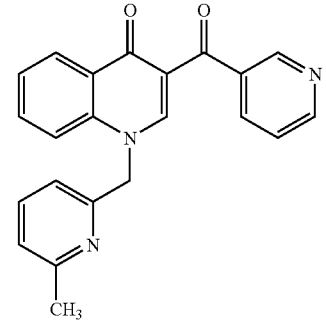

Compound 4p was prepared following the procedure outlined in Step 3 of Example 1 using 16 mg (0.40 mmol) of sodium hydride (60%), 75 mg (0.30 mmol) of 3-(pyridine-3-carbonyl)-1H-quinolin-4-one, 3 mL of anhydrous dimethylformamide, and 74.9 mg (0.4 mmol) of 2-bromomethyl-6-methyl-pyridine. The crude product was purified by flash chromatography to yield 55 mg of 4jj as a colorless solid: LC-MSD, m/z for $C_{23}H_{17}N_3O_2$, [M+H]+=356.4, [M+2H]+=357.4; Reverse phase HPLC (gradient acetonitrile 0.1% TFA 20-95% in 4 min) retention time=0.355 min; $^1$H NMR (400 MHz, CDCl$_3$/HCl): δ 2.56 (s, 3H), 5.44 (s, 2H), 6.87 (d, 1H), 7.10 (d, 1H), 7.34-7.46 (m, 3H), 7.52 (t, 1H), 7.58 (t, 1H), 8.08 (m, 1H), 8.43 (d, 1H), 8.49 (s, 1H), 8.71 (d, 1H), 8.99 (s, 1H).

Example 37

Preparation of 3-(3,4-Dimethyl-benzoyl)-1-(2-trifluoromethyl-benzyl)-1H-quinolin-4-one (4kk)

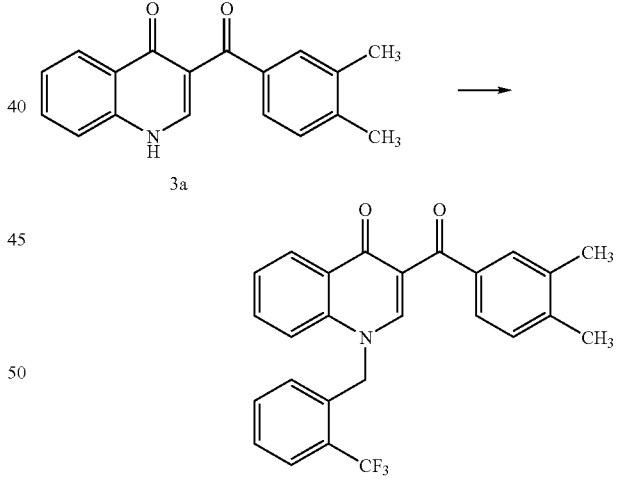

Compound 4kk was prepared following the procedure outlined in Step 3 of Example 1 using 26 mg (0.65 mmol) of sodium hydride (60%), 138.6 mg (0.50 mmol) of 3-(3,4-Dimethyl-benzoyl)-2,3-dihydro-1H-quinolin-4-one 3a, 3 mL of anhydrous dimethylformamide, and 155.4 mg (0.65 mmol) of 2-trifluoromethylbenzylbromide. The crude product was purified by flash chromatography to yield 96 mg of 4kk as a colorless solid: LC-MSD, m/z for $C_{26}H_{20}F_3NO_2$, [M+H]+=436.5, [M+2H]+=437.5; Reverse phase HPLC (gradient acetonitrile 0.1% TFA 20-95% in 4 min) retention time=2.709 min; $^1$H NMR (400 MHz, CDCl$_3$/HCl): δ 2.32 (d, 6H), 5.60 (s, 2H), 6.92 (m, 1H), 7.17 (t, 2H), 7.39-7.47 (m, 3H), 7.54-7.60 (m, 2H), 7.65 (s, 1H), 7.79 (m, 1H), 8.22 (s, 1H), 8.50 (m, 1H).

Example 38

Preparation of 3-(3,4-Dimethyl-benzoyl)-1-(3-fluoro-pyridin-2-ylmethyl)-1H-quinolin-4-one (4ll)

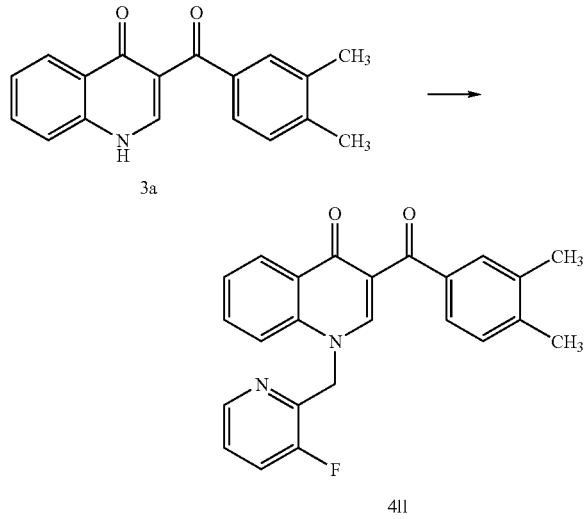

Compound 4ll was prepared following the procedure outlined in Step 3 of Example 1 using 26 mg (0.65 mmol) of sodium hydride (60%), 138.6 mg (0.50 mmol) of 3-(3,4-Dimethyl-benzoyl)-2,3-dihydro-1H-quinolin-4-one 3a, 3 mL of anhydrous dimethylformamide, and 123.5 mg (0.65 mmol) of 2-bromomethyl-3-fluoro-pyridine. The crude product was purified by flash chromatography to yield 96 mg of 4ll as a colorless solid: LC-MSD, m/z for $C_{24}H_{19}FN_2O_2$, [M+H]+=387.5, [M+2H]+=388.5; Reverse phase HPLC (gradient acetonitrile 0.1% TFA 20-95% in 4 min) retention time=2.192 min; $^1$H NMR (400 MHz, CDCl$_3$/HCl): δ 2.30 (d, 6H), 5.56 (s, 2H), 7.17 (d, 1H), 7.31 (m, 1H), 7.38 (t, 1H), 7.46 (t, 1H), 7.56-7.70 (m, 4H), 8.35-8.42 (m, 2H), 8.42-8.47 (m, 1H).

Example 39

Preparation of 3-(3,4-Dimethyl-benzoyl)-1-(6-oxazol-2-yl-pyridin-2-ylmethyl)-1H-quinolin-4-one (4 mm)

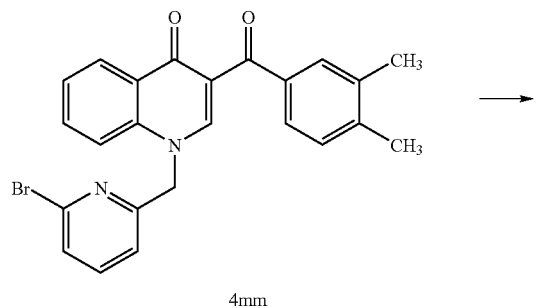

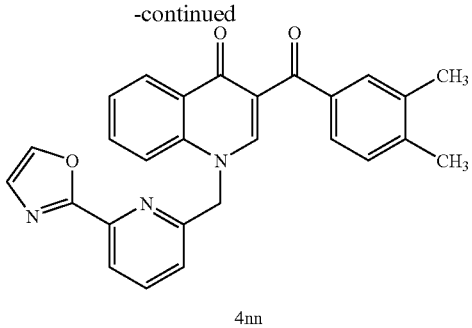

90 mg (0.2 mmol) of 1-(6-Bromo-pyridin-2-ylmethyl)-3-(3,4-dimethyl-benzoyl)-1H-quinolin-4-one, 143 mg (0.40 mmol) of 2-tri-t-butylstannyloxazole, 23 mg (0.02 mmol) of tetrakis(triphenylphosphine)palladium were dissolved in 2 mL of anhydrous tetrahydrofuran. The resultant mixture was stirred at 75° C. for 18 h. The reaction solution was quenched by pouring into a container having 20 mL of water. The crude product precipitated out of solution and was isolated by filtration. The crude product was purified by flash chromatography to yield 16 mg of 4nn as a colorless solid: LC-MSD, m/z for $C_{27}H_{21}N_3O_3$, [M+H]+=436.5, [M+2H]+=437.5; Reverse phase HPLC (gradient acetonitrile 0.1% TFA 20-95% in 4 min) retention time=2.136 min; $^1$H NMR (400 MHz, CDCl$_3$/HCl): δ 2.35 (d, 6H), 5.62 (s, 2H), 7.06 (d, 1H), 7.19 (d, 1H), 7.35-7.44 (m, 3H), 7.54-7.62 (m, 2H), 7.66 (s, 1H), 7.78 (t, 1H), 7.84 (d, 1H), 8.08 (d, 1H), 8.34 (s, 1H), 8.48 (d, 1H).

Example 40

Preparation of 3-(3,4-Dimethyl-benzoyl)-1-(6-pyrimidin-5-yl-pyridin-2-ylmethyl)-1H-quinolin-4-one (4oo)

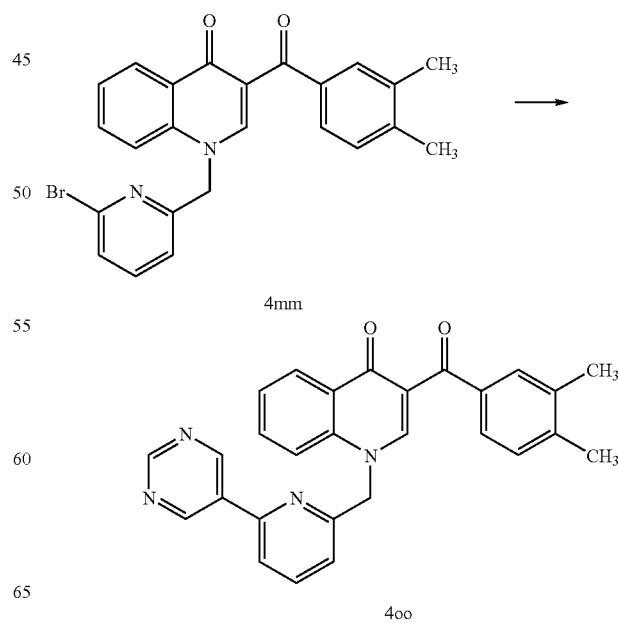

90 mg (0.2 mmol) of 1-(6-Bromo-pyridin-2-ylmethyl)-3-(3,4-dimethyl-benzoyl)-1H-quinolin-4-one 4 mm, 50 mg (0.40 mmol) of pyrimidin-5-boronic acid, 18.3 mg (0.02 mmol) of Pd₂(dba)₃, 21 mg (0.08 mmol) of triphenylphosphine were dissolved in 2 mL of tetrahydrofuran. To the resultant solution was added 0.5 mL (1.0 mmol) of 2N Na₂CO₃ aqueous solution and the mixture was stirred at 75° C. for 18 h. The reaction mixture was quenched by pouring into a container having 20 mL of water. The crude product precipitated out of solution and was isolated by filtration. The crude product 4oo was purified by flash chromatography to yield 14 mg of colorless a solid: LC-MSD, m/z for C₂₈H₂₂N₄O₂, [M+H]+=447.5, [M+2H]+=448.5; Reverse phase HPLC (gradient acetonitrile 0.1% TFA 20-95% in 4 min) retention time=2.055 min; ¹H NMR (400 MHz, CDCl₃/HCl): δ 2.35 (d, 6H), 5.56 (s, 2H), 7.17 (d, 1H), 7.36-7.48 (m, 2H), 7.52-7.66 (m, 3H), 7.72 (d, 1H), 7.81 (t, 1H), 8.37 (s, 1H), 8.42-8.50 (m, 1H), 9.22-9.32 (m, 3H).

Example 41

Preparation of 1-(6-Amino-pyridin-2-ylmethyl)-3-(3,4-dimethyl-benzoyl)-1H-isoquinolin-4-one (4pp)

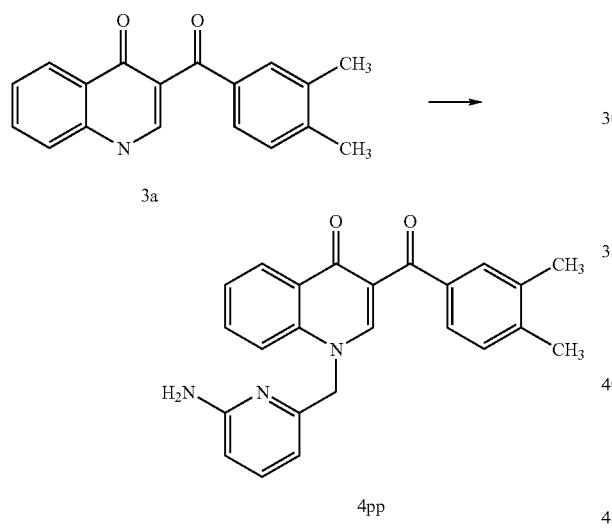

16 mg (0.4 mmol) of sodium hydride (60%) was suspended in 3 mL of anhydrous dimethylformamide. 86 mg (0.31 mmol) of 3-(3,4-dimethyl-benzoyl)-2,3-dihydro-1H-quinolin-4-one 3a was added and the mixture was stirred at rt for 30 min. To the resultant mixture was added 34 mg (0.12 mmol) of (6-bromomethyl-pyridin-2-yl)-carbamic acid tert-butyl ester and the reaction solution was stirred at room temperature for 1 hour. The reaction solution was quenched upon the addition of 100 mL of water. The mixture was extracted with 100 mL of chloroform (2×) and the combined organic layer was dried over anhydrous MgSO₄ and evaporated in vacuo. The crude product was dissolved in 2 mL of dichloromethane and 0.3 mL of trifluoroacetic acid was added. The mixture was stirred at room temperature for 1 hour followed by the addition of 10 mL of saturated NaHCO₃ aqueous solution. The mixture was extracted with 50 mL of chloroform (2×). The combined organic layer was dried over anhydrous MgSO₄ and evaporated in vacuo. The crude product 4pp was purified by preparative HPLC to yield 4 mg of a colorless solid: LC-MSD, m/z for C₂₄H₂₁N₃O₂, [M+H]+=374.5, [M+2H]+=385.5; Reverse phase HPLC (gradient acetonitrile with 0.1% TFA 20-95% in 4 min) retention time=1.902 min; ¹H NMR (400 MHz, CDCl₃/HCl): δ 2.32 (d, 6H), 4.50 (s, 2H), 5.26 (s, 2H), 6.42 (d, 2H), 7.18 (d, 1H), 7.30-7.50 (m, 3H), 7.58 (t, 2H), 7.62 (s, 1H), 8.24 (d, 1H), 8.46 (d, 1H).

Example 42

Preparation of N-{6-[3-(3,4-Dimethyl-benzoyl)-4-oxo-4H-quinolin-1-ylmethyl]-pyridin-2-yl}-acetamide (4qq)

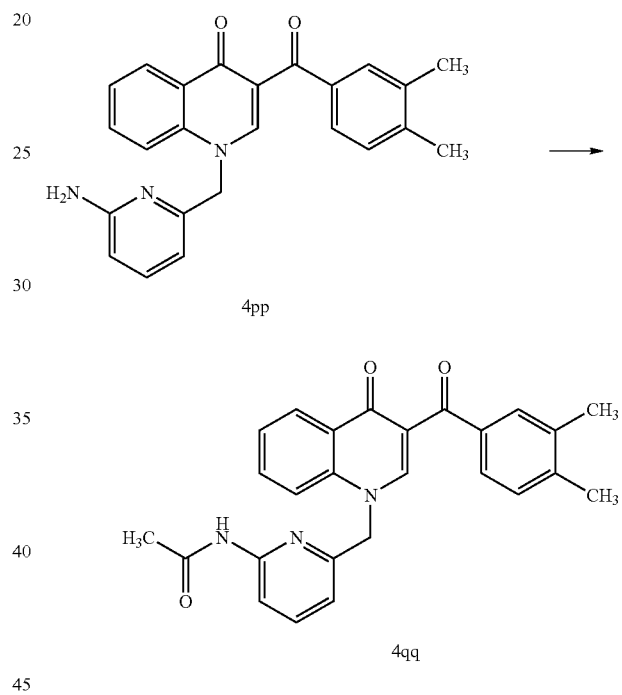

8 mg (0.021 mmol) of 1-(6-amino-pyridin-2-ylmethyl)-3-(3,4-dimethyl-benzoyl)-1H-isoquinolin-4-one 4pp was dissolved in 2 mL of dichloromethane. To the resultant solution was added 10 mg (0.13 mmol) of acetyl chloride and 15 mg (0.15 mmol) of triethylamine and the reaction mixture was stirred for 1 h followed by the addition of 30 mL of water to quench the reaction. The reaction solution was extracted with 30 mL of chloroform (2×) and the combined organic layer was dried over anhydrous MgSO₄ and evaporated in vacuo. The crude product 4qq was purified by preparative HPLC to yield 4 mg of 4qq as a colorless solid: LC-MSD, m/z for C₂₆H₂₃N₃O₃ [M+H]+=426.5, [M+2H]+=427.5; Reverse phase HPLC (gradient acetonitrile with 0.1% TFA 20-95% in 4 min) retention time=2.038 min; ¹H NMR (400 MHz, CDCl₃/HCl): δ 2.20 (s, 3H), 2.34 (d, 6H), 5.32 (s, 2H), 6.94 (d, 1H), 7.18 (d, 1H), 7.32-7.43 (m, 2H), 7.54-7.60 (m, 2H), 7.62-7.72 (m, 2H), 8.20 (s, 1H), 8.14 (d, 1H), 8.30 (s, 1H), 8.47 (d, 1H).

Example 43

Preparation of 3-(3,4-Dimethyl-benzoyl)-1-(2-fluoro-benzyl)-1H-1[1,6]napthyridin-4-one (11a)

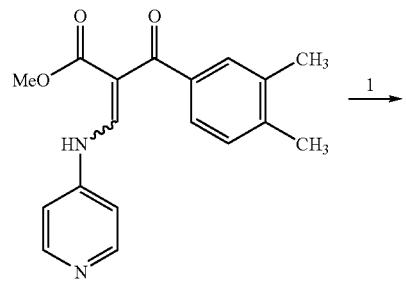

2f

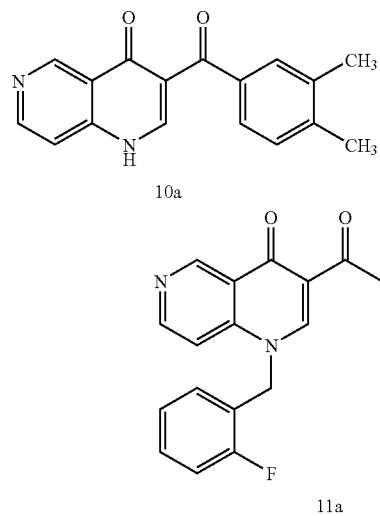

10a

11a

Step 1: 3-(3,4-Dimethyl-benzoyl)-1H-[1,6]napthyridin-4-one (10a)

273 g (0.88 mmol) of 2-(3,4-Dimethyl-benzoyl)-3-(pyridine-4-ylamino)-acrylic acid methyl ester 2f was dissolved in 30 mL of diphenyl ether and the resultant solution was heated at 250° C. After 2.5 h, the reaction solution was cooled to room temperature and diluted with 50 mL of hexane. The crude product precipitated out of solution and was isolated by filtration. The crude product was purified by washing with hexane to yield 119 mg of 3-(3,4-Dimethyl-benzoyl)-1H-[1,6]napthyridin-4-one 10a as white crystals.

Step 2: 3-(3,4-Dimethyl-benzoyl)-1-(2-fluoro-benzyl)-1H-1[1,6]napthyridin-4-one (11a)

8.0 mg (0.32 mmol) of 60% sodium hydride was added to a mixture of 0.045 g (0.162 mmol) of 3-(3,4-Dimethyl-benzoyl)-1H-[1,6]napthyridin-4-one 10a in 0.5 mL of N,N-dimethylformamide and the resultant solution was stirred at rt for 5 min. Then 23.4 μL (0.194 mmol) of 2-fluorobenzyl bromide was added to the solution and the reaction mixture was stirred for 2.5 h at room temperature. The reaction solution was quenched upon the addition of water. The crude product 11a was purified on the reverse phase HPLC (with a C18 column, gradient of 20-70% acetonitrile with 0.1% TFA) to yield 40.8 mg of 3-(3,4-Dimethyl-benzoyl)-1-(2-fluoro-benzyl)-1H-1[1,6]napthyridin-4-one 11a as a white crystalline solid: LC-MSD, m/z for: $C_{24}H_{19}FN_2O_2$, [M+H]=387.5; Reverse phase HPLC gradient, 20-95% acetonitrile with 0.1% TFA in 4 minutes, retention time=2.1 min; $^1$H NMR (400 MHz, CDCl$_3$): δ 9.40 (1H, s), 8.80 (1H, m), 8.56 (1H, m), 7.93 (1H, m), 7.64 (1H, m), 7.59 (1H, m), 7.41 (2H, m), 7.23 (3H, m) 5.59 (2H, s), 2.36 (3H, s), 2.32 (3H, s).

Example 44

Preparation of 3-(3,4-Dimethyl-benzoyl)-1-(3-methyl-benzyl)-1H-1[1,6]napthyridin-4-one (11b)

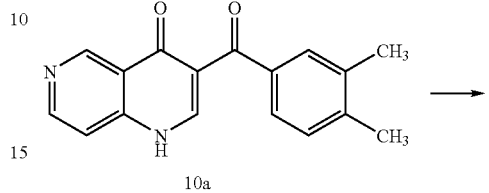

10a

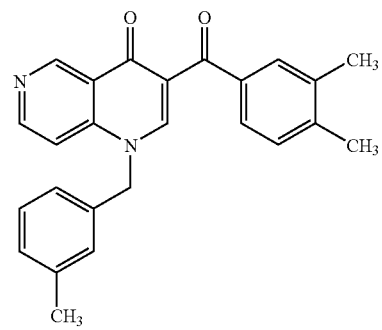

11b

Compound 11a was prepared following the procedure outlined in Step 3 of Example 1 using 0.045 g (0.162 mmol) of 3-(3,4-Dimethyl-benzoyl)-1H-[1,6]napthyridin-4-one 10a, 8.0 mg (0.32 mmol) of 60% sodium hydride, 26.2 μL (0.30 mmol) of 3-methylbenzyl bromide, and 0.5 mL N,N-dimethylformamide. The reaction time was 3 h. Purification of the crude product by reverse phase HPLC using 20-70% acetonitrile yielded 13 mg of 3-(3,4-Dimethyl-benzoyl)-1-(3-methyl-benzyl)-1H-1[1,6]napthyridin-4-one 11b as white solid: LC-MSD, m/z for $C_{25}H_{22}N_2O_2$, [M+H]=383.5; Reverse phase HPLC gradient, 20-95% acetonitrile with 0.1% TFA in 4 minutes, retention time=2.3 min; $^1$H NMR (400 MHz, CDCl$_3$): δ 9.43 (1H, s), 8.67 (1H, m), 8.56 (1H, m), 7.81 (1H, m), 7.64 (1H, m), 7.60 (1H, m), 7.26 (2H, m), 7.17 (2H, m), 7.31 (1H, m), 5.57 (2H, s), 2.34 (9H, m).

Example 45

Preparation of 3-(3,4-Dimethyl-benzoyl)-1-(2-fluoro-3-methyl-benzyl)-1H-1-quinolin-4-one (4rr)

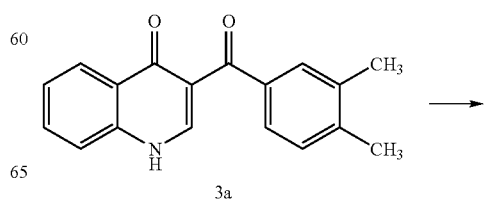

3a

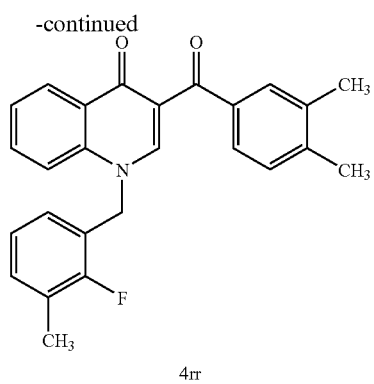

4rr

Compound 4rr was prepared following the procedure outlined in Step 3 of Example 1 using 0.100 g (0.361 mmol) of 3-(3,4-dimethyl-benzoyl)-1H-quinolin-4-one 3a, 17.3 mg (0.721 mmol) of 60% sodium hydride and 87.9 mg (0.433 mmol) of 2-fluoro-3-methylbenzyl bromide, and 0.7 mL N,N-dimethylformamide. The reaction mixture was stirred for 3 h. The crude product was washed with dichloromethane to yield 56.4 mg of 3-(3,4-Dimethyl-benzoyl)-1-(2-fluoro-3-methyl-benzyl)-1H-1-quinolin-4-one 4rr as a yellow solid: LC-MSD, m/z for $C_{26}H_{22}FNO_2$, [M+H]=400.5; Reverse phase HPLC gradient, 20-95% acetonitrile with 0.1% TFA in 4 minutes, retention time=2.6 min; $^1$H NMR (400 MHz, CDCl$_3$): δ 8.57 (1H, s), 8.19 (1H, m), 7.71 (1H, m), 7.63 (1H, m), 7.54 (1H, s), 7.47 (1H, m), 7.42 (1H, m), 7.22 (2H, m), 7.02 (1H, m), 6.98 (1H, m), 5.68 (2H, s), 2.29 (3H, s), 2.49 (6H, m).

Example 46

Preparation of 3-(3,4-Dimethyl-benzoyl)-1-(2,6-dimethyl-benzyl)-1H-1-quinolin-4-one (4ss)

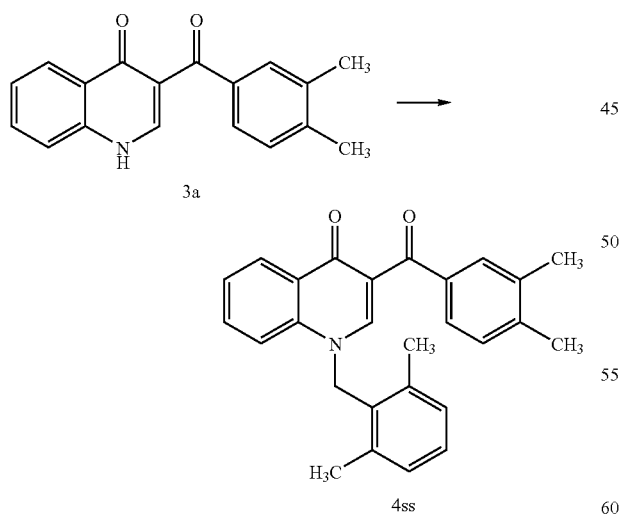

Compound 4ss was prepared following the procedure outlined in Step 3 of Example 1 using 0.100 g (0.361 mmol) of 3-(3,4-dimethyl-benzoyl)-1H-quinolin-4-one 3a, 17.3 mg (0.721 mmol) of 60% sodium hydride and 86.2 mg (0.433 mmol) of 2-Bromomethyl-1,3-dimethyl-benzene (prepared according to literature procedures: Soloshonok, V. A. et al., Tetrahedron 2001, 57, 6375-6382.), and 0.7 mL N,N-dimethylformamide. The reaction solution was stirred at room temperature for 2 h. Purification of the crude product by reverse phase HPLC using 20-70% acetonitrile followed by neutralization with aqueous saturated sodium bicarbonate provided 98 mg of 3-(3,4-Dimethyl-benzoyl)-1-(2,6-dimethyl-benzyl)-1H-1-quinolin-4-one 4ss as a white solid: LC-MSD, m/z for $C_{27}H_{25}NO_2$, [M+H]=396.5; Reverse phase HPLC gradient, 20-95% acetonitrile with 0.1% TFA in 4 minutes, retention time=2.9 min; $^1$H NMR (400 MHz, CDCl$_3$): δ 8.54 (1H, m), 7.79 (2H, m), 7.57 (1H, s), 7.50 (2H, m), 7.43 (1H, m), 7.22 (1H, m), 7.13 (2H, m), 7.09 (1H, m), 5.27 (2H, s), 2.28-2.24 (12H, m).

Example 47

Preparation of 1-(6-Bromo-pyridin-2-ylmethyl)-3-(3,4-dimethyl-benzoyl)-6-fluoro-1H-quinolin-4-one (4tt)

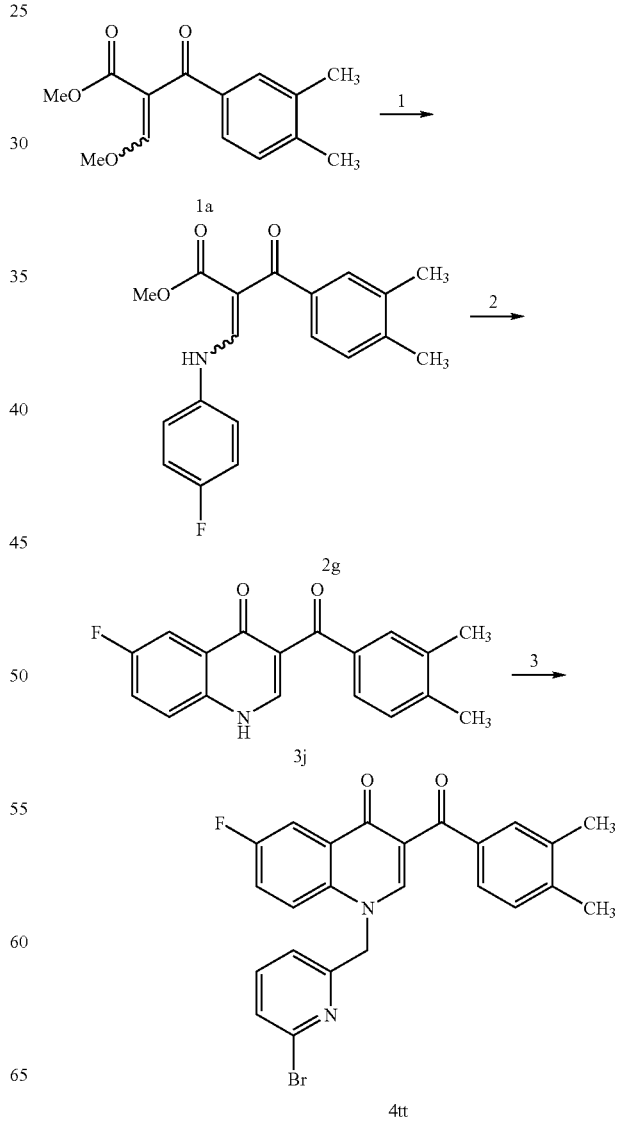

Step 1: 2-(3,4-Dimethyl-benzoyl)-3-(4-fluoro-phenylamino)-acrylic acid methyl ester (2g)

1 g (4.03 mmol) of the crude 2-(3,4-dimethyl-benzoyl)-3-methoxy-acrylic acid methyl ester 1a and 0.40 g (3.63 mmol) of 4-fluoroaniline were heated neat at 100° C. for 2 h. The reaction solution was cooled to room temperature and the crude product precipitated out of solution. The crude material was recrystallized from dichloromethane/hexane to yield 0.70 g of 2-(3,4-dimethyl-benzoyl)-3-(4-fluoro-phenylamino)-acrylic acid methyl ester 2g as brown crystalline solid.

Step 2: 3-(3,4-dimethyl-benzoyl)-6-fluoro-1H-quinolin-4-one (3j)

0.691 g (2.11 mmol) of 2-(3,4-Dimethyl-benzoyl)-3-(4-fluoro-phenylamino)-acrylic acid methyl ester 2g was dissolved in 30 mL of diphenyl ether and the resultant solution was heated at 250° C. After 2.5 h the solution was cooled to room temperature and diluted with 50 mL of hexane. The crude product precipitated out of solution and was isolated by filtration. The crude product was further washed with hexane to yield 0.412 g of 3-(3,4-dimethyl-benzoyl)-6-fluoro-1H-quinolin-4-one 3j as a brown solid.

Step 3: 1-(6-Bromo-pyridin-2-ylmethyl)-3-(3,4-dimethyl-benzoyl)-6-fluoro-1H-quinolin-4-one (4tt)

To a solution of 0.050 g (0.169 mmol) of 3-(3,4-dimethyl-benzoyl)-6-fluoro-1H-quinolin-4-one 4tt in 1.0 mL of tetrahydrofuran was added 0.4 mL (0.5 M in toluene, 0.203 mmol) of potassium hexamethyldisilazide and the reaction solution was stirred for 5 min, followed by the addition of 50.9 mg (0.203 mmol) of 2-bromo-6-bromomethyl-pyridine in 0.5 ml of tetrahydrofuran. The resultant solution was stirred at 60° C. for 3 h. The reaction solution was quenched by the addition of water and the aqueous phase was extracted with 3×5 mL of ether. The combined organic layer was dried over anhydrous magnesium sulfate, filtered and concentrated in vacuo to yield 58 mg of 1-(6-Bromo-pyridin-2-ylmethyl)-3-(3,4-dimethyl-benzoyl)-6-fluoro-1H-quinolin-4-one 4tt as a yellow solid: LC-MSD, m/z for $C_{24}H_{18}BrFN_2O_2$, [M+H]=465.4, 466.5, 467.4, 468.4; Reverse phase HPLC gradient, 20-95% acetonitrile with 0.1% TFA in 4 minutes, retention time=2.8 min; $^1$H NMR (400 MHz, CDCl$_3$): δ 8.27 (1H, s), 8.12 (1H, m), 7.64 (1H, s), 7.56 (1H, m), 7.51 (1H, m), 7.47 (1H, m), 7.40-7.34 (2H, m), 7.19 (1H, m), 7.00 (1H, m), 5.46 (2H, s), 2.32 (3H, s), 2.31 (3H, s).

Example 48

Preparation of 3-(3,4-Dimethyl-benzoyl)-6-fluoro-1-(3-methyl-benzyl)-1H-quinolin-4-one (4uu)

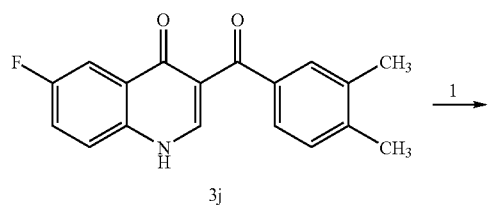

3j

-continued

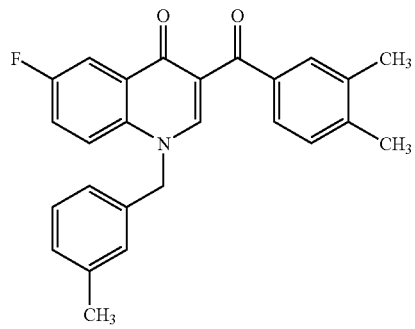

4uu

Compound 4uu was prepared following the procedure outlined in Step 3 of Example 1. Briefly described here, 0.050 g (0.169 mmol) of 3-(3,4-dimethyl-benzoyl)-6-fluoro-1H-quinolin-4-one 3j, 0.4 mL of potassium hexamethyldisilazide (0.5 M in toluene, 0.203 mmol) and 37.6 mg (0.203 mmol) of 3-methylbenzyl bromide were combined in 1.5 mL of tetrahydrofuran and heated at 60° C. for 3 h. Purification of the crude product using flash chromatography (30-50% ethyl acetate in hexane) yielded 52.2 mg of 3-(3,4-dimethyl-benzoyl)-6-fluoro-1-(3-methyl-benzyl)-1H-quinolin-4-one as a white solid 4uu: LC-MSD, m/z for $C_{26}H_{22}FNO_2$, [M+H]=400.5; Reverse phase HPLC gradient, 20-95% acetonitrile with 0.1% TFA in 4 minutes, retention time=2.9 min; $^1$H NMR (400 MHz, CDCl$_3$): δ 8.26 (1H, s), 8.11 (1H, m), 7.64 (1H, s), 7.56 (1H, m), 7.38 (1H, m), 7.32-7.23 (2H, m), 7.18 (1H, m), 7.15 (1H, m), 6.97 (2H, m), 5.37 (2H, s), 2.33 (3H, s), 2.32 (3H, s), 2.31 (3H, s).

Example 49

Preparation of 1-(6-Bromo-pyridin-2-ylmethyl)-3-(3,4-dimethyl-benzoyl)-7-fluoro-1H-quinolin-4-one (4vv)

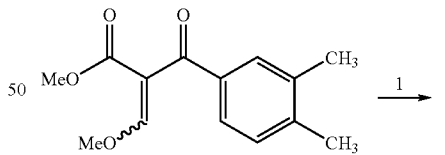

1a

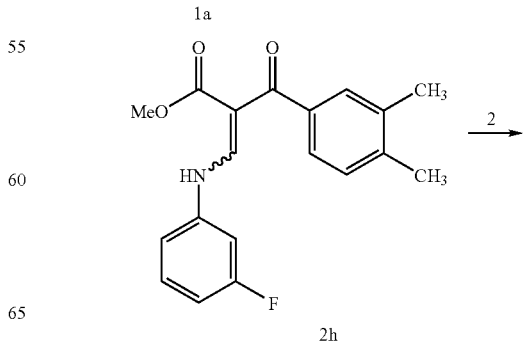

2h

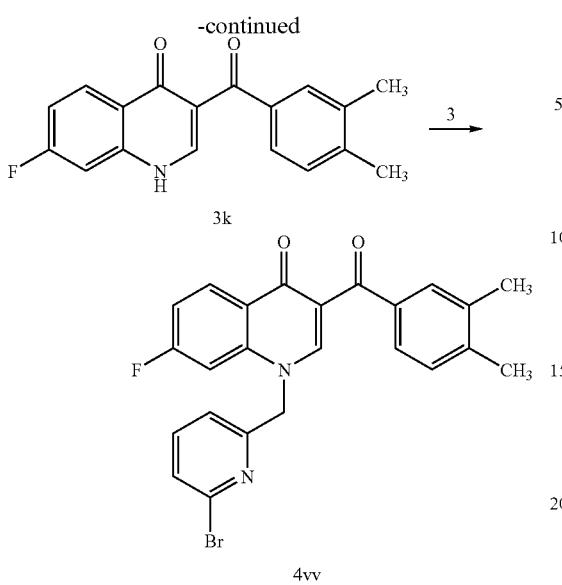

Step 1: 2-(3,4-Dimethyl-benzoyl)-3-(3-fluoro-phenylamino)-acrylic acid methyl ester (2h)

Compound 2h was prepared following the procedure described in Step 1 of Example 1 using from 2g (8.06 mmol) of crude 2-(3,4-Dimethyl-benzoyl)-3-methoxy-acrylic acid methyl ester 1a and 0.806 g (7.26 mmol) 3-fluoroaniline. The crude product 2h was purified by recrystalization with dichloromethane/hexane to yield 1.19 g of 2-(3,4-Dimethyl-benzoyl)-3-(3-fluoro-phenylamino)-acrylic acid methyl ester as a brown solid.

Step 2: 3-(3,4-dimethyl-benzoyl)-7-fluoro-1H-quinolin-4-one (3k)

Compound 3k was prepared following the procedure described in Step 2 of Example 5 using 1.19 g (3.64 mmol) of 2-(3,4-Dimethyl-benzoyl)-3-(3-fluoro-phenylamino)-acrylic acid methyl ester 2h and 30 mL of diphenyl ether to yield 0.858 g of 3-(3,4-dimethyl-benzoyl)-7-fluoro-1H-quinolin-4-one 3k as a brown solid.

Step 3: 1-(6-Bromo-pyridin-2-ylmethyl)-3-(3,4-dimethyl-benzoyl)-7-fluoro-1H-quinolin-4-one (4vv)

Compound 4vv was prepared following the procedure described in Step 3 of Example 1 using 0.050 g (0.169 mmol) of 3-(3,4-dimethyl-benzoyl)-7-fluoro-1H-quinolin-4-one 3k, 0.4 mL of potassium hexamethyldisilazide (0.5 M in toluene, 0.203 mmol) and 50.9 mg (0.203 mmol) of 2-bromo-6-bromomethyl-pyridine in 1.5 mL of tetrahydrofuran and heating the reaction solution at 60° C. for 24 h. The crude product was purified by flash chromatography using 10-80% ethyl acetate in hexane to yield 37.8 mg of 3-(3,4-Dimethyl-benzoyl)-7-fluoro-1-(3-methyl-benzyl)-1H-quinolin-4-one 4vv as a white solid: LC-MSD, m/z for $C_{24}H_{18}BrFN_2O_2$ [M+H]: 465.4, 466.5, 467.4, 468.4; Reverse phase HPLC gradient, 20-95% acetonitrile with 0.1% TFA in 4 minutes, retention time=2.8 min; $^1$H NMR (400 MHz, CDCl$_3$): δ 8.47 (1H, m), 8.23 (1H, s), 7.64 (1H, s), 7.56 (1H, m), 7.53 (1H, m), 7.47 (1H, m), 7.18 (1H, m), 7.12 (1H, m), 7.05-7.02 (2H, m), 5.39 (2H, s), 2.32 (3H, s), 2.31 (3H, s).

Example 50

Preparation of 1-(6-bromo-pyridin-2-ylmethyl)-3-(5,6-dimethyl-pyridine-2-carbonyl)-1H-quinolin-4-one (4ww)

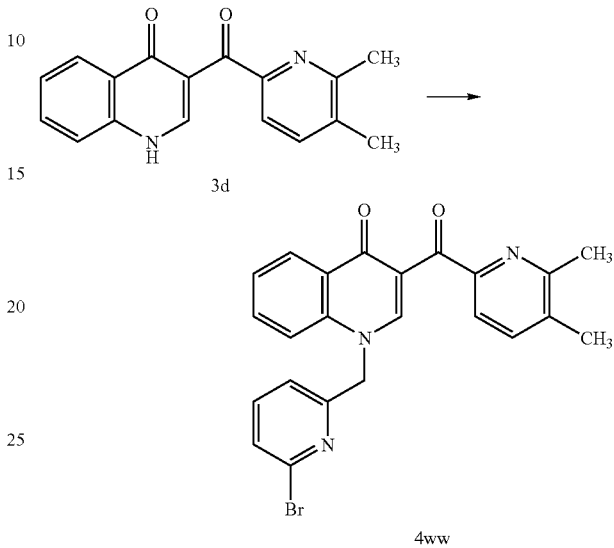

Compound 4ww was prepared following the procedure described in Step 3 of Example using 45 mg (0.16 mmol) of 3-(5,6-dimethyl-pyridine-2-carbonyl)-1H-quinolin-4-one 3d, 8 mg (0.21 mmol) of 60% sodium hydride and 53 mg (0.21 mmol) of 2-bromo-6-bromomethyl-pyridine in 0.7 mL N,N-dimethylformamide and stirring the reaction mixture at rt for 2 h. The product was purified using reverse phase HPLC (mobile phase with a gradient 10-50% acetonitrile in 50 min). The HPLC fractions containing pure product were combined, evaporated under vacuum and neutralized using methanolic ammonia and purified by flash chromatography (using 30-100% ethyl acetate in hexane) to give 18 mg of a pale yellow solid: LC-MSD, m/z for $C_{23}H_{18}BrN_3O_2$ [M+H]+: 448.4, 450.4; Reverse phase HPLC gradient, 20-95% acetonitrile with 0.1% TFA in 4 minutes, retention time=2.1 min; $^1$H NMR (400 MHz, CDCl$_3$): δ 2.35 (s, 3H), 2.5 (s, 3H), 5.5 (s, 2H), 7.0-7.1 (m, 1H), 7.3-7.35 (m, 1H), 7.35-7.4 (m, 1H), 7.4-7.6 (m, 4H), 7.6-7.7 (m, 1H), 8.4-8.45 (m, 1H), 8.5 (s, 1H).

Example 51

Preparation of 3-(3,4-dimethyl-benzoyl)-1-(6-trifluoromethyl-pyridin-2-ylmethyl)-1H-quinolin-4-one (4xx)

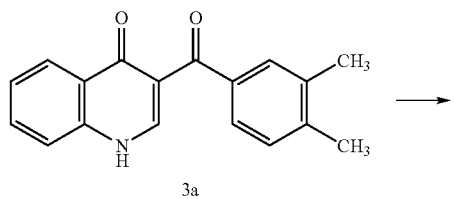

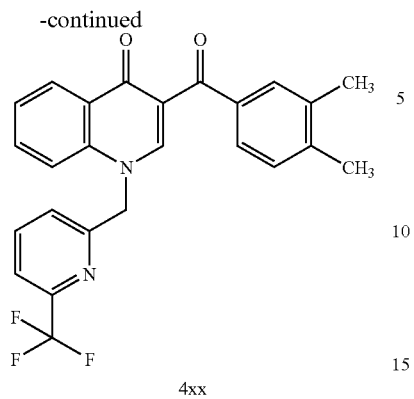

4xx

Compound 4xx was prepared following the procedure described in Step 3 of Example 1 using 55 mg (0.20 mmol) of 3-(3,4-dimethyl-benzoyl)-1H-quinolin-4-one, 10 mg (0.26 mmol) of 60% sodium hydride and 62 mg (0.26 mmol) of 2-bromomethyl-6-trifluoromethyl-pyridine, and 1.7 mL N,N-dimethylformamide and stirring the reaction mixture for 6 h at rt. The crude product was purified by flash chromatography using 20-75% ethyl acetate in hexane yielded to provide 45 mg of the product as white solid: LC-MSD, m/z for $C_{25}H_{19}F_3N_2O_2$ [M+H]+: 437.3; Reverse phase HPLC gradient, 20-95% acetonitrile with 0.1% TFA in 4 minutes, retention time=2.8 min; $^1$H NMR (400 MHz, CDCl$_3$): δ 2.25 (s, 3H), 2.3 (s, 3H), 5.6 (s, 2H), 7.1-7.2 (m, 1H), 7.2-7.3 (m, 1H), 7.3-7.4 (m, 2H), 7.5-7.65 (m, 15 4H), 7.8-7.9 (m, 1H), 8.35 (s, 1H), 8.4-8.5 (m, 1H).

Example 52

Preparation of 1-(6-Bromo-pyridin-2-ylmethyl)-3-(3,4-dimethyl-benzoyl)-1H-[1,5]naphthyridin-4-one

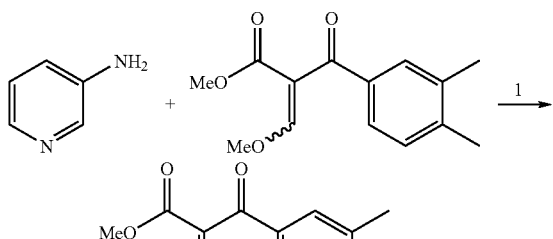

Step 1: 2-(3,4-Dimethyl-benzoyl)-3-(pyridin-3-ylamino)-acrylic acid methyl ester 1g (4.02 mmol) of the crude 2-(3,4-Dimethyl-benzoyl)-3-methoxy-acrylic acid methyl ester and 0.38 g (4.02 mmol) of 3-aminopyridine were heated neat at 100° C. for 2 h. The product crystallized upon cooling the reaction to rt to yield 1.12 g of 2-(3,4-Dimethyl-benzoyl)-3-(pyridin-3-ylamino)-acrylic acid methyl ester as brown crystalline solid.

Step 2: 3-(3,4-Dimethyl-benzoyl)-1H-[1,5]naphthyridin-4-one 1.12 g (3.61 mmol) of 2-(3,4-Dimethyl-benzoyl)-3-(pyridin-3-ylamino)-acrylic acid methyl ester was dissolved in 30 mL of diphenyl ether and the solution was heated at 250° C. After 2.5 h the solution was cooled to rt and 50 mL of hexane was added. The mixture was filtered and the solid washed with hexane to yield 0.67 g of 3-(3,4-Dimethyl-benzoyl)-1H-[1,5]naphthyridin-4-one as a brown solid.

Step 3: 1-(6-Bromo-pyridin-2-ylmethyl)-3-(3,4-dimethyl-benzoyl)-1H-[1,5]naphthyridin-4-one To a solution of 0.060 g (0.216 mmol) of 3-(3,4-Dimethyl-benzoyl)-1H-[1,5]naphthyridin-4-one in 2.0 mL of N,N-dimethylformamide was added 10.4 mg (0.259 mmol, 60% dispersion in oil) of sodium hydride and the reaction was stirred for 5 min. 65 mg (0.259 mmol) of 2-bromo-6-bromomethyl-pyridine was added and the reaction was stirred at room temperature for 3 h. Water was added and the solid collected by filtration. The crude brown solid was purified on the reverse phase HPLC with a C18 column, gradient of 20-70% acetonitrile—0.1% TFA to yield 11.8 mg of 1-(6-Bromo-pyridin-2-ylmethyl)-3-(3,4-dimethyl-benzoyl)-1H-[1,5] naphthyridin-4-one as an off white solid.

LC-MSD, m/z for $C_{23}H_{18}BrN_3O_2$ [M+H]: 448.06 LC retention time on HPLC, C18 column gradient 20-95% acetonitrile with 0.1% TFA in 4 minutes: 2.2 min Example 53

Preparation of 3-(3,4-Dimethyl-benzoyl)-1-(6-methyl-pyridin-2-ylmethyl)-1H-[1,5]naphthyridin-4-one

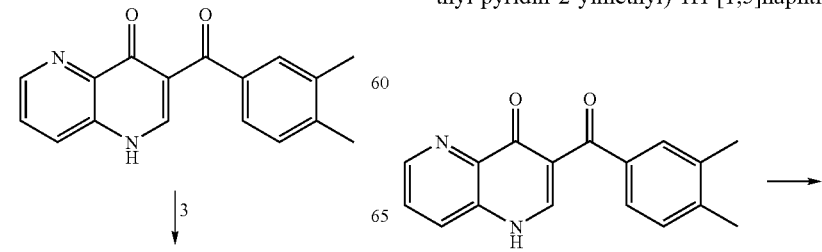

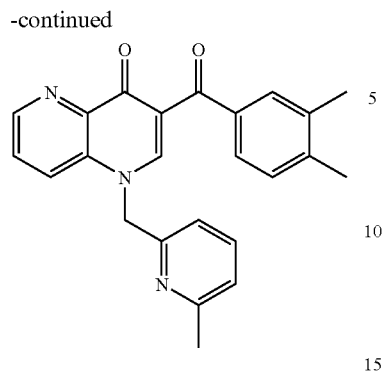

Experimental conditions analogous to those described for Step 3 of Example 1 were used with 0.100 g (0.359 mmol) of 3-(3,4-Dimethyl-benzoyl)-1H-[1,5]naphthyridin-4-one, 17.2 mg (0.431 mmol, 60% dispersion in oil) of sodium hydride, 80.2 mg (0.431 mmol) of 2-methyl-6-bromomethyl-pyridine and 3.5 mL of N,N dimethylformamide. The crude brown solid was purified on the reverse phase HPLC with a C18 column, gradient of 20-70% acetonitrile—0.1% TFA to yield 61.7 mg of 3-(3,4-Dimethyl-benzoyl)-1-(6-methyl-pyridin-2-ylmethyl)-1H-[1,5]naphthyridin-4-one as an off white solid. LC-MSD, m/z for $C_{24}H_{21}N_3O_2$ [M+H]: 384.2 LC retention time on HPLC, C18 column gradient 20-95% acetonitrile with 0.1% TFA in 4 minutes: 1.8 min Example 54

Preparation of 1-(6-Bromo-pyridin-2-ylmethyl)-3-(3, 4-dimethyl-benzoyl)-7-methyl-1H-[1,8]naphthyridin-4-one

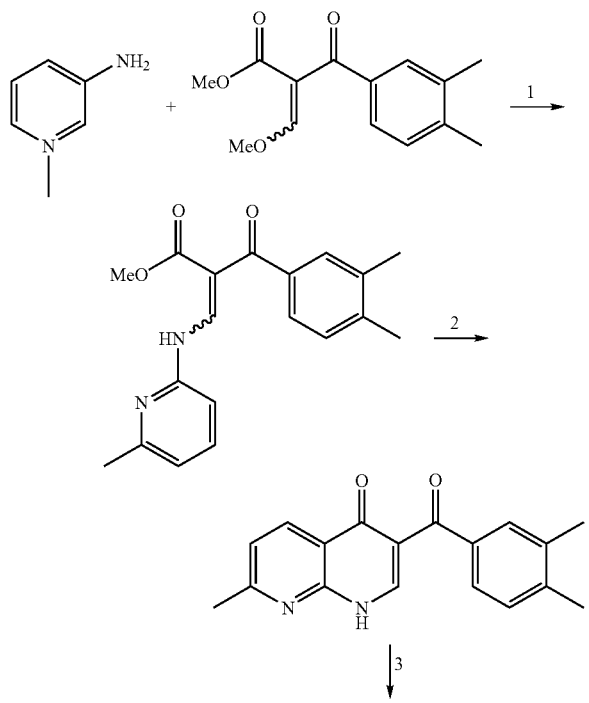

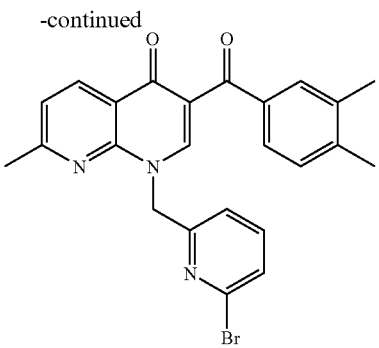

Step 1: 2-(3,4-Dimethyl-benzoyl)-3-(6-methyl-pyridin-2-ylamino)-acrylic acid methyl ester Experimental conditions analogous to those described for Step 1 of Example 1 were used with 0.50 g (2.01 mmol) of the crude 2-(3,4-Dimethyl-benzoyl)-3-methoxy-acrylic acid methyl ester and 0.22 g (2.01 mmol) of 2-amino-6-picoline to yield 1.12 g of 2-(3,4-Dimethyl-benzoyl)-3-(6-methyl-pyridin-2-ylamino)-acrylic acid methyl ester as brown crystalline solid.

Step 2: 3-(3,4-Dimethyl-benzoyl)-7-methyl-1H-[1,8]naphthyridin-4-one

Experimental conditions analogous to those described for Step 2 of Example 1 were used with 0.59 g (1.82 mmol) of 2-(3,4-Dimethyl-benzoyl)-3-(6-methyl-pyridin-2-ylamino)-acrylic acid methyl ester in 30 mL of diphenyl ether to yield 0.33 g of 3-(3,4-Dimethyl-benzoyl)-7-methyl-1H-[1,8]naphthyridin-4-one as a brown solid.

Step 3: 1-(6-Bromo-pyridin-2-ylmethyl)-3-(3,4-dimethyl-benzoyl)-7-methyl-1H-[1,8]naphthyridin-4-one Experimental conditions analogous to those described for Step 3 of Example 1 were used with 0.100 g (0.342 mmol) of 3-(3,4-Dimethyl-benzoyl)-7-methyl-1H-[1,8]naphthyridin-4-one, 16.4 mg (0.410 mmol, 60% dispersion in oil) of sodium hydride, 0.103 g (0.410 mmol) of 2-bromo-6-bromomethyl-pyridine and 3.5 mL of N,N dimethylformamide. The crude brown solid was purified on the reverse phase HPLC with a C18 column, gradient of 20-70% acetonitrile—0.1% TFA to yield 29.5 mg of 1-(6-Bromo-pyridin-2-ylmethyl)-3-(3,4-dimethyl-benzoyl)-7-methyl-1H-[1,8]naphthyridin-4-one as an off white solid. LC-MSD, m/z for $C_{24}H_{20}BrN_3O_2$ [M+H]: 463.07 LC retention time on HPLC, C18 column gradient 20-95% acetonitrile with 0.1% TFA in 4 minutes: 2.7 min Example 55

Preparation of 3-(3,4-Dimethyl-benzoyl)-7-methyl-1-(6-methyl-pyridin-2-ylmethyl)-1H-[1,8]naphthyridin-4-one

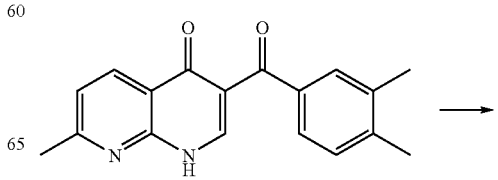

-continued

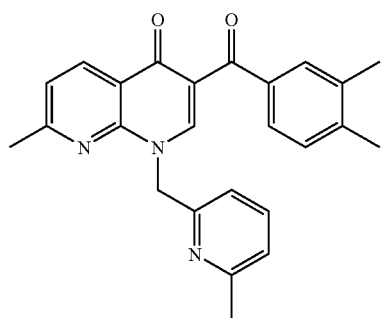

Experimental conditions analogous to those described for Step 3 of Example 1 were used with 0.100 g (0.342 mmol) of 3-(3,4-Dimethyl-benzoyl)-7-methyl-1H-[1,8]naphthyridin-4-one, 16.4 mg (0.410 mmol, 60% dispersion in oil) of sodium hydride, 76.3 mg (0.410 mmol) of 2-methyl-6-bromomethyl-pyridine and 3.5 mL of N,N-dimethylformamide. The crude brown solid was purified by flash column chromatography using 30-100% ethyl acetate in hexane to yield 38 mg of 1-(6-Bromo-pyridin-2-ylmethyl)-3-(3,4-dimethyl-benzoyl)-7-methyl-1H-[1,8]naphthyridin-4-one as an off white solid. LC-MSD, m/z for $C_{25}H_{23}N_3O_2$ [M+H]: 398.2 LC retention time on HPLC, C18 column gradient 20-95% acetonitrile with 0.1% TFA in 4 minutes: 2.3 min Example 56

Preparation of 1-(6-Bromo-pyridin-2-ylmethyl)-3-(3,4-dimethyl-benzoyl)-6,8-dimethyl-1H-[1,7]naphthyridin-4-one

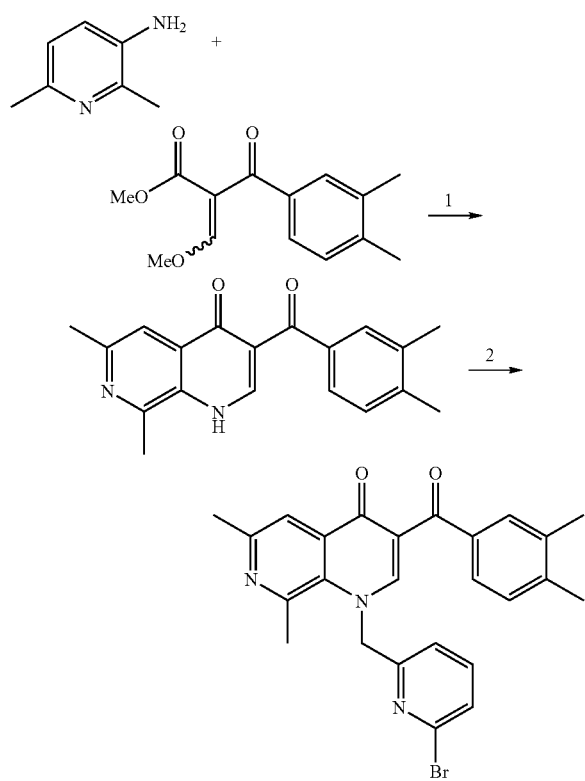

Step 1: 3-(3,4-Dimethyl-benzoyl)-6,8-dimethyl-1H-[1,7]naphthyridin-4-one 0.50 g (2.01 mmol) of 2-(3,4-Dimethyl-benzoyl)-3-methoxy-acrylic acid methyl ester and 0.25 g (2.01 mmol) of 2,6-Dimethyl-pyridin-3-ylamine were heated at 100° C. for two hours. After cooling to room temperature 30 mL of diphenyl ether was added and heated at 250° C. for two hours. The reaction was allowed to cool to room temperature and hexane was added. The brown precipitate was collected by filtration to yield 45 mg of 3-(3,4-Dimethyl-benzoyl)-6,8-dimethyl-1H-[1,7]naphthyridin-4-one.

Step 2: 1-(6-Bromo-pyridin-2-ylmethyl)-3-(3,4-dimethyl-benzoyl)-6,8-dimethyl-1H-[1,7]naphthyridin-4-one Experimental conditions analogous to described for Step 3 of Example 1 were used with 42 mg (0.137 mmol) of 3-(3,4-Dimethyl-benzoyl)-6,8-dimethyl-1H-[1,7]naphthyridin-4-one, 6 mg (0.165 mmol, 60% dispersion in oil) of sodium hydride, 41.3 mg (0.165 mmol) of 2-bromo-6-bromomethyl-pyridine and 1.5 mL of N,N-dimethylformamide. The crude brown solid was purified by flash column chromatography using 30-100% ethyl acetate in hexane to yield 7.9 mg of 1-(6-Bromo-pyridin-2-ylmethyl)-3-(3,4-dimethyl-benzoyl)-6,8-dimethyl-1H-[1,7]naphthyridin-4-one as an off white solid. LC-MSD, m/z for $C_{25}H_{22}BrN_3O_2$ [M+H]: 477.37 LC retention time on HPLC, C18 column gradient 20-95% acetonitrile with 0.1% TFA in 4 minutes: 2.9 min Example 57

Preparation of 1-(6-Bromo-pyridin-2-ylmethyl)-3-(3,4-dimethyl-benzoyl)-8-methyl-1H-[1,5]naphthyridin-4-one

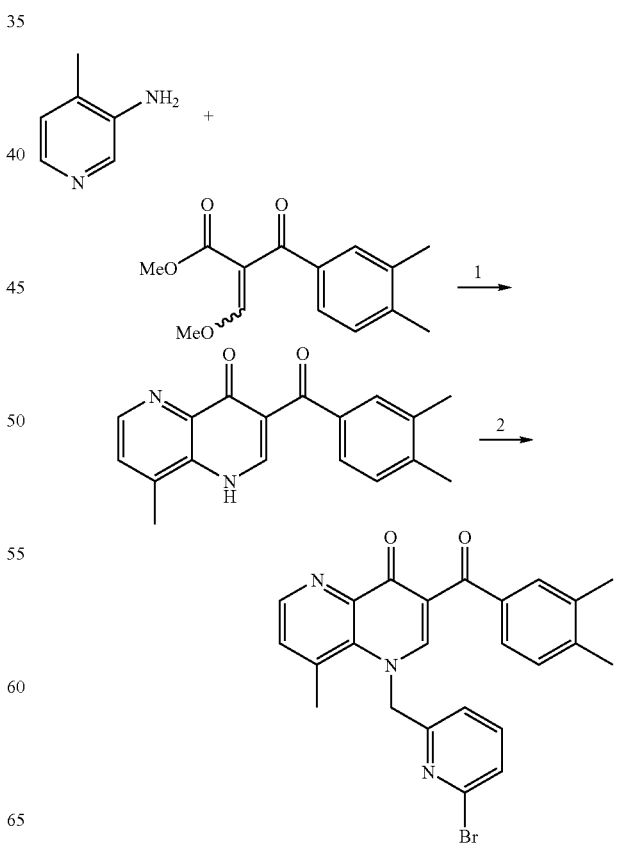

Step 1: 3-(3,4-Dimethyl-benzoyl)-8-methyl-1H-[1,5]naphthyridin-4-one

Experimental conditions analogous to those described for Step 1 of Example 1 were used with 0.50 g (2.01 mmol) 2-(3,4-Dimethyl-benzoyl)-3-methoxy-acrylic acid methyl ester, 0.22 g (2.01 mmol) of 4-Methyl-pyridin-3-ylamine, and 30 mL of diphenyl ether to yield 94.4 mg of 3-(3,4-Dimethyl-benzoyl)-8-methyl-1H-[1,5]naphthyridin-4-one as a brown solid.

Step 2: 1-(6-Bromo-pyridin-2-ylmethyl)-3-(3,4-dimethyl-benzoyl)-8-methyl-1H-[1,5]naphthyridin-4-one Experimental conditions analogous to described for Step 3 of Example 1 were used with 93 mg (0.318 mmol) of 3-(3,4-Dimethyl-benzoyl)-8-methyl-1H-[1,5]naphthyridin-4-one, 15 mg (0.382 mmol, 60% dispersion in oil) of sodium hydride, 95.8 mg (0.382 mmol) of 2-bromo-6-bromomethyl-pyridine and 3.0 mL of N,N-dimethylformamide. The crude brown solid was purified by flash column chromatography using 30-100% ethyl acetate in hexane to yield 1-(6-Bromo-pyridin-2-ylmethyl)-3-(3,4-dimethyl-benzoyl)-8-methyl-1H-[1,5]naphthyridin-4-one as an off white solid. LC-MSD, m/z for $C_{24}H_{20}BrN_3O_2$ [M+H]: 462.07 LC retention time on HPLC, C18 column gradient 20-95% acetonitrile with 0.1% TFA in 4 minutes: 3.0 min.

Example 58

Preparation of 1-(6-Bromo-pyridin-2-ylmethyl)-3-(3,4-dimethyl-benzoyl)-6-methyl-1H-[1,5]naphthyridin-4-one

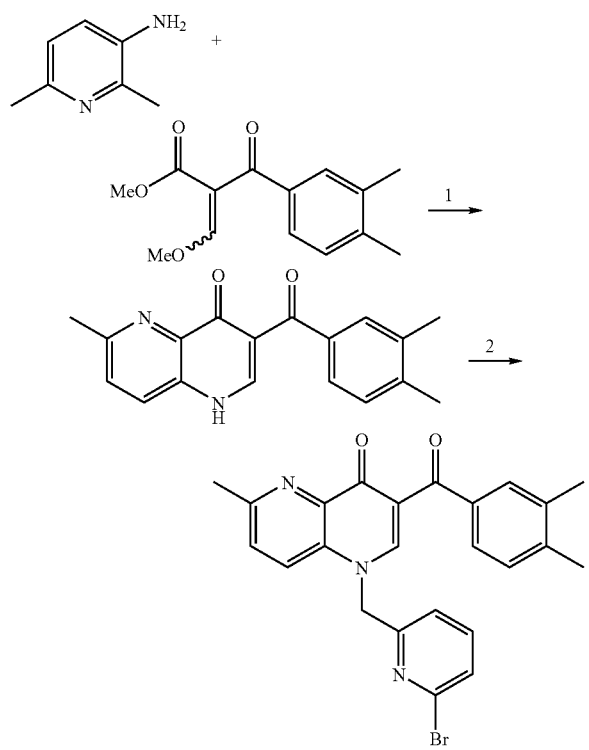

Step 1: 3-(3,4-Dimethyl-benzoyl)-6-methyl-1H-[1,5]naphthyridin-4-one

Experimental conditions analogous to those described for step 1 of Example 1 were used with 0.50 g (2.01 mmol) 2-(3,4-Dimethyl-benzoyl)-3-methoxy-acrylic acid methyl ester, 0.22 g (2.01 mmol) of 6-Methyl-pyridin-3-ylamine, and 15 mL of diphenyl ether to yield 129 mg of 3-(3,4-Dimethyl-benzoyl)-6-methyl-1H-[1,5]naphthyridin-4-one as a brown solid.

Step 2: 1-(6-Bromo-pyridin-2-ylmethyl)-3-(3,4-dimethyl-benzoyl)-6-methyl-1H-[1,5]naphthyridin-4-one Potassium hexamethyldisilazane (0.49 mL, 0.246 mmol, 0.5 M in THF) was added to a solution of 3-(3,4-Dimethyl-benzoyl)-6-methyl-1H-[1,5]naphthyridin-4-one (60 mg, 0.205) in 2 mL of tetrahydrofuran. After the reaction was stirred at room temperature for 20 minutes 2-bromo-6-bromomethyl-pyridine (61.8 mg, 0.246 mmol) was added and stirred overnight at room temperature. Water and ethyl acetate were added and the two phases were separated. The aqueous phase was extracted with ethyl acetate (3×20 mL). The combined organic layers were dried with magnesium sulfate, filtered and concentrated in vacuo. The crude brown solid was purified by reverse phase HPLC with a C18 column, gradient of 20-70% acetonitrile—0.1% TFA to yield 1-(6-Bromo-pyridin-2-ylmethyl)-3-(3,4-dimethyl-benzoyl)-6-methyl-1H-[1,5]naphthyridin-4-one as an off white solid. LC-MSD, m/z for $C_{24}H_{20}BrN_3O_2$ [M+H]: 462.07 LC retention time on HPLC, C18 column gradient 20-95% acetonitrile with 0.1% TFA in 4 minutes: 2.3 min.

Example 59

Preparation of 3-(3,4-Dimethyl-benzoyl)-6-methyl-1-(6-methyl-pyridin-2-ylmethyl)-1H-[1,5]naphthyridin-4-one

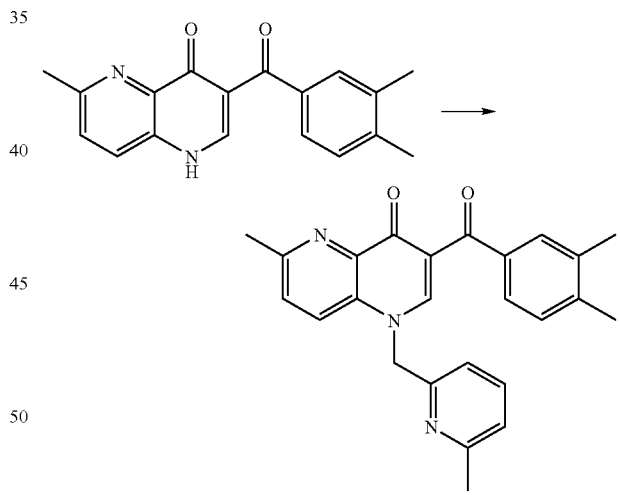

Experimental conditions analogous to those described for Step 3 of Example 1 were used with 65 mg (0.222 mmol) of 3-(3,4-Dimethyl-benzoyl)-6-methyl-1H-[1,5]naphthyridin-4-one, 11 mg (0.267 mmol, 60% dispersion in oil) of sodium hydride, 49.6 mg (0.267 mmol) of 2-methyl-6-bromomethyl-pyridine and 2.0 mL of N,N-dimethylformamide. The crude brown solid was purified by reverse phase HPLC with a C18 column, gradient of 20-70% acetonitrile—0.1% TFA to yield 3-(3,4-Dimethyl-benzoyl)-6-methyl-1-(6-methyl-pyridin-2-ylmethyl)-1H-[1,5]naphthyridin-4-one as an off white solid. LC-MSD, m/z for $C_{25}H_{23}N_3O_2$ [M+H]: 398.18 LC retention time on HPLC, C18 column gradient 20-95% acetonitrile with 0.1% TFA in 4 minutes: 2.0 min.

Example 60

Preparation of 1-(6-Bromo-pyridin-2-ylmethyl)-3-(2,3-dihydro-benzo[1,4]dioxine-6-carbonyl)-7-methyl-1H-[1,8]naphthyridin-4-one

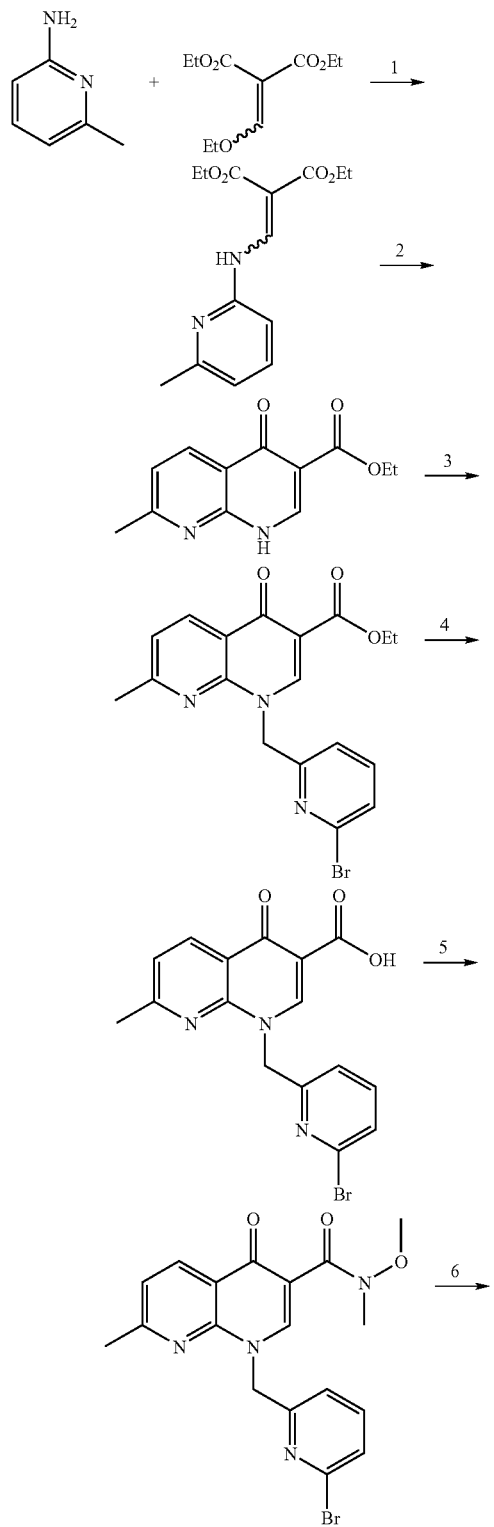

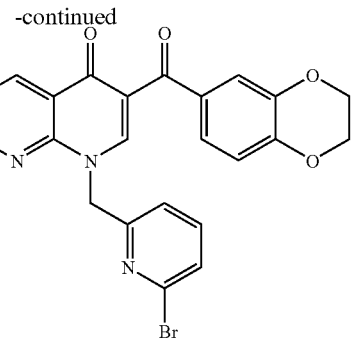

Step 1: 2-[(6-Methyl-pyridin-2-ylamino)-methylene]-malonic acid diethyl ester 20 g (92.5 mmol) of 2-ethoxymethylene-malonic acid diethyl ester and 10 g (92.5 mmol) of 2-amino-6-methylpyridine were heated neat at 110° C. for 2 h. The reaction was allowed to cool to room temperature and the product was recrystallized from dichloromethane and hexane to afford 21.8 g of 2-[(6-Methyl-pyridin-2-ylamino)-methylene]-malonic acid diethyl ester as a white solid.

Step 2: 7-Methyl-4-oxo-1,4-dihydro-[1,8]naphthyridine-3-carboxylic acid ethyl ester 21.8 g (3.61 mmol) of 2-[(6-Methyl-pyridin-2-ylamino)-methylene]-malonic acid diethyl ester was dissolved in 300 mL of diphenyl ether and the solution was heated at 250° C. After 2.5 h the solution was cooled to rt and 50 mL of hexane was added. The mixture was filtered and the solid washed with hexane to yield 18.5 g of -Methyl-4-oxo-1,4-dihydro-[1,8]naphthyridine-3-carboxylic acid ethyl ester as a brown solid.

Step 3: 1-(6-Bromo-pyridin-2-ylmethyl)-7-methyl-4-oxo-1,4-dihydro-[1,8]naphthyridine-3-carboxylic acid ethyl ester 25.6 mL of potassium hexamethyldisilazane (12.91 mmol, 0.5 M in tolene) was added to 2.5 g (10.76 mmol) of 7-Methyl-4-oxo-1,4-dihydro-[1,8]naphthyridine-3-carboxylic acid ethyl ester dissolved in 22 mL of tetrahydrofuran and was stirred at room temperature for 15 minutes. 3.24 g (12.91 mmol) of 2-Bromo-6-bromomethyl-pyridine was added and stirred at room temperature for 2.5 h. Water and ethyl acetate were added and the layers separated. The aqueous layer was extracted with ethyl acetate (3×50 mL). The combined organic layers were dried over magnesium sulfate, filtered and dried in vacuo. The crude product was purified on silica gel eluting with 50/50 ethyl acetate/hexane to yield 0.620 g of 1-(6-Bromo-pyridin-2-ylmethyl)-7-methyl-4-oxo-1,4-dihydro-[1,8]naphthyridine-3-carboxylic acid ethyl ester as a brown solid.

Step 4: 1-(6-Bromo-pyridin-2-ylmethyl)-7-methyl-4-oxo-1,4-dihydro-[1,8]naphthyridine-3-carboxylic acid 0.110 g (4.62 mmol) of lithium hydroxide was added to 0.620 g of 1-(6-Bromo-pyridin-2-ylmethyl)-7-methyl-4-oxo-1,4-dihydro-[1,8]naphthyridine-3-carboxylic acid ethyl ester dissolved in 50 mL methanol and 100 mL of water and was heated at 60° C. for 3 hours. After the reaction was cooled to room temperature 1M HCl was added until the product precipitated from solution. The white solid was collected by vacuum filtration to yield 0.400 g of 1-(6-Bromo-pyridin-2-ylmethyl)-7-methyl-4-oxo-1,4-dihydro-[1,8]naphthyridine-3-carboxylic acid as a white solid.

Step 5: 1-(6-Bromo-pyridin-2-ylmethyl)-7-methyl-4-oxo-1,4-dihydro-[1,8]naphthyridine-3-carboxylic acid methoxy-methyl-amide 0.667 mL (3.75 mmol, 50% solution in ethyl acetate) of 1-propanephosphonic anhydride solution was added to 0.400 g (1.07 mmol) of 1-(6-Bromo-pyridin-2-ylmethyl)-7-methyl-4-oxo-1,4-dihydro-[1,8]naphthyridine-3-carboxylic acid, 0.208 g (2.13 mmol) of N,O-dimethylhydroxyl amine, and 0.653 mL (3.75 mmol) of diisopropylethylamine dissolved in 1 mL of dichloromethane. After the reaction was stirred at room temperature for 1 hour water was added and was extracted with dichloromethane (3×25 mL). The combined organic layers were dried over magnesium sulfate, filtered and concentrated in vacuo. The crude product was purified on silica gel eluting with 100% ethyl acetate to yield 0.355 g of 1-(6-Bromo-pyridin-2-ylmethyl)-7-methyl-4-oxo-1,4-dihydro-[1,8]naphthyridine-3-carboxylic acid methoxy-methyl-amide as a white solid.

Step 6: 1-(6-Bromo-pyridin-2-ylmethyl)-3-(2,3-dihydro-benzo[1,4]dioxine-6-carbonyl)-7-methyl-1H-[1,8]naphthyridin-4-one 0.896 mL of 3,4-(ethylenedioxy)phenylmagnesium bromide (0.448 mmol, 0.5M in THF) was added to 85 mg (0.204 mmol) of 1-(6-Bromo-pyridin-2-ylmethyl)-7-methyl-4-oxo-1,4-dihydro-[1,8]naphthyridine-3-carboxylic acid methoxy-methyl-amide dissolved in 1 mL of THF and the reaction was stirred at room temperature for 1 hour. Saturated ammonium chloride was added and the aqueous layer was extracted with dichloromethane (3×10 mL). The combined organic layers were dried over magnesium sulfate, filtered and concentrated in vacuo. The crude product was purified by flash column chromatography using 20-100% ethyl acetate in hexane and further purified on the reverse phase HPLC with a C18 column, gradient of 20-70% acetonitrile—0.1% TFA to yield 38.2 mg of 1-(6-Bromo-pyridin-2-ylmethyl)-3-(2,3-dihydro-benzo[1,4]dioxine-6-carbonyl)-7-methyl-1H-[1,8]naphthyridin-4-one as a white solid. LC-MSD, m/z for $C_{24}H_{18}BrN_3O_4$ [M+H]: 492.05 LC retention time on HPLC, C18 column gradient 20-95% acetonitrile with 0.1% TFA in 4 minutes: 2.4 min Example 62

Preparation of 1-(6-Bromo-pyridin-2-ylmethyl)-3-(4-methoxy-3-methyl-benzoyl)-7-methyl-1H-[1,8]naphthyridin-4-one

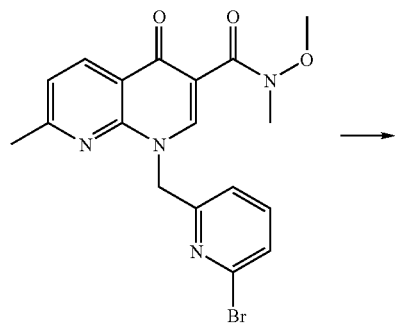

-continued

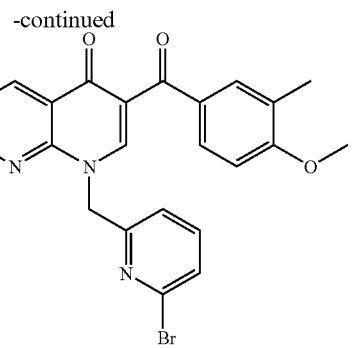

Experimental conditions analogous to those described for Step 6 of Example 60 were used with 85 mg (0.204 mmol) of 1-(6-Bromo-pyridin-2-ylmethyl)-7-methyl-4-oxo-1,4-dihydro-[1,8]naphthyridine-3-carboxylic acid methoxy-methyl-amide and 0.896 mL 0.448 mL, 0.5 M in THF) of 4-methoxy-3-methylphenylmagnesium bromide in 1 mL of THF. The crude product was purified by flash column chromatography using 20-100% ethyl acetate in hexane and further purified on the reverse phase HPLC with a C18 column, gradient of 20-70% acetonitrile—0.1% TFA to afford 27.9 mg of 1-(6-Bromo-pyridin-2-ylmethyl)-3-(4-methoxy-3-methyl-benzoyl)-7-methyl-1H-[1,8]naphthyridin-4-one as a white solid. LC-MSD, m/z for $C_{24}H_{20}BrN_3O_3$ [M+H]: 478.07 LC retention time on HPLC, C18 column gradient 20-95% acetonitrile with 0.1% TFA in 4 minutes: 2.6 min.

Example 63

Preparation of 1-(6-Bromo-pyridin-2-ylmethyl)-3-(5,6-dimethyl-pyridine-3-carbonyl)-7-methyl-1H-[1,8]naphthyridin-4-one

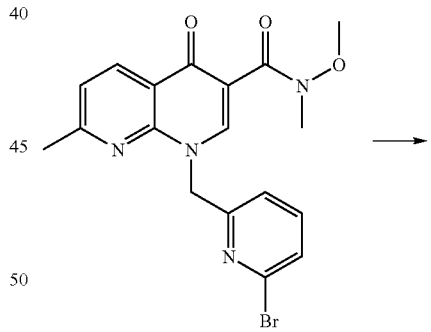

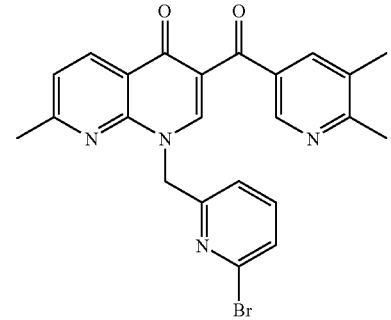

0.23 mL (0.469 mmol, 2M in THF) isopropylmagnesium chloride was added to a solution of 104.4 mg (0.448 mmol) of 5-iodo-2,3-dimethyl-pyridine in 1 mL of tetrahydrofuran. After the reaction was stirred for 40 min at room temperature 85 mg (0.204 mmol) of 1-(6-Bromo-pyridin-2-ylmethyl)-7-methyl-4-oxo-1,4-dihydro-[1,8]naphthyridine-3-carboxylic acid methoxy-methyl-amide in 0.6 mL of tetrahydrofuran was added and the reaction stirred for 1 h. Water was added and was extracted with dichloromethane (3×10 mL). The combined organic layers were dried over magnesium sulfate, filtered and dried in vacuo. The crude product was purified by flash column chromatography using 20-100% ethyl acetate in hexane to yield 37.4 mg of 1-(6-Bromo-pyridin-2-ylmethyl)-3-(5,6-dimethyl-pyridine-3-carbonyl)-7-methyl-1H-[1,8]naphthyridin-4-one. LC-MSD, m/z for $C_{23}H_{19}BrN_4O_2$ [M+H]: 463.07 LC retention time on HPLC, C18 column gradient 20-95% acetonitrile with 0.1% TFA in 4 minutes: 1.7 min

Example 64

Preparation of 1-(6-Bromo-pyridin-2-ylmethyl)-3-(3,4-dimethyl-benzoyl)-6,7-dimethyl-1H-[1,8]naphthyridin-4-one

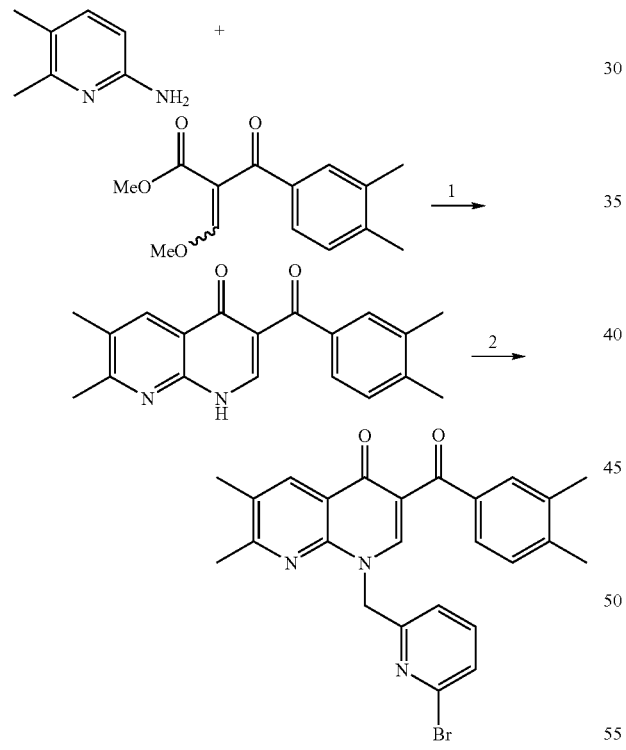

Step 1: 3-(3,4-Dimethyl-benzoyl)-6,7-dimethyl-1H-[1,8]naphthyridin-4-one

Experimental conditions analogous to those described for Step 1 of Example 1 were used with 0.50 g (2.01 mmol) 2-(3,4-Dimethyl-benzoyl)-3-methoxy-acrylic acid methyl ester, 0.25 g (2.01 mmol) of 5,6-Dimethyl-pyridin-2-ylamine, and 15 mL of diphenyl ether to yield 68.7 mg of 3-(3,4-Dimethyl-benzoyl)-6,7-dimethyl-1H-[1,8]naphthyridin-4-one as a brown solid.

Step 2: 1-(6-Bromo-pyridin-2-ylmethyl)-3-(3,4-dimethyl-benzoyl)-6,7-dimethyl-1H-[1,8]naphthyridin-4-one Experimental conditions analogous to those described for Step 2 of Example 1 were used with 69 mg (0.224 mmol) of 3-(3,4-Dimethyl-benzoyl)-6,7-dimethyl-1H-[1,8]naphthyridin-4-one, 11 mg (0.269 mmol, 60% dispersion in oil) of sodium hydride, 67.5 mg (0.269 mmol) of 2-bromo-6-bromomethyl-pyridine and 2.0 mL of N,N dimethylformamide. The crude brown solid was purified by flash column chromatography using 30-100% ethyl acetate in hexane to yield 1-(6-Bromo-pyridin-2-ylmethyl)-3-(3,4-dimethyl-benzoyl)-6,7-dimethyl-1H-[1,8]naphthyridin-4-one as an off white solid. LC-MSD, m/z for $C_{25}H_{22}BrN_3O_2$ [M+H]: 476.09 LC retention time on HPLC, C18 column gradient 20-95% acetonitrile with 0.1% TFA in 4 minutes: 2.8 min

Example 65

Preparation of 1-(6-Bromo-pyridin-2-ylmethyl)-3-(2,3-dihydro-benzo[1,4]dioxine-6-carbonyl)-6,7-dimethyl-1H-[1,8]naphthyridin-4-one

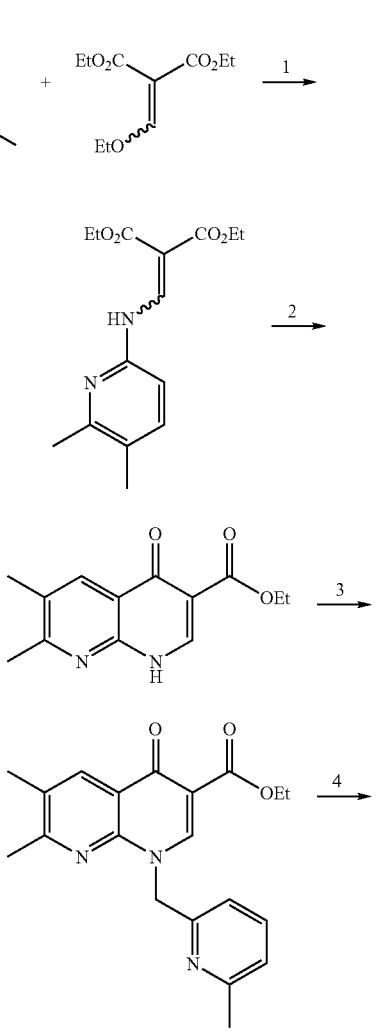

-continued

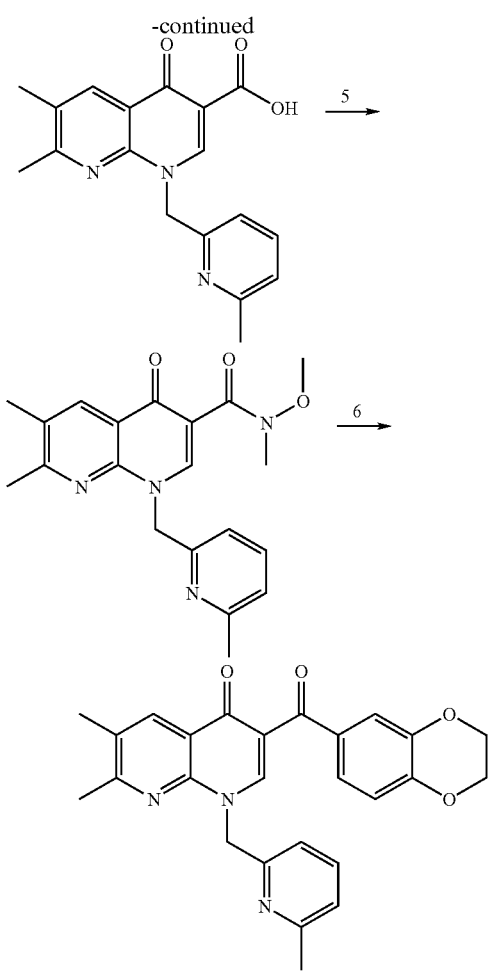

Step 1: 2-[(5,6-Dimethyl-pyridin-2-ylamino)-methylene]-malonic acid diethyl ester Experimental conditions analogous to those described for Step 1 of Example 60 were used with 5 g (40.93 mmol) of 5,6-Dimethyl-pyridin-2-ylamine and 8.2 mL (40.93 mmol) of 2-ethoxymethylene malonic acid diethyl ester to afford 10.61 g of 2-[(5,6-Dimethyl-pyridin-2-ylamino)-methylene]-malonic acid diethyl ester.

Step 2: 6,7-Dimethyl-4-oxo-1,4-dihydro-[1,8]naphthyridine-3-carboxylic acid ethyl ester Experimental conditions analogous to those described for Step 2 of Example 60 were used with 10.61 g (36.29 mmol) of 2-[(5,6-Dimethyl-pyridin-2-ylamino)-methylene]-malonic acid diethyl ester and 150 mL of diphenyl ether to yield 7.21 g of 6,7-Dimethyl-4-oxo-1,4-dihydro-[1,8]naphthyridine-3-carboxylic acid ethyl ester.

Step 3: 6,7-Dimethyl-1-(6-methyl-pyridin-2-ylmethyl)-4-oxo-1,4-dihydro-[1,8]naphthyridine-3-carboxylic acid ethyl ester Experimental conditions analogous to those described for Step 3 of Example 60 were used with 3 g (12.17 mmol) of 6,7-Dimethyl-4-oxo-1,4-dihydro-[1,8]naphthyridine-3-carboxylic acid ethyl ester, 2.49 g (13.39 mmol) of 2-Bromomethyl-6-methyl-pyridine, 0.54 g (13.39 mmol, 60% dispersion in oil), and 60 mL of N,N-dimethylformamide to give 1.61 g of 6,7-Dimethyl-1-(6-methyl-pyridin-2-ylmethyl)-4-oxo-1,4-dihydro-[1,8]naphthyridine-3-carboxylic acid ethyl ester.

Step 4: 6,7-Dimethyl-1-(6-methyl-pyridin-2-ylmethyl)-4-oxo-1,4-dihydro-[1,8]naphthyridine-3-carboxylic acid Experimental conditions analogous to those described for Step 4 of Example 60 were used with 1.60 g (4.55 mmol) of 6,7-Dimethyl-1-(6-methyl-pyridin-2-ylmethyl)-4-oxo-1,4-dihydro-[1,8]naphthyridine-3-carboxylic acid ethyl ester, 0.33 g (13.66 mmol) of lithium hydroxide, 100 mL of water and 50 mL of methanol to afford 1.26 g of 6,7-Dimethyl-1-(6-methyl-pyridin-2-ylmethyl)-4-oxo-1,4-dihydro-[1,8]naphthyridine-3-carboxylic acid.

Step 5: 6,7-Dimethyl-1-(6-methyl-pyridin-2-ylmethyl)-4-oxo-1,4-dihydro-[1,8]naphthyridine-3-carboxylic acid methoxy-methyl amide Experimental conditions analogous to those described for Step 5 of Example 60 were used with 1.26 g (3.89 mmol), 0.76 g (7.79 mmol) of N,O dimethylhydroxylamine, 2.43 mL (4.08 mmol, 50% solution in ethyl acetate), 4.10 mL (23.34 mmol) of diisopropylethylamine and 4 mL of dichloromethane to give 1.32 g of 6,7-Dimethyl-1-(6-methyl-pyridin-2-ylmethyl)-4-oxo-1,4-dihydro-[1,8]naphthyridine-3-carboxylic acid methoxy-methyl amide.

Step 6: 3-(2,3-Dihydro-benzo[1,4]dioxine-6-carbonyl)-6,7-dimethyl-1-(6-methyl-pyridin-2-ylmethyl)-1H-[1,8]naphthyridin-4-one Experimental conditions analogous to those described for Step 6 of Example 60 were used with 100 mg (0.273 mmol) of 6,7-Dimethyl-1-(6-methyl-pyridin-2-ylmethyl)-4-oxo-1,4-dihydro-[1,8]naphthyridine-3-carboxylic acid methoxy-methyl amide, 1.2 mL (0.60 mmol, 0.5M solution in tetrahydrofuran) of 3,4-(ethylenedioxy)phenylmagnesium bromide, and 1 mL of THF. The crude product was purified by flash column chromatography using 20-100% ethyl acetate in hexane and further purified on the reverse phase HPLC with a C18 column, gradient of 20-70% acetonitrile—0.1% TFA to afford 42.7 mg of 3-(2,3-Dihydro-benzo[1,4]dioxine-6-carbonyl)-6,7-dimethyl-1-(6-methyl-pyridin-2-ylmethyl)-1H-[1,8]naphthyridin-4-one. LC-MSD, m/z for $C_{26}H_{23}N_3O_4$ [M+H]: 442.17 LC retention time on HPLC, C18 column gradient 20-95% acetonitrile with 0.1% TFA in 4 minutes: 1.9 min.

Example 66

Preparation of 3-(4-Methoxy-3-methyl-benzoyl)-6,7-dimethyl-1-(6-methyl-pyridin-2-ylmethyl)-1H-[1,8]naphthyridin-4-one

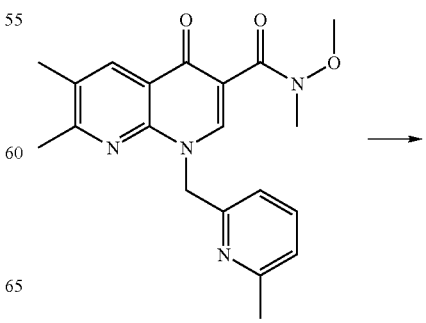

-continued

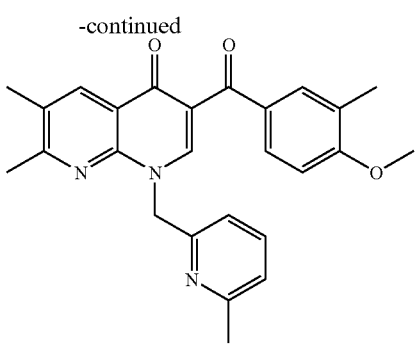

Experimental conditions analogous to those described for Step 6 of Example 60 were used with 100 mg (0.273 mmol) of 6,7-Dimethyl-1-(6-methyl-pyridin-2-ylmethyl)-4-oxo-1,4-dihydro-[1,8]naphthyridine-3-carboxylic acid methoxy-methyl amide, 1.2 mL (0.60 mmol, 0.5 M in tetrahydrofuran) of 4-methoxy-3-methylphenylmagnesium bromide and 1.2 mL of THF. The crude product was purified by flash column chromatography using 20-100% ethyl acetate in hexane and further purified on the reverse phase HPLC with a C18 column, gradient of 20-70% acetonitrile—0.1% TFA to give 40.1 mg of 3-(4-Methoxy-3-methyl-benzoyl)-6,7-dimethyl-1-(6-methyl-pyridin-2-ylmethyl)-1H-[1,8]naphthyridin-4-one. LC-MSD, m/z for $C_{26}H_{25}N_3O_3$ [M+H]: 428.19 LC retention time on HPLC, C18 column gradient 20-95% acetonitrile with 0.1% TFA in 4 minutes: 2.2 min.

Example 67

Preparation of 3-(3-Fluoro-4-methoxy-benzoyl)-6,7-dimethyl-1-(6-methyl-pyridin-2-ylmethyl)-1H-[1,8]naphthyridin-4-one

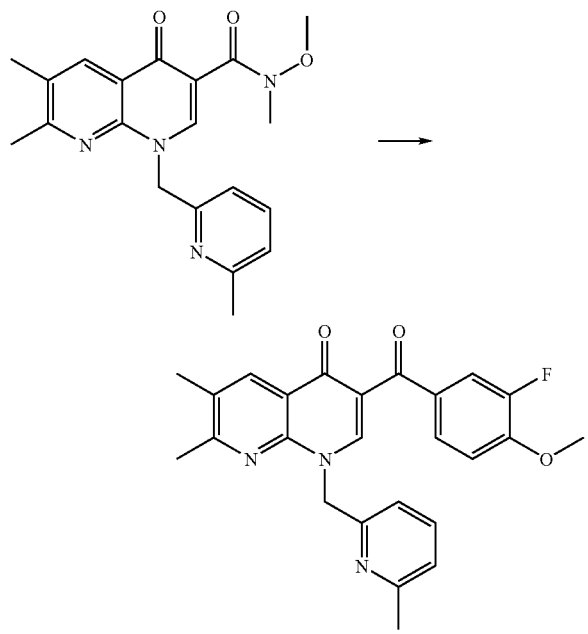

Experimental conditions analogous to those described for Step 6 of Example 60 were used with 100 mg (0.273 mmol) of 6,7-Dimethyl-1-(6-methyl-pyridin-2-ylmethyl)-4-oxo-1,4-dihydro-[1,8]naphthyridine-3-carboxylic acid methoxy-methyl amide, 1.2 mL (0.60 mmol, 0.5 M in tetrahydrofuran) of 3-fluoro-4-methoxyphenylmagnesium bromide and 1.2 mL of THF. The crude product was purified by flash column chromatography using a gradient of 20-100% ethyl acetate in hexane and further purified on the reverse phase HPLC with a C18 column, gradient of 20-70% acetonitrile—0.1% TFA to yield 58.7 mg 3-(3-Fluoro-4-methoxy-benzoyl)-6,7-dimethyl-1-(6-methyl-pyridin-2-ylmethyl)-1H-[1,8]naphthyridin-4-one. LC-MSD, m/z for $C_{25}H_{22}FN_3O_3$ [M+H]: 432.16 LC retention time on HPLC, C18 column gradient 20-95% acetonitrile with 0.1% TFA in 4 minutes: 2.1 min Example 68

Preparation of 1-(6-Bromo-pyridin-2-ylmethyl)-3-(4-methoxy-3-methyl-benzoyl)-1H-[1,5]naphthyridin-4-one

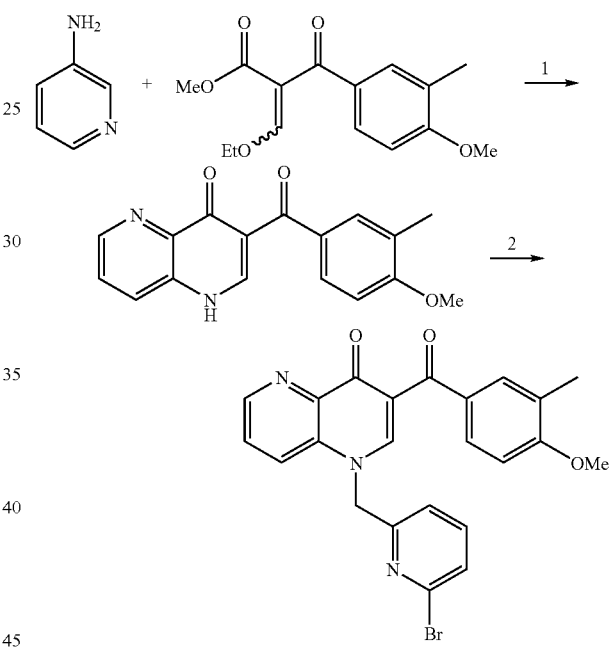

Step 1: 3-(4-Methoxy-3-methyl-benzoyl)-1H-[1,5]naphthyridin-4-one

Experimental conditions analogous to those described for Step 1 of Example 1 were used with 0.60 g (2.27 mmol) of 3-ethoxy-2-(4-methoxy-3-methyl-benzoyl)-acrylic acid methyl ester, 0.214 g (2.27 mmol) of 3-aminopyridine, and 15 mL of diphenyl ether to yield 0.435 g of 3-(4-Methoxy-3-methyl-benzoyl)-1H-[1,5]naphthyridin-4-one.

Step 2: 1-(6-Bromo-pyridin-2-ylmethyl)-3-(4-methoxy-3-methyl-benzoyl)-1H-[1,5]naphthyridin-4-one Experimental conditions analogous to those described for Step 1 of Example 2 using 75 mg (0.255 mmol) of 3-(4-Methoxy-3-methyl-benzoyl)-1H-[1,5]naphthyridin-4-one, 76.8 mg (0.306 mmol) of 2-bromo-6-bromomethyl-pyridine, 0.61 mL (0.306 mmol, 0.5 M in toluene) of potassium hexamethyldisilazane, and 2.5 mL of THF. The crude product was purified by flash column chromatography using a gradient of 20-100% ethyl acetate in hexane and further purified on the reverse phase HPLC with a C18 column, gradient of 20-70% acetonitrile—0.1% TFA to yield 20 mg of 1-(6-Bromo-pyridin-2-ylmethyl)-3-(4-methoxy-3-methyl-benzoyl)-1H-[1,5]naphthyridin-4-one. LC-MSD, m/z for C$_{23}$H$_{18}$BrN$_3$O$_3$ [M+H]: 464.05 LC retention time on HPLC, C18 column gradient 20-95% acetonitrile with 0.1% TFA in 4 minutes: 2.0 min.

Example 69

Preparation of 3-(4-Methoxy-3-methyl-benzoyl)-1-(6-methyl-pyridin-2-ylmethyl)-1H-[1,5]naphthyridin-4-one

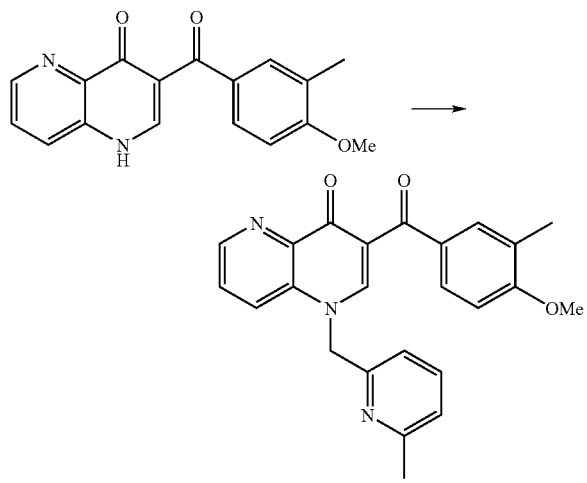

Experimental conditions analogous to those described for Step 3 of Example 1 using 75 mg (0.255 mmol) of 3-(4-Methoxy-3-methyl-benzoyl)-1H-[1,5]naphthyridin-4-one, 56.9 mg (0.306 mmol) of 2-bromomethyl-6-methyl-pyridine, 0.61 mL (0.306 mmol, 0.5 M in toluene) of potassium hexamethyldisilazane, and 2.5 mL of THF. The crude product was purified by flash column chromatography using a gradient of 20-100% ethyl acetate in hexane and further purified on the reverse phase HPLC with a C18 column, gradient of 20-70% acetonitrile—0.1% TFA to yield 38.6 mg of 3-(4-Methoxy-3-methyl-benzoyl)-1-(6-methyl-pyridin-2-ylmethyl)-1H-[1,5]naphthyridin-4-one. LC-MSD, m/z for C$_{24}$H$_{21}$N$_3$O$_3$ [M+H]: 400.16 LC retention time on HPLC, C18 column gradient 20-95% acetonitrile with 0.1% TFA in 4 minutes: 1.8 min.

Example 70

Preparation of 6-[3-(4-Methoxy-3-methyl-benzoyl)-4-oxo-4H-quinolin-1-ylmethyl]-pyridine-2-carbonitrile

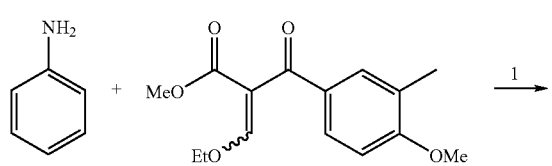

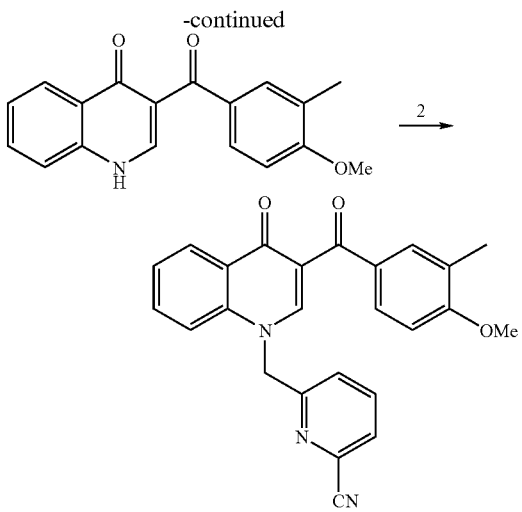

Step 1: 3-(4-Methoxy-3-methyl-benzoyl)-1H-quinolin-4-one

Experimental conditions analogous to those described for Step 1 of Example 1 were used with 1 g (3.78 mmol) of 3-ethoxy-2-(4-methoxy-3-methyl-benzoyl)-acrylic acid methyl ester, 0.214 g (3.78 mmol) of aniline, and 20 mL of diphenyl ether to yield 1.12 g of 3-(4-Methoxy-3-methyl-benzoyl)-1H-quinolin-4-one.

Step 2: 6-[3-(4-Methoxy-3-methyl-benzoyl)-4-oxo-4H-quinolin-1-ylmethyl]-pyridine-2-carbonitrile Experimental conditions analogous to those described for Step 3 of Example 1 were used with 100 mg (0.341 mmol) of 3-(4-Methoxy-3-methyl-benzoyl)-1H-quinolin-4-one, 80.6 mg (0.409 mmol) of 6-bromomethyl-pyridine-2-carbonitrile, 16.4 mg (0.409 mmol, 60% dispersion in oil), and 3.5 mL of N,N-dimethylformamide. The crude product was purified by flash column chromatography using a gradient of 20-100% ethyl acetate in hexane to yield 58 mg of 6-[3-(4-Methoxy-3-methyl-benzoyl)-4-oxo-4H-quinolin-1-ylmethyl]-pyridine-2-carbonitrile. LC-MSD, m/z for C$_{25}$H$_{19}$N$_3$O$_3$ [M+H]: 410.14 LC retention time on HPLC, C18 column gradient 20-95% acetonitrile with 0.1% TFA in 4 minutes: 2.3 min.

Example 71

Preparation of 3-(4-Methoxy-3-methyl-benzoyl)-1-(6-trifluoromethyl-pyridin-2-ylmethyl)-1H-quinolin-4-one

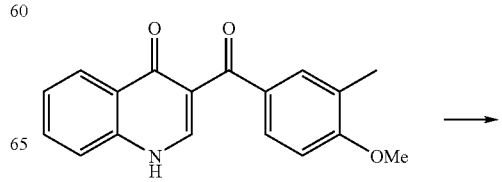

-continued

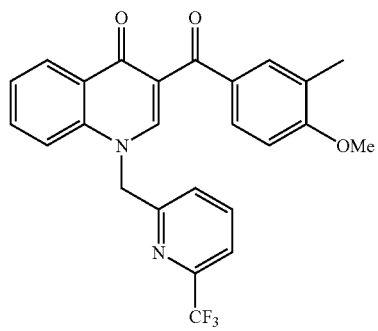

Experimental conditions analogous to those described for Step 3 of Example 1 were used with 100 mg (0.341 mmol) of 3-(4-Methoxy-3-methyl-benzoyl)-1H-quinolin-4-one, 98.2 mg (0.409 mmol) of 2-bromomethyl-6-trifluoromethyl-pyridine, 16.4 mg (0.409 mmol, 60% dispersion in oil), and 3.5 mL of N,N-dimethylformamide. The crude product was purified by flash column chromatography using a gradient of 20-100% ethyl acetate in hexane to yield 39 mg of 3-(4-Methoxy-3-methyl-benzoyl)-1-(6-trifluoromethyl-pyridin-2-ylmethyl)-1H-quinolin-4-one. LC-MSD, m/z for $C_{25}H_{19}F_3N_2O_3$ [M+H]: 453.13 LC retention time on HPLC, C18 column gradient 20-95% acetonitrile with 0.1% TFA in 4 minutes: 2.5 min.

Example 72

Preparation of 1-(6-Amino-pyridin-2-ylmethyl)-3-(4-methoxy-3-methyl-benzoyl)-1H-quinolin-4-one

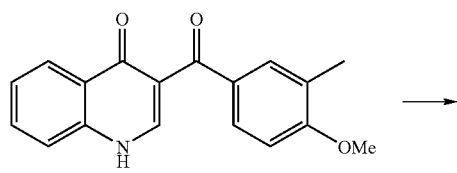

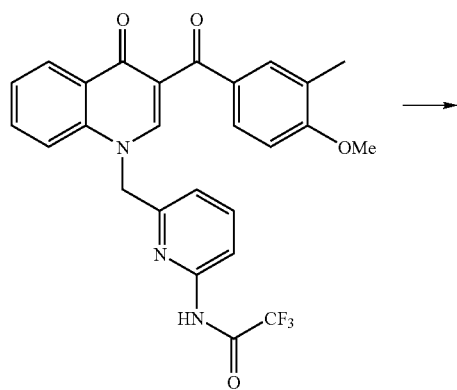

-continued

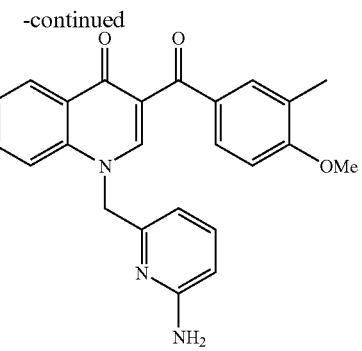

Step 1: 2,2,2-Trifluoro-N-{6-[3-(4-methoxy-3-methyl-benzoyl)-4-oxo-4H-quinolin-1-ylmethyl]-pyridin-2-yl}-acetamide Potassium hexamethyldisilazane (2.44 mL, 1.22 mmol, 0.5 M in THF) was added to a solution of 3-(4-Methoxy-3-methyl-benzoyl)-1H-quinolin-4-one (0.30 g, 1.02) in 10 mL of tetrahydrofuran. After the reaction was stirred at rt for 20 minutes, N-(6-Bromomethyl-pyridin-2-yl)-2,2,2-trifluoroacetamide (0.35 g, 0.246 mmol) was added and stirred overnight at room temperature. Water and ethyl acetate were added and the two phases were separated. The aqueous phase was extracted with ethyl acetate (3×20 mL). The combined organic layers were dried with magnesium sulfate, filtered and concentrated in vacuo. The crude brown solid was purified by reverse phase HPLC with a C18 column, gradient of 20-70% acetonitrile—0.1% TFA to yield 212 mg of 2,2,2-Trifluoro-N-{6-[3-(4-methoxy-3-methyl-benzoyl)-4-oxo-4H-quinolin-1-ylmethyl]-pyridin-2-yl}-acetamide Step 2: 1-(6-Amino-pyridin-2-ylmethyl)-3-(4-methoxy-3-methyl-benzoyl)-1H-quinolin-4-one A solution of 212 mg (0.43 mmol) 2,2,2-Trifluoro-N-{6-[3-(4-methoxy-3-methyl-benzoyl)-4-oxo-4H-quinolin-1-ylmethyl]-pyridin-2-yl}-acetamide, excess diethylamine and 5 mL of methanol were heated at 45° C. overnight. The solid was collected by filtration and purified by reverse phase HPLC with a C18 column, gradient of 20-70% acetonitrile—0.1% TFA to yield 32.4 mg of 1-(6-Amino-pyridin-2-ylmethyl)-3-(4-methoxy-3-methyl-benzoyl)-1H-quinolin-4-one. LC-MSD, m/z for $C_{24}H_{21}N_3O_3$ [M+H]: 400.16 LC retention time on HPLC, C18 column gradient 20-95% acetonitrile with 0.1% TFA in 4 minutes: 1.5 min.

Example 73

Preparation of 1-(6-Bromo-pyridin-2-ylmethyl)-3-(4-methoxy-3-methyl-benzoyl)-6-methyl-1H-[1,5]naphthyridin-4-one

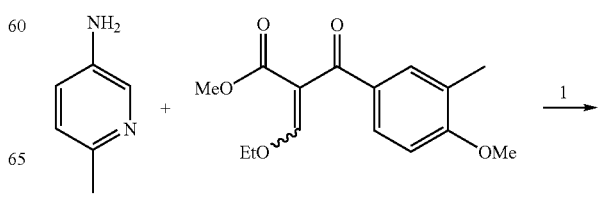

Example 74

Preparation of 3-(4-Methoxy-3-methyl-benzoyl)-6-methyl-1-(6-methyl-pyridin-2-ylmethyl)-1H-[1,5]naphthyridin-4-one

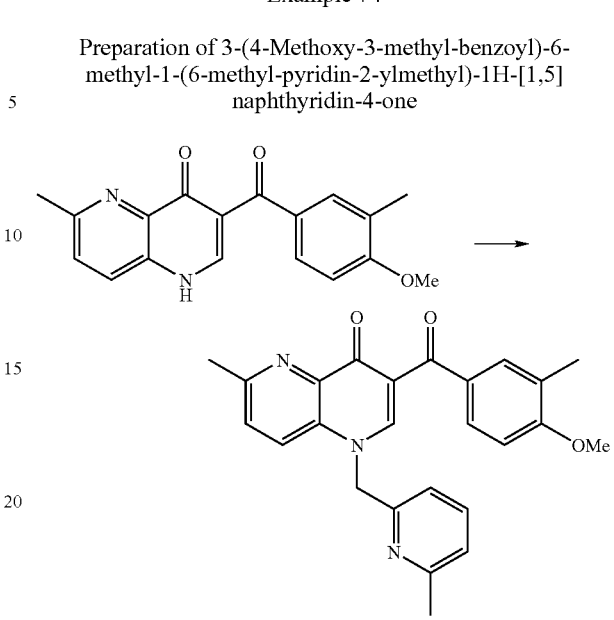

Experimental conditions analogous to those described for Step 3 of Example 1 were used with 100 mg (0.324 mmol) of 3-(4-Methoxy-3-methyl-benzoyl)-6-methyl-1H-[1,5]naphthyridin-4-one, 72.4 mg (0.389 mmol) of 2-Bromomethyl-6-methyl-pyridine, 15.6 mg (0.389 mmol, 60% dispersion in oil), and 1 mL of N,N-dimethylformamide. The crude product was purified by flash column chromatography using a gradient of 20-100% ethyl acetate in hexane and further purified on the reverse phase HPLC with a C18 column, gradient of 20-70% acetonitrile—0.1% TFA to yield 34.8 mg of 3-(4-Methoxy-3-methyl-benzoyl)-6-methyl-1-(6-methyl-pyridin-2-ylmethyl)-1H-[1,5]naphthyridin-4-one. LC-MSD, m/z for $C_{25}H_{23}N_3O_3$ [M+H]: 414.17 LC retention time on HPLC, C18 column gradient 20-95% acetonitrile with 0.1% TFA in 4 minutes: 1.8 min.

Example 75

Preparation of 1-(3-Bromo-benzyl)-3-(4-methoxy-3-methyl-benzoyl)-6-methyl-1H-[1,5]naphthyridin-4-one

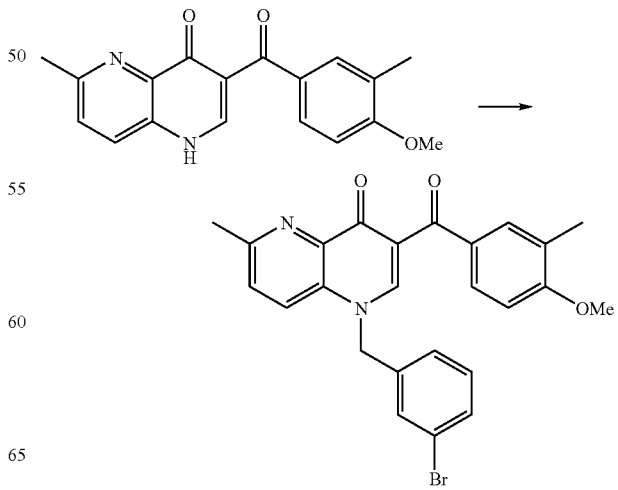

---

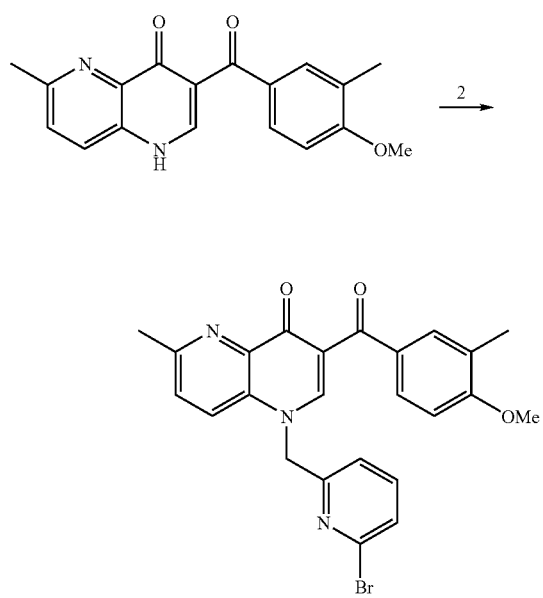

Step 1: 3-(4-Methoxy-3-methyl-benzoyl)-6-methyl-1H-[1,5]naphthyridin-4-one

Experimental conditions analogous to those described for Step 1 of Example 1 were used with 0.50 g (1.88 mmol) of 3-ethoxy-2-(4-methoxy-3-methyl-benzoyl)-acrylic acid methyl ester, 0.20 g (1.88 mmol) of 6-Methyl-pyridin-3-ylamine, and 10 mL of diphenyl ether to yield 0.33 g of 3-(4-Methoxy-3-methyl-benzoyl)-6-methyl-1H-[1,5]naphthyridin-4-one.

Step 2: 1-(6-Bromo-pyridin-2-ylmethyl)-3-(4-methoxy-3-methyl-benzoyl)-6-methyl-1H-[1,5]naphthyridin-4-one Experimental conditions analogous to those described for Step 3 of Example 1 were used with 100 mg (0.324 mmol) of 3-(4-Methoxy-3-methyl-benzoyl)-6-methyl-1H-[1,5]naphthyridin-4-one, 97.7 mg (0.389 mmol) of 2-bromo-6-bromomethyl-pyridine, 15.6 mg (0.389 mmol, 60% dispersion in oil), and 1 mL of N,N-dimethylformamide. The crude product was purified by flash column chromatography using a gradient of 20-100% ethyl acetate in hexane and further purified on the reverse phase HPLC with a C18 column, gradient of 20-70% acetonitrile—0.1% TFA to yield 52.6 mg of 1-(6-Bromo-pyridin-2-ylmethyl)-3-(4-methoxy-3-methyl-benzoyl)-6-methyl-1H-[1,5]naphthyridin-4-one. LC-MSD, m/z for $C_{24}H_{20}BrN_3O_3$ [M+H]: 478.07 LC retention time on HPLC, C18 column gradient 20-95% acetonitrile with 0.1% TFA in 4 minutes: 2.1 min Experimental conditions analogous to those described for Step 3 of Example 1 were used with 120 mg (0.390 mmol) of 3-(4-Methoxy-3-methyl-benzoyl)-6-methyl-1H-[1,5]naphthyridin-4-one, 116.8 mg (0.467 mmol) of 1-bromo-3-bromomethyl-benzene, 19 mg (0.467 mmol, 60% dispersion in oil), and 1 mL of N,N dimethylformamide. The crude product was purified by flash column chromatography using a gradient of 20-100% ethyl acetate in hexane and further purified on the reverse phase HPLC with a C18 column, gradient of 20-70% acetonitrile—0.1% TFA to yield 36.6 mg of 1-(3-Bromo-benzyl)-3-(4-methoxy-3-methyl-benzoyl)-6-methyl-1H-[1,5]naphthyridin-4-one. LC-MSD, m/z for $C_{25}H_{21}BrN_2O_3$ [M+H]: 477.07 LC retention time on HPLC, C18 column gradient 20-95% acetonitrile with 0.1% TFA in 4 minutes: 2.4 min.

Example 76

Preparation of 1-(3-Chloro-benzyl)-3-(4-methoxy-3-methyl-benzoyl)-6-methyl-1H-[1,5]naphthyridin-4-one

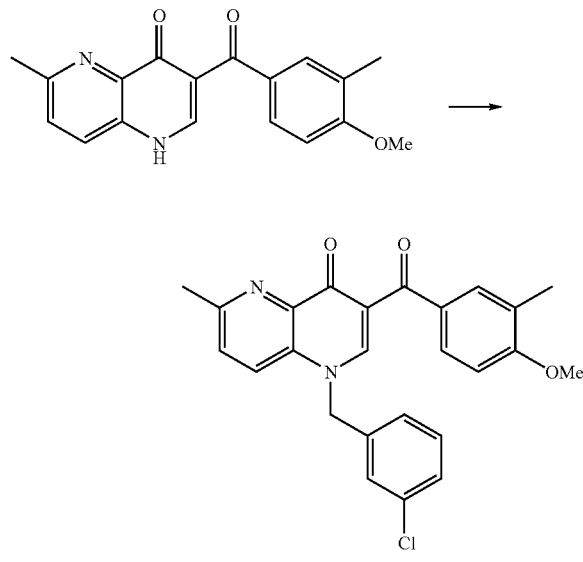

Experimental conditions analogous to those described for Step 3 of Example 1 were used with 120 mg (0.390 mmol) of 3-(4-Methoxy-3-methyl-benzoyl)-6-methyl-1H-[1,5]naphthyridin-4-one, 75.2 mg (0.467 mmol) of 3-chlorobenzyl chloride, 19 mg (0.467 mmol, 60% dispersion in oil), and 1 mL of N,N dimethylformamide. The solid was collected by filtration and was purified by flash column chromatography using a gradient of 20-100% ethyl acetate in hexane to yield 65.7 mg of 1-(3-Chloro-benzyl)-3-(4-methoxy-3-methyl-benzoyl)-6-methyl-1H-[1,5]naphthyridin-4-one. LC-MSD, m/z for $C_{25}H_{21}ClN_2O_3$ [M+H]: 433.12 LC retention time on HPLC, C18 column gradient 20-95% acetonitrile with 0.1% TFA in 4 minutes: 2.5 min.

Example 77

Preparation of 3-(3-Fluoro-4-methoxy-benzoyl)-1-(6-trifluoromethyl-pyridin-2-ylmethyl)-1H-quinolin-4-one

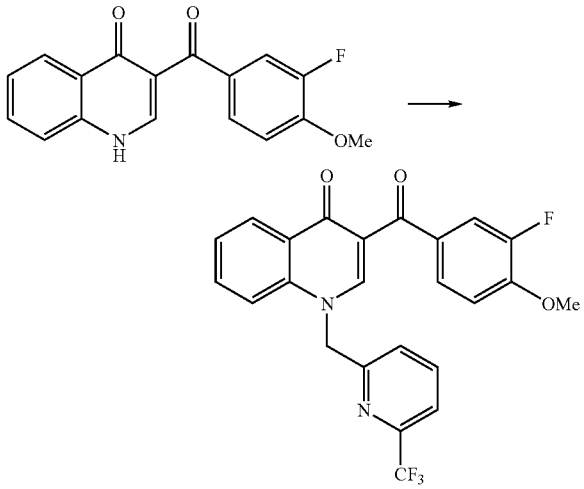

Experimental conditions analogous to those described for Step 3 of Example 1 were used with 150 mg (0.505 mmol) of 3-(3-Fluoro-4-methoxy-benzoyl)-1H-quinolin-4-one, 145.3 mg (0.605 mmol) of 2-bromomethyl-6-trifluoromethyl-pyridine, 24.2 mg (0.605 mmol, 60% dispersion in oil), and 1 mL of N,N dimethylformamide. Water was added and the solid was collected by filtration. The crude product was purified by flash column chromatography using a gradient of 20-100% ethyl acetate in hexane to yield 195.9 mg of 3-(3-Fluoro-4-methoxy-benzoyl)-1-(6-trifluoromethyl-pyridin-2-ylmethyl)-1H-quinolin-4-one. LC-MSD, m/z for $C_{24}H_{16}F_4N_2O_3$ [M+H]: 457.11 LC retention time on HPLC, C18 column gradient 20-95% acetonitrile with 0.1% TFA in 4 minutes: 2.5 min.

Example 78

Preparation of 1-(6-Bromo-pyridin-2-ylmethyl)-3-(3-fluoro-4-methoxy-benzoyl)-6-methyl-1H-[1,5]naphthyridin-4-one

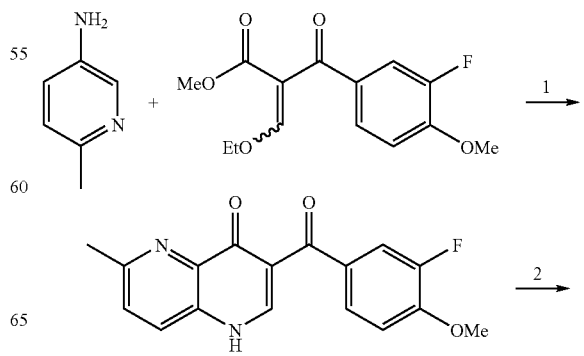

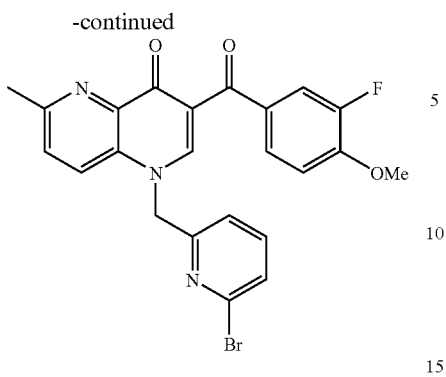
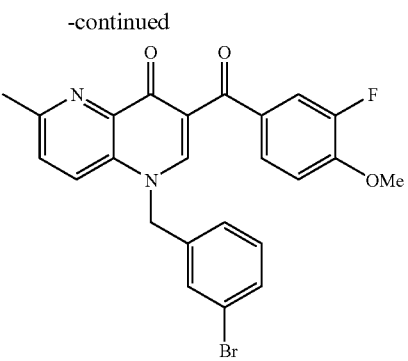

Step 1: 3-(3-Fluoro-4-methoxy-benzoyl)-6-methyl-1H-[1,5]naphthyridin-4-one

Experimental conditions analogous to those described for Step 1 of Example 1 were used with 0.50 g (1.86 mmol) of 3-Ethoxy-2-(3-fluoro-4-methoxy-benzoyl) acrylic acid methyl ester, 0.20 g (1.86 mmol) of 6-Methyl-pyridin-3-ylamine, and 15 mL of diphenyl ether to yield 0.233 g of 3-(3-Fluoro-4-methoxy-benzoyl)-6-methyl-1H-[1,5]naphthyridin-4-one.

Step 2: 1-(6-Bromo-pyridin-2-ylmethyl)-3-(3-fluoro-4-methoxy-benzoyl)-6-methyl-1H-[1,5]naphthyridin-4-one Experimental conditions analogous to those described for Step 3 of Example 1 were used with 110 mg (0.352 mmol) of 3-(3-Fluoro-4-methoxy-benzoyl)-6-methyl-1H-[1,5]naphthyridin-4-one, 106.1 mg (0.423 mmol) of 2-bromo-6-bromomethyl-pyridine, 16.9 mg (0.423 mmol, 60% dispersion in oil), and 2 mL of N,N dimethylformamide. The crude product was purified by flash column chromatography using a gradient of 20-100% ethyl acetate in hexane and further purified on the reverse phase HPLC with a C18 column, gradient of 20-70% acetonitrile—0.1% TFA to yield 1-(6-Bromo-pyridin-2-ylmethyl)-3-(3-fluoro-4-methoxy-benzoyl)-6-methyl-1H-[1,5]naphthyridin-4-one. LC-MSD, m/z for $C_{23}H_{17}BrFN_3O_3$ [M+H]: 482.04 LC retention time on HPLC, C18 column gradient 20-95% acetonitrile with 0.1% TFA in 4 minutes: 2.6 min.

Example 79

Preparation of 1-(3-Bromo-benzyl)-3-(3-fluoro-4-methoxy-benzoyl)-6-methyl-1H-[1,5]naphthyridin-4-one

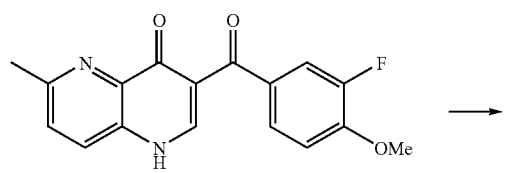

Experimental conditions analogous to those described for Step 3 of Example 1 were used with 112 mg (0.358 mmol) of 3-(3-Fluoro-4-methoxy-benzoyl)-6-methyl-1H-[1,5]naphthyridin-4-one, 107.5 mg (0.430 mmol) of 3-bromobenzyl bromide, 17.2 mg (0.430 mmol, 60% dispersion in oil), and 2 mL of N,N-dimethylformamide. The crude product was purified on the reverse phase HPLC with a C18 column, gradient of 20-70% acetonitrile—0.1% TFA to yield 67 mg of 1-(3-Bromo-benzyl)-3-(3-fluoro-4-methoxy-benzoyl)-6-methyl-1H-[1,5]naphthyridin-4-one. LC-MSD, m/z for $C_{24}H_{18}BrFN_2O_3$ [M+H]: 481.05. LC retention time on HPLC, C18 column gradient 20-95% acetonitrile with 0.1% TFA in 4 minutes: 2.7 min

Example 80

Preparation of 1-(6-Bromo-pyridin-2-ylmethyl)-3-(3-fluoro-4-methoxy-benzoyl)-1H-[1,5]naphthyridin-4-one

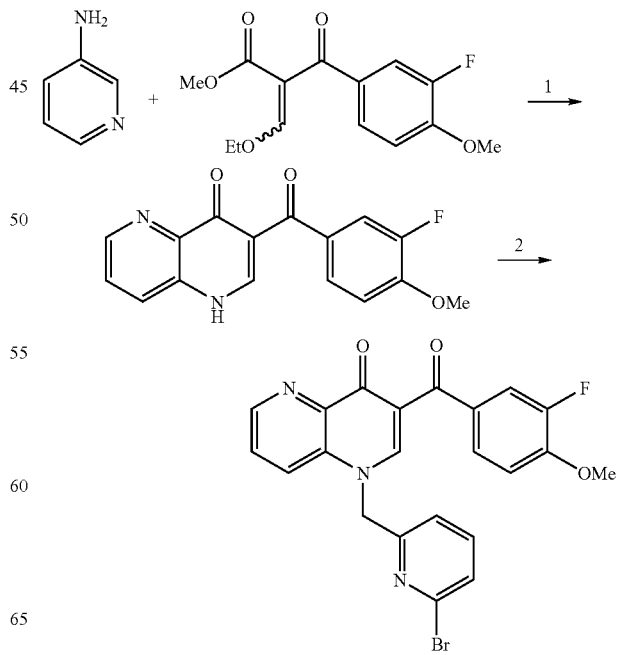

Step 1: 3-(3-Fluoro-4-methoxy-benzoyl)-1H-[1,5]naphthyridin-4-one

Experimental conditions analogous to those described for Step 1 of Example 1 were used with 0.70 g (2.61 mmol) of 3-Ethoxy-2-(3-fluoro-4-methoxy-benzoyl)acrylic acid methyl ester, 0.25 g (2.61 mmol) of 3-aminopyridine, and 15 mL of diphenyl ether to yield 3-(3-Fluoro-4-methoxy-benzoyl)-6-methyl-1H-[1,5]naphthyridin-4-one.

Step 2: 1-(6-Bromo-pyridin-2-ylmethyl)-3-(3-fluoro-4-methoxy-benzoyl)-1H-[1,5]naphthyridin-4-one Experimental conditions analogous to those described for Step 3 of Example 1 were used with 120 mg (0.402 mmol) of 3-(3-Fluoro-4-methoxy-benzoyl)-1H-[1,5]naphthyridin-4-one, 121.1 mg (0.483 mmol) of 2-bromo-6-bromomethyl-pyridine, 19.3 mg (0.483 mmol, 60% dispersion in oil), and 2 mL of N,N dimethylformamide. The crude product was purified by flash column chromatography using a gradient of 20-100% ethyl acetate in hexane and further purified on the reverse phase HPLC with a C18 column, gradient of 20-70% acetonitrile—0.1% TFA to yield 1-(6-Bromo-pyridin-2-ylmethyl)-3-(3-fluoro-4-methoxy-benzoyl)-6-methyl-1H-[1,5]naphthyridin-4-one. LC-MSD, m/z for $C_{22}H_{15}BrFN_3O_3$ [M+H]: 468.03.

Example 81

Preparation of 1-(3-Bromo-benzyl)-3-(3-fluoro-4-methoxy-benzoyl)-1H-[1,5]naphthyridin-4-one

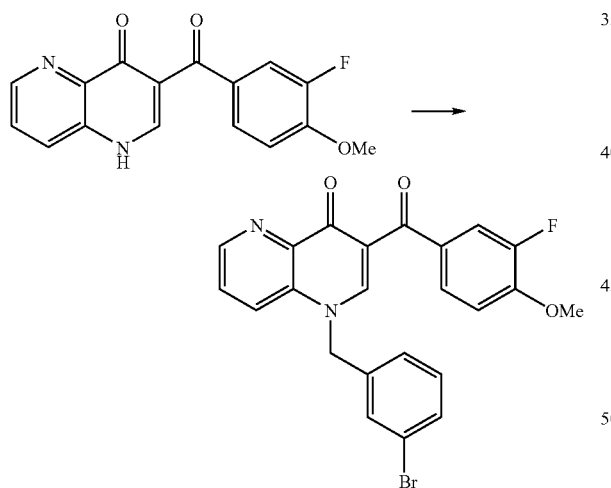

Experimental conditions analogous to those described for Step 3 of Example 1 were used with 120 mg (0.402 mmol) of 3-(3-Fluoro-4-methoxy-benzoyl)-1H-[1,5]naphthyridin-4-one, 120.7 mg (0.483 mmol) of 3-bromobenzyl bromide, 19.3 mg (0.483 mmol, 60% dispersion in oil), and 2 mL of N,N dimethylformamide. The crude product was purified by flash column chromatography using a gradient of 20-100% ethyl acetate in hexane and further purified on the reverse phase HPLC with a C18 column, gradient of 20-70% acetonitrile—0.1% TFA to yield 1-(6-Bromo-pyridin-2-ylmethyl)-3-(3-fluoro-4-methoxy-benzoyl)-6-methyl-1H-[1,5]naphthyridin-4-one. LC-MSD, m/z for $C_{23}H_{16}BrFN_2O_3$ [M+H]: 467.03.

Example 82

Preparation of 1-(3-Bromo-benzyl)-3-(5-methyl-pyridine-2-carbonyl)-1H-quinolin-4-one

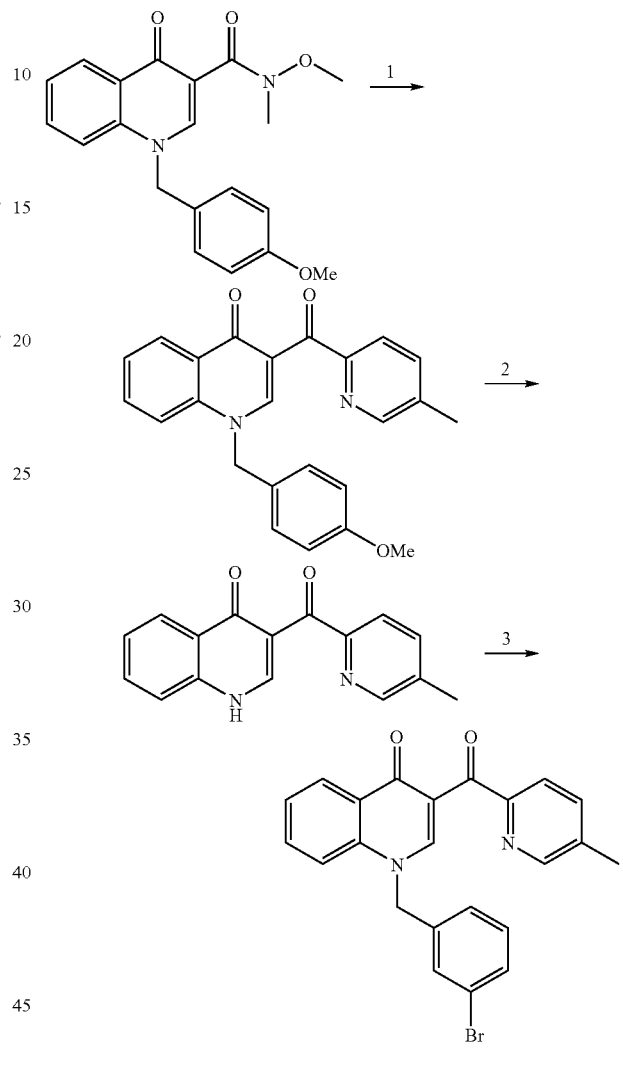

Step 1: 1-(4-Methoxy-benzyl)-3-(5-methyl-pyridine-2-carbonyl)-1H-quinolin-4-one Experimental conditions analogous to those described for Step 6 of Example 60 with 0.82 mg (2.33 mmol), 20.5 mL (5.12 mmol, 0.25 M in tetrahydrofuran) of 2-methyl-2-pyridylmagnesium bromide, and 10 mL of tetrahydrofuran. The crude product was purified by flash column chromatography using a gradient of 70:30 ethyl acetate/methanol to obtain 0.381 g of 1-(4-Methoxy-benzyl)-3-(5-methyl-pyridine-2-carbonyl)-1H-quinolin-4-one.

Step 2: 3-(5-Methyl-pyridine-2-carbonyl)-1H-quinolin-4-one

A 4M solution of hydrochloric acid in dioxane (4 mL) was added to 381 mg (0.991 mmol) of 1-(4-Methoxy-benzyl)-3-(5-methyl-pyridine-2-carbonyl)-1H-quinolin-4-one and was heated in a pressure tube at 120° C. for 18 h. The reaction was concentrated and saturated sodium bicarbonate was added and the aqueous phase was extracted with dichloromethane (3×20 mL). The crude product was purified by flash column chromatography using a gradient of 70:30 ethyl acetate/methanol to afford 68.4 mg of 3-(5-Methyl-pyridine-2-carbonyl)-1H-quinolin-4-one.

Step 3: 1-(3-Bromo-benzyl)-3-(5-methyl-pyridine-2-carbonyl)-1H-quinolin-4-one

Experimental conditions analogous to those described for Example 1 step 3 were used with 68 mg (0.257 mmol) of 3-(5-Methyl-pyridine-2-carbonyl)-1H-quinolin-4-one, 77.2 mg (0.309 mmol) of 3-bromobenzyl bromide, 12.4 mg (0.309 mmol, 60% dispersion in oil), and 1 mL of DMF. The crude product was purified by reverse phase HPLC with a C18 column, gradient of 20-70% acetonitrile—0.1% TFA to yield 39.1 mg of 1-(3-Bromo-benzyl)-3-(5-methyl-pyridine-2-carbonyl)-1H-quinolin-4-one as a white solid. LC-MSD, m/z for $C_{23}H_{17}BrN_2O_2$ [M+H]: 433.05 LC retention time on HPLC, C18 column gradient 20-95% acetonitrile with 0.1% TFA in 4 minutes: 2.5 min.

Example 83

Preparation of 3-(5-Methyl-pyridine-2-carbonyl)-1-(6-methyl-pyridin-2-ylmethyl)-1H-quinolin-4-one

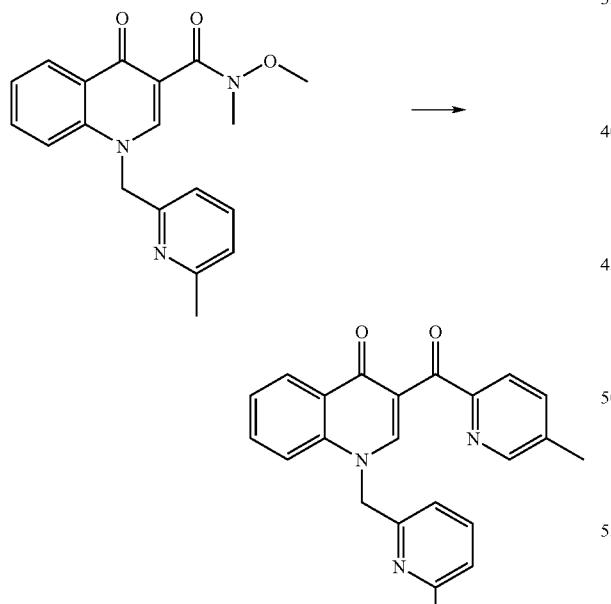

Experimental conditions analogous to those described for Step 6 of Example 60 with 200 mg (0.593 mmol) of 1-(6-Methyl-pyridin-2-ylmethyl)-4-oxo-1,4-dihydro-quinoline-3-carboxylic acid methoxy-methyl amide, 5.2 mL (1.30 mmol, 0.25 M in tetrahydrofuran) of 5-methyl-2-pyridylmagnesium bromide, and 2.6 mL of tetrahydrofuran. The crude product was purified by flash column chromatography using a gradient of 20-100% ethyl acetate in hexane and further purified on the reverse phase HPLC with a C18 column, gradient of 20-70% acetonitrile—0.1% TFA to yield 77.6 mg of 3-(5-Methyl-pyridine-2-carbonyl)-1-(6-methyl-pyridin-2-ylmethyl)-1H-quinolin-4-one. LC-MSD, m/z for $C_{23}H_{19}N_3O_2$ [M+H]: 370.15 LC retention time on HPLC, C18 column gradient 20-95% acetonitrile with 0.1% TFA in 4 minutes: 0.91 min.

Example 84

Preparation of 1-(6-Bromo-pyridin-2-ylmethyl)-3-(5,6-dimethyl-pyridine-3-carbonyl)-1H-quinolin-4-one

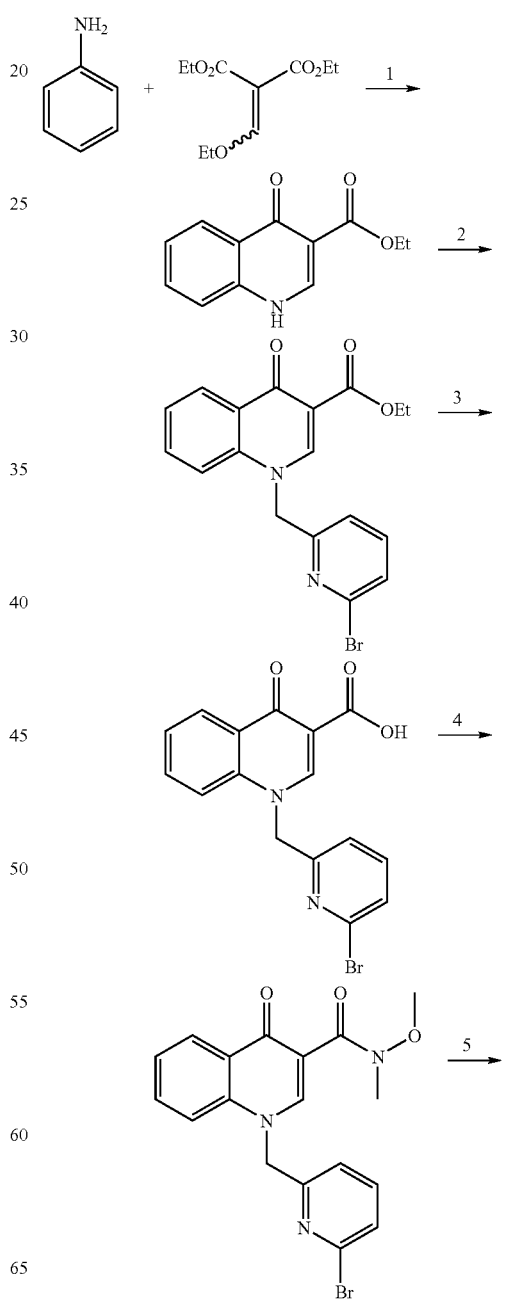

-continued

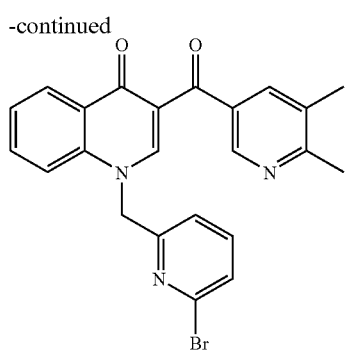

Step 1: 4-Oxo-1,4-dihydro-quinoline-3-carboxylic acid ethyl ester 31.7 g (147 mmol) of 2-Ethoxymethylene-malonic acid diethyl ester and 13.7 g (147 mmol) of aniline were stirred neat at 110° C. for 1 h, then 300 mL of diphenyl ether was added and the temperature of the oil bath was raised to 260° C. for 2 h. The solution was then cooled down to rt, diluted with 600 mL of hexanes and filtered. The solids were washed with 200 mL of hexanes and dried to yield 23.7 g of the product as a light brown powder. LC-MSD, m/z for $C_{12}H_{11}NO_3$ [M+H]+=218.2, HPLC retention time: 2.5 min.

Step 2: 1-(6-Bromo-pyridin-2-ylmethyl)-4-oxo-1,4-dihydro-quinoline-3-carboxylic acid ethyl ester 8.75 g (40.3 mmol) of 4-oxo-1,4-dihydro-quinoline-3-carboxylic acid ethyl ester was dissolved/suspended in 100 mL DMF followed by the addition of 1.93 g (48.3 mmol) of 60% sodium hydride. After the bubbling has ceased 12.1 g (48.3 mmol) of 2-bromo-6-bromomethyl-pyridine was added and the solution was stirred at r.t. overnight. The reaction was quenched using 900 mL of water, filtered and washed with 200 mL of water. The solid was further washed with 100 mL DCM. The DCM washes were evaporated and chromatographed on silica using 0-30% methanol in DCM. The purified compound was combined with the washed solid to give 14.9 g of the product as an off-white solid.

Step 3: 1-(6-Bromo-pyridin-2-ylmethyl)-4-oxo-1,4-dihydro-quinoline-3-carboxylic acid 14.9 g (38.5 mmol) of 1-(6-bromo-pyridin-2-ylmethyl)-4-oxo-1,4-dihydro-quinoline-3-carboxylic acid ethyl ester was dissolved/suspended in 300 mL of a 1:1 methanol-water mixture. 1.11 g (46.2 mmol) of lithium hydroxide was added and the mixture was heated up to 65° C. and stirred overnight. The mixture was cooled down to r.t., 300 mL of methanol and 4 mL of concentrated aqueous HCl were added and the solids were filtered off. The solids were then dissolved/suspended in 300 mL ethanol, brought to reflux, cooled down to rt, filtered, washed with 50 mL diethyl ether and dried to yield 9.5 g of the product as a white solid.

Step 4: 1-(6-Bromo-pyridin-2-ylmethyl)-4-oxo-1,4-dihydro-quinoline-3-carboxylic acid methoxy-methyl-amide 9.45 g (26.3 mmol) of 1-(6-bromo-pyridin-2-ylmethyl)-4-oxo-1,4-dihydro-quinoline-3-carboxylic acid, 2.82 g (28.9 mmol) of N,O-dimethylhydroxylamine hydrochloride, 22 mL (16 g, 158 mmol) of triethylamine and 18.8 mL (20.1 g, 31.6 mmol) of 50% 1-propanephosphonic acid cyclic anhydride were sequentially added to 250 mL acetonitrile at rt. After 1 h 400 mL of water were added and the mixture was extracted two times with 300 mL DCM. Combined organic layers were evaporated and the residue purified on silica flash column using 0-15% methanol in EtOAc to give 9.62 g of the product as an off-white solid.

Step 5: 1-(6-Bromo-pyridin-2-ylmethyl)-3-(5,6-dimethyl-pyridine-3-carbonyl)-1H-quinolin-4-one Prepared from 402 mg (1.0 mmol) of 1-(6-bromo-pyridin-2-ylmethyl)-4-oxo-1,4-dihydro-quinoline-3-carboxylic acid methoxy-methyl-amide in 3 mL THF and 513 mg (2.2 mmol) of 5-iodo-2,3-dimethyl-pyridine in 5 mL THF with 1.15 mL 2M isopropylmagnesium chloride. Yield: 296 mg of a white powder. LC-MSD, m/z for $C_{23}H_{18}BrN_3O_2$ [M+H]+=448.0, 450.0; HPLC retention time: 1.9 min.

Example 85

Preparation of 1-(6-Bromo-pyridin-2-ylmethyl)-3-(5,6,7,8-tetrahydro-quinoline-2-carbonyl)-1H-quinolin-4-one

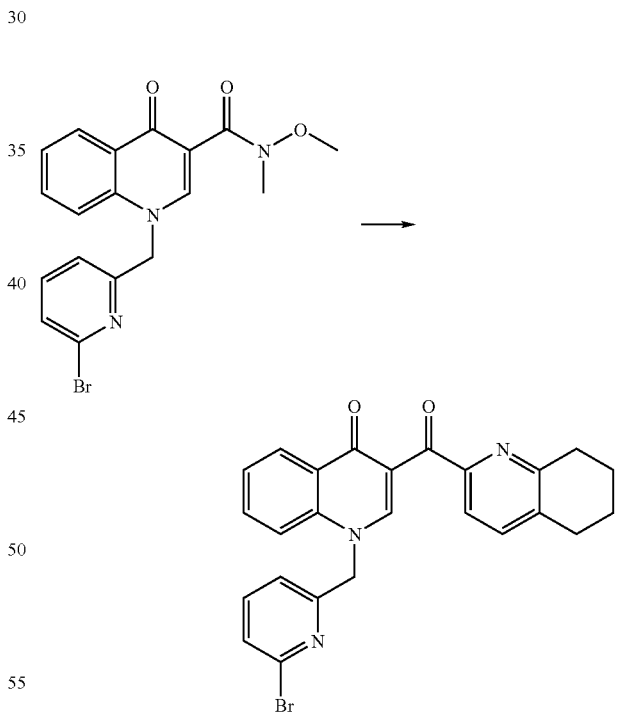

Experimental conditions analogous to those described for Step 6 of Example 60 from 327 mg (0.81 mmol) of 1-(6-bromo-pyridin-2-ylmethyl)-4-oxo-1,4-dihydro-quinoline-3-carboxylic acid methoxy-methyl-amide in 4 mL THF and 527 mg (2.03 mmol) of 2-iodo-5,6,7,8-tetrahydro-quinoline in 2 mL THF with 1.01 mL 2M isopropylmagnesium chloride. Yield: 28 mg of a white powder. LC-MSD, m/z for $C_{25}H_{20}BrN_3O_2$ [M+H]+=474.0, 476.0; HPLC retention time: 2.5 min.

Example 86

Preparation of 1-(6-Bromo-pyridin-2-ylmethyl)-3-(4,5-dimethyl-pyridine-2-carbonyl)-1H-quinolin-4-one

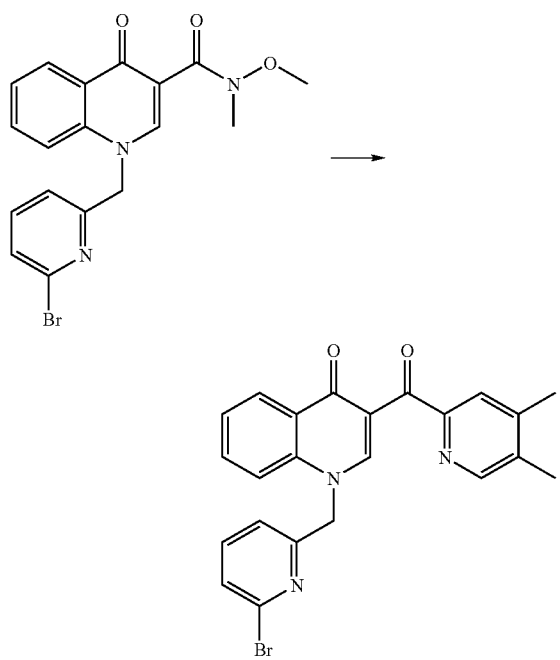

Experimental conditions analogous to those described for Step 6 of Example 60 from 86 mg (0.21 mmol) of 1-(6-bromo-pyridin-2-ylmethyl)-4-oxo-1,4-dihydro-quinoline-3-carboxylic acid methoxy-methyl-amide in 1 mL THF and 125 mg (0.54 mmol) of 2-iodo-4,5-dimethyl-pyridine in 1 mL THF with 0.28 mL 2M isopropylmagnesium chloride using. Yield: 21 mg of a white powder. LC-MSD, m/z for $C_{23}H_{18}BrN_3O_2$ [M+H]+=448.0, 450.0; HPLC retention time: 2.2 min.

Example 87

Preparation of 1-(6-Bromo-pyridin-2-ylmethyl)-3-(3-dimethylamino-benzoyl)-1H-quinolin-4-one

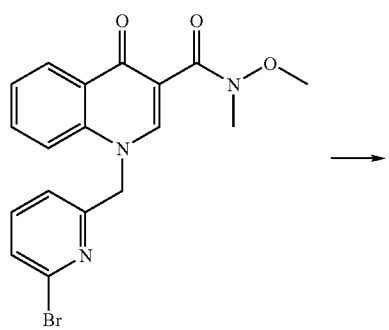

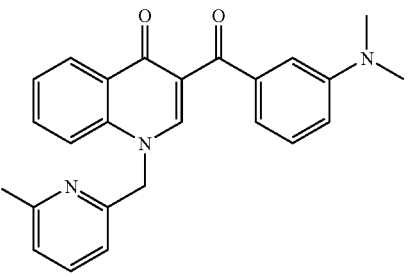

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 1.3 mL 0.5M 3-N,N-dimethylanilinemagnesium bromide. Yield: 97 mg of a yellow solid. LC-MSD, m/z for $C_{24}H_{20}BrN_3O_2$ [M+H]+=462.0, 464.0; HPLC retention time: 2.2 min.

Example 88

Preparation of 1-(6-Bromo-pyridin-2-ylmethyl)-3-(4-methoxy-3-methyl-benzoyl)-1H-quinolin-4-one Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 1.3 mL 0.5M 4-methoxy-3-methylphenylmagnesium bromide. Yield: 102 mg of a white solid. LC-MSD, m/z for $C_{24}H_{19}BrN_2O_3$ [M+H]+=463.0, 465.0; HPLC retention time: 2.5 min.

Example 89

Preparation of 1-(6-Bromo-pyridin-2-ylmethyl)-3-(3,4-dichloro-benzoyl)-1H-quinolin-4-one

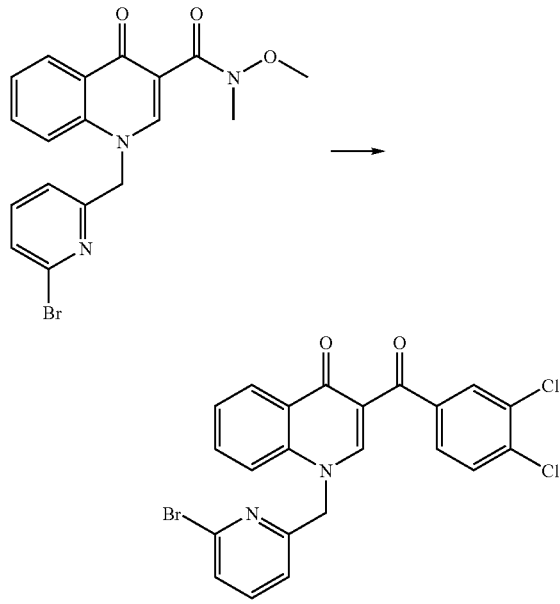

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 3,4-dichlorophenylmagnesium bromide. Yield: 64 mg of a white solid. LC-MSD, m/z for $C_{22}H_{13}BrCl_2N_2O_2$ [M+H]+=487.0, 489.0, 491.0; HPLC retention time: 2.9 min.

Example 90

Preparation of 1-(6-Bromo-pyridin-2-ylmethyl)-3-(2,4-dimethyl-benzoyl)-1H-quinolin-4-one

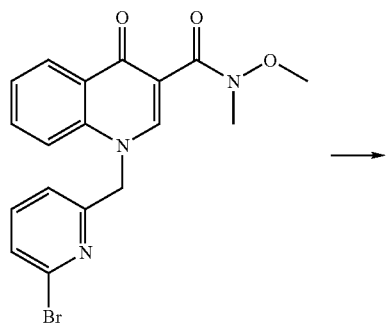

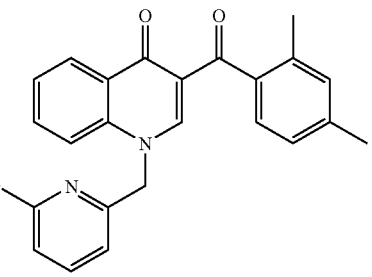

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 2,4-dimethylphenylmagnesium bromide. Yield: 57 mg of a white solid. LC-MSD, m/z for $C_{24}H_{19}BrN_2O_2$ [M+H]+=447.0, 449.0; HPLC retention time: 2.7 min.

Example 91

Preparation of 1-(6-Bromo-pyridin-2-ylmethyl)-3-(2,5-dimethyl-benzoyl)-1H-quinolin-4-one

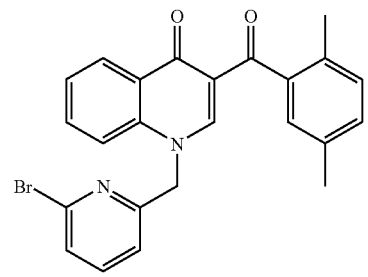

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 2,5-dimethylphenylmagnesium bromide. Yield: 57 mg of a white solid. LC-MSD, m/z for $C_{24}H_{19}BrN_2O_2$ [M+H]+=447.0, 449.0; HPLC retention time: 2.7 min.

Example 92

Preparation of 1-(6-Bromo-pyridin-2-ylmethyl)-3-(2,3-dimethyl-benzoyl)-1H-quinolin-4-one

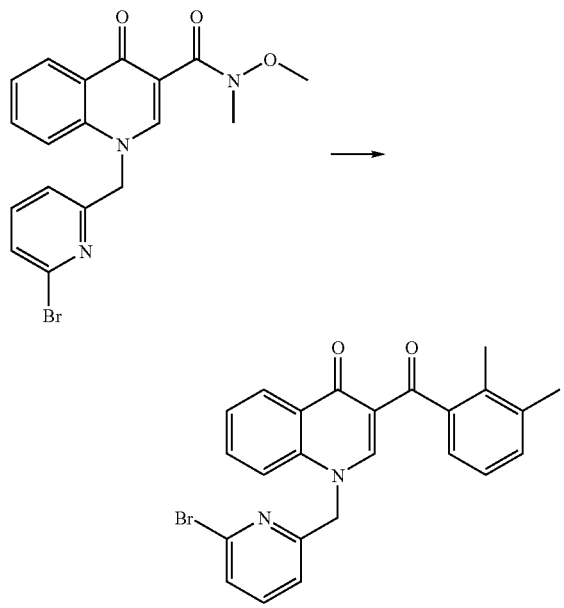

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 2,3-dimethylphenylmagnesium bromide. Yield: 54 mg of a white solid. LC-MSD, m/z for $C_{24}H_{19}BrN_2O_2$ [M+H]+=447.0, 449.0; HPLC retention time: 2.6 min.

Example 93

Preparation of 1-(6-Bromo-pyridin-2-ylmethyl)-3-(3,5-dimethyl-benzoyl)-1H-quinolin-4-one

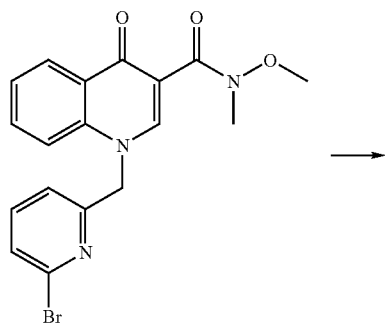

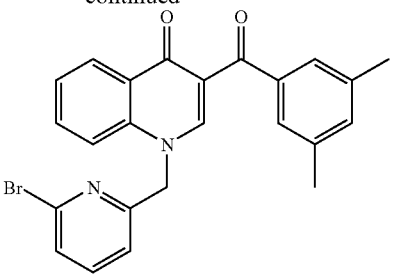

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 3,5-dimethylphenylmagnesium bromide. Yield: 66 mg of a white solid. LC-MSD, m/z for $C_{24}H_{19}BrN_2O_2$ [M+H]+=447.0, 449.0; HPLC retention time: 2.7 min.

Example 94

Preparation of 1-(6-Bromo-pyridin-2-ylmethyl)-3-(2,3-dihydro-benzo[1,4]dioxine-6-carbonyl)-1H-quinolin-4-one Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 3,4-(ethylenedioxy)phenylmagnesium bromide. Yield: 77 mg of a white solid. LC-MSD, m/z for $C_{24}H_{17}BrN_2O_4$ [M+H]+=477.0, 479.0; HPLC retention time: 2.4 min.

Example 95

Preparation of 1-(6-Bromo-pyridin-2-ylmethyl)-3-(4-tert-butyl-benzoyl)-1H-quinolin-4-one

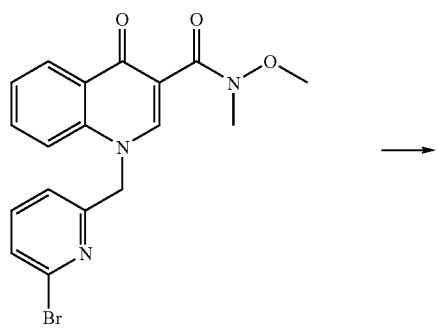

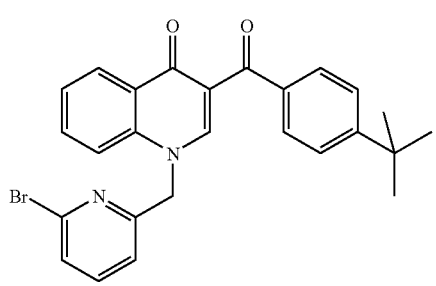

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.25 mL 2M 4-tert-butylphenylmagnesium bromide. Yield: 80 mg of a white solid. LC-MSD, m/z for $C_{26}H_{23}BrN_2O_2$ [M+H]+=475.0, 477.0; HPLC retention time: 2.9 min.

Example 96

Preparation of 1-(6-Bromo-pyridin-2-ylmethyl)-3-(4-ethyl-benzoyl)-1H-quinolin-4-one

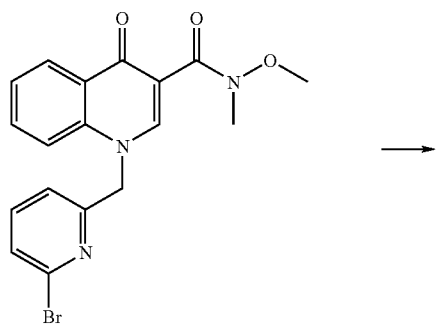

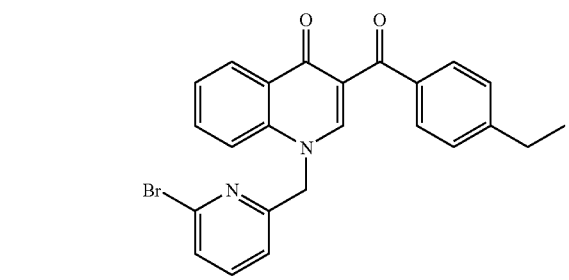

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 4-ethylphenylmagnesium bromide. Yield: 80 mg of a white solid. LC-MSD, m/z for $C_{24}H_{19}BrN_2O_2$ [M+H]+=447.0, 449.0; HPLC retention time: 2.7 min.

Example 97

Preparation of 1-(6-Bromo-pyridin-2-ylmethyl)-3-(4-dimethylamino-benzoyl)-1H-quinolin-4-one

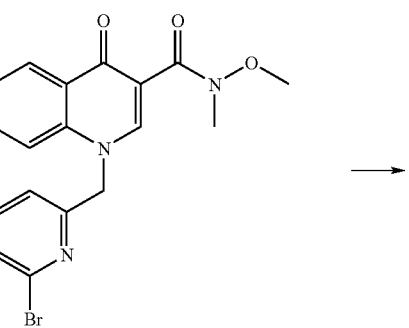

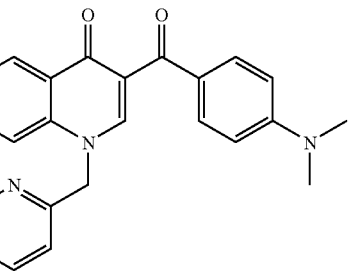

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 4-N,N-dimethylanilinemagnesium bromide. Yield: 52 mg of a yellow solid. LC-MSD, m/z for $C_{24}H_{20}BrN_3O_2$ [M+H]+=462.0, 464.0; HPLC retention time: 2.6 min.

Example 98

Preparation of 1-(6-Bromo-pyridin-2-ylmethyl)-3-(2-methyl-benzoyl)-1H-quinolin-4-one

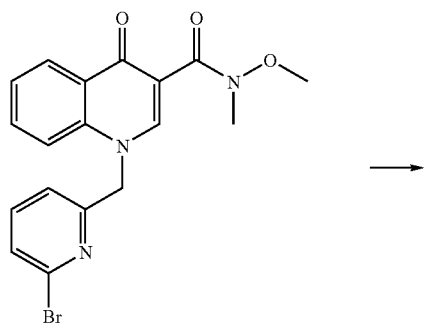

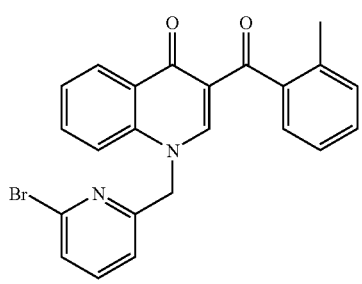

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.49 mL 1M 4-ethylphenylmagnesium bromide. Yield: 55 mg of a white solid. LC-MSD, m/z for $C_{23}H_{17}BrN_2O_2$ [M+H]+=433.0, 435.0; HPLC retention time: 2.5 min.

Example 99

Preparation of 1-(6-Bromo-pyridin-2-ylmethyl)-3-(4-ethoxy-3-methyl-benzoyl)-1H-quinolin-4-one

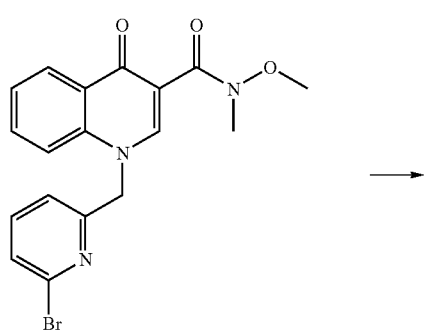

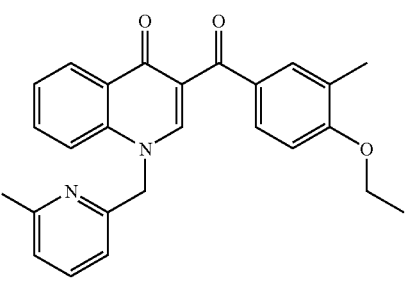

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 172 mg (0.66 mmol) of 1-ethoxy-4-iodo-2-methyl-benzene in 1 mL THF with 0.34 mL 2M isopropylmagnesium chloride. Yield: 53 mg of a white powder. LC-MSD, m/z for $C_{25}H_{21}BrN_2O_3$ [M+H]+=477.0, 479.0; HPLC retention time: 2.6 min.

Example 100

Preparation of 1-(6-Bromo-pyridin-2-ylmethyl)-3-[4-(2-methoxy-ethoxy)-3-methyl-benzoyl]-1H-quinolin-4-one

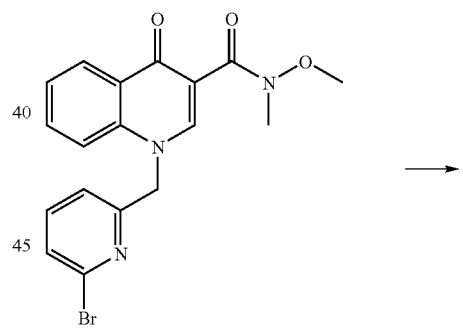

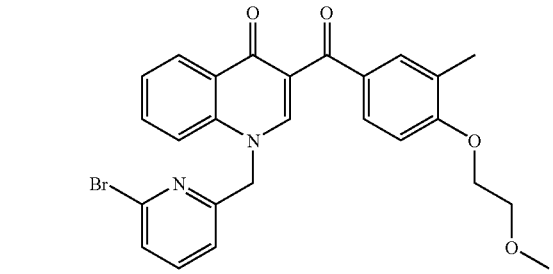

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 2 mL THF and 192 mg (0.66 mmol) of 4-iodo-1-(2-methoxy-ethoxy)-2-methyl-benzene in 2 mL THF with 0.34 mL 2M isopropylmagnesium chloride. Yield: 39 mg of a white powder. LC-MSD, m/z for C$_{26}$H$_{23}$BrN$_2$O$_4$ [M+H]+=507.0, 509.0; HPLC retention time: 2.5 min.

Example 101

Preparation of 1-(6-Bromo-pyridin-2-ylmethyl)-3-(5-bromo-pyrimidine-2-carbonyl)-1H-quinolin-4-one

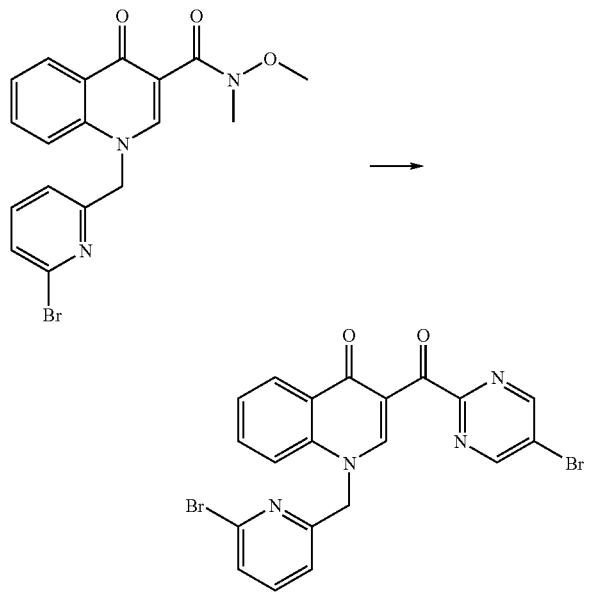

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 187 mg (0.66 mmol) of 5-bromo-2-iodo-pyrimidine in 2 mL THF with 0.34 mL 2M isopropylmagnesium chloride. Yield: 31 mg of a white powder. LC-MSD, m/z for C$_{20}$H$_{12}$Br$_2$N$_4$O$_2$ [M+H]+=498.9, 500.9, 502.9; HPLC retention time: 2.2 min.

Example 102

Preparation of 1-(6-Bromo-pyridin-2-ylmethyl)-3-(6-trifluoromethyl-pyridine-3-carbonyl)-1H-quinolin-4-one

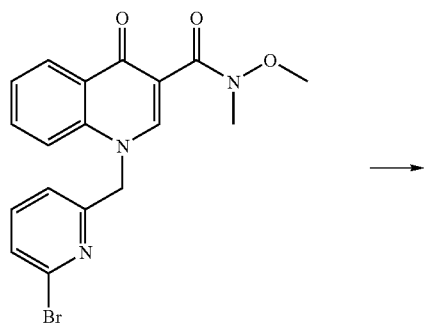

-continued

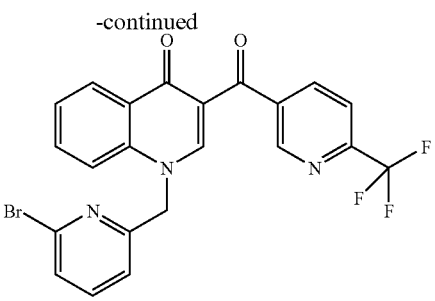

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 179 mg (0.66 mmol) of 5-iodo-2-trifluoromethyl-pyridine in 1 mL THF with 0.34 mL 2M isopropylmagnesium chloride. Yield: 76 mg of a white powder. LC-MSD, m/z for C$_{22}$H$_{13}$BrF$_3$N$_3$O$_2$ [M+H]+=488.0, 490.0; HPLC retention time: 2.5 min.

Example 103

Preparation of 1-(6-Bromo-pyridin-2-ylmethyl)-3-(6-trifluoromethyl-pyridine-2-carbonyl)-1H-quinolin-4-one

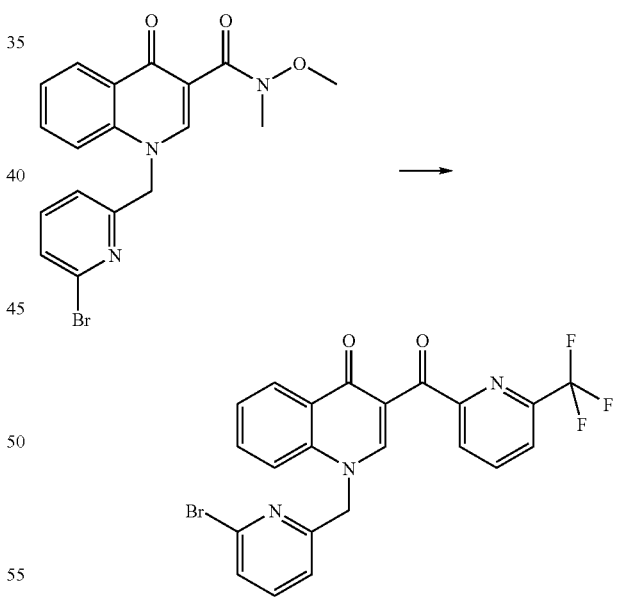

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 239 mg (0.66 mmol) of 75% 5-iodo-2-trifluoromethyl-pyridine in 1 mL THF with 0.37 mL 2M isopropylmagnesium chloride. Yield: 78 mg of a white powder. LC-MSD, m/z for C$_{22}$H$_{13}$BrF$_3$N$_3$O$_2$ [M+H]+=488.0, 490.0; HPLC retention time: 2.4 min.

Example 104

Preparation of 1-(6-Bromo-pyridin-2-ylmethyl)-3-(3,4-dimethoxy-benzoyl)-1H-quinolin-4-one

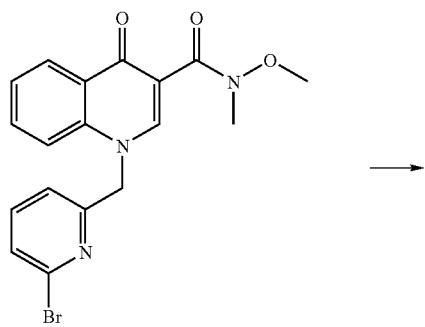

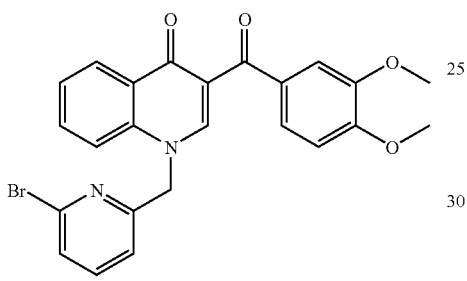

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 3,4-dimethoxyphenylmagnesium bromide. Yield: 55 mg of a white solid. LC-MSD, m/z for $C_{24}H_{19}BrN_2O_4$ [M+H]+=479.0, 481.0; HPLC retention time: 2.1 min.

Example 105

Preparation of 1-(6-Bromo-pyridin-2-ylmethyl)-3-(3-methoxy-benzoyl)-1H-quinolin-4-one

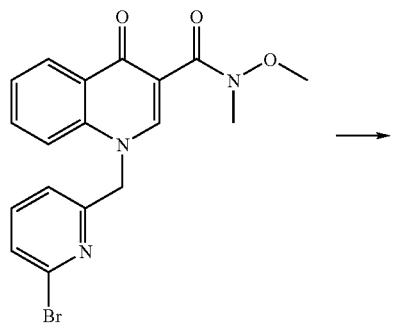

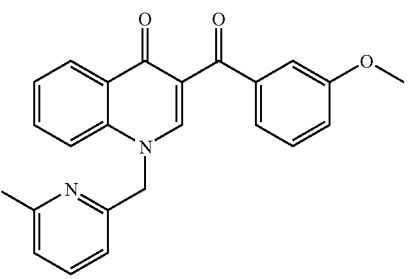

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1.5 mL THF and 0.49 mL 1M 3-methoxyphenylmagnesium bromide. Yield: 53 mg of a white solid. LC-MSD, m/z for $C_{23}H_{17}BrN_2O_3$ [M+H]+=449.0, 451.0; HPLC retention time: 2.3 min.

Example 106

Preparation of 1-(6-Bromo-pyridin-2-ylmethyl)-3-(4,5-dimethyl-thiazole-2-carbonyl)-1H-quinolin-4-one

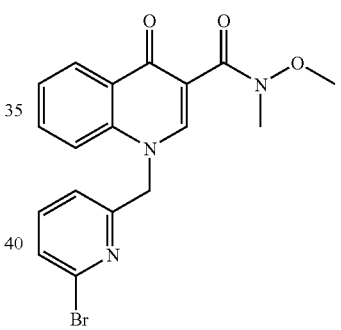

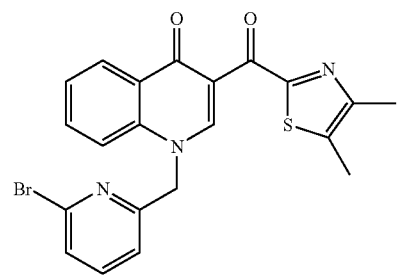

585 mg (5.17 mmol) of 4,5-dimethylthiazole was dissolved in 10 mL of anhydrous THF and cooled down to −78° C. 2.07 mL of 2.5 M BuLi in hexanes was added dropwise, followed after 15 minutes by 1.0 g of anhydrous magnesium bromide. The solution was warmed up to rt. The final compound was prepared from 120 mg (0.30 mmol) of 1-(6-bromo-pyridin-2-ylmethyl)-4-oxo-1,4-dihydro-quinoline-3-carboxylic acid methoxy-methyl-amide in 2 mL THF and 1.64 mL of the thiazole salt solution. Yield: 13 mg of a white solid. LC-MSD, m/z for $C_{21}H_{16}BrN_3O_2S$ [M+H]+=454.0, 456.0; HPLC retention time: 2.2 min.

Example 107

Preparation of 1-(6-Bromo-pyridin-2-ylmethyl)-3-(4-methoxy-benzoyl)-1H-quinolin-4-one

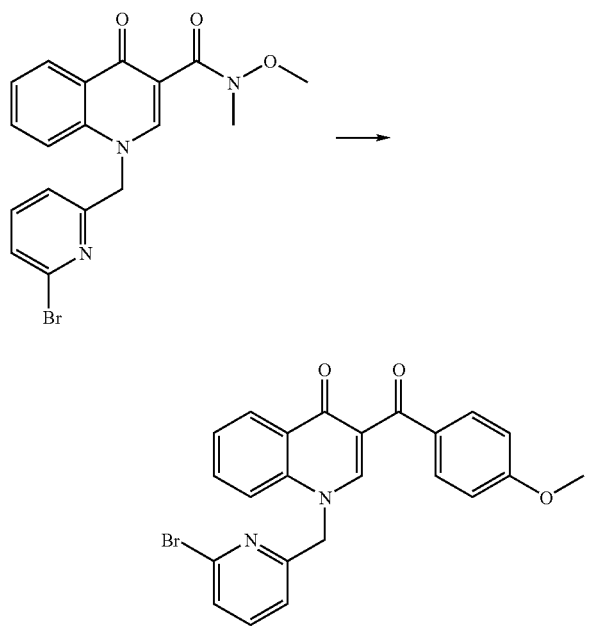

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 4-methoxyphenylmagnesium bromide. Yield: 51 mg of a white solid. LC-MSD, m/z for $C_{23}H_{17}BrN_2O_3$ [M+H]+=449.0, 451.0; HPLC retention time: 2.3 min.

Example 108

Preparation of 1-(6-Bromo-pyridin-2-ylmethyl)-3-(3-fluoro-4-methoxy-benzoyl)-1H-quinolin-4-one

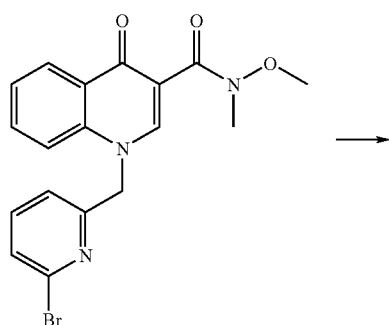

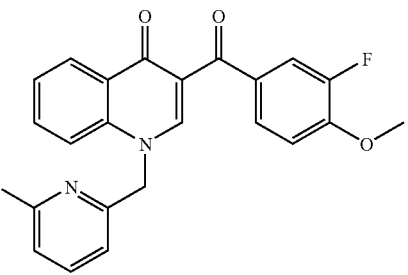

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 3-fluoro-4-methoxyphenylmagnesium bromide. Yield: 57 mg of a white solid. $^1$H NMR (400 MHz, CDCl$_3$): δ 4.0 (s, 3H), 5.5 (s, 2H), 6.9-7.0 (m, 2H), 7.3-7.4 (m, 1H), 7.4-7.6 (m, 3H), 7.6-7.7 (m, 3H), 8.3 (s, 1H), 8.4-8.5 (m, 1H). LC-MSD, m/z for $C_{23}H_{16}BrFN_2O_3$ [M+H]+=467.0, 469.0; HPLC retention time: 2.3 min.

Example 109

Preparation of 1-(6-Bromo-pyridin-2-ylmethyl)-3-(4-isopropyl-benzoyl)-1H-quinolin-4-one

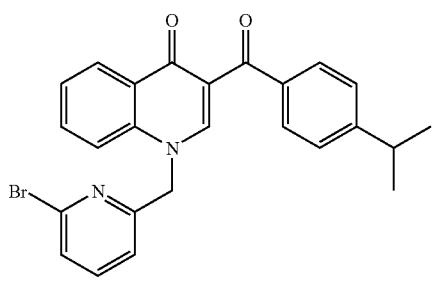

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 4-iso-propylphenylmagnesium bromide. Yield: 52 mg of a white solid. LC-MSD, m/z for $C_{25}H_{21}N_2O_2$ [M+H]+=461.0, 463.0; HPLC retention time: 2.7 min.

Example 110

Preparation of 1-(6-Bromo-pyridin-2-ylmethyl)-3-(3-methyl-pyridine-2-carbonyl)-1H-quinolin-4-one

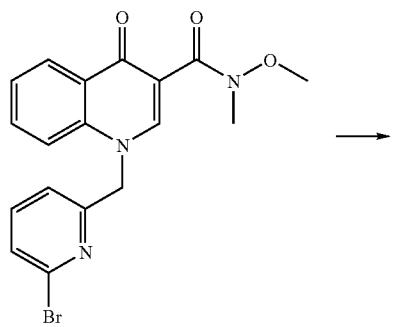

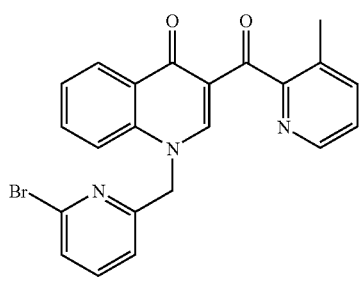

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 1.96 mL 0.25M 3-methyl-2-pyridylmagnesium bromide. Yield: 22 mg of a white solid. LC-MSD, m/z for $C_{22}H_{16}BrN_3O_2$ [M+H]+=434.0, 436.0; HPLC retention time: 1.8 min.

Example 111

Preparation of 1-(6-Bromo-pyridin-2-ylmethyl)-3-(4-methyl-pyridine-2-carbonyl)-1H-quinolin-4-one

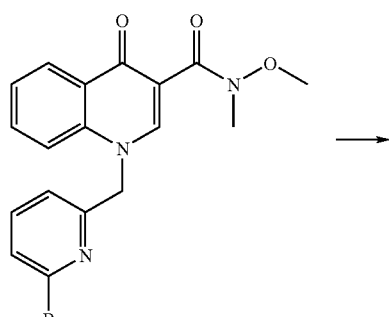

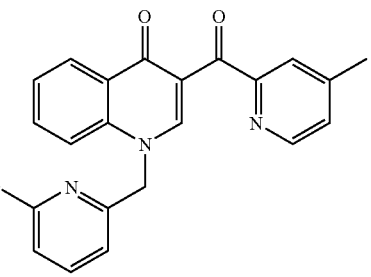

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 1.96 mL 0.25M 4-methyl-2-pyridylmagnesium bromide. Yield: 17 mg of a white solid. LC-MSD, m/z for $C_{22}H_{16}BrN_3O_2$ [M+H]+=434.0, 436.0; HPLC retention time: 1.8 min.

Example 112

Preparation of 1-(6-Bromo-pyridin-2-ylmethyl)-3-(5-methyl-pyridine-2-carbonyl)-1H-quinolin-4-one

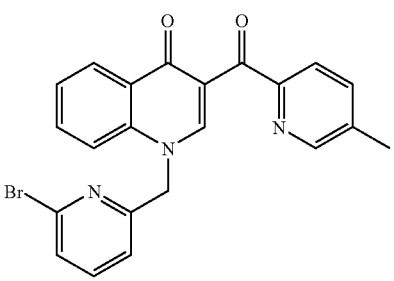

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 1.96 mL 0.25M 5-methyl-2-pyridylmagnesium bromide. Yield: 33 mg of a white solid. LC-MSD, m/z for $C_{22}H_{16}BrN_3O_2$ [M+H]+=434.0, 436.0; HPLC retention time: 2.0 min.

Example 113

Preparation of 1-(6-Bromo-pyridin-2-ylmethyl)-3-(2,3-dimethyl-3H-imidazole-4-carbonyl)-1H-quinolin-4-one

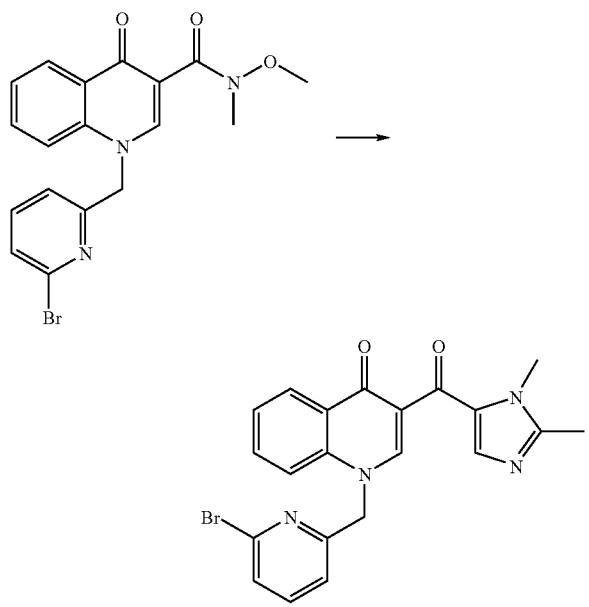

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 3 mL DCM and 146 mg (0.66 mmol) of 5-iodo-1,2-dimethyl-1H-imidazole in 1 mL DCM with 0.34 mL 2M isopropylmagnesium chloride. Yield: 36 mg of a white powder. LC-MSD, m/z for $C_{21}H_{17}BrN_4O_2$ [M+H]+=437.0, 439.0; HPLC retention time: 0.4 min.

Example 114

Preparation of 1-(6-Bromo-pyridin-2-ylmethyl)-3-(6-ethyl-pyridine-3-carbonyl)-1H-quinolin-4-one

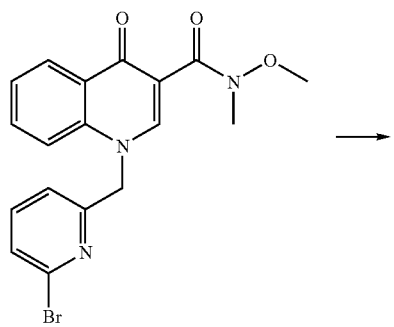

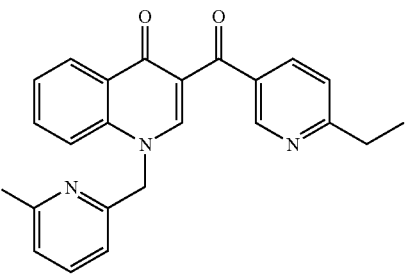

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 153 mg (0.66 mmol) of 2-ethyl-5-iodo-pyridine in 1 mL THF with 0.34 mL 2M isopropylmagnesium chloride. Yield: 62 mg of a white powder. LC-MSD, m/z for $C_{23}H_{18}BrN_3O_2$ [M+H]+=448.0, 450.0; HPLC retention time: 1.6 min.

Example 115

Preparation of 1-(6-Bromo-pyridin-2-ylmethyl)-3-(4-methoxy-2-methyl-benzoyl)-1H-quinolin-4-one

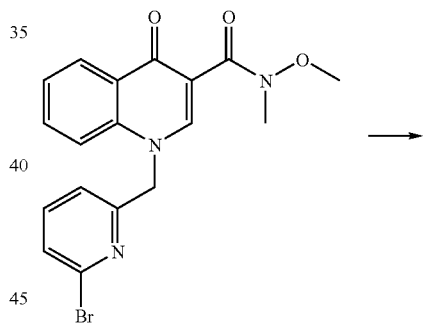

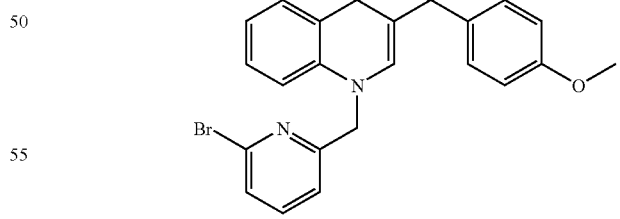

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1.5 mL THF and 0.98 mL 0.5M 4-methoxy-2-methylphenylmagnesium bromide. Yield: 41 mg of a white solid. LC-MSD, m/z for $C_{24}H_{19}BrN_2O_3$ [M+H]+=463.0, 465.0; HPLC retention time: 2.4 min.

Example 116

Preparation of 1-(6-Bromo-pyridin-2-ylmethyl)-3-(4-chloro-3-fluoro-benzoyl)-1H-quinolin-4-one

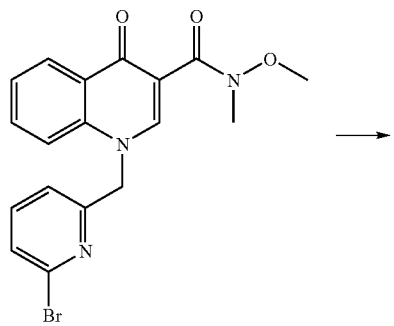

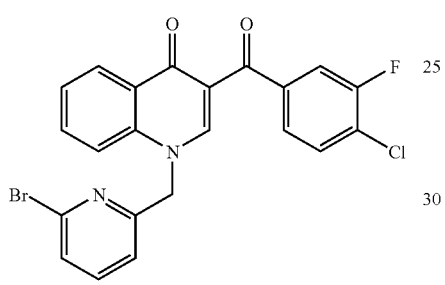

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1.5 mL THF and 0.98 mL 0.5M 4-chloro-3-fluorophenylmagnesium bromide. Yield: 52 mg of a white solid. LC-MSD, m/z for $C_{22}H_{13}BrClFN_2O_2$ [M+H]+=471.0, 473.0; HPLC retention time: 2.6 min.

Example 117

Preparation of 1-(6-Bromo-pyridin-2-ylmethyl)-3-(2,6-dimethyl-pyridine-3-carbonyl)-1H-quinolin-4-one

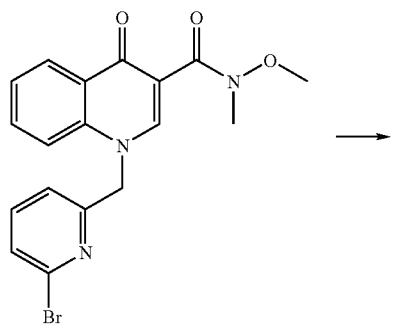

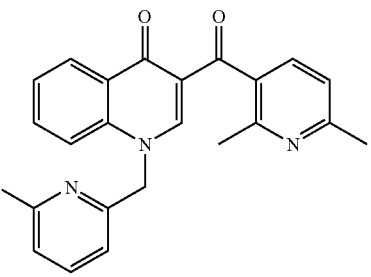

Experimental conditions analogous to those described for Step 6 of Example 60 from 105 mg (0.26 mmol) of 1-(6-bromo-pyridin-2-ylmethyl)-4-oxo-1,4-dihydro-quinoline-3-carboxylic acid methoxy-methyl-amide in 1 mL THF and 134 mg (0.58 mmol) of 2,6-dimethyl-5-iodo-pyridine in 1 mL THF with 0.30 mL 2M isopropylmagnesium chloride. Yield: 19 mg of a white powder. LC-MSD, m/z for $C_{23}H_{18}BrN_3O_2$ [M+H]+=448.0, 450.0; HPLC retention time: 1.2 min.

Example 118

Preparation of 1-(6-Bromo-pyridin-2-ylmethyl)-3-(4-chloro-3-methyl-benzoyl)-1H-quinolin-4-one

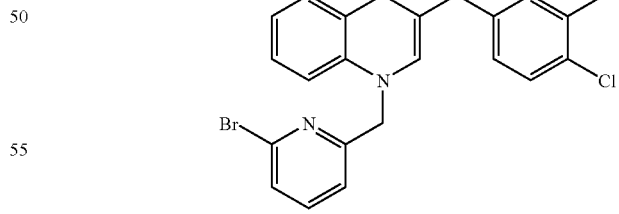

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 1 mL THF and 0.98 mL 0.5M 4-chloro-3-methylphenylmagnesium bromide. Yield: 54 mg of a white solid. LC-MSD, m/z for $C_{23}H_{16}BrClN_2O_2$ [M+H]+=467.0, 469.0; HPLC retention time: 2.6 min.

Example 119

Preparation of 1-(6-Bromo-pyridin-2-ylmethyl)-3-(4-methylsulfanyl-benzoyl)-1H-quinolin-4-one

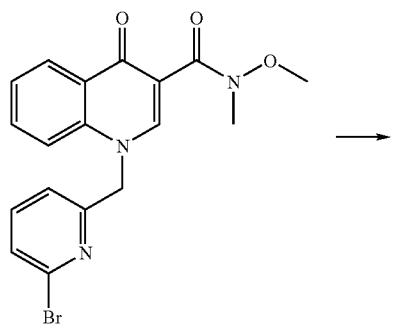

→

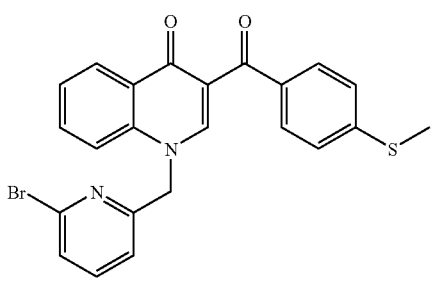

Experimental conditions analogous to those described for Step 6 of Example 60 from 210 mg (0.52 mmol) of 1-(6-bromo-pyridin-2-ylmethyl)-4-oxo-1,4-dihydro-quinoline-3-carboxylic acid methoxy-methyl-amide in 3 mL THF and 2.3 mL 0.5M 4-thioanisolemagnesium bromide. Yield: 111 mg of a white solid. LC-MSD, m/z for $C_{23}H_{17}BrN_2O_2S$ [M+H]+=465.0, 467.0; HPLC retention time: 2.4 min.

Example 120

Preparation of 1-(6-Bromo-pyridin-2-ylmethyl)-3-(5-chloro-thiophene-2-carbonyl)-1H-quinolin-4-one

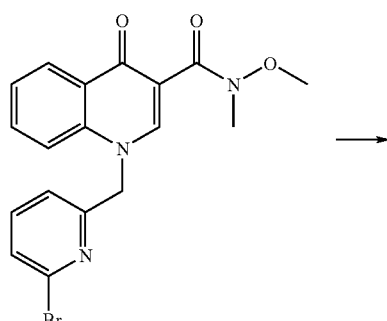

→

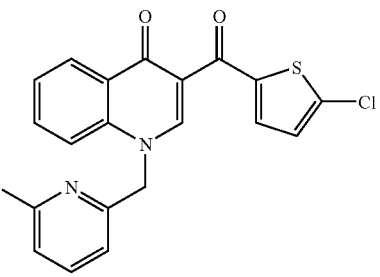

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 0.5 mL THF and 2.0 mL 0.25M 5-chloro-2-thienylmagnesium bromide. Yield: 56 mg of a white solid. LC-MSD, m/z for $C_{20}H_{12}BrClN_2O_2S$ [M+H]+=458.9, 460.9, 462.9; HPLC retention time: 2.5 min.

Example 121

Preparation of 1-(6-Bromo-pyridin-2-ylmethyl)-3-(6-chloro-pyridine-3-carbonyl)-1H-quinolin-4-one

→

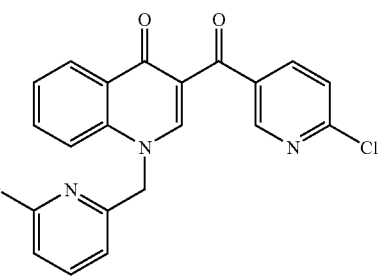

Experimental conditions analogous to those described for Step 6 of Example 60 from 275 mg (0.68 mmol) of 1-(6-bromo-pyridin-2-ylmethyl)-4-oxo-1,4-dihydro-quinoline-3-carboxylic acid methoxy-methyl-amide in 3 mL THF and 360 mg (1.51 mmol) of 2-chloro-5-iodo-pyridine in 2 mL THF with 0.79 mL 2M isopropylmagnesium chloride. Yield: 187 mg of a white powder. LC-MSD, m/z for $C_{21}H_{13}BrClN_3O_2$ [M+H]+=454.0, 456.0; HPLC retention time: 2.2 min.

Example 122

Preparation of 1-(6-Bromo-pyridin-2-ylmethyl)-3-(6-methoxy-5-methyl-pyridine-3-carbonyl)-1H-quinolin-4-one

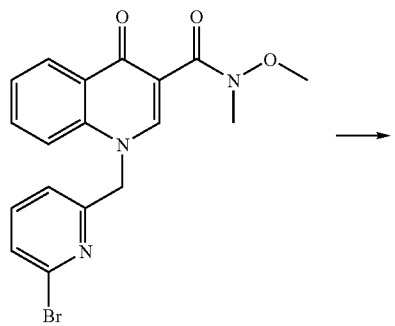

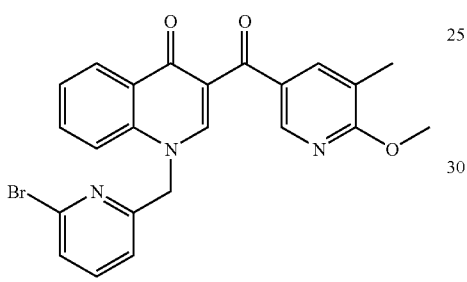

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 164 mg (0.66 mmol) of 5-iodo-2-methoxy-3-methyl-pyridine in 1 mL THF with 0.34 mL 2M isopropylmagnesium chloride. Yield: 40 mg of a white powder. LC-MSD, m/z for C$_{23}$H$_{18}$BrN$_3$O$_3$ [M+H]+=464.0, 466.0; HPLC retention time: 2.4 min.

Example 123

Preparation of 1-(6-Bromo-pyridin-2-ylmethyl)-3-(4-fluoro-3-methyl-benzoyl)-1H-quinolin-4-one

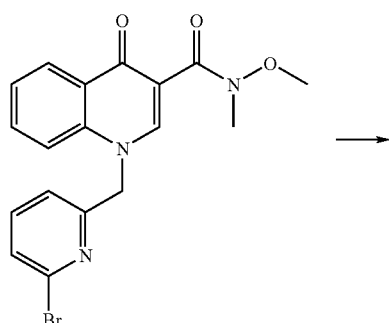

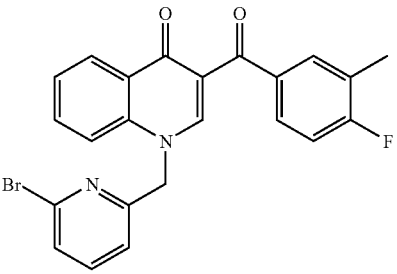

Experimental conditions analogous to those described for Step 6 of Example 60 from 90 mg (0.22 mmol) of 1-(6-bromo-pyridin-2-ylmethyl)-4-oxo-1,4-dihydro-quinoline-3-carboxylic acid methoxy-methyl-amide in 2 mL THF and 0.49 mL 1M 4-fluoro-3-methylphenylmagnesium bromide. Yield: 40 mg of a white solid. LC-MSD, m/z for C$_{23}$H$_{16}$BrFN$_2$O$_2$ [M+H]+=451.0, 453.0; HPLC retention time: 2.5 min.

Example 124

Preparation of 1-(6-Bromo-pyridin-2-ylmethyl)-3-(4-chloro-3-methoxy-benzoyl)-1H-quinolin-4-one

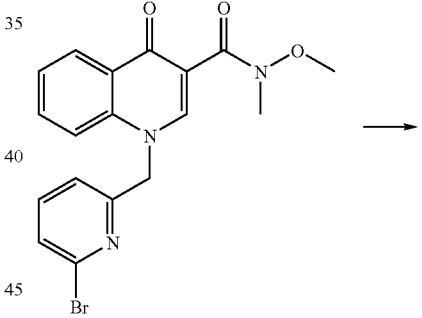

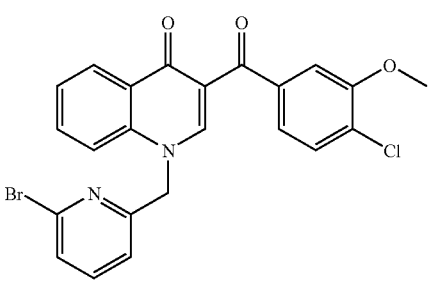

Experimental conditions analogous to those described for Step 6 of Example 60 from 92 mg (0.22 mmol) of 1-(6-bromo-pyridin-2-ylmethyl)-4-oxo-1,4-dihydro-quinoline-3-carboxylic acid methoxy-methyl-amide in 1 mL THF and 2.01 mL 0.25M 4-chloro-3-methoxyphenylmagnesium bromide. Yield: 40 mg of a white solid. LC-MSD, m/z for C$_{23}$H$_{16}$BrClN$_2$O$_3$ [M+H]+=483.0, 485.0; HPLC retention time: 2.5 min.

Example 125

Preparation of 1-(6-Bromo-pyridin-2-ylmethyl)-3-(4-chloro-benzoyl)-1H-quinolin-4-one

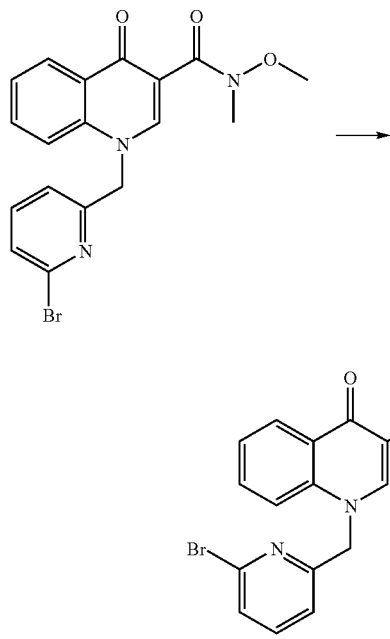

Experimental conditions analogous to those described for Step 6 of Example 60 from 150 mg (0.37 mmol) of 1-(6-bromo-pyridin-2-ylmethyl)-4-oxo-1,4-dihydro-quinoline-3-carboxylic acid methoxy-methyl-amide in 3 mL THF and 0.82 mL 1M 4-chlorophenylmagnesium bromide. Yield: 73 mg of a white solid. LC-MSD, m/z for $C_{22}H_{14}BrClN_2O_2$ [M+H]+=453.0, 455.0; HPLC retention time: 2.6 min.

Example 126

Preparation of 1-(6-Bromo-pyridin-2-ylmethyl)-3-(5-methoxy-6-methyl-pyridine-2-carbonyl)-1H-quinolin-4-one

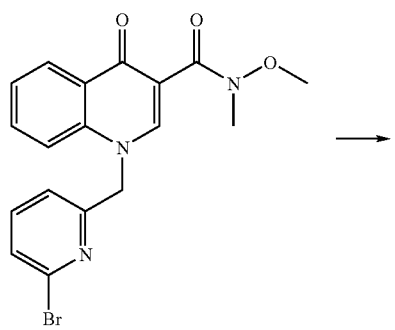

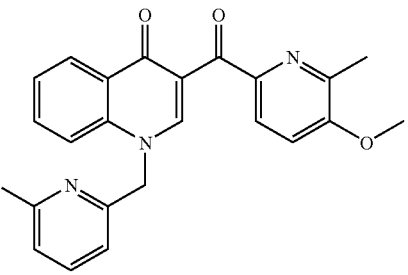

Experimental conditions analogous to those described for Step 6 of Example 60 from 120 mg (0.30 mmol) of 1-(6-bromo-pyridin-2-ylmethyl)-4-oxo-1,4-dihydro-quinoline-3-carboxylic acid methoxy-methyl-amide in 1 mL THF and 164 mg (0.66 mmol) of 6-iodo-3-methoxy-2-methyl-pyridine in 1 mL THF with 0.34 mL 2M isopropylmagnesium chloride. Yield: 60 mg of a white powder. LC-MSD, m/z for $C_{23}H_{18}BrN_3O_3$ [M+H]+=464.0, 466.0; HPLC retention time: 1.9 min.

Example 127

Preparation of 3-(4-Methoxy-3-methyl-benzoyl)-1-(6-methyl-pyridin-2-ylmethyl)-1H-quinolin-4-one

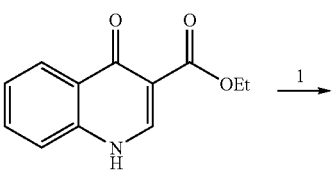

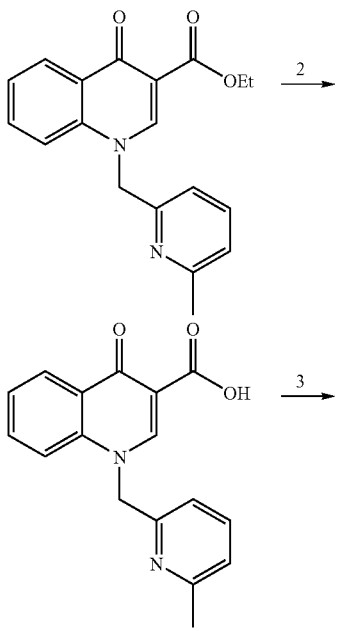

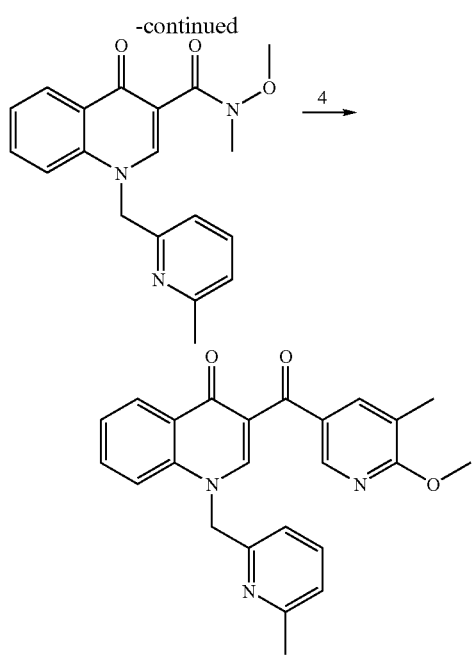

Step 1: 1-(6-Methyl-pyridin-2-ylmethyl)-4-oxo-1,4-dihydro-quinoline-3-carboxylic acid ethyl ester Experimental conditions analogous to those described for Step 3 of Example 1, from 2.87 g (13.2 mmol) of 4-oxo-1,4-dihydro-quinoline-3-carboxylic acid ethyl ester, 0.64 g (15.9 mmol) of 60% sodium hydride, 2.95 g (15.9 mmol) of 2-bromomethyl-6-methyl-pyridine in 30 mL DMF to give 3.18 g of the product as an off-white solid.

Step 2: 1-(6-Methyl-pyridin-2-ylmethyl)-4-oxo-1,4-dihydro-quinoline-3-carboxylic acid Experimental conditions analogous to those described for Step 4 of Example 60, from 3.15 g (9.77 mmol) of 1-(6-methyl-pyridin-2-ylmethyl)-4-oxo-1,4-dihydro-quinoline-3-carboxylic acid ethyl ester, 80 mL of 1:1 methanol-water mixture and 0.28 g (11.7 mmol) of lithium hydroxide with a work-up consisting only of thorough evaporation of solvents.

Step 3: 1-(6-Methyl-pyridin-2-ylmethyl)-4-oxo-1,4-dihydro-quinoline-3-carboxylic acid methoxy-methyl-amide Experimental conditions analogous to those described for Step 5 of Example 60, from crude 1-(6-Methyl-pyridin-2-ylmethyl)-4-oxo-1,4-dihydro-quinoline-3-carboxylic acid, 1.27 g (12.7 mmol) of N,O-dimethylhydroxylamine hydrochloride, 9 mL (6.5 g, 64.7 mmol) of triethylamine and 9.2 mL (9.83 g, 15.5 mmol) of 50% 1-propanephosphonic acid cyclic anhydride in 50 mL acetonitrile to give 2.30 g of the product as an off-white solid.

Step 4: 3-(4-Methoxy-3-methyl-benzoyl)-1-(6-methyl-pyridin-2-ylmethyl)-1H-quinolin-4-one Experimental conditions analogous to those described for Step 6 of Example 60, from 168 mg (0.50 mmol) of 1-(6-methyl-pyridin-2-ylmethyl)-4-oxo-1,4-dihydro-quinoline-3-carboxylic acid methoxy-methyl-amide in 2.5 mL THF and 2.5 mL 0.5M 4-methoxy-3-methylphenylmagnesium bromide. Yield: 107 mg of a white solid. LC-MSD, m/z for $C_{25}H_{22}N_2O_3$ [M+H]+=399.1; HPLC retention time: 2.1 min.

Example 128

Preparation of 3-(2,3-Dihydro-benzo[1,4]dioxine-6-carbonyl)-1-(6-methyl-pyridin-2-ylmethyl)-1H-quinolin-4-one

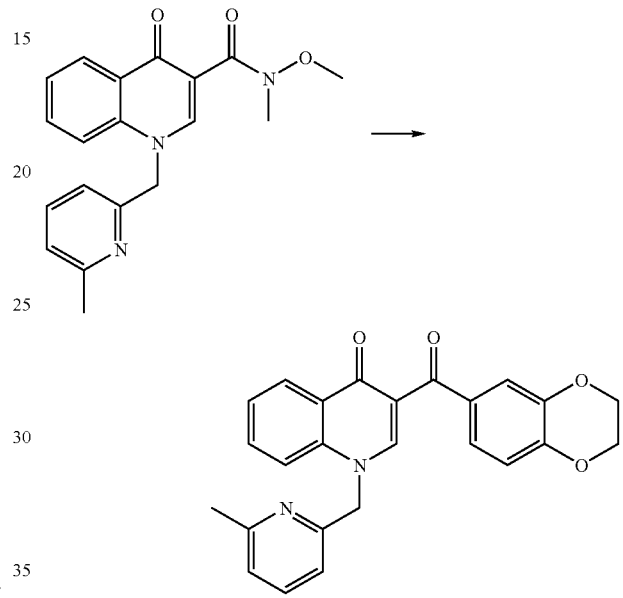

Experimental conditions analogous to those described for Step 6 of Example 60, from 161 mg (0.48 mmol) of 1-(6-methyl-pyridin-2-ylmethyl)-4-oxo-1,4-dihydro-quinoline-3-carboxylic acid methoxy-methyl-amide in 2.5 mL THF and 2.4 mL 0.5M 3,4-(ethylenedioxy)phenylmagnesium bromide. Yield: 65 mg of a white solid. LC-MSD, m/z for $C_{25}H_{20}N_2O_4$ [M+H]+=413.1; HPLC retention time: 1.8 min.

Example 129

Preparation of 3-(4-Dimethylamino-benzoyl)-1-(6-methyl-pyridin-2-ylmethyl)-1H-quinolin-4-one

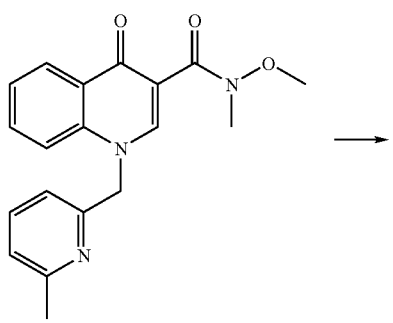

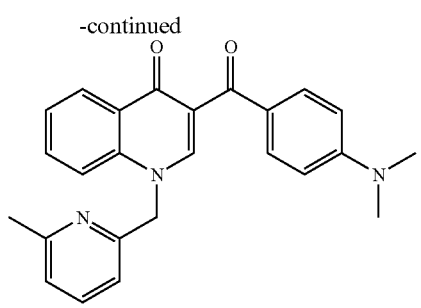

Experimental conditions analogous to those described for Step 6 of Example 60, from 138 mg (0.41 mmol) of 1-(6-methyl-pyridin-2-ylmethyl)-4-oxo-1,4-dihydro-quinoline-3-carboxylic acid methoxy-methyl-amide in 2 mL THF and 2 mL 0.5M 4-N,N-dimethylanilinemagnesium bromide. Yield: 17 mg of a white solid. LC-MSD, m/z for $C_{25}H_{23}N_3O_2$ [M+H]+=398.1; HPLC retention time: 1.9 min.

Example 130

Preparation of 1-(6-Methyl-pyridin-2-ylmethyl)-3-(6-trifluoromethyl-pyridine-3-carbonyl)-1H-quinolin-4-one

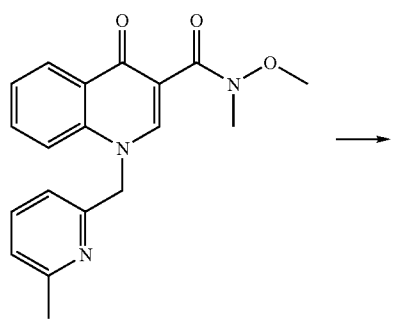

Experimental conditions analogous to those described for Step 6 of Example 60, from 120 mg (0.36 mmol) of 1-(6-methyl-pyridin-2-ylmethyl)-4-oxo-1,4-dihydro-quinoline-3-carboxylic acid methoxy-methyl-amide in 1 mL THF and 214 mg (0.78 mmol) of 5-iodo-2-trifluoromethyl-pyridine in 1.5 mL THF with 0.41 mL 2M isopropylmagnesium chloride. Yield: 81 mg of a white powder. LC-MSD, m/z for $C_{23}H_{16}F_3N_3O_2$ [M+H]+=424.1; HPLC retention time: 2.2 min.

Example 131

Preparation of 3-(3-Fluoro-4-methoxy-benzoyl)-1-(6-methyl-pyridin-2-ylmethyl)-1H-quinolin-4-one

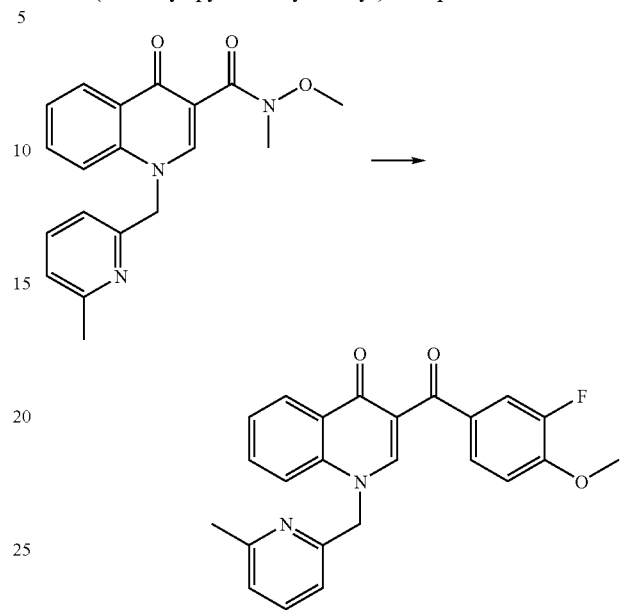

Experimental conditions analogous to those described for Step 6 of Example 60, from 120 mg (0.36 mmol) of 1-(6-methyl-pyridin-2-ylmethyl)-4-oxo-1,4-dihydro-quinoline-3-carboxylic acid methoxy-methyl-amide in 2 mL THF and 1.6 mL 0.5M 3-fluoro-4-methoxyphenylmagnesium bromide. Yield: 95 mg of a white solid. LC-MSD, m/z for $C_{24}H_{19}FN_2O_3$ [M+H]+=403.1; HPLC retention time: 1.9 min.

Example 132

Preparation of 3-(6-Ethyl-pyridine-3-carbonyl)-1-(6-methyl-pyridin-2-ylmethyl)-1H-quinolin-4-one

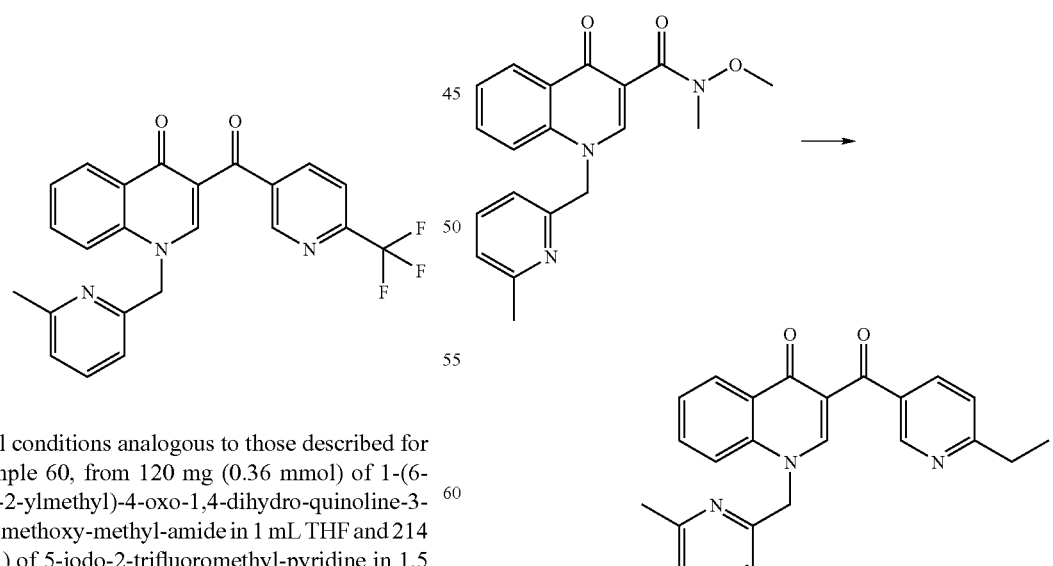

Experimental conditions analogous to those described for Step 6 of Example 60, from 85 mg (0.25 mmol) of 1-(6- methyl-pyridin-2-ylmethyl)-4-oxo-1,4-dihydro-quinoline-3-carboxylic acid methoxy-methyl-amide in 2.5 mL THF and 129 mg (0.56 mmol) of 2-ethyl-5-iodo-pyridine in 1 mL THF with 0.29 mL 2M isopropylmagnesium chloride. Yield: 41 mg of a white powder. LC-MSD, m/z for $C_{24}H_{21}N_3O_2$ [M+H]+=384.1; HPLC retention time: 0.7 min.

Example 133

Preparation of 3-(6-Chloro-pyridine-3-carbonyl)-1-(6-methyl-pyridin-2-ylmethyl)-1H-quinolin-4-one

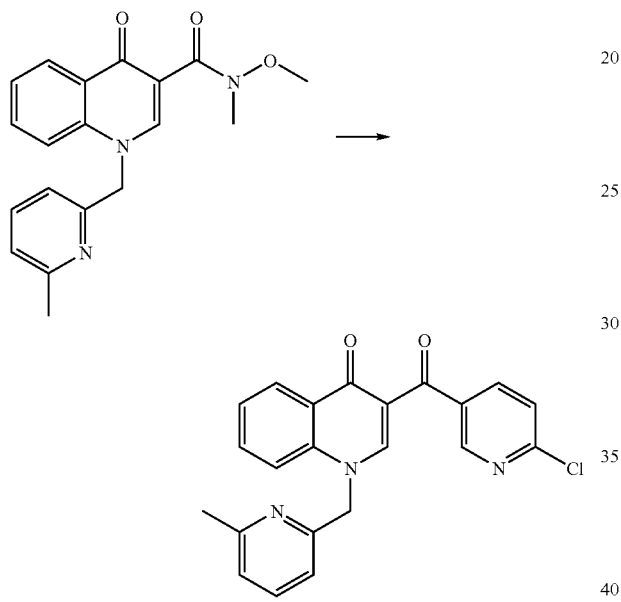

Experimental conditions analogous to those described for Step 6 of Example 60, from 800 mg (2.37 mmol) of 1-(6-methyl-pyridin-2-ylmethyl)-4-oxo-1,4-dihydro-quinoline-3-carboxylic acid methoxy-methyl-amide in 25 mL THF and 1.25 g (5.22 mmol) of 2-chloro-5-iodo-pyridine in 7 mL THF with 2.73 mL 2M isopropylmagnesium chloride. Yield: 635 mg of a white powder. LC-MSD, m/z for $C_{22}H_{16}ClN_3O_2$ [M+H]+=390.1, 392.0; HPLC retention time: 2.0 min.

Example 134

Preparation of 1-(3-Chloro-benzyl)-3-(6-chloro-pyridine-3-carbonyl)-1H-quinolin-4-one

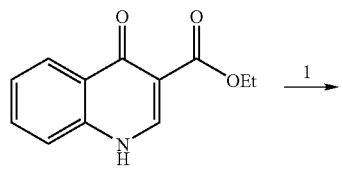

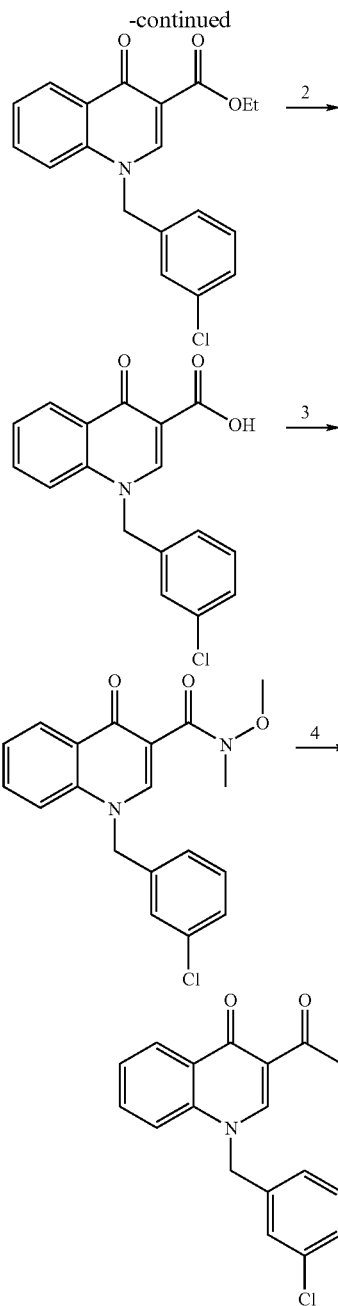

Step 1: 1-(3-Chloro-benzyl)-4-oxo-1,4-dihydro-quinoline-3-carboxylic acid ethyl ester Experimental conditions analogous to those described for Step 1 of Example 3, from 5.08 g (23.4 mmol) of 4-oxo-1,4-dihydro-quinoline-3-carboxylic acid ethyl ester, 1.12 g (28.1 mmol) of 60% sodium hydride, 4.52 g (28.1 mmol) of 3-chlorobenzyl chloride in 60 mL DMF at 60° C. to give 7.01 g of the product as an off-white solid.

Step 2: 1-(3-Chloro-benzyl)-4-oxo-1,4-dihydro-quinoline-3-carboxylic acid

Experimental conditions analogous to those described for Step 4 of Example 60, from 7.00 g (20.5 mmol) of 1-(3- chloro-benzyl)-4-oxo-1,4-dihydro-quinoline-3-carboxylic acid ethyl ester, 200 mL of 1:1 methanol-water mixture and 0.98 g (41.0 mmol) of lithium hydroxide with a work-up consisting only of thorough evaporation of solvents. The residue was directly taken to step 3.

Step 3: 1-(3-Chloro-benzyl)-4-oxo-1,4-dihydro-quinoline-3-carboxylic acid methoxy-methyl-amide Experimental conditions analogous to those described for Step 5 of Example 60, from crude 1-(3-Chloro-benzyl)-4-oxo-1,4-dihydro-quinoline-3-carboxylic acid, 2.21 g (22.6 mmol) of N,O-dimethylhydroxylamine hydrochloride, 14.3 mL (10.4 g, 103 mmol) of triethylamine and 14.6 mL (15.6 g, 24.5 mmol) of 50% 1-propanephosphonic acid cyclic anhydride in 100 mL acetonitrile to give 3.10 g of the product as an off-white solid.

Step 4: Preparation of 1-(3-Chloro-benzyl)-3-(6-chloro-pyridine-3-carbonyl)-1H-quinolin-4-one Experimental conditions analogous to those described for Step 6 of Example 60, from 600 mg (1.68 mmol) of 1-(3-chloro-benzyl)-4-oxo-1,4-dihydro-quinoline-3-carboxylic acid methoxy-methyl-amide in 4 mL THF and 887 mg (3.70 mmol) of 2-chloro-5-iodo-pyridine in 4 mL THF with 1.93 mL 2M isopropylmagnesium chloride. Yield: 418 mg of a white powder. LC-MSD, m/z for $C_{22}H_{14}Cl_2N_2O_2$ [M+H]+=409.0, 411.0; HPLC retention time: 3.3 min.

Example 135

Preparation of 1-(3-Chloro-benzyl)-3-(6-methoxy-5-methyl-pyridine-3-carbonyl)-1H-quinolin-4-one

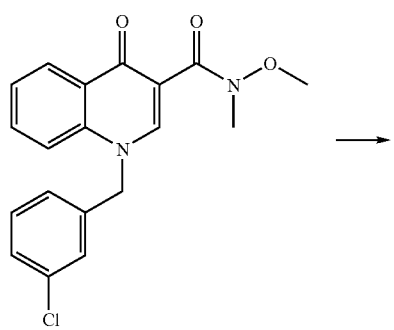

Experimental conditions analogous to those described for Step 6 of Example 60, from 119 mg (0.33 mmol) of 1-(3-chloro-benzyl)-4-oxo-1,4-dihydro-quinoline-3-carboxylic acid methoxy-methyl-amide in 1 mL THF and 183 mg (0.73 mmol) of 5-iodo-2-methoxy-3-methyl-pyridine in 1 mL THF with 0.38 mL 2M isopropylmagnesium chloride. Yield: 86 mg of a white powder. LC-MSD, m/z for $C_{24}H_{19}ClN_2O_3$ [M+H]+=419.1, 421.1; HPLC retention time: 3.1 min.

Example 136

Preparation of 1-(3-Chloro-benzyl)-3-(4-methoxy-benzoyl)-1H-quinolin-4-one

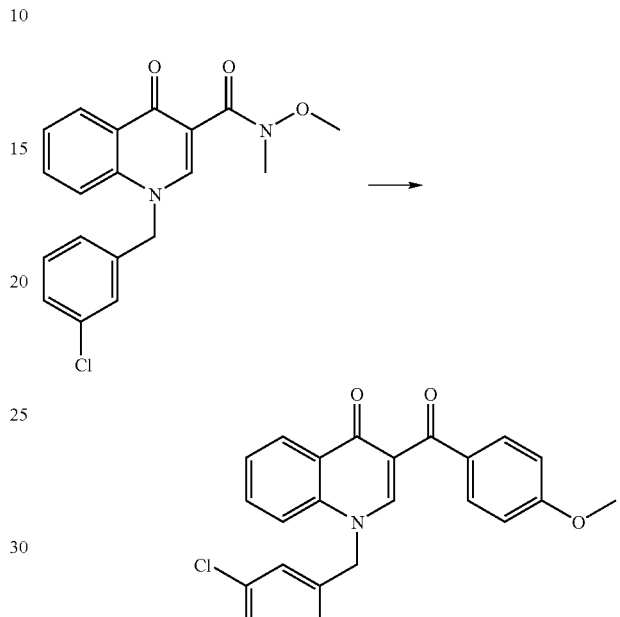

Experimental conditions analogous to those described for Step 6 of Example 60, from 300 mg (0.84 mmol) of 1-(3-chloro-benzyl)-4-oxo-1,4-dihydro-quinoline-3-carboxylic acid methoxy-methyl-amide in 3 mL THF and 3.7 mL 0.5M 4-methoxyphenylmagnesium bromide. Yield: 168 mg of a white solid. LC-MSD, m/z for $C_{24}H_{18}ClNO_3$ [M+H]+=404.1, 406.0; HPLC retention time: 2.4 min.

Example 137

Preparation of 1-(3-Chloro-benzyl)-3-(6-ethyl-pyridine-3-carbonyl)-1H-quinolin-4-one

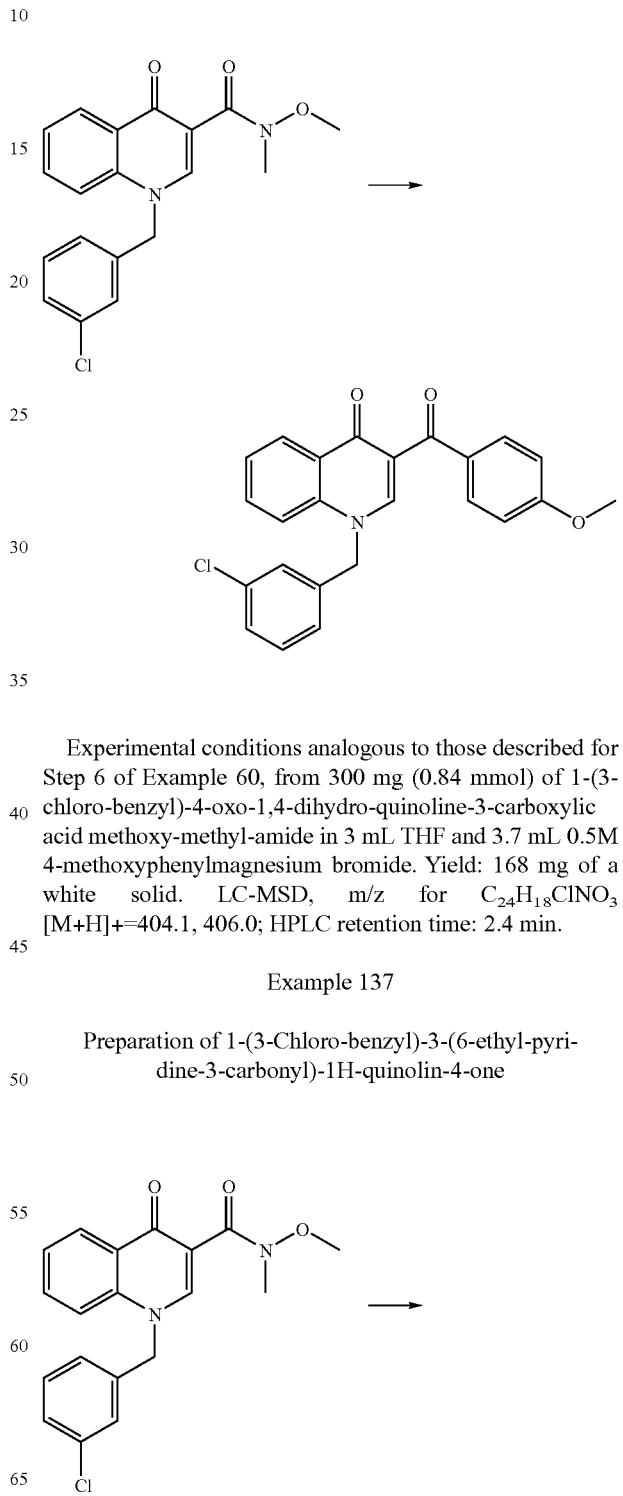

-continued

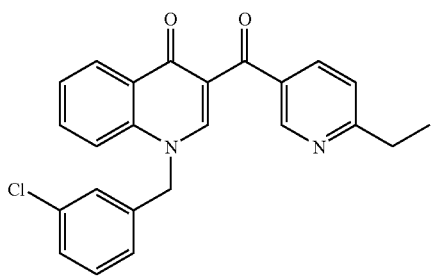

Experimental conditions analogous to those described for Step 6 of Example 60, from 300 mg (0.84 mmol) of 1-(3-chloro-benzyl)-4-oxo-1,4-dihydro-quinoline-3-carboxylic acid methoxy-methyl-amide in 2 mL THF and 433 mg (1.86 mmol) of 2-ethyl-5-iodo-pyridine in 2 mL THF with 0.97 mL 2M isopropylmagnesium chloride. Yield: 127 mg of a white powder. LC-MSD, m/z for $C_{24}H_{19}ClN_2O_2$ [M+H]+=403.1, 405.1; HPLC retention time: 1.8 min.

Example 138

Preparation of 1-(3-Chloro-benzyl)-3-(6-methoxy-pyridine-3-carbonyl)-1H-quinolin-4-one

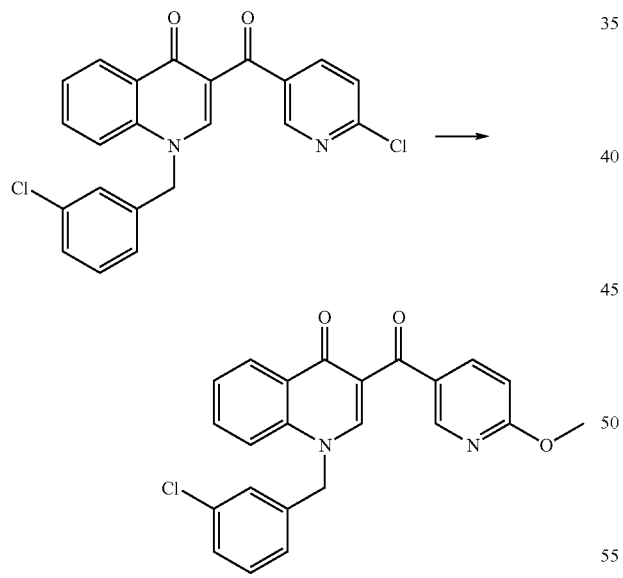

Experimental conditions analogous to those described for Step 6 of Example 60, from 151 mg (0.37 mmol) of 1-(3-chloro-benzyl)-3-(6-chloro-pyridine-3-carbonyl)-1H-quinolin-4-one and 170 mg (3.15 mmol) of sodium methoxide were stirred in 2 mL of dry methanol in a sealed vessel at 75° C. for 2 h. The reaction mixture was evaporated and purified by flash chromatography to give 134 mg of a white powder. LC-MSD, m/z for $C_{23}H_{17}ClN_2O_3$ [M+H]+=405.1, 407.1; HPLC retention time: 2.3 min.

Example 139

Preparation of 1-(4-Methoxy-benzyl)-3-(6-trifluoromethyl-pyridine-3-carbonyl)-1H-quinolin-4-one

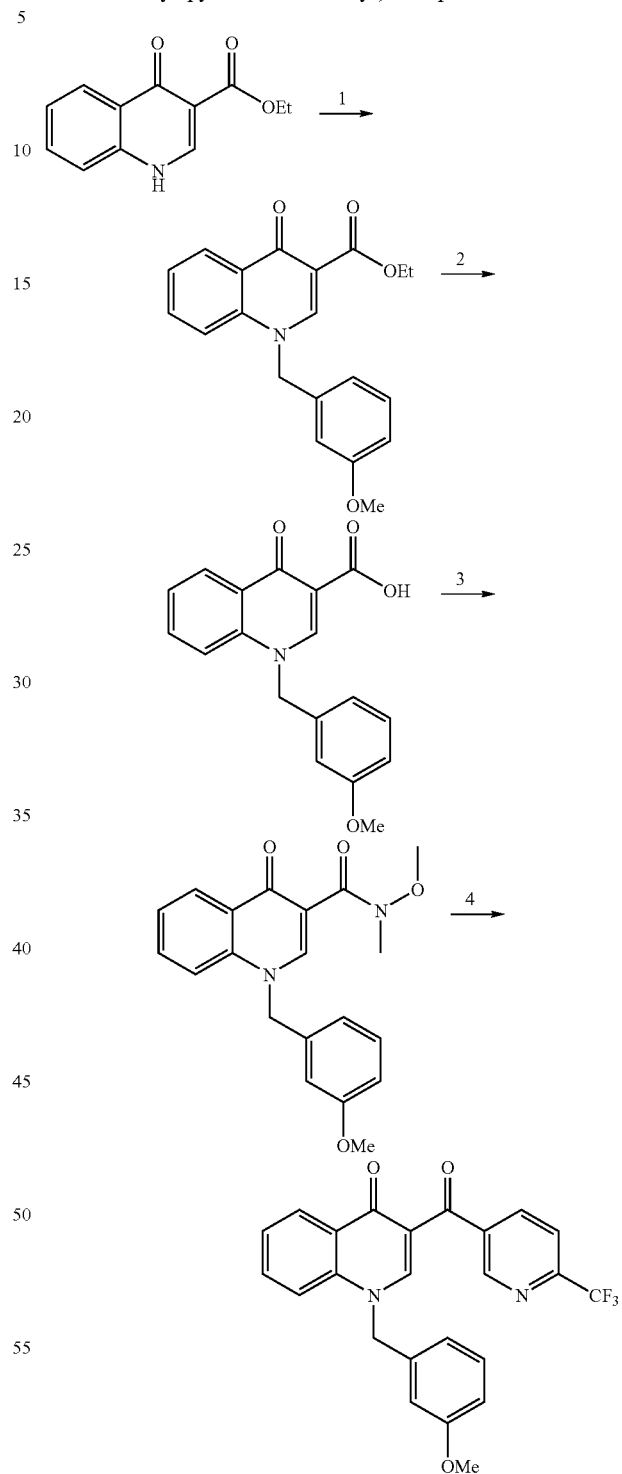

Step 1: 1-(4-Methoxy-benzyl)-4-oxo-1,4-dihydro-quinoline-3-carboxylic acid ethyl ester Experimental conditions analogous to those described for Step 3 of Example 1, from 03.00 g (13.8 mmol) of 4-oxo-1, 4-dihydro-quinoline-3-carboxylic acid ethyl ester, 0.66 g (16.6 mmol) of 60% sodium hydride, 2.60 g (16.6 mmol) of 4-methoxybenzyl chloride in 30 mL DMF to give 3.10 g of the product as an off-white solid.

Step 2: 1-(4-Methoxy-benzyl)-4-oxo-1,4-dihydro-quinoline-3-carboxylic acid

Experimental conditions analogous to those described for Step 4 of Example 60, from 3.10 g (8.80 mmol) of 1-(4-methoxy-benzyl)-4-oxo-1,4-dihydro-quinoline-3-carboxylic acid ethyl ester, 40 mL of 1:1 methanol-water mixture and 0.44 g (18.3 mmol) of lithium hydroxide with a work-up consisting only of thorough evaporation of solvents.

Step 3: 1-(4-Methoxy-benzyl)-4-oxo-1,4-dihydro-quinoline-3-carboxylic acid methoxy-methyl-amide Experimental conditions analogous to those described for Step 5 of Example 60, from crude 1-(4-Methoxy-benzyl)-4-oxo-1,4-dihydro-quinoline-3-carboxylic acid, 1.03 g (10.6 mmol) of N,O-dimethylhydroxylamine hydrochloride, 6.1 mL (4.43 g, 43.8 mmol) of triethylamine and 6.3 mL (6.80 g, 10.7 mmol) of 50% 1-propanephosphonic acid cyclic anhydride in 30 mL acetonitrile to give 1.90 g of the product as an off-white solid.

Step 4: 1-(4-Methoxy-benzyl)-3-(6-trifluoromethyl-pyridine-3-carbonyl)-1H-quinolin-4-one Experimental conditions analogous to those described for Step 6 of Example 60, from 864 mg (2.45 mmol) of 1-(4-methoxy-benzyl)-4-oxo-1,4-dihydro-quinoline-3-carboxylic acid methoxy-methyl-amide in 8 mL THF and 1.47 g (5.40 mmol) of 2-ethyl-5-iodo-pyridine in 8 mL THF with 2.82 mL 2M isopropylmagnesium chloride. Yield: 800 mg of a white powder. LC-MSD, m/z for $C_{24}H_{17}F_3N_2O_3$ [M+H]+=439.1; HPLC retention time: 2.6 min.

Example 140

Preparation of 1-(3-Bromo-benzyl)-3-(6-trifluoromethyl-pyridine-3-carbonyl)-1H-quinolin-4-one

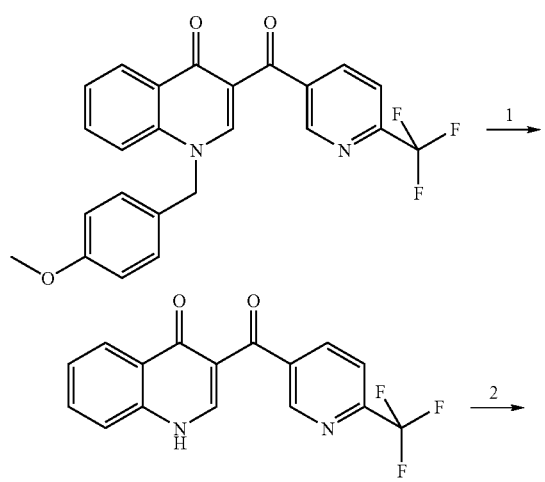

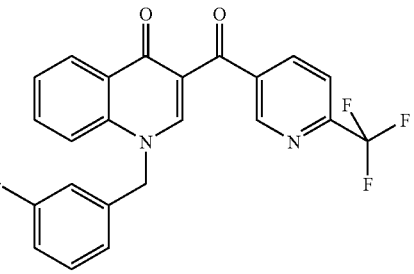

Step 1: 3-(6-Trifluoromethyl-pyridine-3-carbonyl)-1H-quinolin-4-one 800 mg (1.83 mmol) of 1-(4-methoxy-benzyl)-3-(6-trifluoromethyl-pyridine-3-carbonyl)-1H-quinolin-4-one was heated in a sealed tube to 120° C. in 15 mL of 4 M HCl in dioxane for 20 h. The solution was evaporated and the residue ultrasonicated in 20 mL saturated aqueous $NaHCO_3$. Filtration of the solid followed by aqueous wash, DCM wash and drying gave 340 mg of a light-brown powder. LC-MSD, m/z for $C_{16}H_9F_3N_2O_2$ [M+H]+=319.0; HPLC retention time: 1.8 min.

Step 2: 1-(3-Bromo-benzyl)-3-(6-trifluoromethyl-pyridine-3-carbonyl)-1H-quinolin-4-one Experimental conditions analogous to those described for Step 6 of Example 60, from 71 mg (0.22 mmol) of 3-(6-trifluoromethyl-pyridine-3-carbonyl)-1H-quinolin-4-one, 11 mg (0.27 mmol) of 60% sodium hydride, 67 mg (0.27 mmol) of 3-bromobenzyl bromide and 1 mL of N,N-dimethylformamide. Yield: 85 mg of a white solid: LC-MSD, m/z for $C_{23}H_{14}BrF_3N_2O_2$ [M+H]+=487.0, 489.0; HPLC retention time: 2.7 min.

Example 141

Preparation of 3-(6-Dimethylamino-pyridine-3-carbonyl)-1-(6-methyl-pyridin-2-ylmethyl)-1H-quinolin-4-one

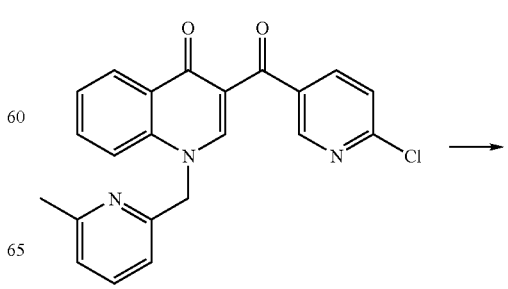

-continued

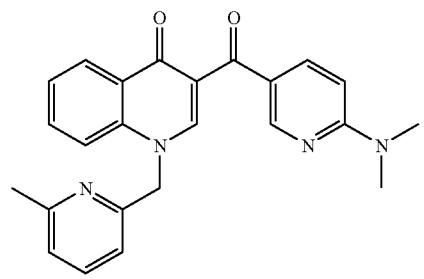

95 mg (0.37 mmol) of 3-(6-chloro-pyridine-3-carbonyl)-1-(6-methyl-pyridin-2-ylmethyl)-1H-quinolin-4-one was heated with 3 mL of 2 M solution of dimethylaamine in THF in a sealed vessel at 70° C. for 2 h. The reaction mixture was evaporated and purified by flash chromatography to give 88 mg of a yellow powder. LC-MSD, m/z for $C_{24}H_{22}N_4O_2$ [M+H]+=399.1; HPLC retention time: 0.5 min.

Example 142

Preparation of 1-(3-Chloro-benzyl)-3-(6-dimethylamino-pyridine-3-carbonyl)-1H-quinolin-4-one

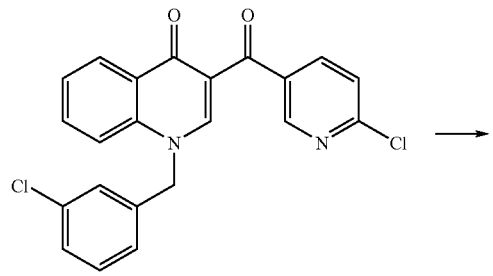

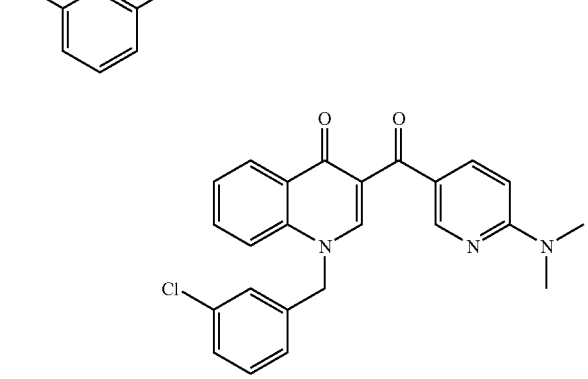

Experimental conditions analogous to those described for Example 141, from 151 mg (0.37 mmol) of 1-(3-chloro-benzyl)-3-(6-chloro-pyridine-3-carbonyl)-1H-quinolin-4-one and 2 mL 2 M dimethylamine solution. Yield: 127 mg of a yellow powder. LC-MSD, m/z for $C_{24}H_{20}ClN_3O_2$ [M+H]+=418.1, 420.1; HPLC retention time: 1.6 min.

Example 143

Preparation of 1-(6-Bromo-pyridin-2-ylmethyl)-3-(6-dimethylamino-pyridine-3-carbonyl)-1H-quinolin-4-one

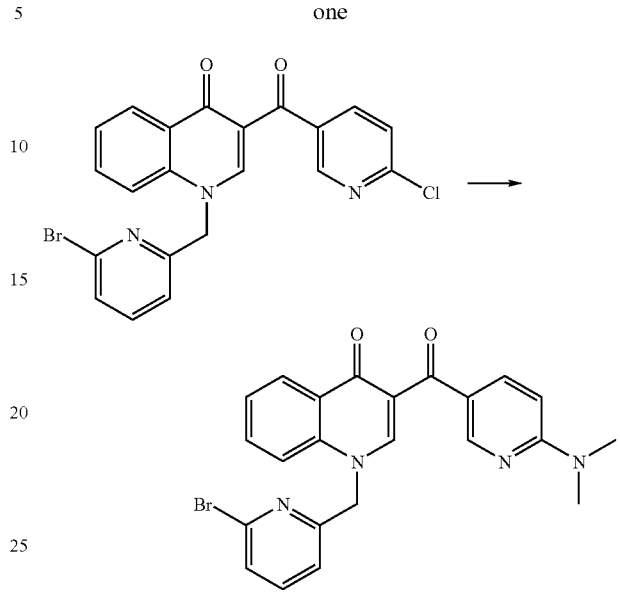

Experimental conditions analogous to those described for Example 141, from 42 mg (0.092 mmol) of 1-(6-bromo-pyridin-2-ylmethyl)-3-(6-chloro-pyridine-3-carbonyl)-1H-quinolin-4-one and 1 mL 2 M dimethylamine solution. Yield: 17 mg of a yellow powder. LC-MSD, m/z for $C_{23}H_{19}BrN_4O_2$ [M+H]+=463.0, 465.0; HPLC retention time: 0.6 min.

Example 144

Preparation of 1-(6-Bromo-pyridin-2-ylmethyl)-3-(6-pyrrolidin-1-yl-pyridine-3-carbonyl)-1H-quinolin-4-one

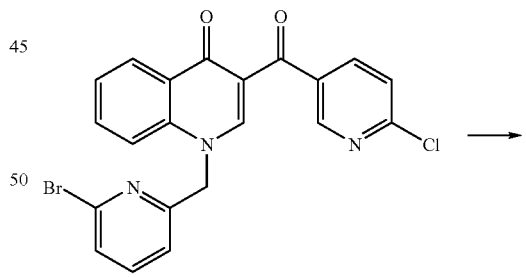

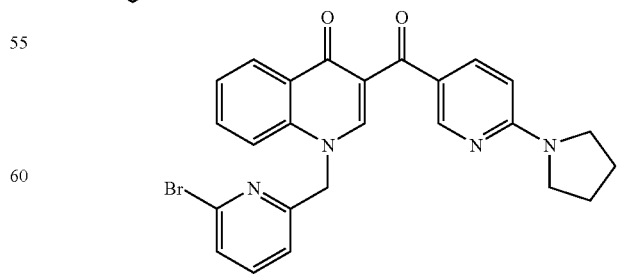

Experimental conditions analogous to those described for Example 141, from 103 mg (0.23 mmol) of 1-(6-bromopyridin-2-ylmethyl)-3-(6-chloro-pyridine-3-carbonyl)-1H-quinolin-4-one and 0.5 mL pyrrolidine in 2 mL THF. Yield: 50 mg of a yellow powder. LC-MSD, m/z for C$_{25}$H$_{21}$BrN$_4$O$_2$ [M+H]+=489.0, 491.0; HPLC retention time: 1.1 min.

Example 145

Preparation of 1-(6-Bromo-pyridin-2-ylmethyl)-3-(6-diethylamino-pyridine-3-carbonyl)-1H-quinolin-4-one

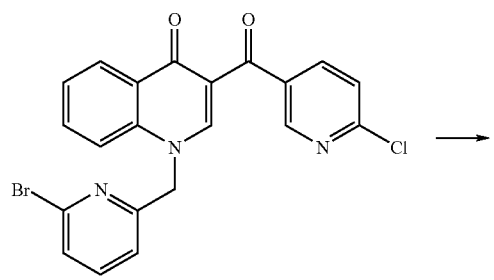

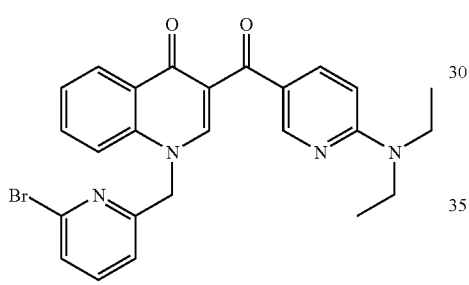

Experimental conditions analogous to those described for Example 141, from 97 mg (0.21 mmol) of 1-(6-bromo-pyridin-2-ylmethyl)-3-(6-chloro-pyridine-3-carbonyl)-1H-quinolin-4-one and 3 mL diethylamine in 7 mL THF. Yield: 50 mg of a yellow powder. LC-MSD, m/z for C$_{25}$H$_{23}$BrN$_4$O$_2$ [M+H]+=491.0, 493.0; HPLC retention time: 2.9 min.

Example 146

Preparation of 3-(6-Amino-pyridine-3-carbonyl)-1-(6-bromo-pyridin-2-ylmethyl)-1H-quinolin-4-one

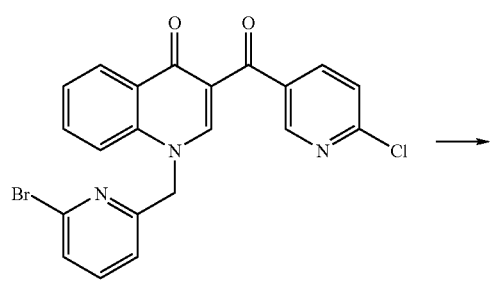

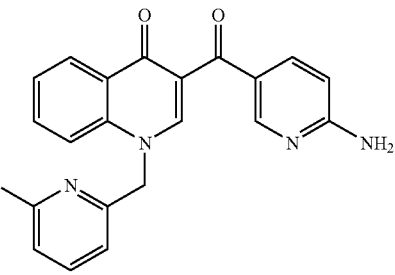

100 mg (0.22 mmol) of 1-(6-bromo-pyridin-2-ylmethyl)-3-(6-chloro-pyridine-3-carbonyl)-1H-quinolin-4-one and 72 mg (1.1 mmol) of sodium azide were heated at 100° C. in 1 mL of DMF for 1 h. The temperature of the solution was lowered to 70° C. and 1 mL of water was added, followed by 214 uL (155 mg, 1.54 mmol) of triethylamine and 378 mg (1.32 mmol) of tris(2-carboxyethyl)phosphine hydrochloride. After 1 h of reaction time the mixture was purified on reverse-phase HPLC, followed by flash chromatography to give 60 mg of a yellow powder. LC-MSD, m/z for C$_{21}$H$_{15}$BrN$_4$O$_2$ [M+H]+=435.0, 437.0; HPLC retention time: 0.6 min.

Example 147

Preparation of 1-(6-Bromo-pyridin-2-ylmethyl)-3-(6-methoxy-pyridine-3-carbonyl)-1H-quinolin-4-one

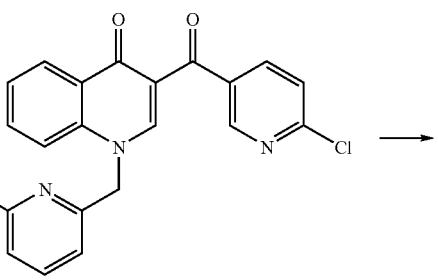

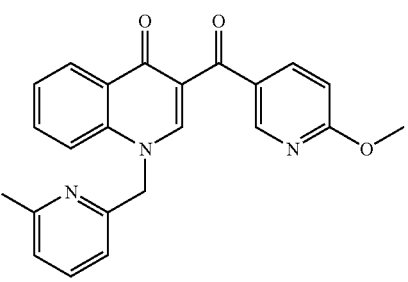

Experimental conditions analogous to those described for Example 141, from 38 mg (0.084 mmol) of 1-(6-bromo-pyridin-2-ylmethyl)-3-(6-chloro-pyridine-3-carbonyl)-1H-quinolin-4-one, 90 mg (1.67 mmol) of sodium methoxide and 1 mL dry methanol. Yield: 19 mg of a white powder. LC-MSD, m/z for C$_{22}$H$_{16}$BrN$_3$O$_3$ [M+H]+=450.0, 452.0; HPLC retention time: 2.3 min.

Example 148

Preparation of 1-(6-Bromo-pyridin-2-ylmethyl)-3-(6-oxo-1,6-dihydro-pyridine-3-carbonyl)-1H-quinolin-4-one

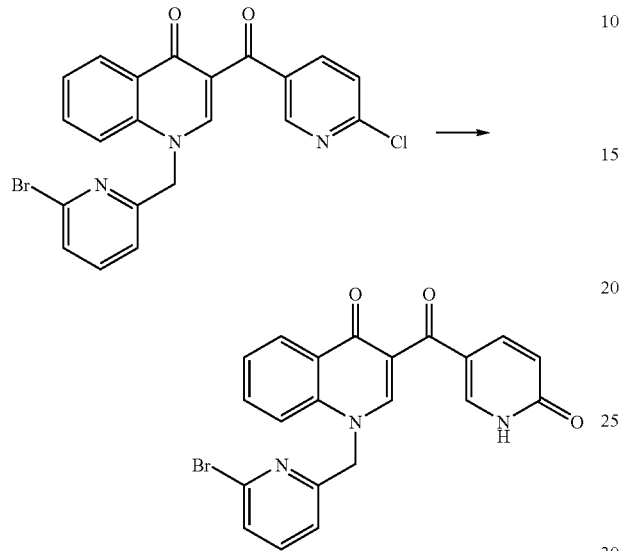

70 mg (0.22 mmol) of 1-(6-bromo-pyridin-2-ylmethyl)-3-(6-chloro-pyridine-3-carbonyl)-1H-quinolin-4-one was heated at 100° C. in 2 mL of concentrated aqueous hydrobromic acid in a sealed tube for 20 h. The solution was evaporated and purified on reverse-phase HPLC and free-based to give 36 mg of a yellow powder. LC-MSD, m/z for $C_{21}H_{14}BrN_3O_3$ [M+H]+=436.0, 438.0; HPLC retention time: 1.4 min.

Example 149

Preparation of 7-(3,4-dimethyl-benzoyl)-5-pyridin-2-ylmethyl-5H-[1,3]dioxolo[4,5-g]quinolin-8-one

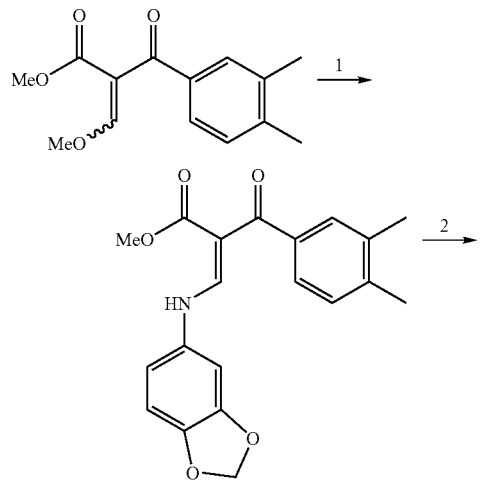

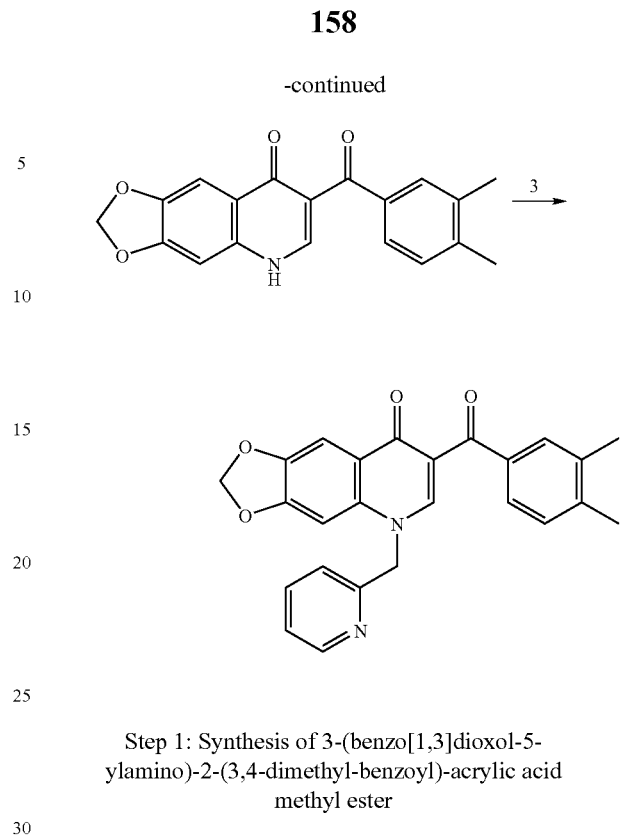

Step 1: Synthesis of 3-(benzo[1,3]dioxol-5-ylamino)-2-(3,4-dimethyl-benzoyl)-acrylic acid methyl ester Experimental conditions analogous to those described for Step 1 of Example 1, from crude 2-(3,4-dimethyl-benzoyl)-3-methoxy-acrylic acid methyl ester (4.03 g, 16.3 mmol) and benzo[1,3]dioxol-5-ylamine (2.45 g, 17.9 mmol). Yield: 3.14 g of a yellow crystalline solid: LC-MSD, m/z for $C_{20}H_{20}NO_5$ [M+H]+=354.4; HPLC retention time: 2.8 min.

Step 2: Synthesis of 7-(3,4-dimethyl-benzoyl)-5H-[1,3]dioxolo[4,5-g]quinolin-8-one Experimental conditions analogous to those described for Step 2 of Example 1, from 3-(benzo[1,3]dioxol-5-ylamino)-2-(3,4-dimethyl-benzoyl)-acrylic acid methyl ester (1.69 g, 4.78 mmol). Yield: 0.95 g of off-white crystals: LC-MSD, m/z for $C_{19}H_{15}NO_4$ [M+H]+=322.4; HPLC retention time: 1.7 min.

Step 3: Synthesis of 7-(3,4-dimethyl-benzoyl)-5-pyridin-2-ylmethyl-5H-[1,3]dioxolo[4,5-g]quinolin-8-one Experimental conditions analogous to those described for Step 3 of Example 1, from 71 mg (0.22 mmol) of 7-(3,4-dimethyl-benzoyl)-5H-[1,3]dioxolo[4,5-g]quinolin-8-one, 23 mg of 60% sodium hydride, 72 mg of 2-bromomethylpyridine hydrobromide and 1.3 mL of N,N-dimethylformamide. Yield: 75 mg of a white solid: LC-MSD, m/z for $C_{25}H_{20}N_2O_4$ [M+H]+=413.5; HPLC retention time: 2.1 min.

Example 150

Preparation of 7-(3,4-Dimethyl-benzoyl)-5-pyridin-3-ylmethyl-5H-[1,3]dioxolo[4,5-g]quinolin-8-one

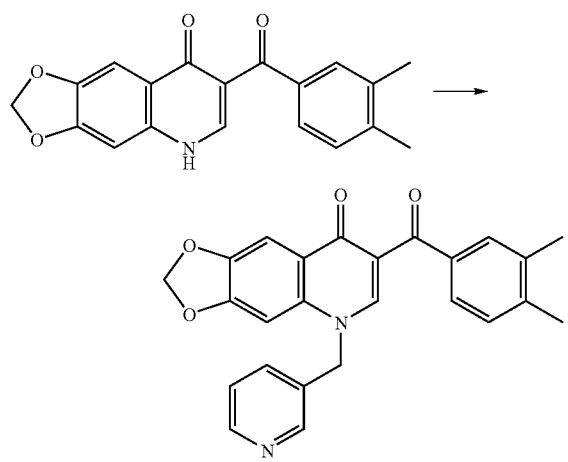

Experimental conditions analogous to those described for Step 3 of Example 1, from 71 mg (0.22 mmol) of 7-(3,4-dimethyl-benzoyl)-5H-[1,3]dioxolo[4,5-g]quinolin-8-one, 23 mg of 60% sodium hydride, 72 mg of 3-bromomethylpyridine hydrobromide and 1.3 mL of N,N-dimethylformamide. Yield: 45 mg of a white solid: LC-MSD, m/z for $C_{25}H_{20}N_2O_4$ [M+H]+=413.5; HPLC retention time: 1.5 min.

Example 151

Preparation of 7-(3,4-Dimethyl-benzoyl)-5-pyridin-4-ylmethyl-5H-[1,3]dioxolo[4,5-g]quinolin-8-one

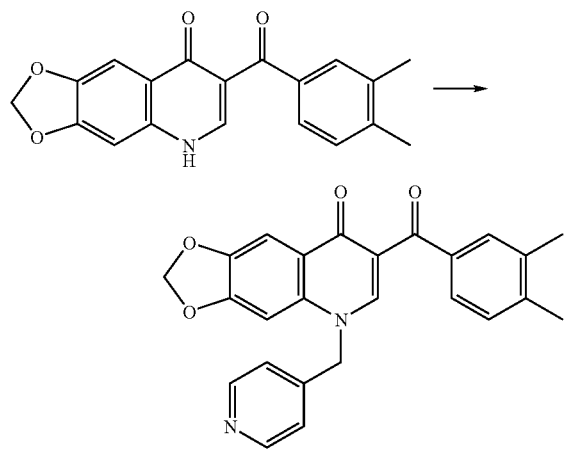

Experimental conditions analogous to those described for Step 3 of Example 1, from 71 mg (0.22 mmol) of 7-(3,4-dimethyl-benzoyl)-5H-[1,3]dioxolo[4,5-g]quinolin-8-one, 23 mg of 60% sodium hydride, 72 mg of 4-bromomethylpyridine hydrobromide and 1.3 mL of N,N-dimethylformamide. Yield: 61 mg of a white solid: LC-MSD, m/z for $C_{25}H_{20}N_2O_4$ [M+H]+=413.5; HPLC retention time: 1.2 min.

Example 152

Preparation of 8-(3,4-Dimethyl-benzoyl)-6-pyridin-2-ylmethyl-2,3-dihydro-6H-[1,4]dioxino[2,3-g]quinolin-9-one

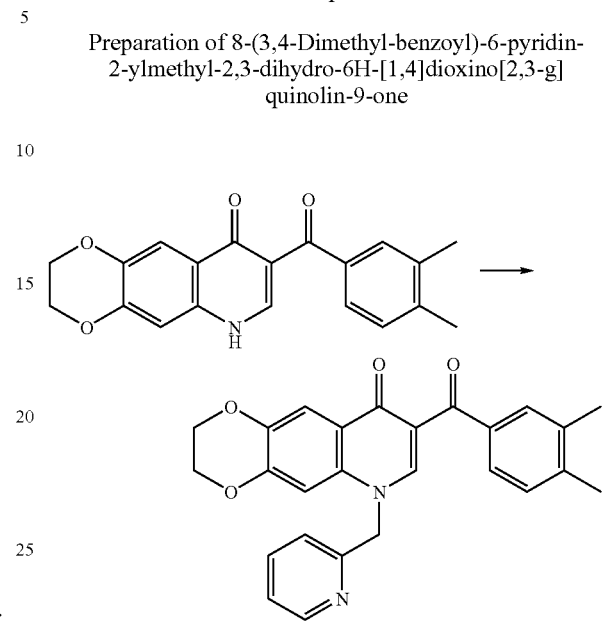

Experimental conditions analogous to those described for Step 3 of Example 1, from 58 mg (0.17 mmol) of 8-(3,4-dimethyl-benzoyl)-2,3-dihydro-6H-[1,4]dioxino[2,3-g]quinolin-9-one, 18 mg of 60% sodium hydride, 57 mg of 2-bromomethylpyridine hydrobromide and 1.2 mL of N,N-dimethylformamide. Yield: 63 mg of a white solid: LC-MSD, m/z for $C_{26}H_{22}N_2O_4$ [M+H]+=427.5; HPLC retention time: 2.1 min.

Example 153

Preparation of 8-(3,4-Dimethyl-benzoyl)-6-pyridin-3-ylmethyl-2,3-dihydro-6H-[1,4]dioxino[2,3-g]quinolin-9-one

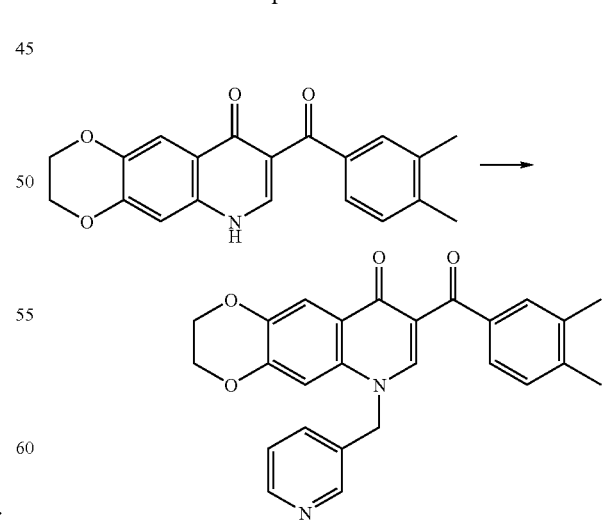

Experimental conditions analogous to those described for Step 3 of Example 1, from 58 mg (0.17 mmol) of 8-(3,4-dimethyl-benzoyl)-2,3-dihydro-6H-[1,4]dioxino[2,3-g]

quinolin-9-one, 18 mg of 60% sodium hydride, 57 mg of 3-bromomethylpyridine hydrobromide and 1.2 mL of N,N-dimethylformamide. Yield: 55 mg of a white solid: LC-MSD, m/z for $C_{26}H_{22}N_2O_4$ [M+H]+=427.5; HPLC retention time: 1.6 min.

Example 154

Preparation of 8-(3,4-Dimethyl-benzoyl)-6-pyridin-4-ylmethyl-2,3-dihydro-6H-[1,4]dioxino[2,3-g]quinolin-9-one

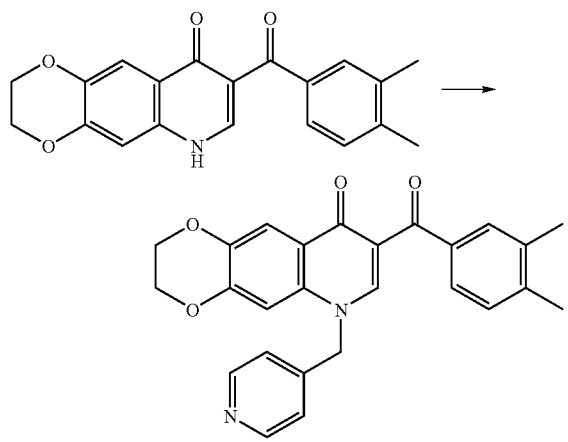

Experimental conditions analogous to those described for Step 3 of Example 1, from 58 mg (0.17 mmol) of 8-(3,4-dimethyl-benzoyl)-2,3-dihydro-6H-[1,4]dioxino[2,3-g]quinolin-9-one, 18 mg of 60% sodium hydride, 57 mg of 4-bromomethylpyridine hydrobromide and 1.2 mL of N,N-dimethylformamide. Yield: 52 mg of a white solid: LC-MSD, m/z for $C_{26}H_{22}N_2O_4$ [M+H]+=427.5; HPLC retention time: 1.4 min.

Example 156

Preparation of 1-(6-bromo-pyridin-2-ylmethyl)-3-(3,4-dimethyl-benzoyl)-2-methyl-1H-quinolin-4-one

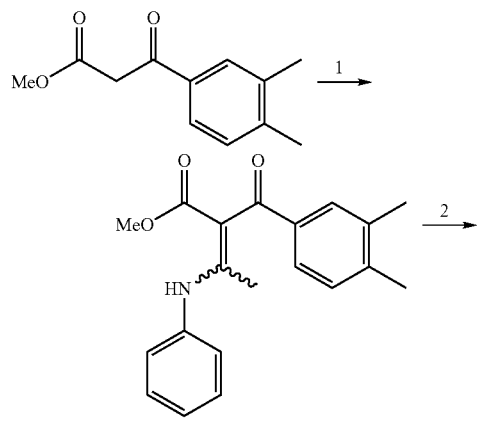

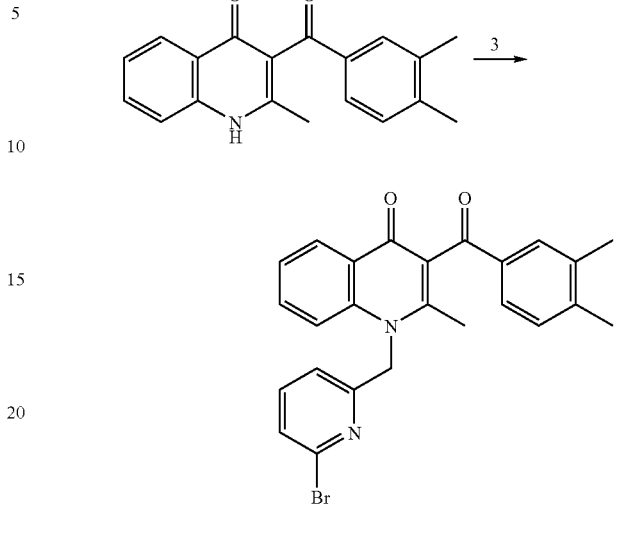

Step 1: Synthesis of 2-(3,4-dimethyl-benzoyl)-3-phenylamino-but-2-enoic acid methyl ester 10.6 g (51.4 mmol) of 3-(3,4-dimethyl-phenyl)-3-oxo-propionic acid methyl ester was heated with 12.4 g (103 mmol) of trimethyl orthoacetate and 5.51 g (54.0 mmol) of acetic anhydride at 115° C. for 3 days. The mixture was evaporated and combined with 4.69 mL (51.4 mmol) of aniline. Yield: 8.60 g of a yellow solid (after flash chromatography contains inseparable 3-(3,4-dimethyl-phenyl)-3-oxo-propionic acid methyl ester): LC-MSD, m/z for $C_{20}H_{21}NO_3$ [M+H]+=324.2; HPLC retention time: 2.1 min.

Step 2: Synthesis of 3-(3,4-Dimethyl-benzoyl)-2-methyl-1H-quinolin-4-one

Experimental conditions analogous to those described for Step 2 of Example 1, from 2-(3,4-dimethyl-benzoyl)-3-phenylamino-but-2-enoic acid methyl ester (8.60 g, 26.6 mmol). Yield: 0.92 g of off-white crystals after recrystallization from hot methanol: LC-MSD, m/z for $C_{19}H_{17}NO_2$ [M+H]+=292.1; HPLC retention time: 1.7 min.

Step 3: Synthesis of 1-(6-bromo-pyridin-2-ylmethyl)-3-(3,4-dimethyl-benzoyl)-2-methyl-1H-quinolin-4-one Experimental conditions analogous to those described for Step 3 of Example 1, from 57 mg (0.20 mmol) of 3-(3,4-dimethyl-benzoyl)-2-methyl-1H-quinolin-4-one, 9 mg (0.24 mmol) of 60% sodium hydride, 59 mg of 2-bromo-6-bromomethyl-pyridine and 0.7 mL of N,N-dimethylformamide. Yield: 44 mg of a white solid: LC-MSD, m/z for $C_{25}H_{21}BrN_2O_2$ [M+H]+=461.1, 463.1; HPLC retention time: 2.7 min.

Example 157

Preparation of 1-(6-bromo-pyridin-2-ylmethyl)-3-(3,4-dimethyl-benzoyl)-6,7-difluoro-1H-quinolin-4-one

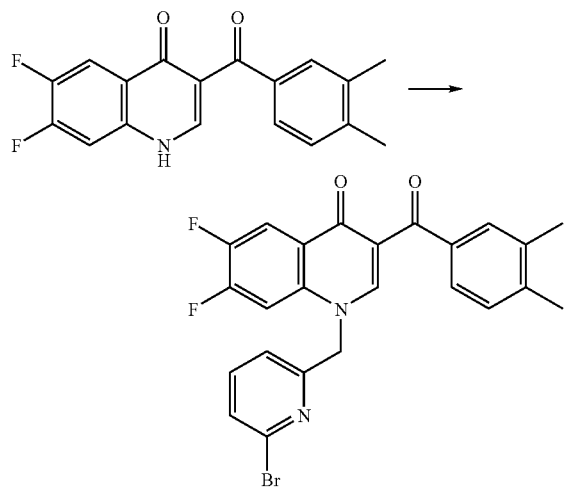

Experimental conditions analogous to those described for Step 3 of Example 1, from 74 mg (0.24 mmol) of 3-(3,4-dimethyl-benzoyl)-6,7-difluoro-1H-quinolin-4-one, 71 mg (0.28 mmol) of 2-bromo-6-bromomethyl-pyridine, 0.57 mL of 0.5M toluene solution of potassium bis(trimethylsilyl)amide and 2 mL of THF. Yield: 73 mg of a white solid: LC-MSD, m/z for $C_{24}H_{17}BrF_2N_2O_2$ [M+H]+=483.4, 485.4; HPLC retention time: 2.6 min.

Example 158

Preparation of 1-(6-bromo-pyridin-2-ylmethyl)-3-(5,6-dimethyl-pyridine-3-carbonyl)-6-fluoro-1H-quinolin-4-one

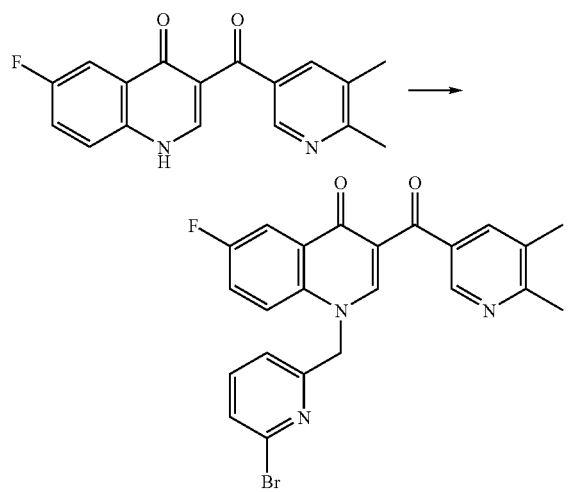

Experimental conditions analogous to those described for Step 3 of Example 1, from 50 mg (0.17 mmol) of 3-(5,6-dimethyl-pyridine-3-carbonyl)-6-fluoro-1H-quinolin-4-one, 8 mg (0.20 mmol) of 60% sodium hydride and 51 mg (0.20 mmol) of 2-bromo-6-bromomethyl-pyridine and 0.7 mL of N,N-dimethylformamide. Yield: 38 mg of a white solid: LC-MSD, m/z for $C_{23}H_{17}BrFN_3O_2$ [M+H]+=466.2, 468.1; HPLC retention time: 2.1 min.

Example 159

Preparation of 3-(5,6-Dimethyl-pyridine-3-carbonyl)-6-fluoro-1-(6-methyl-pyridin-2-ylmethyl)-1H-quinolin-4-one

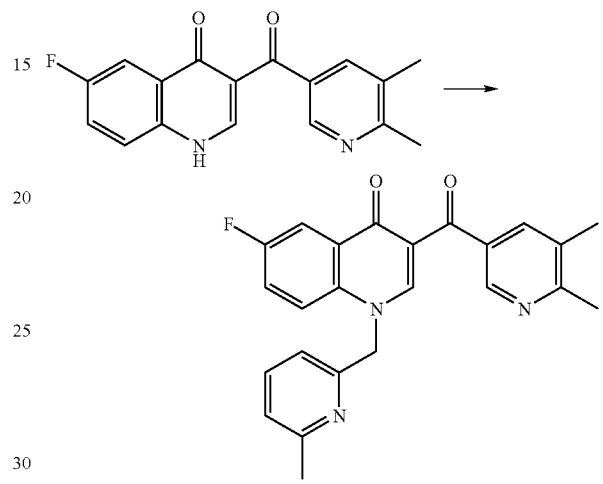

Experimental conditions analogous to those described for Step 3 of Example 1, from 71 mg (0.24 mmol) 3-(5,6-dimethyl-pyridine-3-carbonyl)-6-fluoro-1H-quinolin-4-one, 12 mg (0.29 mmol) of 60% sodium hydride, 53 mg (0.29 mmol) of 2-bromomethyl-6-methyl-pyridine and 1 mL of N,N-dimethylformamide. Yield: 67 mg of a white solid: LC-MSD, m/z for $C_{24}H_{20}FN_3O_2$ [M+H]+=402.1; HPLC retention time: 0.7 min.

Example 160

Preparation of 3-(3,4-Dimethyl-benzoyl)-1-pyridin-2-ylmethyl-6-trifluoromethyl-1H-quinolin-4-one

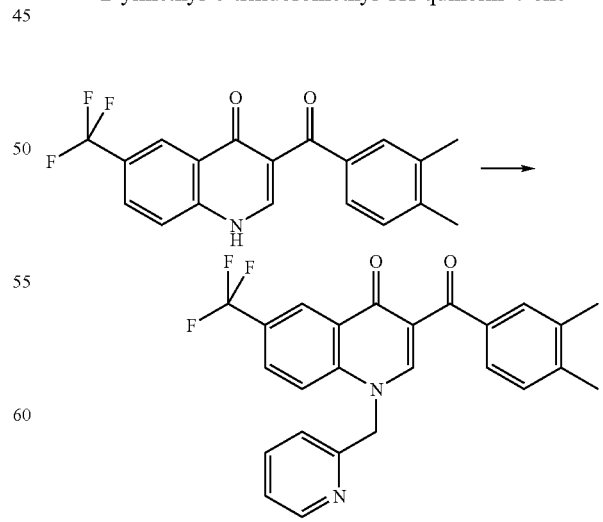

Experimental conditions analogous to those described for Step 3 of Example 1, from 55 mg (0.16 mmol) of 3-(3,4- dimethyl-benzoyl)-6-trifluoromethyl-1H-quinolin-4-one, 18 mg of 60% sodium hydride, 52 mg of 2-bromomethylpyridine hydrobromide and 1 mL of N,N-dimethylformamide. Yield: 49 mg of a white solid: LC-MSD, m/z for $C_{25}H_{19}F_2N_2O_2$ [M+H]+=437.5; HPLC retention time: 2.6 min.

Example 161

Preparation of 3-(3,4-Dimethyl-benzoyl)-1-(5-trifluoromethyl-furan-2-ylmethyl)-1H-quinolin-4-one

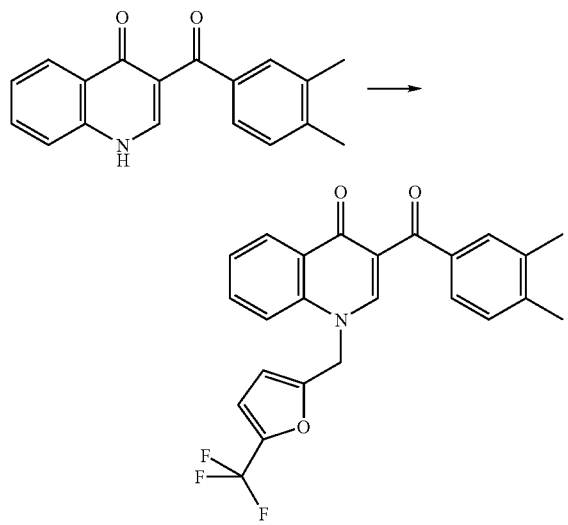

Experimental conditions analogous to those described for Step 3 of Example 1, from 55 mg (0.20 mmol) of 3-(3,4-dimethyl-benzoyl)-1H-quinolin-4-one, 10 mg of 60% sodium hydride, 55 mg (0.24 mmol) 2-bromomethyl-5-trifluoromethyl-furan and 0.7 mL of N,N-dimethylformamide. Yield: 70 mg of a white solid: LC-MSD, m/z for $C_{24}H_{18}F_3NO_3$ [M+H]+=426.4; HPLC retention time: 2.7 min.

Example 162

Preparation of 3-(3,4-Dimethyl-benzoyl)-1-(6-methoxy-pyridin-2-ylmethyl)-1H-quinolin-4-one

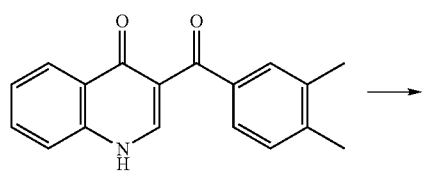

-continued

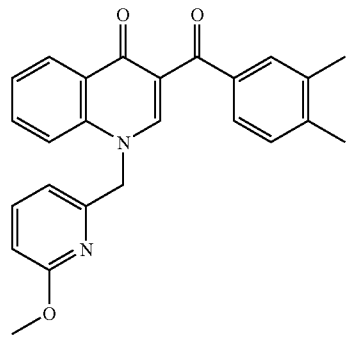

Experimental conditions analogous to those described for Step 3 of Example 1, from 50 mg (0.18 mmol) of 3-(3,4-dimethyl-benzoyl)-1H-quinolin-4-one, 9 mg (0.21 mmol) of 60% sodium hydride, 44 mg (0.22 mmol) 2-bromomethyl-6-methoxy-pyridine and 0.8 mL of N,N-dimethylformamide. Yield: 45 mg of a white solid: LC-MSD, m/z for $C_{25}H_{22}N_2O_3$ [M+H]+=399.3; HPLC retention time: 2.8 min.

Example 163

Preparation of 3-(3,4-Dimethyl-benzoyl)-1-(6-fluoro-pyridin-2-ylmethyl)-1H-quinolin-4-one Experimental conditions analogous to those described for Step 3 of Example 1, from 49 mg (0.18 mmol) of 3-(3,4-dimethyl-benzoyl)-1H-quinolin-4-one, 8 mg (0.21 mmol) of 60% sodium hydride, 40 mg (0.21 mmol) 2-bromomethyl-6-fluoro-pyridine and 0.8 mL of N,N-dimethylformamide. Yield: 28 mg of a white solid: LC-MSD, m/z for $C_{24}H_{19}FN_2O_2$ [M+H]+=387.3; HPLC retention time: 2.6 min.

Example 164

Preparation of 3-(3,4-Dimethyl-benzoyl)-1-(6-oxo-1,6-dihydro-pyridin-2-ylmethyl)-1H-quinolin-4-one

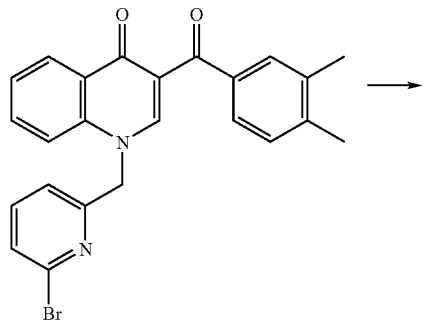

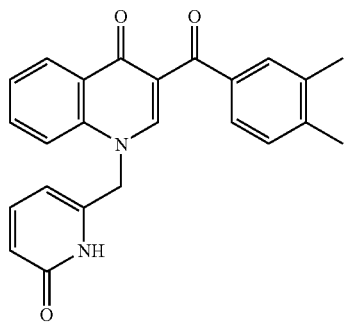

182 mg (0.41 mmol) of 1-(6-bromo-pyridin-2-ylmethyl)-3-(3,4-dimethyl-benzoyl)-1H-quinolin-4-one in a solution of 3 mL acetic acid and 3 mL concentrated aqueous hydrochloric acid was heated in a sealed tube at 150° C. for 24 h. Purification on reverse-phase HPLC and free-basing gave 95 mg of a white solid: LC-MSD, m/z for $C_{24}H_{20}N_2O_3$ [M+H]+=385.1; HPLC retention time: 0.4 min.

Example 165

Preparation of 1-(6-Bromo-pyridin-2-ylmethyl)-3-(4-methanesulfanyl-benzoyl)-1H-quinolin-4-one

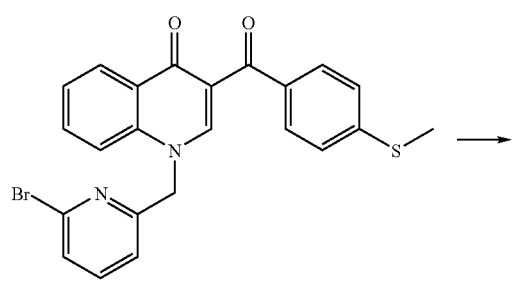

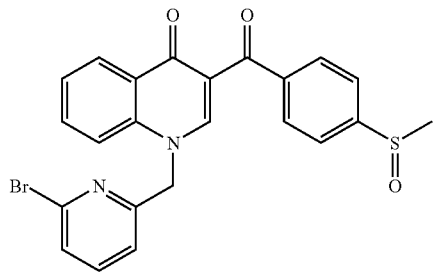

42 mg (0.09 mmol) of 1-(6-bromo-pyridin-2-ylmethyl)-3-(4-methylsulfanyl-benzoyl)-1H-quinolin-4-one was dissolved in 1 mL acetic acid followed by the addition of 16 uL of 35% aqueous hydrogen peroxide. The reaction was stirred at r.t for 20 h and evaporated. Purification using flash chromatography gave 33 mg of a white solid. LC-MSD, m/z for $C_{23}H_{17}BrN_2O_3S$ [M+H]+=481.0, 483.0; HPLC retention time: 1.8 min.

Example 166

Preparation of 1-(6-Amino-pyridin-2-ylmethyl)-3-(5,6-dimethyl-pyridine-2-carbonyl)-1H-quinolin-4-one

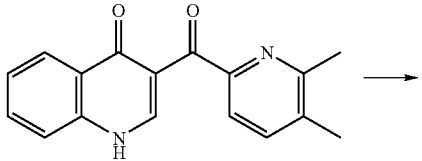

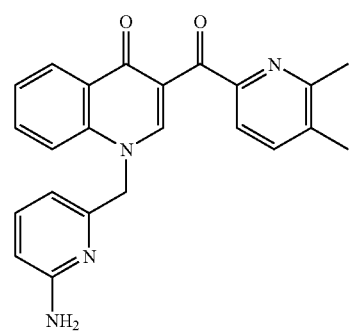

Experimental conditions analogous to those described for Step 3 of Example 1, from 127 mg (0.46 mmol) of 3-(5,6-dimethyl-pyridine-2-carbonyl)-1H-quinolin-4-one, 22 mg (0.55 mmol) of 60% sodium hydride, 155 mg (0.55 mmol) of N-(6-bromomethyl-pyridin-2-yl)-2,2,2-trifluoro-acetamide and 1 mL of N,N-dimethylformamide. The 130 mg of trifluoroacetamide product were heated to 60° C. in a mixture of 1 mL of methanol and 4 mL of diethylamine for 3 h, then overnight at 45° C. The product was filtered off and washed with a small amount of DCM. Yield: 36 mg of a white solid: LC-MSD, m/z for $C_{23}H_{20}N_4O_2$ [M+H]+=385.2; HPLC retention time: 0.8 min.

Example 167

Preparation of 1-(6-Amino-pyridin-2-ylmethyl)-3-(5,6-dimethyl-pyridine-3-carbonyl)-1H-quinolin-4-one

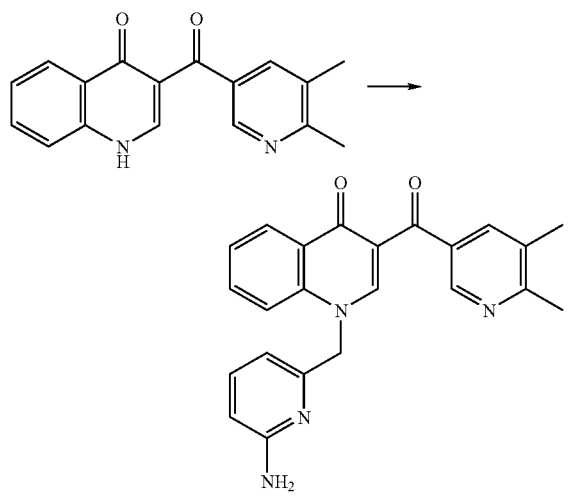

Experimental conditions analogous to those described for Step 3 of Example 1, from 75 mg (0.27 mmol) of 3-(5,6-dimethyl-pyridine-3-carbonyl)-1H-quinolin-4-one, 13 mg (0.32 mmol) of 60% sodium hydride, 92 mg (0.32 mmol) of N-(6-bromomethyl-pyridin-2-yl)-2,2,2-trifluoro-acetamide and 0.7 mL of N,N-dimethylformamide. Yield: 20 mg of a white solid: LC-MSD, m/z for $C_{23}H_{20}N_4O_2$ [M+H]+=385.1; HPLC retention time: 0.3 min.

Example 168

Preparation of 3-(5,6-Dimethyl-pyridine-2-carbonyl)-1-(6-methyl-pyridin-2-ylmethyl)-1H-quinolin-4-one

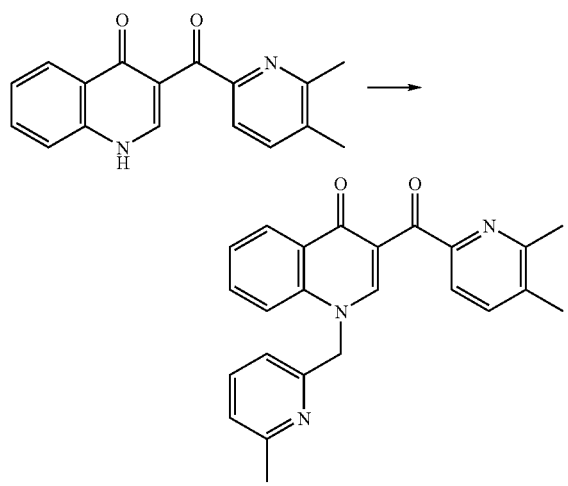

Experimental conditions analogous to those described for Step 3 of Example 1, from 95 mg (0.34 mmol) of 3-(5,6-dimethyl-pyridine-2-carbonyl)-1H-quinolin-4-one, 16 mg (0.41 mmol) of 60% sodium hydride, 77 mg (0.41 mmol) of 2-bromomethyl-6-methyl-pyridine and 1 mL of N,N-dimethylformamide. Yield: 14 mg of a white solid: LC-MSD, m/z for $C_{24}H_{21}N_3O_2$ [M+H]+=384.1; HPLC retention time: 1.9 min.

Example 169

Preparation of 1-[1-(6-Bromo-pyridin-2-yl)-ethyl]-3-(5,6-dimethyl-pyridine-3-carbonyl)-1H-quinolin-4-one

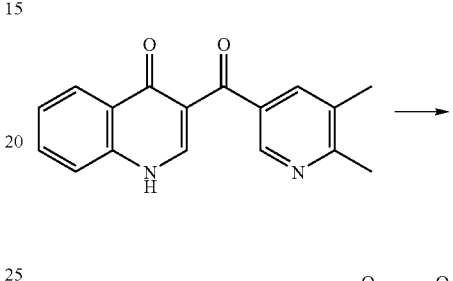

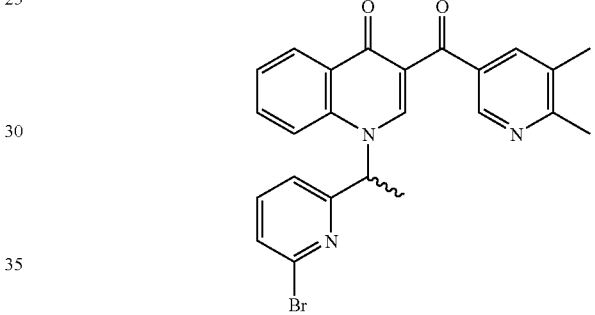

Experimental conditions analogous to those described for Step 3 of Example 1, from 55 mg (0.20 mmol) of 3-(5,6-dimethyl-pyridine-3-carbonyl)-1H-quinolin-4-one, 10 mg (0.26 mmol) of 60% sodium hydride, 68 mg (0.26 mmol) of 2-bromo-6-(1-bromo-ethyl)-pyridine and 0.7 mL of N,N-dimethylformamide. Yield: 24 mg of a white solid: LC-MSD, m/z for $C_{24}H_{20}BrN_3O_2$ [M+H]+=462.0, 464.0; HPLC retention time: 1.4 min.

Example 170

Preparation of 1-[1-(6-Bromo-pyridin-2-yl)-ethyl]-3-(5,6-dimethyl-pyridine-2-carbonyl)-1H-quinolin-4-one

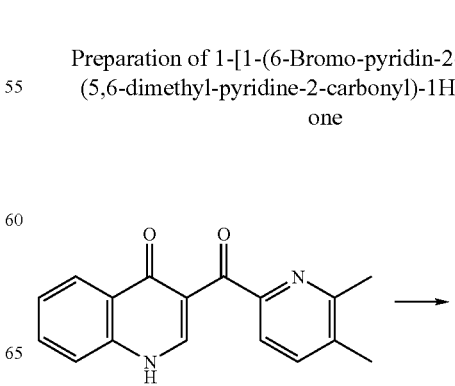

-continued

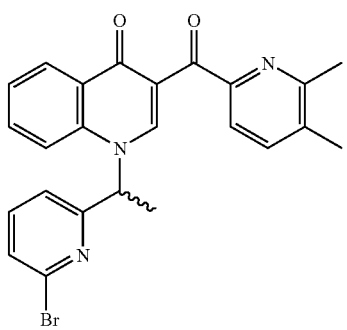

Experimental conditions analogous to those described for Step 3 of Example 1, from 50 mg (0.18 mmol) of 3-(5,6-dimethyl-pyridine-2-carbonyl)-1H-quinolin-4-one, 9 mg (0.22 mmol) of 60% sodium hydride, 57 mg (0.22 mmol) of 2-bromo-6-(1-bromo-ethyl)-pyridine and 0.7 mL of N,N-dimethylformamide. Yield: 4.4 mg of a white solid: LC-MSD, m/z for $C_{24}H_{20}BrN_3O_2$ [M+H]+=462.0, 464.0; HPLC retention time: 2.0 min.

Example 171

Preparation of 1-[1-(6-Bromo-pyridin-2-yl)-ethyl]-3-(3,4-dimethyl-benzoyl)-1H-quinolin-4-one

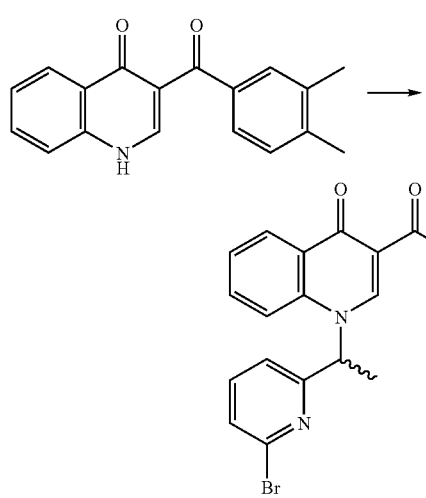

Experimental conditions analogous to those described for Step 3 of Example 1, from 52 mg (0.19 mmol) of 3-(3,4-dimethyl-benzoyl)-1H-quinolin-4-one, 9 mg (0.23 mmol) of 60% sodium hydride, 60 mg (0.23 mmol) of 2-bromo-6-(1-bromo-ethyl)-pyridine and 0.7 mL of N,N-dimethylformamide. Yield: 32 mg of a white solid: LC-MSD, m/z for $C_{25}H_{21}BrN_2O_2$ [M+H]+=461.0, 463.0; HPLC retention time: 2.6 min.

Example 172

Preparation of 3-(5,6-Dimethyl-pyridine-3-carbonyl)-1-(6-trifluoromethyl-pyridin-2-ylmethyl)-1H-quinolin-4-one

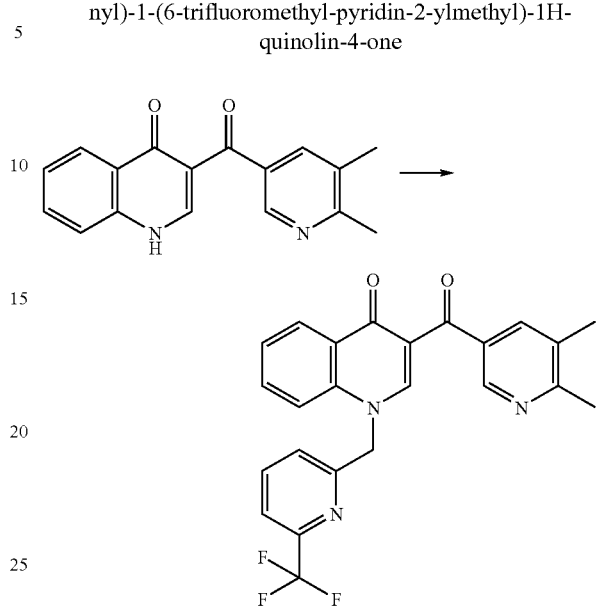

Experimental conditions analogous to those described for Step 3 of Example 1, from 60 mg (0.22 mmol) of 3-(5,6-dimethyl-pyridine-3-carbonyl)-1H-quinolin-4-one, 10 mg (0.26 mmol) of 60% sodium hydride, 62 mg (0.26 mmol) of 2-bromomethyl-6-trifluoromethyl-pyridine and 0.7 mL of N,N-dimethylformamide. Yield: 29 mg of a white solid: LC-MSD, m/z for $C_{24}H_{18}F_3N_3O_2$ [M+H]+=438.1; HPLC retention time: 1.4 min.

Example 173

Preparation of 3-(5,6-Dimethyl-pyridine-2-carbonyl)-1-(6-trifluoromethyl-pyridin-2-ylmethyl)-1H-quinolin-4-one

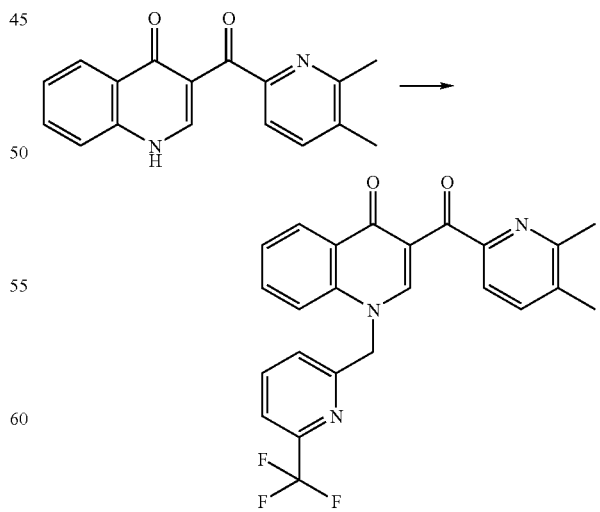

Experimental conditions analogous to those described for Step 3 of Example 1, from 63 mg (0.23 mmol) of 3-(5,6- dimethyl-pyridine-2-carbonyl)-1H-quinolin-4-one, 11 mg (0.27 mmol) of 60% sodium hydride, 65 mg (0.27 mmol) of 2-bromomethyl-6-trifluoromethyl-pyridine and 0.7 mL of N,N-dimethylformamide. Yield: 31 mg of a white solid: LC-MSD, m/z for $C_{24}H_{18}F_3N_3O_2$ [M+H]+=438.1; HPLC retention time: 1.6 min.

Example 174

Preparation of 6-[3-(5,6-Dimethyl-pyridine-2-carbonyl)-4-oxo-4H-quinolin-1-ylmethyl]-pyridine-2-carbonitrile

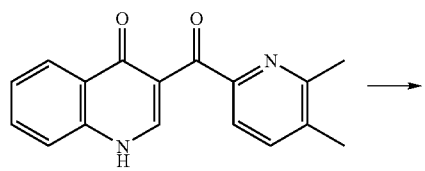

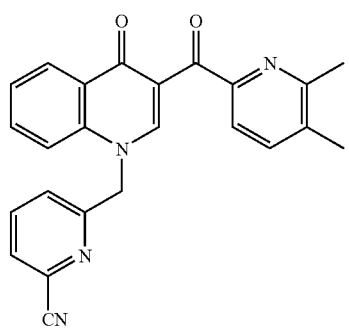

Experimental conditions analogous to those described for Step 3 of Example 1, from 67 mg (0.24 mmol) of 3-(5,6-dimethyl-pyridine-2-carbonyl)-1H-quinolin-4-one, 12 mg (0.29 mmol) of 60% sodium hydride, 57 mg (0.29 mmol) of 6-bromomethyl-pyridine-2-carbonitrile and 0.7 mL of N,N-dimethylformamide. Yield: 34 mg of a white solid: LC-MSD, m/z for $C_{24}H_{18}N_4O_2$ [M+H]+=395.1; HPLC retention time: 1.0 min.

Example 175

Preparation of 6-[3-(3,4-Dimethyl-benzoyl)-4-oxo-4H-quinolin-1-ylmethyl]-pyridine-2-carbonitrile

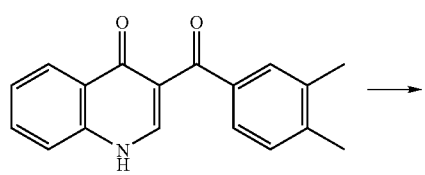

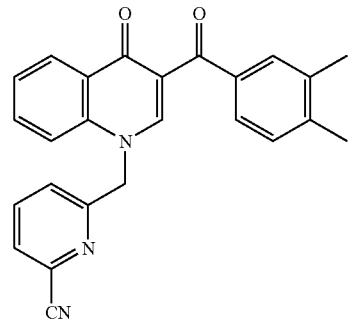

Experimental conditions analogous to those described for Step 3 of Example 1, from 51 mg (0.18 mmol) of 3-(3,4-dimethyl-benzoyl)-1H-quinolin-4-one, 9 mg (0.22 mmol) of 60% sodium hydride, 44 mg (0.22 mmol) of 6-bromomethyl-pyridine-2-carbonitrile and 0.7 mL of N,N-dimethylformamide. Yield: 27 mg of a white solid: LC-MSD, m/z for $C_{25}H_{19}N_3O_2$ [M+H]+=394.1; HPLC retention time: 2.1 min.

Example 176

Preparation of 6-[3-(3,4-Dimethyl-benzoyl)-4-oxo-4H-quinolin-1-ylmethyl]-pyridine-2-carboxylic acid

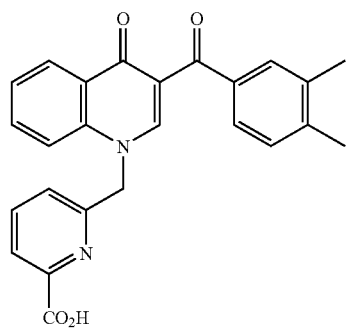

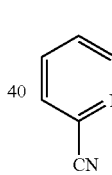

49 mg (0.12 mmol) of 6-[3-(3,4-dimethyl-benzoyl)-4-oxo-4H-quinolin-1-ylmethyl]-pyridine-2-carbonitrile was heated to 100° C. for 1 h in 3 g of 70% aqueous sulfuric acid. The solution was then cooled down, diluted with 20 mL of water and filtered. The residue was purified on reverse-phase HPLC and converted to HCl salt to give 28 mg of a white solid. LC-MSD, m/z for $C_{25}H_{21}N_2O_4$ [M+H]+=413.1; HPLC retention time: 1.7 min.

Example 177

Preparation of 6-[3-(3,4-Dimethyl-benzoyl)-4-oxo-4H-quinolin-1-ylmethyl]-pyridine-2-carboxylic acid amide

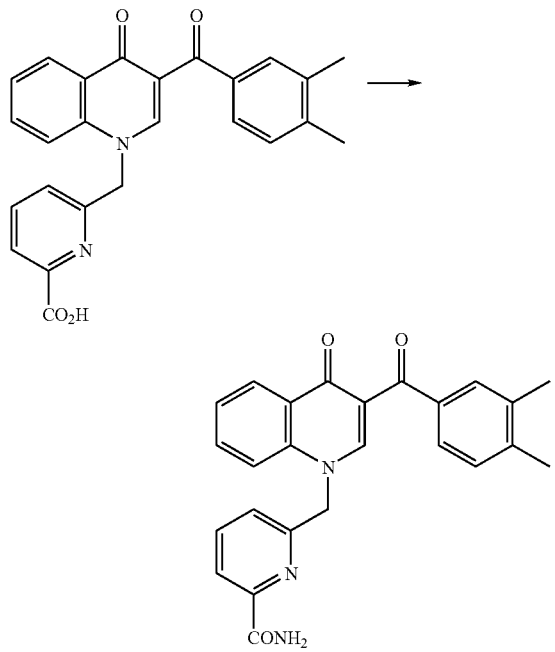

27 mg (0.06 mmol) of 6-[3-(3,4-dimethyl-benzoyl)-4-oxo-4H-quinolin-1-ylmethyl]-pyridine-2-carboxylic acid hydrochloride was dissolved in a mixture of 2 mL DMSO and 0.2 mL 2 M methanolic ammonia followed by the addition of 100 mg (0.36 mmol) of 4-(4,6-dimethoxy-1,3,5-triazin-2-yl)-4-methylmorpholinium chloride. The mixture was stirred for 1 h at r.t. followed by purification on reverse-phase HPLC and flash chromatography to give 17 mg of a white solid. LC-MSD, m/z for $C_{25}H_{21}N_3O_3$ [M+H]+=412.2; HPLC retention time: 1.7 min.

Example 178

Preparation of 1-(2-Fluoro-benzyl)-3-(pyrazine-2-carbonyl)-1H-quinolin-4-one

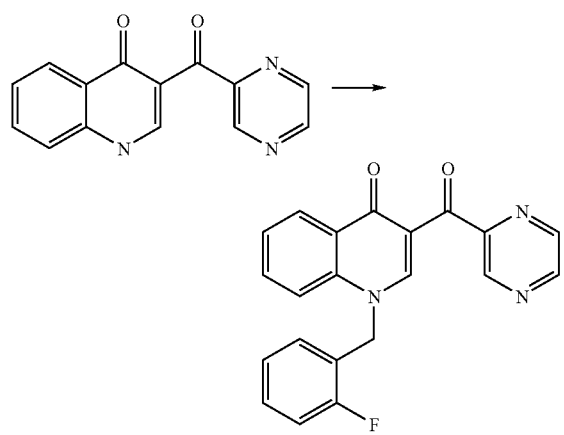

Experimental conditions analogous to those described for Step 3 of Example 1, from 15.6 mg (0.39 mmol) of NaH (60%), 75 mg (0.30 mmol) of 3-(Pyrazine-2-carbonyl)-1H-quinolin-4-one, 3 mL of anhydrous DMF, 78 mg (0.4 mmol) of 2-fluorobenzylbromide. The crude product was purified by flash chromatography to yield 37 mg of colorless solid. LC-MSD, m/z for $C_{21}H_{14}FN_3O_2$ [M+H]+: 360.5, [M+2H]+: 361.5. Reverse phase HPLC gradient acetonitrile 0.1% TFA 20-95% in 4 min: 2.287 min.

Example 179

Preparation of 1-(3-methyl-benzyl)-3-(pyrazine-2-carbonyl)-1H-quinolin-4-one

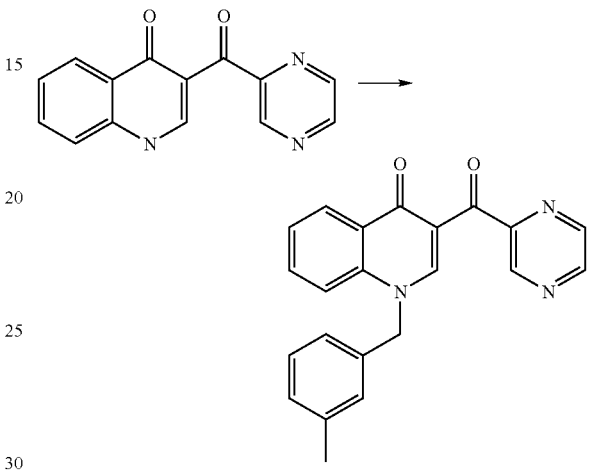

Experimental conditions analogous to those described for Step 3 of Example 1, from 15.6 mg (0.39 mmol) of NaH (60%), 75 mg (0.30 mmol) of 3-(Pyrazine-2-carbonyl)-1H-quinolin-4-one, 3 mL of anhydrous DMF, 76 mg (0.4 mmol) of 3-methylbenzylbromide. The crude product was purified by flash chromatograph to yield 35 mg of colorless solid. LC-MSD, m/z for $C_{22}H_{17}N_3O_2$ [M+H]+: 356.5, [M+2H]+: 357.5. Reverse phase HPLC gradient acetonitrile 0.1% TFA 20-95% in 4 min: 2.394 min.

Example 180

Preparation of 1-(2-methyl-benzyl)-3-(pyrazine-2-carbonyl)-1H-quinolin-4-one

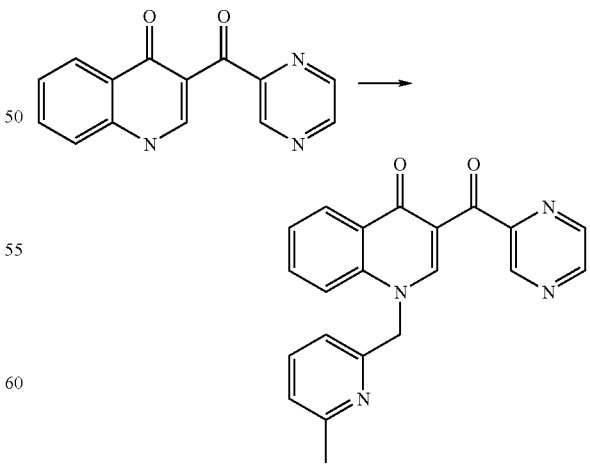

Experimental conditions analogous to those described for Step 3 of Example 1, from 15.6 mg (0.39 mmol) of NaH (60%), 75 mg (0.30 mmol) of 3-(Pyrazine-2-carbonyl)-1H-quinolin-4-one, 3 mL of anhydrous DMF, 76 mg (0.4 mmol) of 2-methylbenzylbromide. The crude product was purified by flash chromatograph to yield 41 mg of colorless solid. LC-MSD, m/z for $C_{21}H_{16}N_4O_2$ [M+H]+: 357.5, [M+2H]+: 358.5. Reverse phase HPLC gradient acetonitrile 0.1% TFA 20-95% in 4 min: 1.895 min Example 181

Preparation of 3-(3,4-Dimethyl-benzoyl)-1-(6-hydroxymethyl-pyridin-2-ylmethyl)-1H-quinolin-4-one

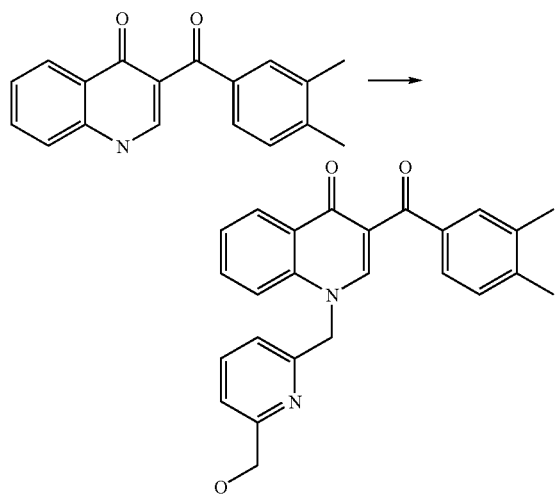

Experimental conditions analogous to those described for Step 3 of Example 1, from 104 mg (2.6 mmol) of NaH (60%), 470 mg (1.70 mmol) of 3-(3,4-Dimethyl-benzoyl)-1H-quinolin-4-one, 12 mL of anhydrous DMF, 470 mg (2.33 mmol) of (3-Bromomethyl-phenyl)-methanol. The crude product was purified by flash chromatograph to yield 350 mg of colorless solid. LC-MSD, m/z for $C_{25}H_{22}N_2O_3$ [M+H]+: 399.5, [M+2H]+: 400.5. Reverse phase HPLC gradient acetonitrile 0.1% TFA 20-95% in 4 min: 2.226 min.

Example 182

Preparation of 3-(3,4-Dimethyl-benzoyl)-1-(6-methoxymethyl-pyridin-2-ylmethyl)-1H-quinolin-4-one

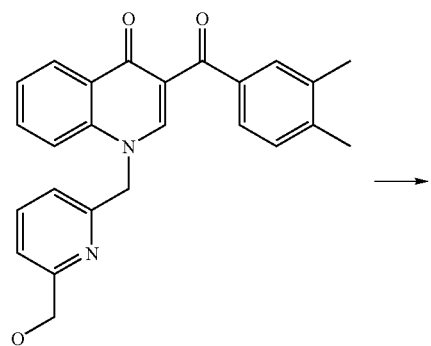

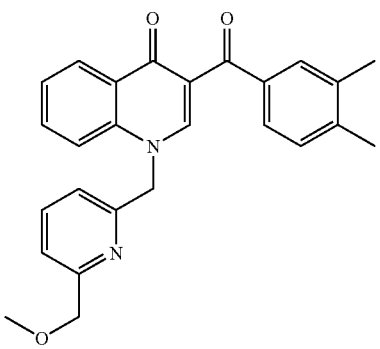

50 mg (0.13 mmol) of 3-(3,4-Dimethyl-benzoyl)-1-(6-hydroxymethyl-pyridin-2-ylmethyl)-1H-quinolin-4-one was dissolved in 3 mL of DMSO. 28 mg (0.5 mmol) of potassium hydroxide was added into the solution and the mixture was stirred at 50° C. overnight. The reaction mixture was poured into 20 mL of ice-water. The mixture was extracted with 30 mL of ethyl acetate. The organic layer was concentrated to dryness. The crude product was purified by preparatory HPLC to yield 30 mg of colorless solid. LC-MSD, m/z for $C_{26}H_{24}N_2O_3$ [M+H]+: 413.5, [M+2H]+: 414.5. Reverse phase HPLC gradient acetonitrile 0.1% TFA 20-95% in 4 min: 2.492 min.

Example 183

Preparation of 3-(3,4-Dimethyl-benzoyl)-1-(3-methylaminomethyl-benzyl)-1H-quinolin-4-one

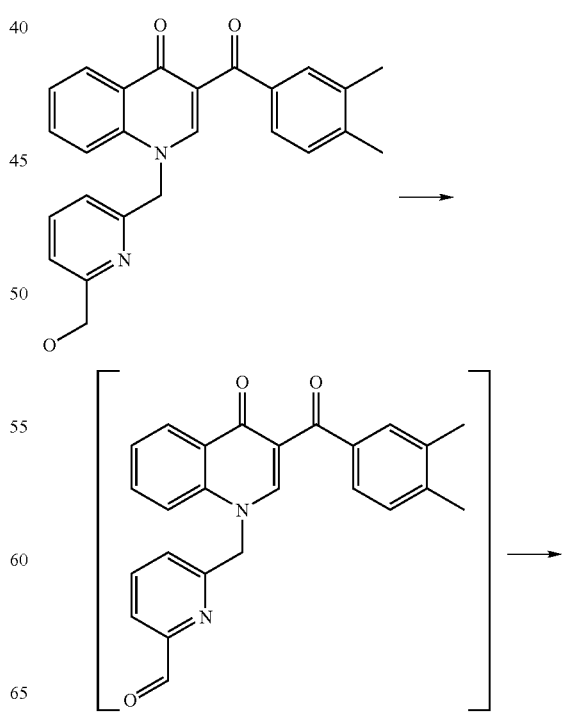

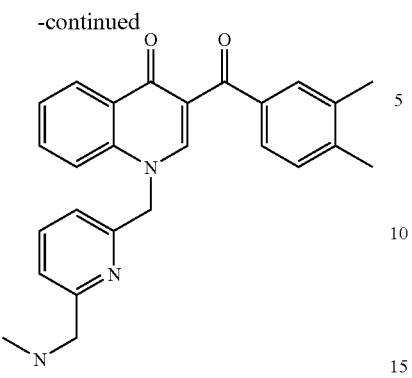

80 mg (0.2 mmol) of 3-(3,4-Dimethyl-benzoyl)-1-(6-hydroxymethyl-pyridin-2-ylmethyl)-1H-quinolin-4-one was dissolved in 6 mL of dichloromethane. 200 mg (0.5 mmol) Dess-Martin reagent was added into the solution and the mixture was stirred at rt for 4 hours. The reaction was quenched by adding 20 mL of water, 4 mL of sat. aqueous sodium bicarbonate solution and 200 mg of sodium thiosulfate. The mixture was extracted with 20 mL of ethyl acetate and the organic layer was separated and dried over magnesium sulfate. The solid was filtered and the filtrate was concentrated to dryness. The obtained crude product was used directly for the next step.

40 mg (0.1 mmol) of crude 6-[3-(3,4-Dimethyl-benzoyl)-4-oxo-4H-quinolin-1-ylmethyl]-pyridine-2-carbaldehyde, 0.06 mL (2.0 M, 0.12 mmol) of methylamine in THF and 44 mg (0.2 mmol) of sodium triacetoxyborohydride were mixed in 3 mL of dichloromethane and the mixture was stirred at rt for 2 hours. The reaction was quenched by adding 20 mL of sat. aqueous sodium bicarbonate. The mixture was extracted with 30 mL of ethyl acetate. The organic layer was concentrated to dryness. The crude product was purified by preparatory HPLC to yield 22 mg of colorless solid. LC-MSD, m/z for $C_{26}H_{25}N_3O_2$ [M+H]+: 412.5, [M+2H]+: 413.5. Reverse phase HPLC gradient acetonitrile 0.1% TFA 20-95% in 4 min: 1.963 min.

Example 184

Preparation of 1-(6-Dimethylaminomethyl-pyridin-2-ylmethyl)-3-(3,4-dimethyl-benzoyl)-1H-quinolin-4-one

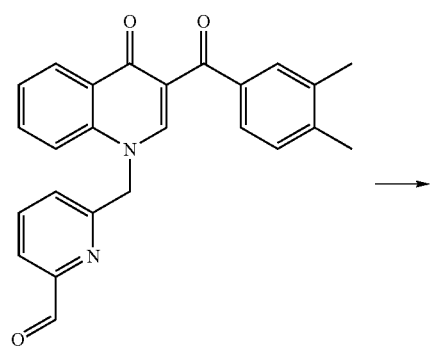

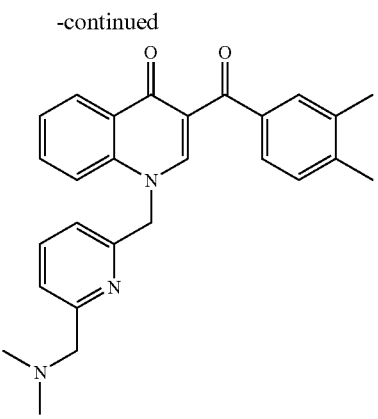

Experimental conditions analogous to those described for Example 183, from 140 mg (0.1 mmol) of crude 6-[3-(3,4-Dimethyl-benzoyl)-4-oxo-4H-quinolin-1-ylmethyl]-pyridine-2-carbaldehyde, 0.06 mL (2.0 M, 0.12 mmol) of dimethylamine in THF and 44 mg (0.2 mmol) of sodium triacetoxyborohydride in 3 mL of dichoromethane. The crude product was purified by preparatory HPLC to yield 19 mg of colorless solid. LC-MSD, m/z for $C_{27}H_{27}N_3O_2$ [M+H]+: 426.5, [M+2H]+: 427.5. Reverse phase HPLC gradient acetonitrile 0.1% TFA 20-95% in 4 min: 1.826 min.

Example 185

Preparation of 3-(5,6-Dimethyl-pyridine-3-carbonyl)-1-(6-hydroxymethyl-pyridin-2-ylmethyl)-1H-quinolin-4-one

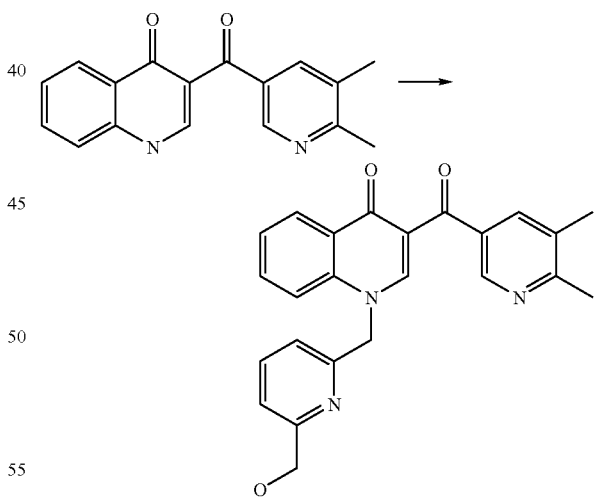

Experimental conditions analogous to those described for Step 3 of Example 1, from 104 mg (2.6 mmol) of NaH (60%), 470 mg (1.7 mmol) of 3-(Pyrazine-2-carbonyl)-1H-quinolin-4-one, 12 mL of anhydrous DMF, 470 mg (2.33 mmol) of (6-Bromomethyl-pyridin-2-yl)-methanol. The crude product was purified by flash chromatograph to yield 350 mg of colorless solid. LC-MSD, m/z for $C_{24}H_{21}N_3O_3$ [M+H]+: 400.5, [M+2H]+: 401.5. Reverse phase HPLC gradient acetonitrile 0.1% TFA 20-95% in 4 min: 0.517 min

Example 186

Preparation 1-(6-Bromo-pyridin-2-ylmethyl)-3-(2-[1,3]dioxan-2-yl-benzoyl)-1H-quinolin-4-one

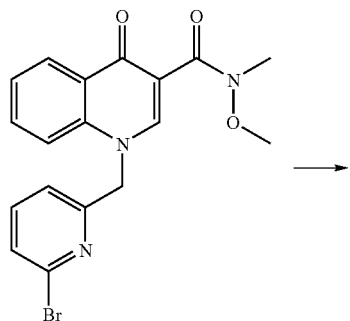

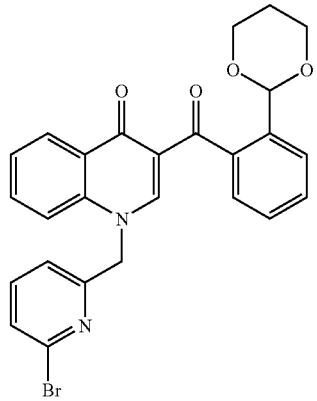

Experimental conditions analogous to those described for Step 6 of Example 60, from 1.01 g (2.5 mmol) of 1-(6-Bromo-pyridin-2-ylmethyl)-4-oxo-1,4-dihydro-quinoline-3-carboxylic acid methoxy-methyl-amide was dissolved in 10 mL of anhydrous THF. 22 mL (0.25 M, 5.5 mmol) of 2-(1,3-dioxan-2-yl)-phenylmegnesium bromide solution in THF was added slowly at 0° C. The mixture was stirred at rt for 2 hours. 20 mL of sat. aqueous ammonium chloride was added and the mixture was extracted with 30 mL of ethyl acetate 2 times. The combined organic layer was collected and combined, dried over MgSO$_4$ overnight. MgSO$_4$ solid was filtered and the filtrate was concentrated to dryness. The crude was purified by flash chromatograph to yield 1.1 g of product as colorless solid. LC-MSD, m/z for $C_{26}H_{21}N_2O_4Br$ [M+H]+: 505.5, [M+2H]+: 506.5. Reverse phase HPLC gradient acetonitrile 0.1% TFA 20-95% in 4 min: 2.337 min.

Example 187

Preparation of 1-(6-Bromo-pyridin-2-ylmethyl)-3-(2-dimethylaminomethyl-benzoyl)-1H-quinolin-4-one

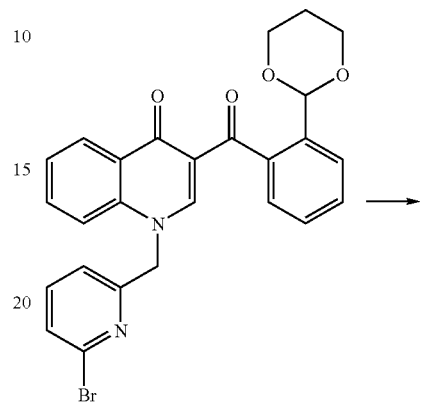

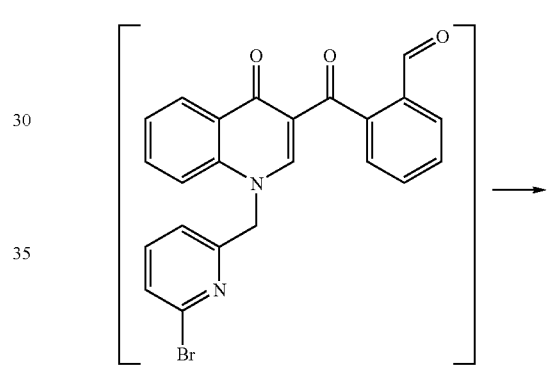

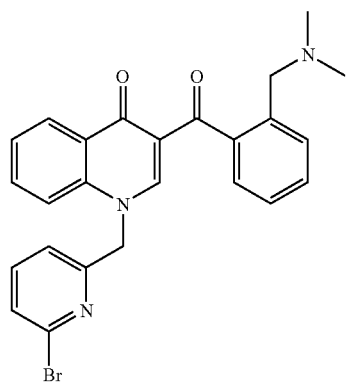

1.01 g of 1-(6-Bromo-pyridin-2-ylmethyl)-3-(2-[1,3]dioxan-2-yl-benzoyl)-1H-quinolin-4-one was dissolved in 10 mL of 4 N HCl in Dioxane and the mixture was stirred at rt for 2 hours. The mixture was concentrated to dryness, re-dissolved in 50 mL of ethyl acetate and washed with sat. aqueous NaHCO$_3$ (50 mL, 2 times), sat. aqueous NaCl (50 mL, 2 times), then concentrated to dryness. The crude was used directly for the next step reaction. 92 mg (0.2 mmol) of the crude 2-[1-(6-Bromo-pyridin-2-ylmethyl)-4-oxo-1,4-dihydro-quinoline-3-carbonyl]-benzaldehyde was dissolved in 3 mL of dichloromethane. 150 μL (2.0 M, 0.3 mmol) of N,N-dimethylamine, 221 mg (1.0 mmol) of sodium triacetoxyborohydride were added into the solution and the mixture was stirred at rt for 2 hours. 5 mL of sat. aqueous sodium bicarbonate was added to quench the reaction. The mixture was extracted with ethyl acetate (10 mL, 2 times). The organic layer was combined and concentrated to dryness. The crude product was purified by preparatory HPLC to yield 51 mg of product as colorless solid. LC-MSD, m/z for $C_{25}H_{22}N_3O_2Br$ [M+H]+: 476.4, [M+2H]+: 477.4. Reverse phase HPLC gradient acetonitrile 0.1% TFA 20-95% in 4 min: 1.796 min Example 188

Preparation of 1-(6-Bromo-pyridin-2-ylmethyl)-3-(3-[1,3]dioxan-2-yl-benzoyl)-1H-quinolin-4-one

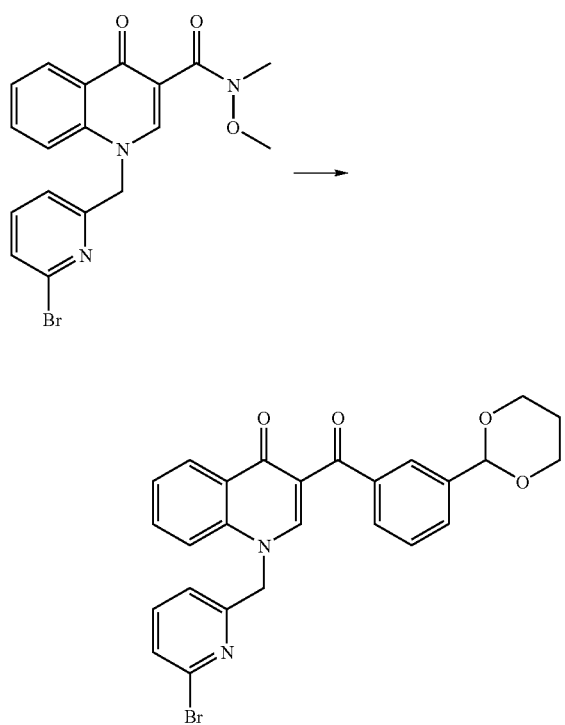

Experimental conditions analogous to those described for Step 6 of Example 60, from 143 mg (0.33 mmol) of 1-(6-Bromo-pyridin-2-ylmethyl)-4-oxo-1,4-dihydro-quinoline-3-carboxylic acid methoxy-methyl-amide, 4 mL (0.25 M, 1 mmol) of 3-(1,3-dioxan-2-yl)-phenylmegnesium bromide in THF solution, 4 mL of THF. The crude product was purified by flash chromatograph to yield 110 mg of colorless solid. LC-MSD, m/z for $C_{26}H_{21}N_2O_4Br$ [M+H]+: 505.5, [M+2H]+: 506.5. Reverse phase HPLC gradient acetonitrile 0.1% TFA 20-95% in 4 min: 2.317 min.

Example 189

Preparation of 1-(6-Bromo-pyridin-2-ylmethyl)-3-(3-[1,3]dioxan-2-yl-4-methoxy-benzoyl)-1H-quinolin-4-one

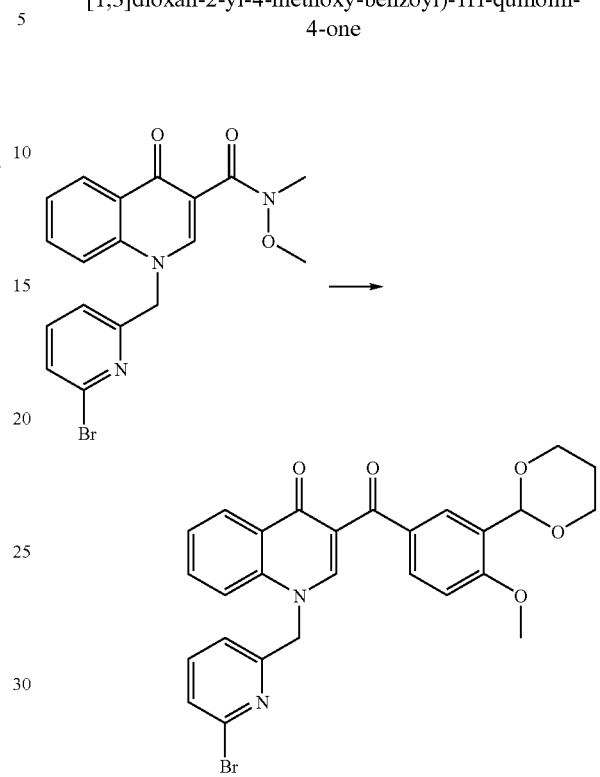

Experimental conditions analogous to those described for Step 6 of Example 60, from 143 mg (0.33 mmol) of 1-(6-Bromo-pyridin-2-ylmethyl)-4-oxo-1,4-dihydro-quinoline-3-carboxylic acid methoxy-methyl-amide, 4 mL (0.25 M, 1 mmol) of 3-(1,3-dioxan-2-yl)-4-methoxyphenylmegnesium bromide in THF solution, 4 mL of THF. The crude product was purified by flash chromatograph to yield 120 mg of colorless solid. LC-MSD, m/z for $C_{27}H_{23}N_2O_5Br$ [M+H]+: 535.5, [M+2H]+: 536.5. Reverse phase HPLC gradient acetonitrile 0.1% TFA 20-95% in 4 min: 2.254 min Example 190

Preparation of 1-(6-Bromo-pyridin-2-ylmethyl)-3-(4-[1,3]dioxan-2-yl-benzoyl)-1H-quinolin-4-one

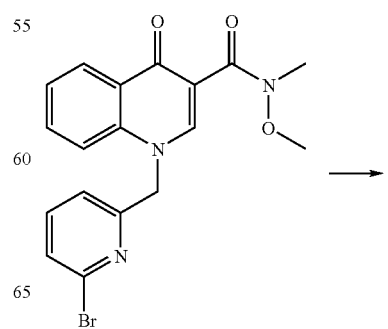

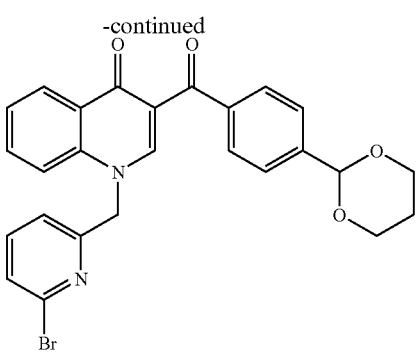

Experimental conditions analogous to those described for Step 6 of Example 60, from 143 mg (0.33 mmol) of 1-(6-Bromo-pyridin-2-ylmethyl)-4-oxo-1,4-dihydro-quinoline-3-carboxylic acid methoxy-methyl-amide, 4 mL (0.25 M, 1 mmol) of 3-(1,3-dioxan-2-yl)-phenylmegnesium bromide solution in THF, 4 mL of THF. The crude product was purified by flash chromatograph to yield 110 mg of colorless solid. LC-MSD, m/z for $C_{26}H_{21}N_2O_4Br$ [M+H]+: 505.5, [M+2H]+: 506.5. Reverse phase HPLC gradient acetonitrile 0.1% TFA 20-95% in 4 min: 2.308 min.

Example 191

Preparation of 2-[1-(6-Bromo-pyridin-2-ylmethyl)-4-oxo-1,4-dihydro-quinoline-3-carbonyl]-benzoic acid

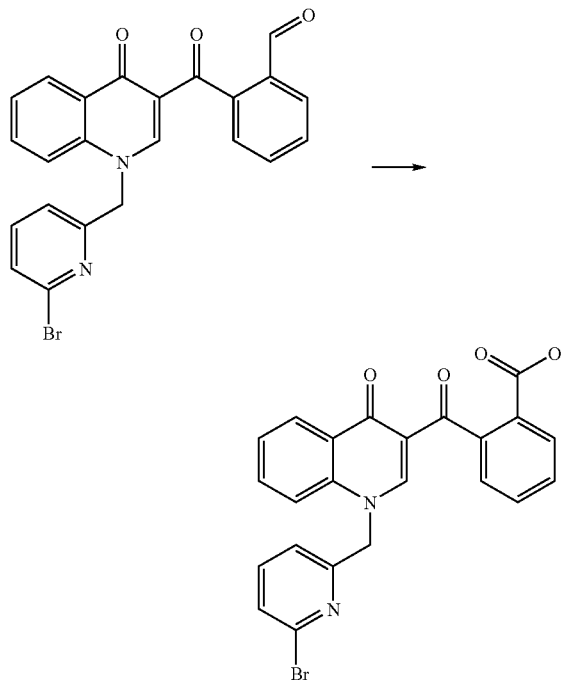

720 mg (1.6 mmol) of 2-[1-(6-Bromo-pyridin-2-ylmethyl)-4-oxo-1,4-dihydro-quinoline-3-carbonyl]-benzaldehyde was dissolved in 30 mL of acetone. 316 mg (2 mmol) of potassium permanganate was added and the mixture was stirred at rt for 2 hours. The reaction was quenched by adding 300 mg of solid sodium thiosulfate and 50 mL of water. The mixture was extracted with dichloromethane (50 mL, 2 times). The organic layer was combined and dried over anhydrous magnesium sulfate overnight. Magnesium sulfate was filtered and the filtrate was concentrated to dryness. The crude was purified by flash chromatograph to yield 360 mg of product as colorless solid. LC-MSD, m/z for $C_{23}H_{15}N_2O_4Br$ [M+H]+: 463.3, [M+2H]+: 464.3. Reverse phase HPLC gradient acetonitrile 0.1% TFA 20-95% in 4 min: 1.973 min.

Example 192

Preparation of 1-(6-Bromo-pyridin-2-ylmethyl)-3-(4-methylaminomethyl-benzoyl)-1H-quinolin-4-one

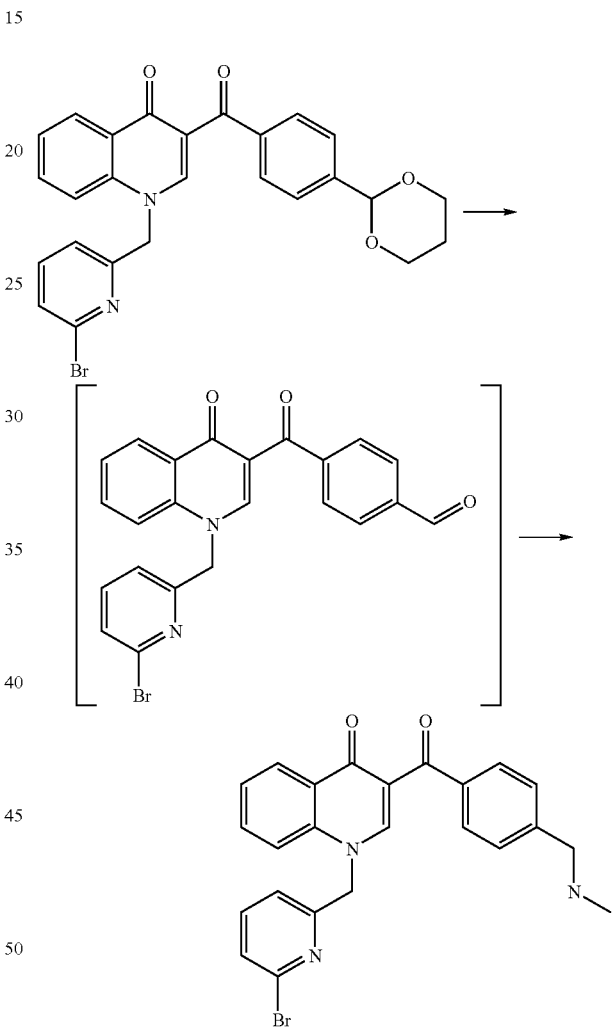

4-[1-(6-Bromo-pyridin-2-ylmethyl)-4-oxo-1,4-dihydro-quinoline-3-carbonyl]-benzaldehyde was synthesized analogous to example 10 with 90 mg (0.18 mmol) of 1-(6-Bromo-pyridin-2-ylmethyl)-3-(4-[1,3]dioxan-2-yl-benzoyl)-1H-quinolin-4-one, 4 mL of 4 N HCl in dioxane. The crude product obtained was used directly for next step with 84 mg (0.4 mmol) of sodium triacetoxyborohydride, 0.2 mL (2.0 M, 0.4 mmol) of methylamine in THF, 2 mL of DCM. The crude product was purified by flash chromatograph to yield 35 mg of colorless solid. LC-MSD, m/z for $C_{24}H_{20}N_3O_2Br$ [M+H]+: 462.3, [M+2H]+: 463.3. Reverse phase HPLC gradient acetonitrile 0.1% TFA 20-95% in 4 min: 0.581 min.

Example 193

Preparation of 2-[1-(6-Bromo-pyridin-2-ylmethyl)-4-oxo-1,4-dihydro-quinoline-3-carbonyl]-benzoic acid methyl ester

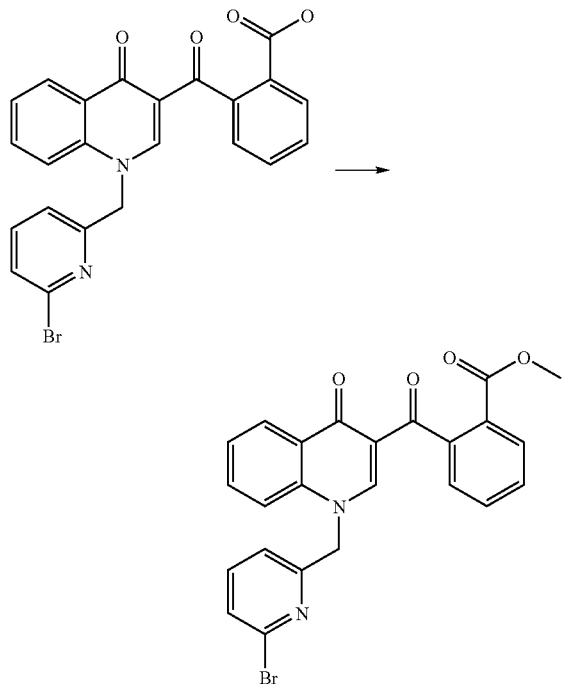

93 mg (0.2 mmol) of 2-[1-(6-Bromo-pyridin-2-ylmethyl)-4-oxo-1,4-dihydro-quinoline-3-carbonyl]-benzoic acid was dissolved in 4 mL of methanol. 0.1 mL of concentrated sulfuric acid was added into the solution and the mixture was heated at 80° C. in the sealed tube for 6 hours. The solution was diluted with 50 mL of ethyl acetate, washed with sat. aqueous sodium bicarbonate (50 mL, 2 times), sat. aqueous sodium chloride (50 mL, 2 times). The organic layer was concentrated to dryness. The crude product was purified by flash chromatograph to yield 50 mg of colorless solid. LC-MSD, m/z for $C_{24}H_{17}N_2O_4Br$ [M+H]+: 477.3, [M+2H]+: 478.3. Reverse phase HPLC gradient acetonitrile 0.1% TFA 20-95% in 4 min: 2.252 min

Example 194

Preparation of 1-(6-Bromo-pyridin-2-ylmethyl)-3-(2-oxazol-2-yl-benzoyl)-1H-quinolin-4-one

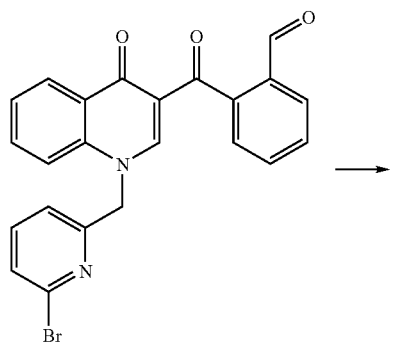

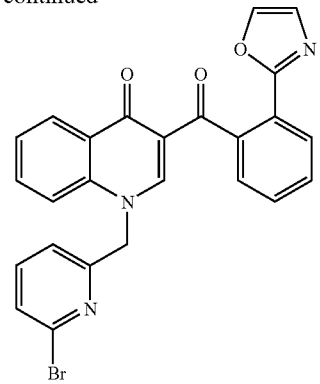

108 mg (0.24 mmol) of 2-[1-(6-Bromo-pyridin-2-ylmethyl)-4-oxo-1,4-dihydro-quinoline-3-carbonyl]-benzaldehyde 47 mg (0.24 mmol) of toluenesulfonylmethyl isocyanate, 20 mg (0.29 mmol) of sodium ethoxide were dissolved in 5 mL of THF and the mixture was stirred at rt for 3 h. The reaction was quenched with 50 mL of water and the mixture was extracted with 50 mL of ethyl acetate. The organic layer was separated and concentrated to dryness. The crude product purified by flash chromatograph to yield 30 mg of colorless solid. LC-MSD, m/z for $C_{25}H_{16}N_3O_3Br$ [M+H]+: 486.4, [M+2H]+: 487.4. Reverse phase HPLC gradient acetonitrile 0.1% TFA 20-95% in 4 min: 3.091 min.

Example 196

Preparation of 2-[1-(6-Bromo-pyridin-2-ylmethyl)-4-oxo-1,4-dihydro-quinoline-3-carbonyl]-N,N-dimethyl-benzamide

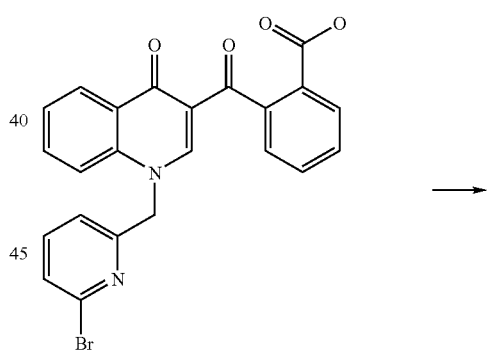

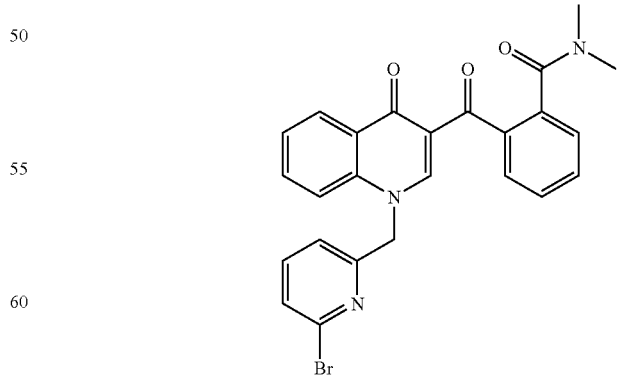

93 mg (0.2 mmol) of 2-[1-(6-Bromo-pyridin-2-ylmethyl)-4-oxo-1,4-dihydro-quinoline-3-carbonyl]-benzoic acid was dissolved in 5 mL of THF. 0.2 mL (2 M, 0.4 mmol) of

Example 197

Preparation of 2-[1-(6-Bromo-pyridin-2-ylmethyl)-4-oxo-1,4-dihydro-quinoline-3-carbonyl]-N-methyl-benzamide

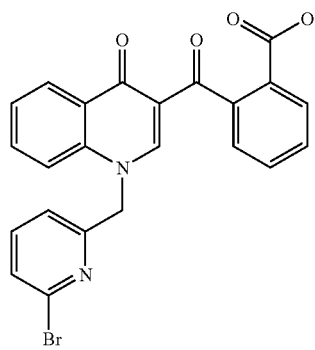

dimethylamine, 0.636 mg (50%, 1 mmol) of propylphosphonic anhydride in ethyl acetate solution, 129 mg (1 mmol) of diisopropylethylamine were added into the solution and the mixture was stirred at rt for 2 hours. The reaction was quenched by adding 50 mL of water and the mixture was extracted with 50 mL of ethyl acetate. The organic layer was separated and concentrated to dryness. The crude was purified by flash chromatograph to yield 55 mg of colorless solid. LC-MSD, m/z for $C_{25}H_{20}N_3O_3Br$ [M+H]+: 490.3, [M+2H]+: 491.3. Reverse phase HPLC gradient acetonitrile 0.1% TFA 20-95% in 4 min: 1.922 min

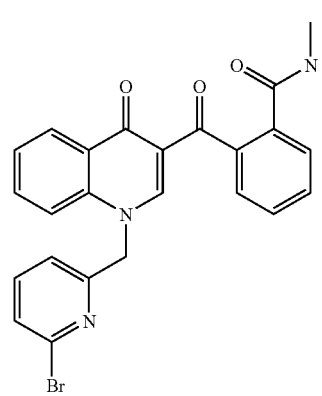

Experimental conditions analogous to those described for Example 196, from 93 mg (0.2 mmol) of 2-[1-(6-Bromo-pyridin-2-ylmethyl)-4-oxo-1,4-dihydro-quinoline-3-carbonyl]-benzoic acid, 5 mL of THF, 0.2 mL (2 M, 0.4 mmol) of methylamine, 0.636 mg (50%, 1 mmol) of propylphosphonic anhydride in ethyl acetate solution, 129 mg (1 mmol) of diisopropylethylamine. The crude was purified by flash chromatograph to yield 34 mg of colorless solid. LC-MSD, m/z for $C_{24}H_{18}N_3O_3Br$ [M+H]+: 476.3, [M+2H]+: 477.3. Reverse phase HPLC gradient acetonitrile 0.1% TFA 20-95% in 4 min: 1.980 min.

Example 198

Preparation of 2-[1-(6-Bromo-pyridin-2-ylmethyl)-4-oxo-1,4-dihydro-quinoline-3-carbonyl]-N-cyclopropyl-benzamide

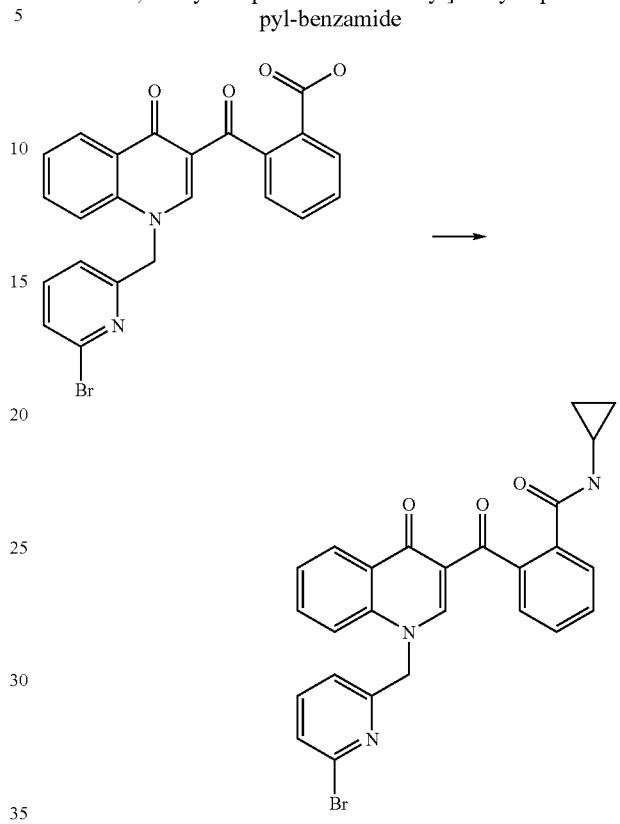

Experimental conditions analogous to those described for Example 196, from 93 mg (0.2 mmol) of 2-[1-(6-Bromo-pyridin-2-ylmethyl)-4-oxo-1,4-dihydro-quinoline-3-carbonyl]-benzoic acid, 5 mL of THF, 0.2 mL (2 M, 0.4 mmol) of cyclopropylamine, 0.636 mg (50%, 1 mmol) of propylphosphonic anhydride in ethyl acetate solution, 129 mg (1 mmol) of diisopropylethylamine. The crude was purified by flash chromatograph to yield 40 mg of colorless solid. LC-MSD, m/z for $C_{26}H_{20}N_3O_3Br$ [M+H]+: 502.4, [M+2H]+: 503.4. Reverse phase HPLC gradient acetonitrile 0.1% TFA 20-95% in 4 min: 2.107 min

Example 199

Preparation of 3-[2-(Azetidine-1-carbonyl)-benzoyl]-1-(6-bromo-pyridin-2-ylmethyl)-1H-quinolin-4-one

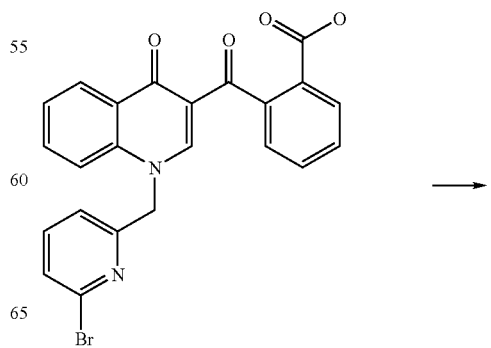

-continued

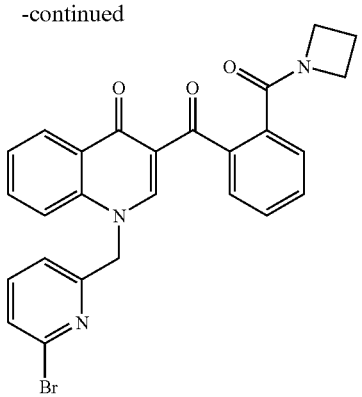

Experimental conditions analogous to those described for Example 196, from 93 mg (0.2 mmol) of 2-[1-(6-Bromo-pyridin-2-ylmethyl)-4-oxo-1,4-dihydro-quinoline-3-carbonyl]-benzoic acid, 5 mL of THF, 22.8 mg (0.4 mmol) of azetidine in THF, 0.636 mg (50%, 1 mmol) of propylphosphonic anhydride in ethyl acetate solution, 129 mg (1 mmol) of diisopropylethylamine. The crude was purified by flash chromatograph to yield 50 mg of colorless solid. LC-MSD, m/z for $C_{26}H_{20}N_3O_3Br$ [M+H]+: 502.4, [M+2H]+: 503.4. Reverse phase HPLC gradient acetonitrile 0.1% TFA 20-95% in 4 min: 1.997 min Example 200

Preparation of 3-(2-Bromo-benzoyl)-1-(6-methyl-pyridin-2-ylmethyl)-1H-quinolin-4-one

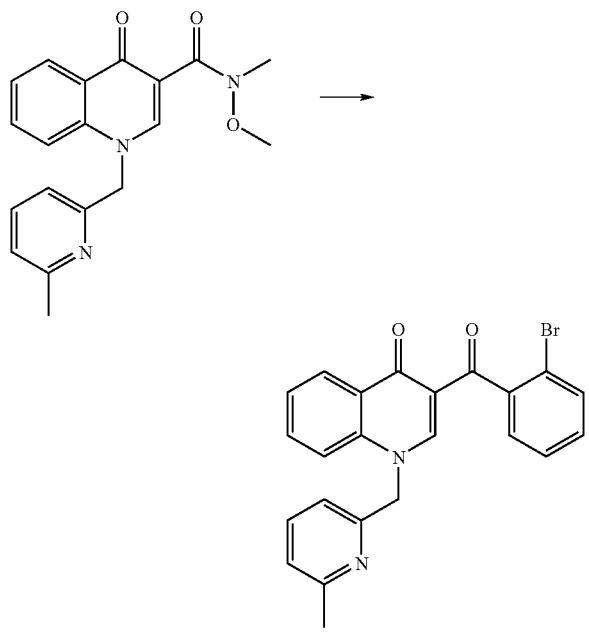

Experimental conditions analogous to those described for Step 6 of Example 60, from 1.41 g (5 mmol) of 2-bromo-iodobenzene was dissolved 10 mL of anhydrous THF. 2.5 mL (2.0 M, 5 mmol) of isopropylmagnesium chloride was added into the solution at −10° C. The mixture was stirred at −10° C. for 1 hour then added slowly into a prepared solution of 674 mg (2 mmol) of 1-(6-Methyl-pyridin-2-ylmethyl)-4-oxo-1,4-dihydro-quinoline-3-carboxylic acid methoxy-methyl-amide in 10 mL of anhydrous THF at −10° C. The mixture was stirred at 0° C. for 2 hours. 50 mL of sat. aqueous ammonium chloride was added to quenched the reaction. The mixture was extracted with 50 mL of ethyl acetate. The organic layer was dried over magnesium sulfate overnight. The solid was filtered and the filtrate was concentrated to dryness. The crude product was purified by flash chromatograph to yield 850 mg of colorless solid. LC-MSD, m/z for $C_{23}H_{17}N_2O_2Br$ [M+H]+: 433.5, [M+2H]+: 434.5. Reverse phase HPLC gradient acetonitrile 0.1% TFA 20-95% in 4 min: 2.076 min.

Example 201

Preparation of 3-[1-(6-Bromo-pyridin-2-ylmethyl)-4-oxo-1,4-dihydro-quinoline-3-carbonyl]-N,N-dimethyl-benzamide

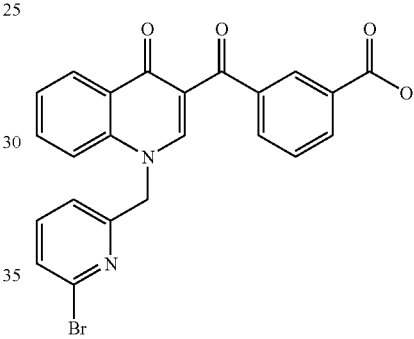

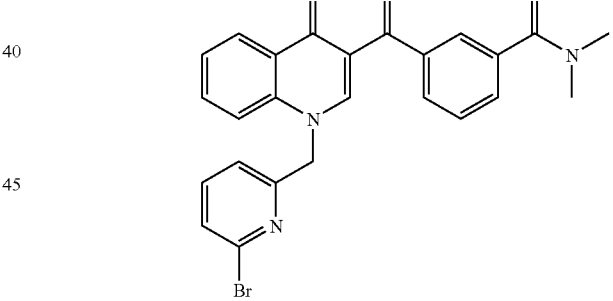

Experimental conditions analogous to those described for Example 196, from 93 mg (0.2 mmol) of 3-[1-(6-Bromo-pyridin-2-ylmethyl)-4-oxo-1,4-dihydro-quinoline-3-carbonyl]-benzoic acid was dissolved in 5 mL of THF. 0.2 mL (2 M, 0.4 mmol) of dimethylamine, 0.636 mg (50%, 1 mmol) of propylphosphonic anhydride in ethyl acetate solution, 129 mg (1 mmol) of diisopropylethylamine were added into the solution and the mixture was stirred at rt for 2 hours. The reaction was quenched by adding 50 mL of water and the mixture was extracted with 50 mL of ethyl acetate. The organic layer was separated and concentrated to dryness. The crude was purified by flash chromatograph to yield 50 mg of colorless solid. LC-MSD, m/z for $C_{25}H_{20}N_3O_3Br$ [M+H]+: 490.3, [M+2H]+: 491.3. Reverse phase HPLC gradient acetonitrile 0.1% TFA 20-95% in 4 min: 1.990 min.

Example 202

Preparation of 3-(2-Bromo-benzoyl)-1-(6-methyl-pyridin-2-ylmethyl)-1H-quinolin-4-one

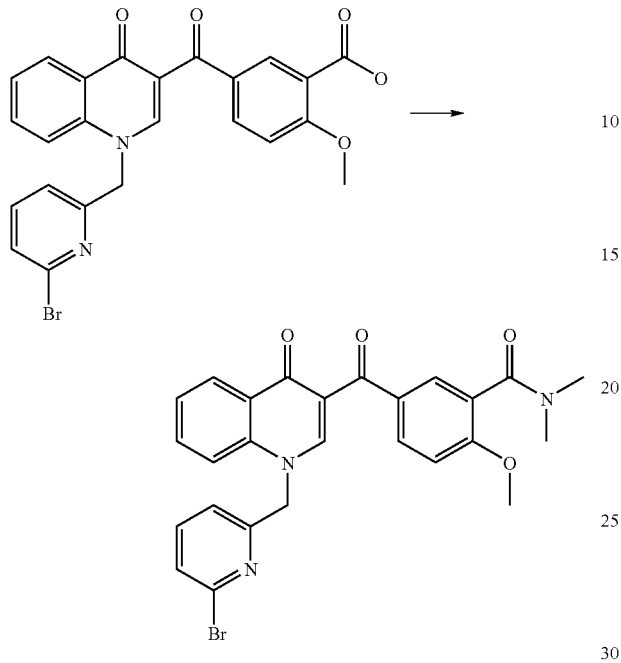

Experimental conditions analogous to those described for Example 196, from 96 mg (0.2 mmol) of 2-methoxyl-3-[1-(6-Bromo-pyridin-2-ylmethyl)-4-oxo-1,4-dihydro-quinoline-3-carbonyl]-benzoic acid was dissolved in 5 mL of THF. 0.2 mL (2 M, 0.4 mmol) of dimethylamine, 0.636 mg (50%, 1 mmol) of propylphosphonic anhydride in ethyl acetate solution, 129 mg (1 mmol) of diisopropylethylamine were added into the solution and the mixture was stirred at rt for 2 hours. The reaction was quenched by adding 50 mL of water and the mixture was extracted with 50 mL of ethyl acetate. The organic layer was separated and concentrated to dryness. The crude product was purified by flash chromatography to yield 51 mg of colorless solid. LC-MSD, m/z for $C_{26}H_{22}N_3O_4Br$ [M+H]+: 520.5, [M+2H]+: 521.5. Reverse phase HPLC gradient acetonitrile 0.1% TFA 20-95% in 4 min: 2.010 min.

Example 203

Preparation of 1-(6-Methyl-pyridin-2-ylmethyl)-3-(2-morpholin-4-yl-benzoyl)-1H-quinolin-4-one

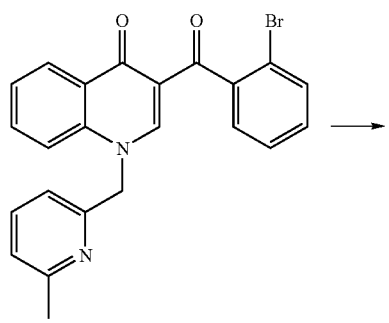

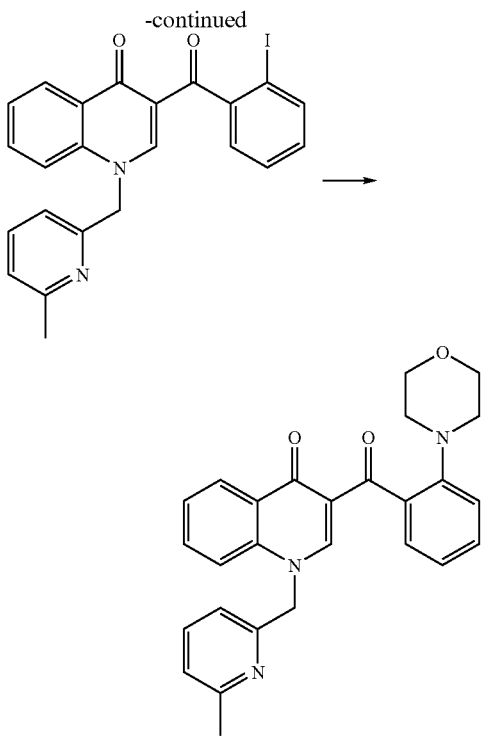

Step 1: 3-(2-Iodo-benzoyl)-1-(6-methyl-pyridin-2-ylmethyl)-1H-quinolin-4-one 443 mg (1 mmol) of 3-(2-Bromo-benzoyl)-1-(6-methyl-pyridin-2-ylmethyl)-1H-quinolin-4-one, 9.5 mg (0.05 mmol) of copper iodide, 14.2 mg (0.1 mmol) (1S,2S)-1-hydroxy-2-methylaminocyclohexane and 300 mg (2 mmol) of sodium iodide were mixed in 5 mL of dioxane. The mixture was stirred at 110° C. in a sealed tube for 18 hours. The reaction was quenched by adding 50 mL of water. The mixture was extracted with 50 mL of ethyl acetate. The organic layer was washed with 50 mL of water, 50 mL of sat. brine, dried over magnesium sulfate overnight. The solid was filtered and the filtrate was concentrated to dryness. The crude product was purified with flash chromatography to yield 270 mg of 3-(2-Iodo-benzoyl)-1-(6-methyl-pyridin-2-ylmethyl)-1H-quinolin-4-one as colorless solid.

Step 2: 1-(6-Methyl-pyridin-2ylmethyl)-3-(2-morpholin-4-yl-benzoyl)-1H-quinolin-4-one 200 mg (0.4 mmol) of 3-(2-Iodo-benzoyl)-1-(6-methyl-pyridin-2-ylmethyl)-1H-quinolin-4-one The obtained compound was mixed with 87 mg (1.0 mmol) of morpholine, 96 mg (1.0 mmol) of sodium butoxide, 13 mg (0.05 mmol) of 18-C-6 crown ether, 9 mg (0.01 mmol) of Tris(dibenzylideneacetone)dipalladium(0) and 18 mg of 2,2'-bis(diphenylphosphino)-1,1'-binaphthyl in 5 mL of THF. The mixture was stirred at 70° C. overnight. The mixture was diluted with 20 mL of ethyl acetate and washed with 20 mL of water. The organic layer was concentrated to dryness and purified by preparatory HPLC to yield 12 mg of product as colorless solid. LC-MSD, m/z for $C_{27}H_{25}N_3O_3$ [M+H]+: 440.5,

[M+2H]+: 441.5. Reverse phase HPLC gradient acetonitrile 0.1% TFA 20-95% in 4 min: 1.858 min.

Example 204

Preparation of 3-(3-Fluoro-4-methoxy-benzoyl)-1-(6-cyano-pyridin-2-ylmethyl)-1H-quinolin-4-one

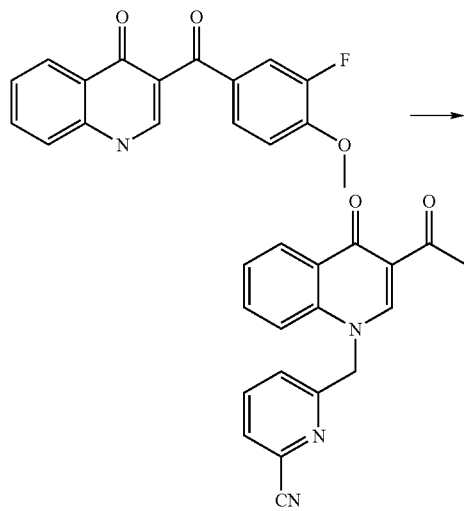

Experimental conditions analogous to those described for Step 3 of Example 1, from 10.4 mg (0.26 mmol) of NaH (60%), 60 mg (0.20 mmol) of 3-(3-Fluoro-4-methoxy-benzoyl)-1H-quinolin-4-one, 2 mL of anhydrous DMF, 60 mg (0.32 mmol) of 2-bromomethyl-6-cyanopyridine. The crude product was purified by flash chromatography to yield 28 mg of colorless solid. LC-MSD, m/z for $C_{24}H_{16}FN_3O_3$ [M+H]+: 414.3, [M+2H]+: 415.3. Reverse phase HPLC gradient acetonitrile 0.1% TFA 20-95% in 4 min: 2.191 min

Example 205

Preparation of 3-(3-Fluoro-4-methoxy-benzoyl)-1-(6-methyl-pyrazin-2-ylmethyl)-1H-quinolin-4-one

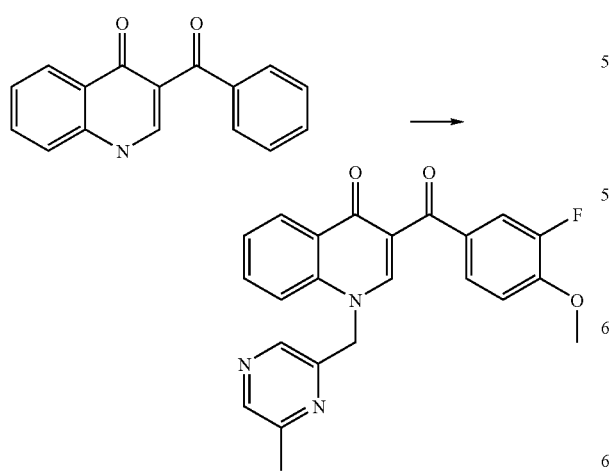

Experimental conditions analogous to those described for Step 3 of Example 1, from 10.4 mg (0.26 mmol) of NaH (60%), 60 mg (0.20 mmol) of 3-(3-Fluoro-4-methoxy-benzoyl)-1H-quinolin-4-one, 2 mL of anhydrous DMF, 60 mg (0.32 mmol) of 2-bromomethyl-6-methylpyrazine. The crude product was purified by flash chromatography to yield 27 mg of colorless solid. LC-MSD, m/z for $C_{23}H_{18}FN_3O_3$ [M+H]+: 404.4, [M+2H]+: 405.4 Reverse phase HPLC gradient acetonitrile 0.1% TFA 20-95% in 4 min: 1.961 min.

Example 206

Preparation of 1-(3-Bromo-benzyl)-3-(6-methoxy-pyridine3-carbonyl)-1H-quinolin-4-one

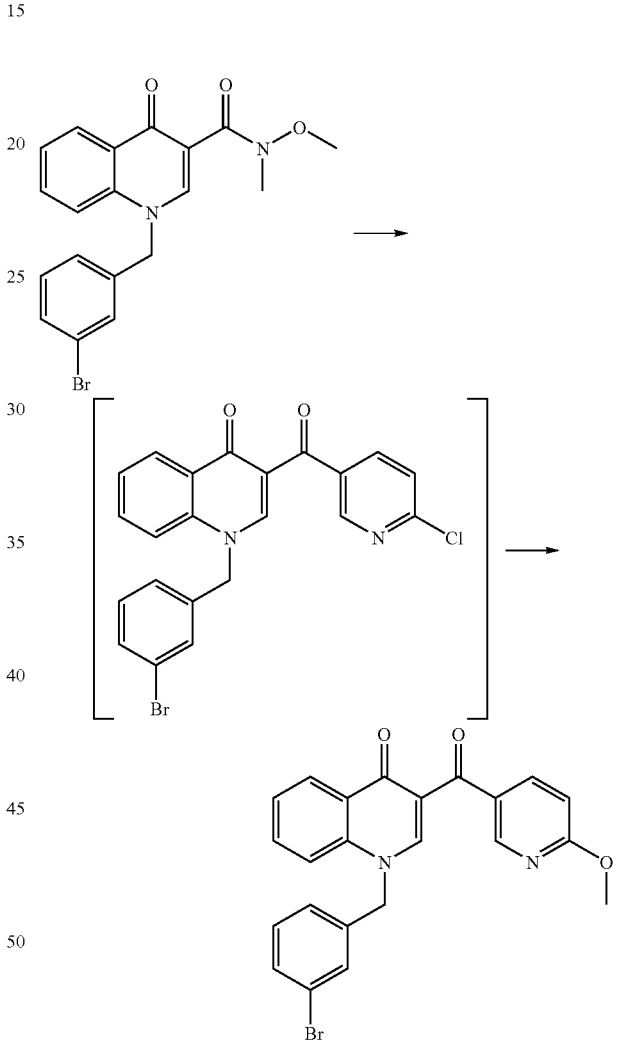

Experimental conditions analogous to those described for Step 3 of Example 1, from 201 mg (0.5 mmol) of 1-(3-Bromo-benzyl)-4-oxo-1,4-dihydro-quinoline-3-carboxylic acid methoxy-methyl-amide, 237 mg (1 mmol) of 2-Chloro-5-iodo-pyridine, 0.55 mL (2M, 1.1 mmol) of isopropylmagnesium bromide in THF solution, 8 mL of anhydrous THF. The crude 1-(3-Bromo-benzyl)-3-(6-chloro-pyridine-3-carbonyl)-1H-quinolin-4-one was dissolved in 10 mL of methanol, 450 mg of sodium methoxide was added and the mixture was stirred at 75° C. for 2 hours. The solvent was removed under vacuum and the crude product was purified by flash chromatography to yield 103 mg of colorless solid. LC-MSD, m/z for $C_{23}H_{17}N_2O_3Br$ [M+H]+: 449.4, [M+2H]$^+$: 450.4. Reverse phase HPLC gradient acetonitrile 0.1% TFA 20-95% in 4 min: 2.988 min.

Example 207

Preparation of 1-(6-Bromo-pyridin-2-ylmethyl)-3-(3-fluoro-4-methoxy-benzoyl)-7-trifluoromethyl-1H-[1,8]naphthyridin-4-one

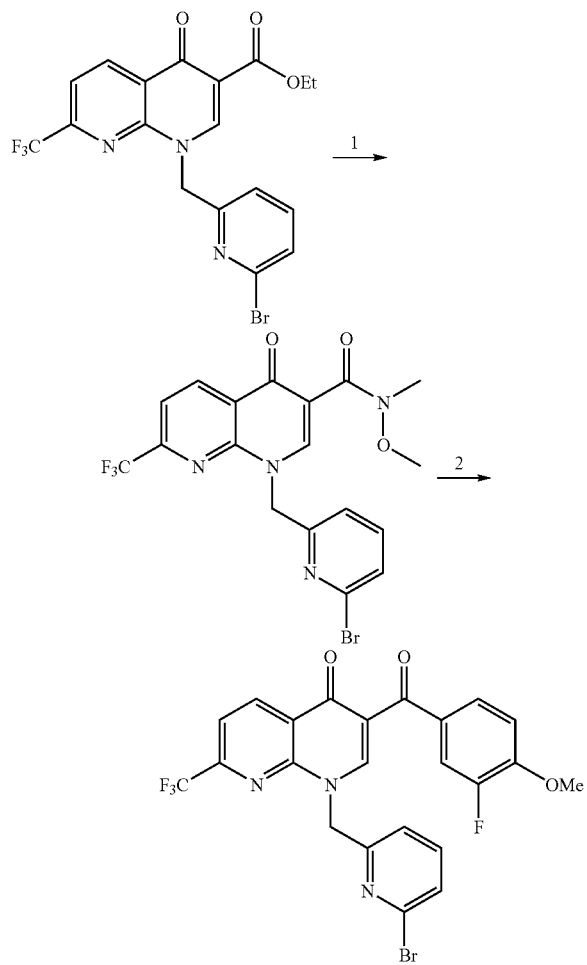

Step 1: 1-(6-bromo-pyridin-2-ylmethyl)-4-oxo-7-trifluoromethyl-1,4-dihydro-[1,8]naphthyridine-3carboxylic acid methoxy-methyl-amide A mixture of 1-(6-bromo-pyridin-2-ylmethyl)-4-oxo-7-trifluoromethyl-1,4-dihydro-[1,8]naphthyridine-3-carboxylic acid ethyl ester (0.72 g, 1.6 mmol, 1 equiv) and methyl-methoxyamine hydrochloride (0.16 g, 1 equiv) in 2 mL of toluene was treated with AlMe$_3$ (0.5 M in toluene, 3.5 mL, 1.1 equiv) at rt for 1 h. The reaction was quenched by slow addition of saturated aqueous solution of sodium potassium tartrate. The organic layer was dried over sodium sulfate, filtered and evaporated to give crude 1-(6-bromo-pyridin-2-ylmethyl)-4-oxo-7-trifluoromethyl-1,4-dihydro-[1,8]naphthyridine-3carboxylic acid methoxy-methyl-amide.

Step 2: 1-(6-Bromo-pyridin-2-ylmethyl)-3-(3-fluoro-4-methoxy-benzoyl)-7-trifluoromethyl-1H-[1,8]naphthyridin-4-one Experimental conditions analogous to those described for Step 6 of Example 60, from 80 mg of 1-(6-bromo-pyridin-2-ylmethyl)-4-oxo-7-trifluoromethyl-1,4-dihydro-[1,8]naphthyridine-3-carboxylic acid methoxy-methyl-amide, 2 mL of THF was treated with 3-fluoro-4-methoxyphenyl magnesium chloride (0.5 M in THF, 1.3 mL, 2 equiv) at rt for 2 h. The reaction was quenched by slow addition of saturated aqueous ammonium chloride. The mixture was subjected to HPLC and then preparative TLC purification to give 1-(6-Bromo-pyridin-2-ylmethyl)-3-(3-fluoro-4-methoxy-benzoyl)-7-trifluoromethyl-1H-[1,8]naphthyridin-4-one. LCMS (ES) M+H 536.0.

Example 208

Preparation of 3-(4-Chloro-benzoyl)-1-(6-methyl-pyridin-2-ylmethyl)-1H-quinolin-4-one

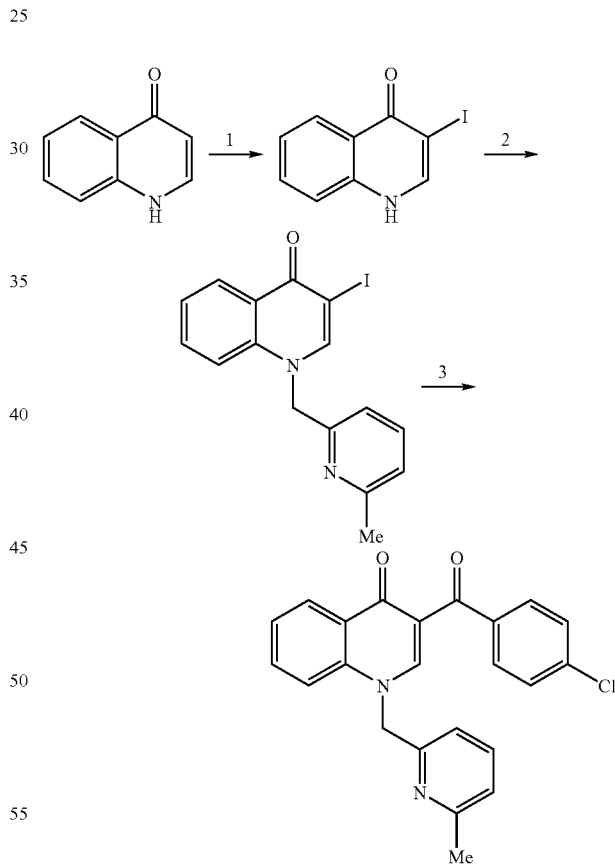

Step 1: 3-Iodo-1H-quinolon-4-one

1H-Quinolin-4-one (2.90 g, 20 mmol, 1 equiv) in 5 mL of DMF was treated with 1.12 g of KOH (2 equiv) and 5.30 g of iodine (1.05 equiv) for 2 hours. The reaction was quenched by slow addition of saturated aqueous solution of $Na_2S_2O_3$. Filtration gave 3-iodo-1H-quinolin-4-one as an off-white solid.

Step 2: 3-iodo-1-(6-methyl-pyridin-2-ylmethyl)-1H-quinolin-4-one 3-iodo-1H-quinolin-4-one (1.36 g, 5 mmol, 1 equiv) in 5 mL of DMF was treated with 0.22 g of NaH (1.1 equiv) for 10 min. 2-Bromomethyl-6-methyl-pyridine (1.11 g, 1.2 equiv) was then added and stirring continued for 3 h. The reaction was quenched by slow addition of saturated aqueous solution of $NH_4Cl$. Standard workup followed by flash chromatography gave 3-iodo-1-(6-methyl-pyridin-2-ylmethyl)-1H-quinolin-4-one as a white solid.

Step 3: Preparation of 3-(4-Chloro-benzoyl)-1-(6-methyl-pyridin-2-ylmethyl)-1H-quinolin-4-one A –78° C. solution of 3-iodo-1-(6-methyl-pyridin-2-ylmethyl)-1H-quinolin-4-one (113 mg, 0.3 mmol, 1 equiv) in 3 mL of THF was treated with 1.65 mL of isopropyl magnesium chloride (1.1 equiv) for 2 hours. Then 4-chloro-N-methoxy-N-methyl-benzamide (46 µL, 1.2 equiv) was added and stirring continued at rt for 2 hours. The reaction was quenched by slow addition of saturated aqueous solution of $NH_4Cl$. Standard workup followed by HPLC purification gave 3-(4-chloro-benzoyl)-1-(6-methyl-pyridin-2-ylmethyl)-1H-quinolin-4-one. LCMS (ES) M+H 389.1

Example 209

Preparation of 1-(6-Bromo-pyridin-2-ylmethyl)-3-(3,4-dimethoxy-benzoyl)-1H-[1,8]naphthyridin-4-one

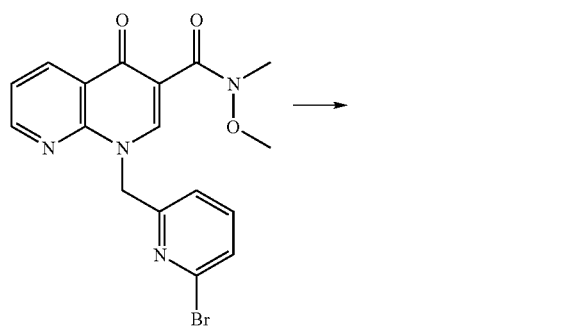

Experimental conditions analogous to those described for Step 6 of Example 60, from 100 mg (0.248 mmol) of 1-(6-Bromo-pyridin-2-ylmethyl)-4-oxo-1,4-dihydro-[1,8]naphthyridine-3-carboxylic acid methoxy-methyl-amide in THF 2 ml, was added 1.09 ml (0.545 mmol) 3,4-dimethoxyphenyl-magnesium bromide. The reaction mixture was stirred at room temperature for 30 min, then quenched with saturated solution of $NH_4Cl$, extracted with ethyl acetate and purified with flash chromatography to give the desired product 22 mg. LCMS observed for (M+H)+: 480.

Example 210

Preparation of 6-[3-(4-Methoxy-3-methyl-benzoyl)-4-oxo-4H-[1,8]naphthyridin-1-ylmethyl]-pyridine-2-carbonitrile

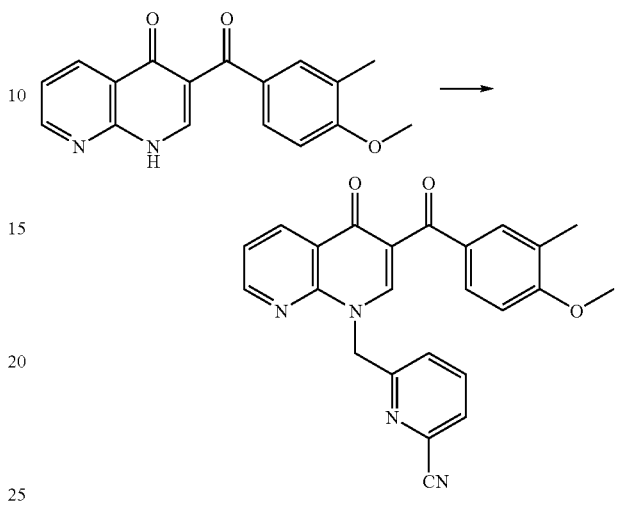

Experimental conditions analogous to those described for Step 3 of Example 1, from 50 mg (0.17 mmol) of 3-(4-Methoxy-3-methyl-benzoyl)-1H-[1,8]naphthyridin-4-one in THF 2 ml, was added KHMDS in THF 0.4 ml (0.2 mmol) slowly. The reaction mixture was stirred at room temperature for 60 min, followed by the addition of 40 mg (0.2 mmol) of 6-Bromomethyl-pyridine-2-carbonitrile. The mixture was heated to 60° C. for 60 min, then quenched with water and purified with HPLC to give the desired product (15 mg). LCMS (M+H)+: 411.1.

Example 211

Preparation of 3-(4-Methoxy-3-methyl-benzoyl)-1-(6-trifluoromethyl-pyridin-2-ylmethyl)-1H-[1,8]naphthyridin-4-one

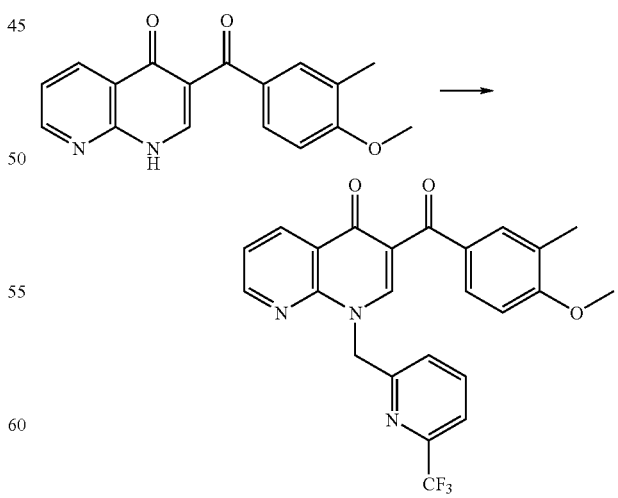

Experimental conditions analogous to those described for Step 3 of Example 1, from 50 mg (0.17 mmol) of 3-(4-Methoxy-3-methyl-benzoyl)-1H-[1,8]naphthyridin-4-one, and 2-Bromomethyl-6-trifluoromethyl-pyridine 53 mg (0.22 mmol), to give 14 mg of desired compound. LCMS (M+H)+: 454.1.

Example 212

Preparation of 3-(4-Methoxy-3-methyl-benzoyl)-1-(3-trifluoromethyl-benzyl)-1H-[1,8]naphthyridin-4-one

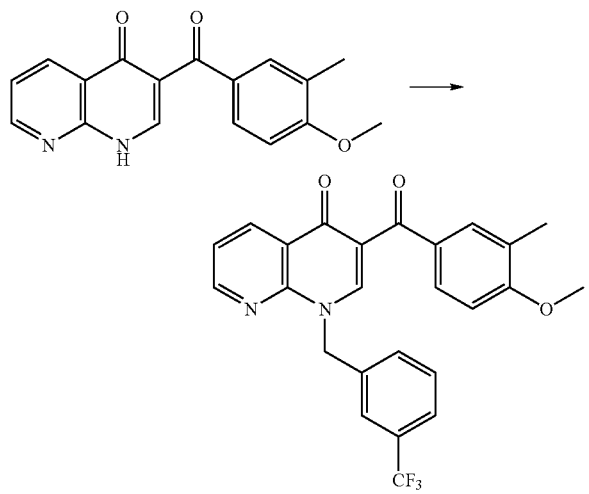

Experimental conditions analogous to those described for Step 3 of Example 1, from 50 mg (0.17 mmol) of 3-(4-Methoxy-3-methyl-benzoyl)-1H-[1,8]naphthyridin-4-one, and 1-Bromomethyl-3-trifluoromethyl-benzene 53 mg (0.22 mmol), to give 12 mg of desired compound. LCMS (M+H)+: 453.1.

Example 213

Preparation of 1-(3-Bromo-benzyl)-3-(4-methoxy-3-methyl-benzoyl)-1H-[1,8]naphthyridin-4-one

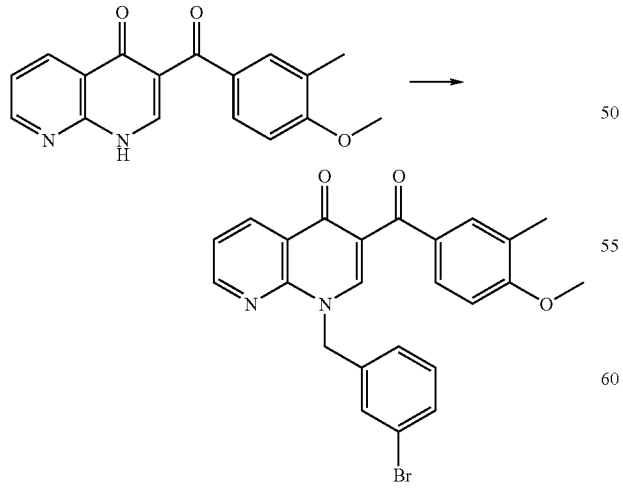

Experimental conditions analogous to those described for Step 3 of Example 1, from 50 mg (0.17 mmol) of 3-(4-Methoxy-3-methyl-benzoyl)-1H-[1,8]naphthyridin-4-one, and 1-Bromo-3-bromomethyl-benzene 55 mg (0.22 mmol), to give 17 mg of desired compound. LCMS (M+H)+: 463.1.

Example 214

Preparation of 3-(5-Methyl-isoxazole-3-carbonyl)-1-(6-methyl-pyridin-2-ylmethyl)-1H-quinolin-4-one

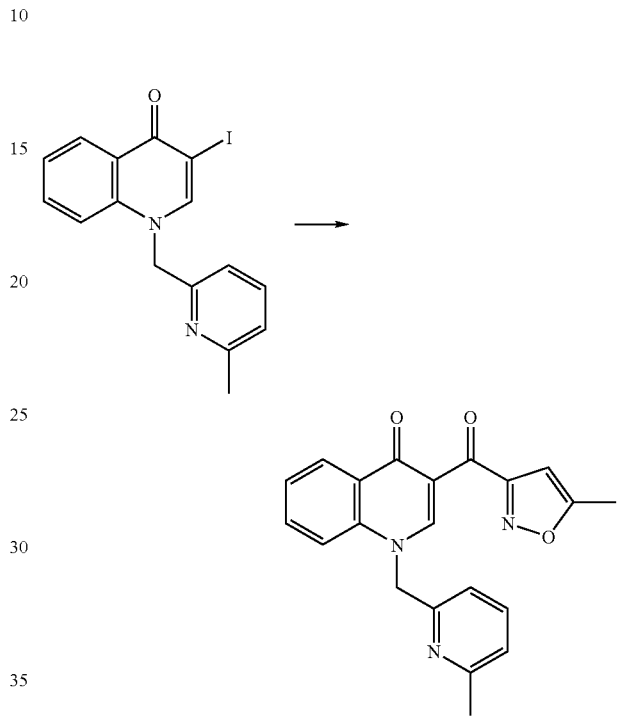

To the solution of 3-Iodo-1-(6-methyl-pyridin-2-ylmethyl)-1H-quinolin-4-one (300 mg, 0.82 mmol, 1.2 eq) in THF (2 ml), was added isopropylmagnesium chloride in THF (0.88 mL, 1.76 mmol, 2.1 eq) slowly at −40° C. The reaction mixture was warmed to room temperature and stirred for 60 min, followed by the addition of 5-Methyl-isoxazole-3-carboxylic acid methoxy-methyl-amide (116 mg, 0.0.68 mmol, 1 eq). The mixture was stirred overnight, quenched with water and purified with HPLC to give the desired product (25 mg). LCMS observed for (M+H)+: 360.1.

Example 216

Preparation of 6-[3-(2,3-Dihydro-benzo[1,4]dioxine-6-carbonyl)-4-oxo-4H-quinolin-1-ylmethyl]-pyridine-2-carbonitrile

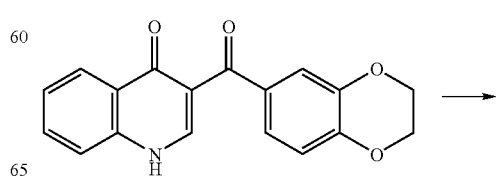

-continued

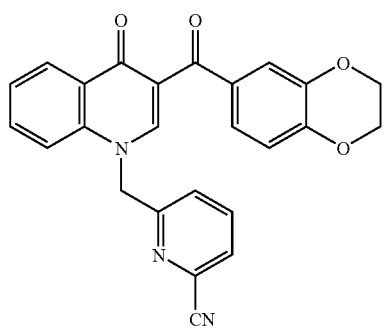

The mixture of 3-(2,3-Dihydro-benzo[1,4]dioxine-6-carbonyl)-1H-quinolin-4-one (70 mg, 0.228 mmol, 1 eq) in DMF (1 ml) and sodium hydride (11.8 mg, 0.296 mmol, 1.3 eq) was stirred at room temperature for 60 min, followed by the addition of 6-Bromomethyl-pyridine-2-carbonitrile (74.1 mg, 0.296 mmol, 1.3 eq). The mixture was stirred for 60 min, quenched with water, taken up with ethyl acetate, dried over sodium sulfate and purified with flash chromatography to give the desired product (17 mg). LCMS observed for (M+H)$^+$: 424.1.

Example 217

Preparation of 3-(2,3-Dihydro-benzo[1,4]dioxine-6-carbonyl)-1-(6-trifluoromethyl-pyridin-2-ylmethyl)-1H-quinolin-4-one

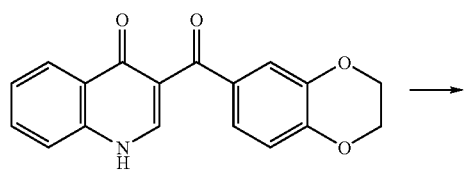

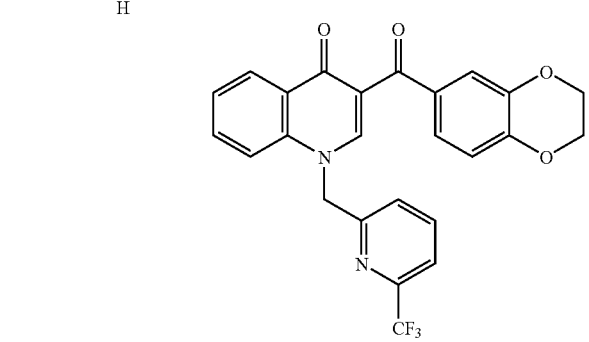

Experimental conditions analogous to those described for Step 3 of Example 1, from 3-(2,3-Dihydro-benzo[1,4]dioxine-6-carbonyl)-1H-quinolin-4-one 70 mg (0.228 mmol) and 71.1 mg (0.296 mmol) of 2-Bromomethyl-6-trifluoromethyl-pyridine, to give 20 mg of desired compound. LCMS (M+H)$^+$: 467.1.

Example 218

Preparation of 1-(6-Amino-pyridin-2-ylmethyl)-3-(2,3-dihydro-benzo[1,4]dioxine-6-carbonyl)-1H-quinolin-4-one

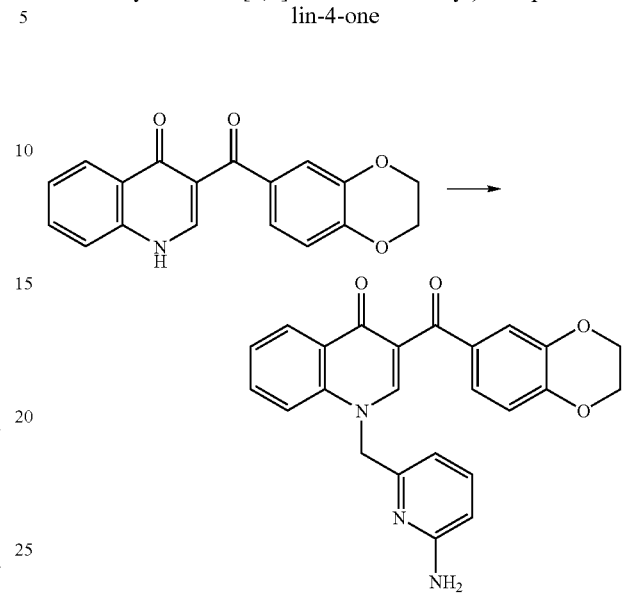

The mixture of 3-(2,3-Dihydro-benzo[1,4]dioxine-6-carbonyl)-1H-quinolin-4-one 70 mg (0.228 mmol) in DMF (1 mL) and sodium hydride 11.8 mg (0.296 mmol) was stirred at room temperature for 60 min, followed by the addition of N-[1-(2-Bromo-1-methyl-ethylideneamino)-vinyl]-2,2,2-trifluoro-acetamide 83.8 mg (0.296 mmol). The mixture was stirred for 60 min, quenched with water, taken up with ethyl acetate, dried over sodium sulfate and purified with flash chromatography. The purified product was treated with Diethylamine in methanol over weekend, filtered to give the desired product 10 mg. LCMS observed for (M+H)$^+$: 414.

Example 219

Preparation of 1-(3-Bromo-benzyl)-3-(2,3-dihydro-benzo[1,4]dioxine-6-carbonyl)-1H-quinolin-4-one

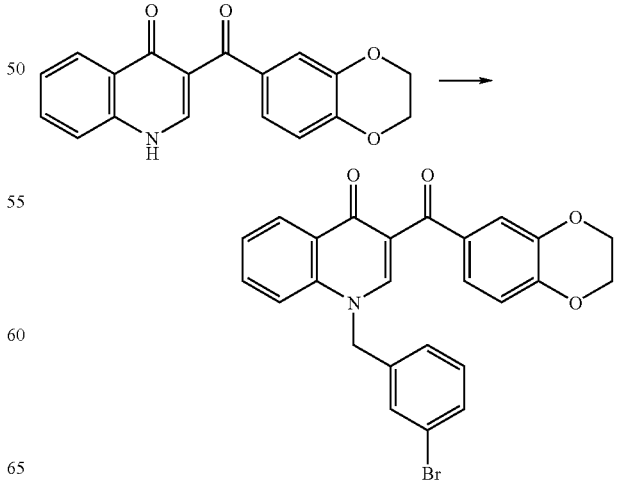

Experimental conditions analogous to those described for Step 3 of Example 1, from 3-(2,3-Dihydro-benzo[1,4]dioxine-6-carbonyl)-1H-quinolin-4-one (70 mg, 0.228 mmol) and 74 mg (0.296 mmol) of 1-Bromo-3-bromomethyl-benzene, to give 25 mg of desired compound. LCMS (M+H)+: 476.

Example 220

Preparation of 3-(2,3-Dihydro-benzo[1,4]dioxine-6-carbonyl)-1-(3-trifluoromethyl-benzyl)-1H-quinolin-4-one

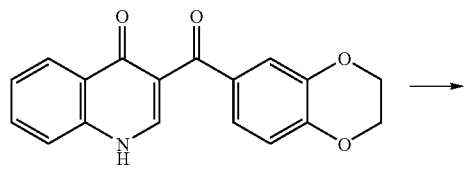

Experimental conditions analogous to those described for Step 3 of Example 1, from 3-(2,3-Dihydro-benzo[1,4]dioxine-6-carbonyl)-1H-quinolin-4-one 70.7 mg (0.296 mmol) and 71.1 mg (0.296 mmol) of 1-Bromomethyl-3-trifluoromethyl-benzene, to give 21 mg of desired compound. LCMS (M+H)+: 466.

Example 221

Preparation of 1-(3-Chloro-benzyl)-3-(2,3-dihydro-benzo[1,4]dioxine-6-carbonyl)-1H-quinolin-4-one

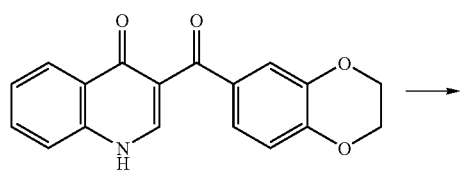

-continued

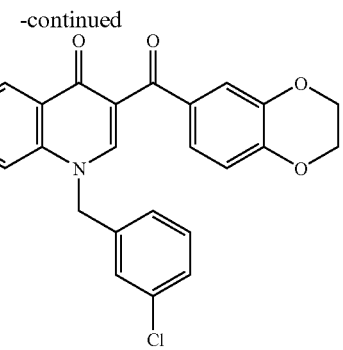

Experimental conditions analogous to those described for Step 3 of Example 1, from 3-(2,3-Dihydro-benzo[1,4]dioxine-6-carbonyl)-1H-quinolin-4-one 70 mg (0.228 mmol) and 71.1 mg (0.296 mmol) 1-Chloro-3-chloromethyl-benzene, to give 24 mg of desired compound. LCMS (M+H)+: 432.

Example 222

Preparation of 1-(6-Bromo-pyridin-2-ylmethyl)-3-(4-methoxy-3-methyl-benzoyl)-1H-[1,8]naphthyridin-4-one Experimental conditions analogous to those described for Step 6 of Example 60, from 55 mg (0.136 mmol) of 1-(6-Bromo-pyridin-2-ylmethyl)-4-oxo-1,4-dihydro-[1,8]naphthyridine-3-carboxylic acid methoxy-methyl-amide, and 0.5 ml (0.285 mmol) of 4-methoxy-3-methylphenyl magnesium chloride, to give desired compound as a white solid. LCMS (M+H)+: 464.

Biological Example 1

To demonstrate that the compounds described above are useful modulators for chemokine binding to CCXCKR2, the compounds were screened in vitro to determine their ability to displace SDF-1 from the CCXCKR2 receptor at multiple concentrations. The compounds were combined with mammary gland cells expressing the CCXCKR2 receptor in the presence of the $^{125}$I-labeled chemokine as detailed in Determination of $IC_{50}$ values, Reagents and Cells (see below). The ability of the compounds to displace the labeled chemokine from the CCXCKR2 receptor sites at multiple concentrations was then determined with the screening process.

Compounds that were deemed effective modulators were able to displace at least 50% of the SDF-1 from the CCX-CKR2 receptor at concentrations at or below 20 micromolar (µM) but >500 nM (+); and more preferably at concentrations from >100 nM to ≦500 nM (++). At present, especially preferred compounds can displace at least 50% of the SDF-1 from the CCXCKR2 receptor at concentrations at or below 100 nM (+++). Exemplary compounds that met these criteria are reproduced in Table 4 below. All compounds were prepared as described in the Examples above, or by related methods substituting readily available starting materials.

TABLE 4

| No | Structure | Activity |
|---|---|---|
| 1 | 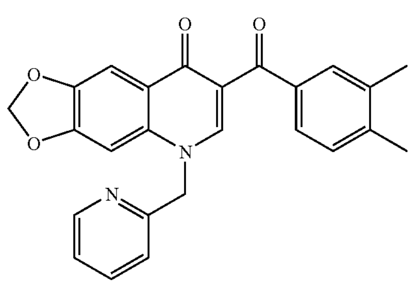 | ++ |
| 2 | 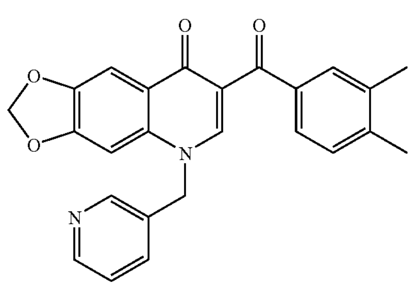 | + |
| 3 | 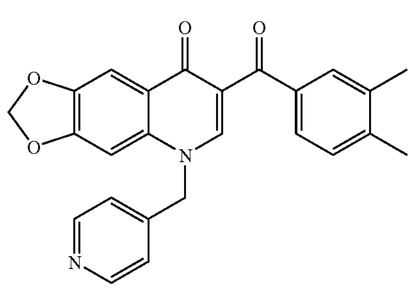 | + |

TABLE 4-continued

| No | Structure | Activity |
|---|---|---|
| 4 | 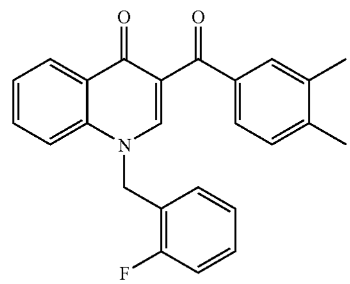 | +++ |
| 5 | 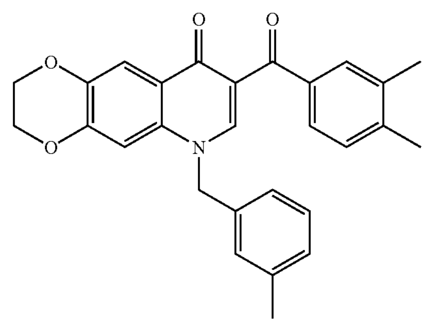 | + |
| 6 | 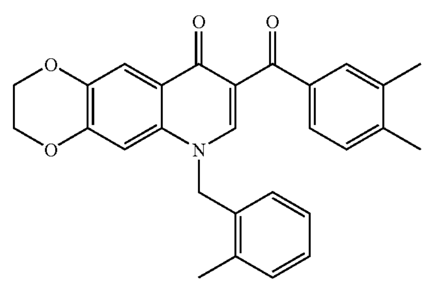 | + |
| 7 | 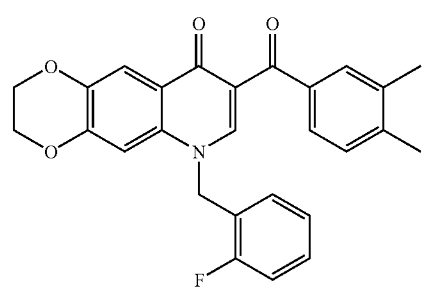 | + |
| 8 | 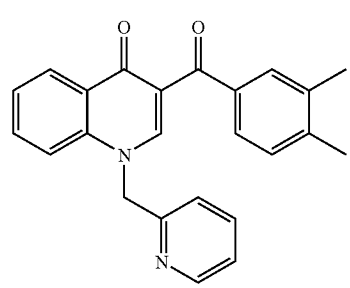 | +++ |

TABLE 4-continued

| No | Structure | Activity |
|----|-----------|----------|
| 9  | 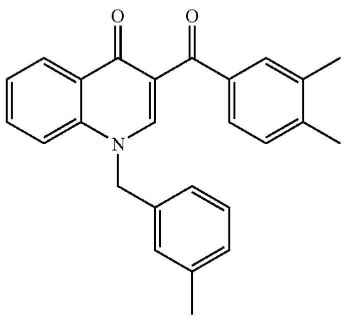 | +++ |
| 10 | 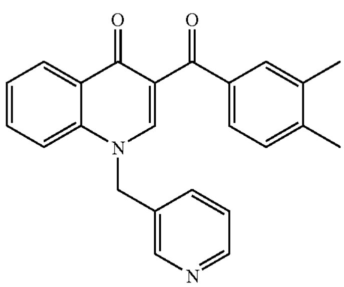 | + |
| 11 | 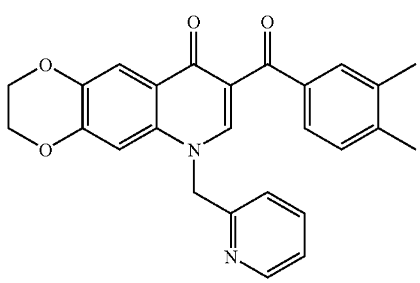 | + |
| 12 | 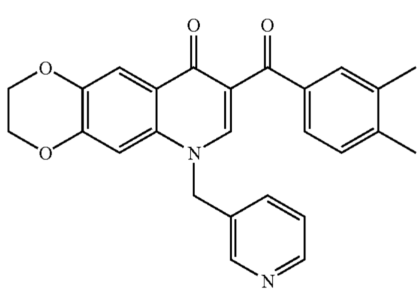 | + |
| 13 | 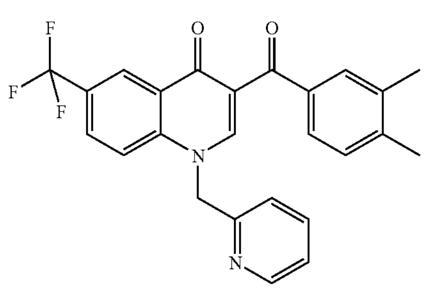 | + |
| 14 | | + |
| 15 | | + |
| 16 | | + |
| 17 | | + |
| 18 | | ++ |

TABLE 4-continued

| No | Structure | Activity |
|----|-----------|----------|
| 19 | 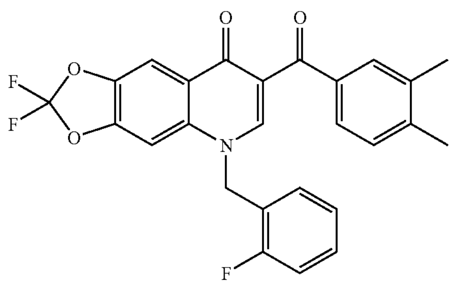 | + |
| 20 | 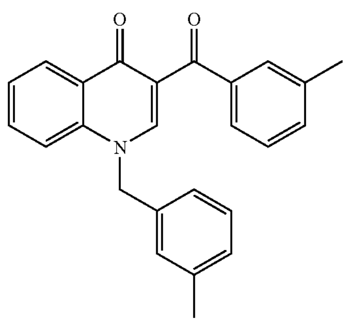 | +++ |
| 21 | 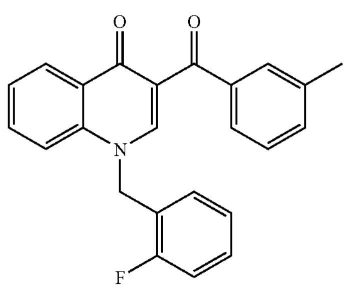 | +++ |
| 22 | 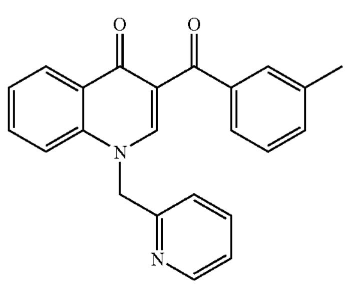 | +++ |
| 23 | 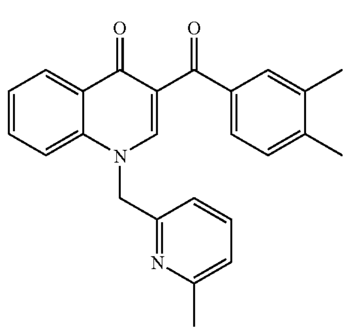 | +++ |
| 24 | | + |
| 25 | | + |
| 26 | | + |
| 27 | | + |
| 28 | | +++ |

TABLE 4-continued

| No | Structure | Activity |
|----|-----------|----------|
| 29 | 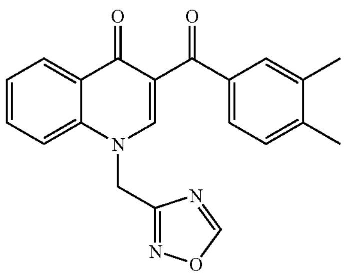 | +++ |
| 30 | 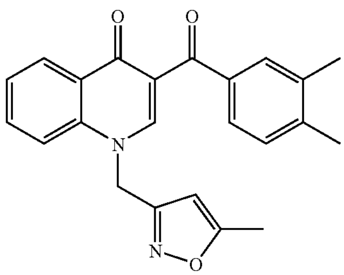 | ++ |
| 31 | 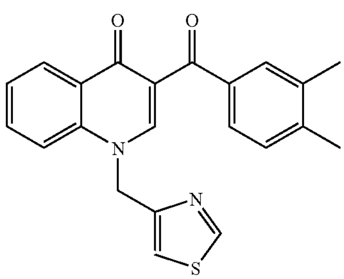 | +++ |
| 32 | 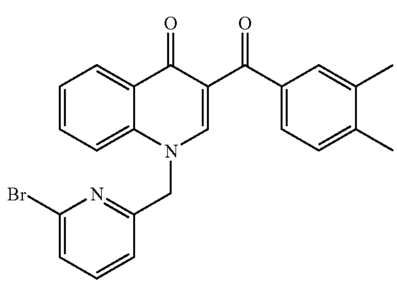 | +++ |
| 33 | 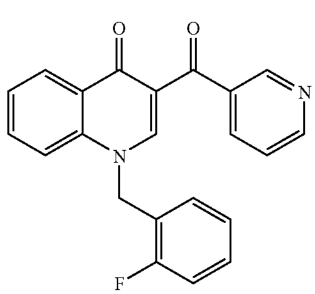 | + |
| 34 | | + |
| 35 | | + |
| 36 | | + |
| 37 | | +++ |
| 38 | | + |

TABLE 4-continued
| No | Structure | Activity |
|----|-----------|----------|
| 39 | 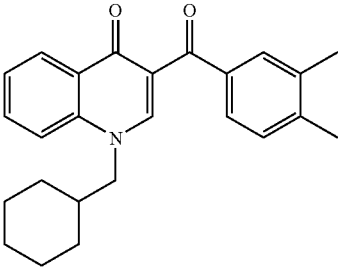 | +++ |
| 40 | 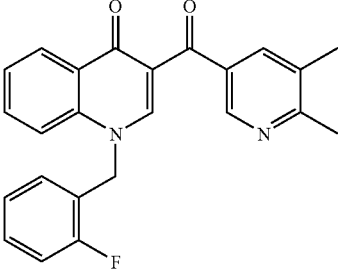 | +++ |
| 41 | 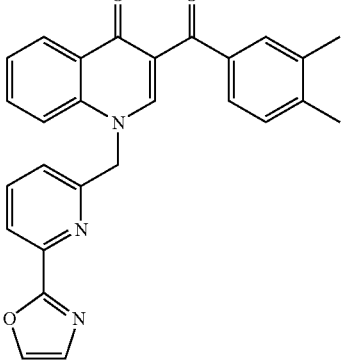 | ++ |
| 42 | 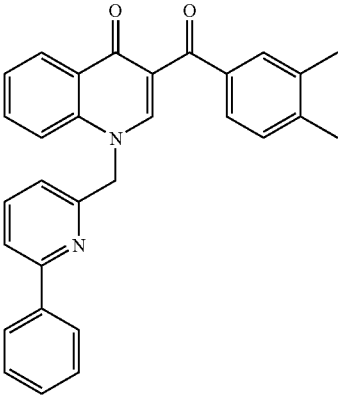 | ++ |
TABLE 4-continued
| No | Structure | Activity |
|----|-----------|----------|
| 43 | 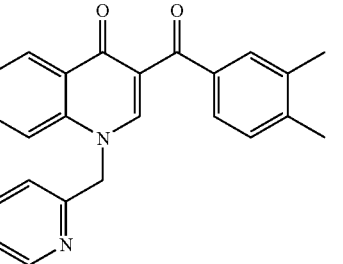 | ++ |
| 44 | 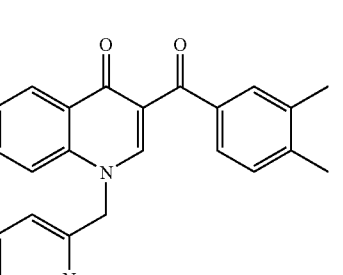 | +++ |
| 45 | 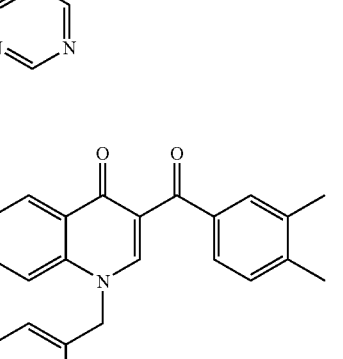 | +++ |
| 46 | 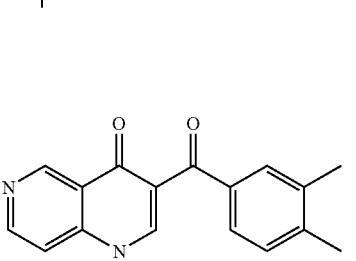 | + |

TABLE 4-continued
| No | Structure | Activity |
|----|-----------|----------|
| 47 | 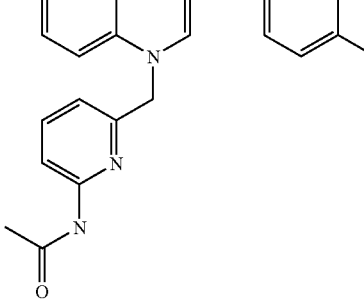 | ++ |
| 48 | 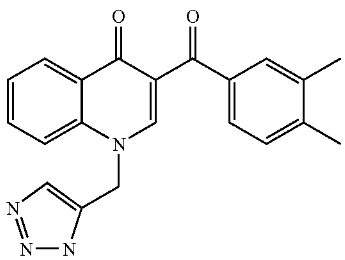 | ++ |
| 49 | 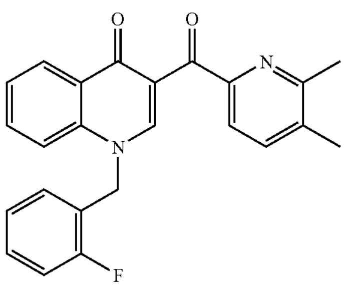 | +++ |
| 50 | 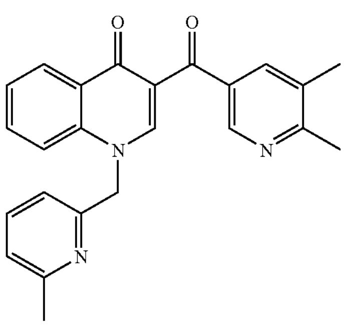 | +++ |
| 51 | 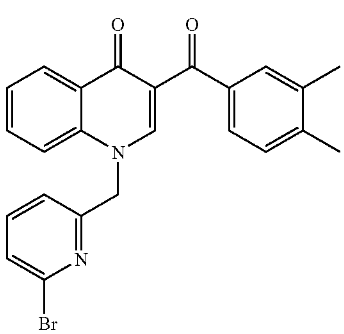 | +++ |
TABLE 4-continued
| No | Structure | Activity |
|----|-----------|----------|
| 52 | 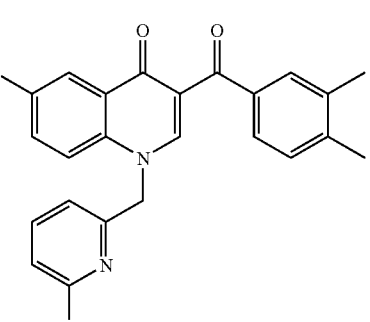 | ++ |
| 53 | 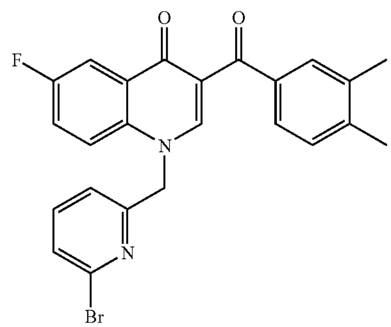 | +++ |
| 54 | 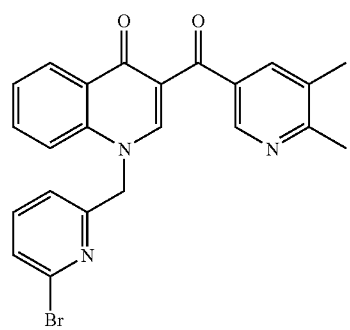 | +++ |
| 55 | 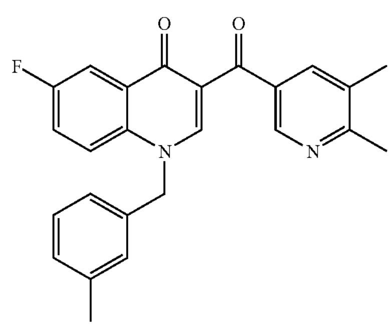 | +++ |

TABLE 4-continued

| No | Structure | Activity |
|----|-----------|----------|
| 56 | 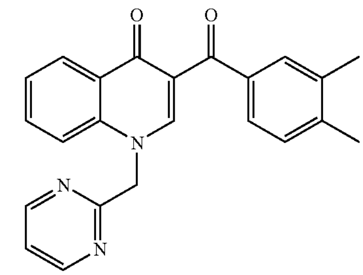 | +++ |
| 57 | 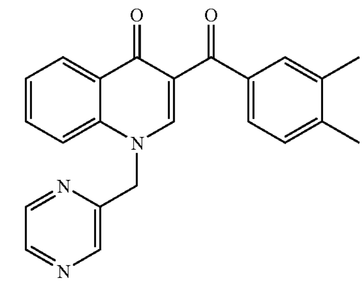 | +++ |
| 58 | 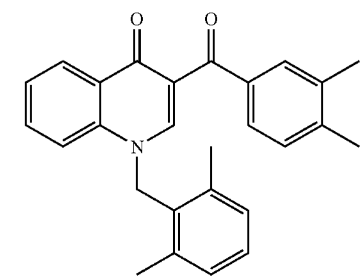 | + |
| 59 | 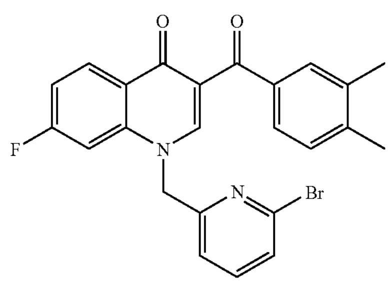 | +++ |
| 60 | 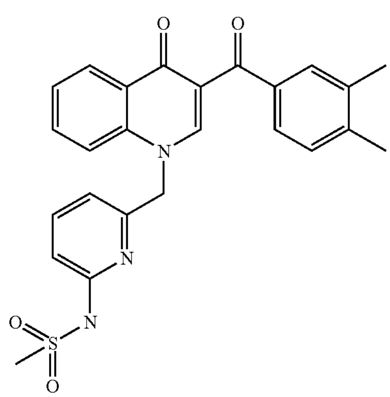 | ++ |
| 61 | | + |
| 62 | | + |
| 63 | | + |
| 64 | | +++ |

TABLE 4-continued
| No | Structure | Activity |
|----|-----------|----------|
| 65 | 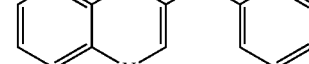 | +++ |
| 66 | 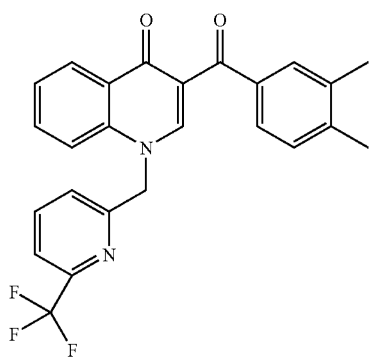 | +++ |
| 67 | 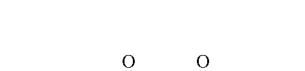 | +++ |
| 68 | 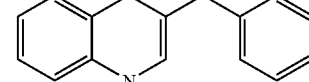 | +++ |
| 69 |  | +++ |
| 70 | 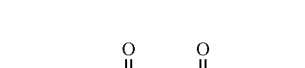 | +++ |
| 71 | 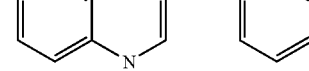 | ++ |
| 72 |  | + |

TABLE 4-continued
| No | Structure | Activity |
|----|-----------|----------|
| 73 | 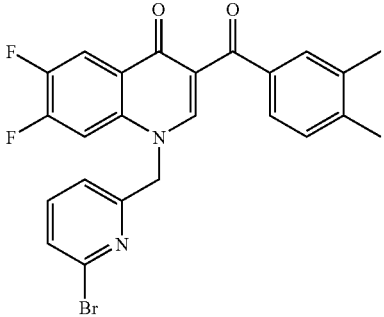 | +++ |
| 74 | 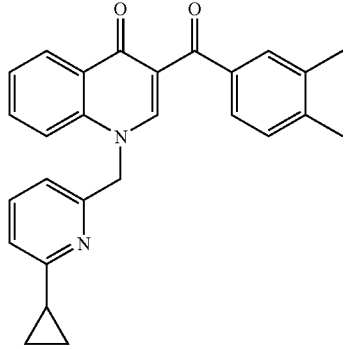 | +++ |
| 75 | 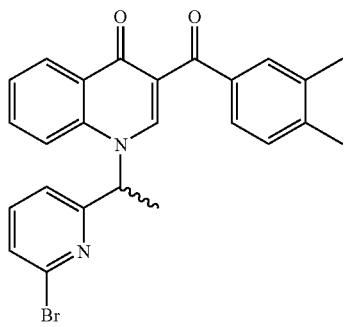 | +++ |
| 76 | 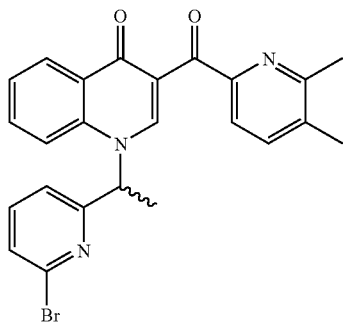 | +++ |
| 77 | 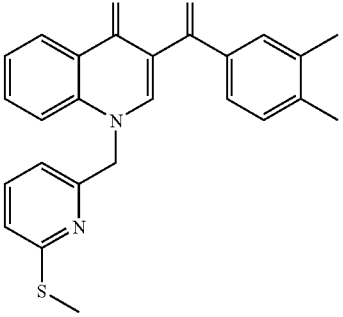 | +++ |
| 78 | 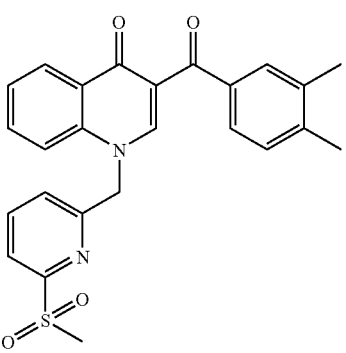 | ++ |
| 79 | 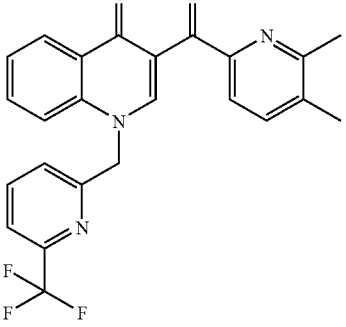 | +++ |
| 80 | 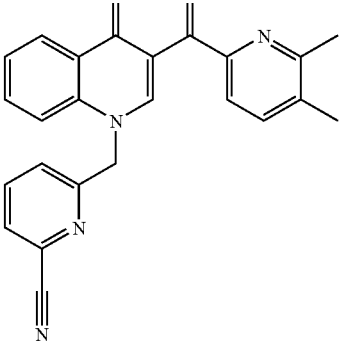 | +++ |

TABLE 4-continued

| No | Structure | Activity |
|----|-----------|----------|
| 81 | 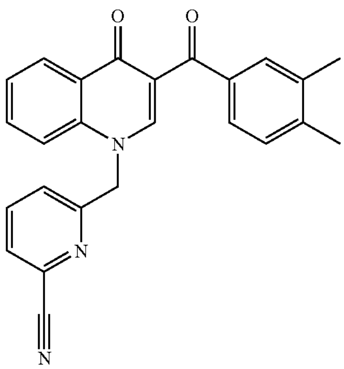 | +++ |
| 82 | 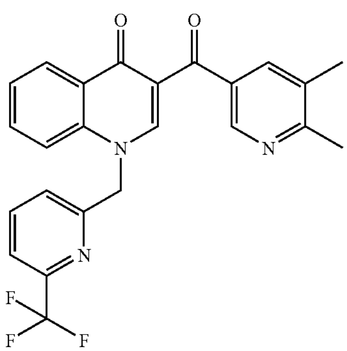 | +++ |
| 83 | 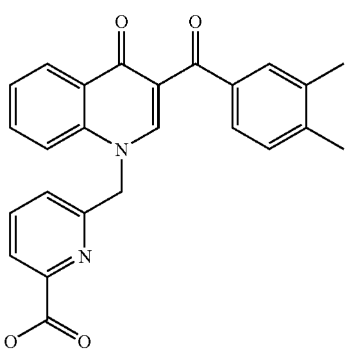 | + |
| 84 | 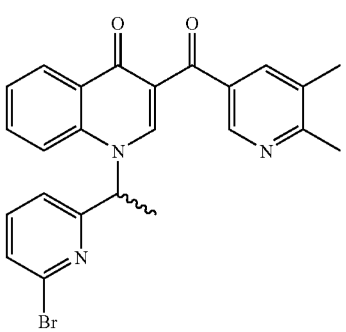 | + |
| 85 | | +++ |
| 86 | | + |
| 87 | | +++ |
| 88 | | ++ |

TABLE 4-continued
| No | Structure | Activity |
|----|-----------|----------|
| 89 | 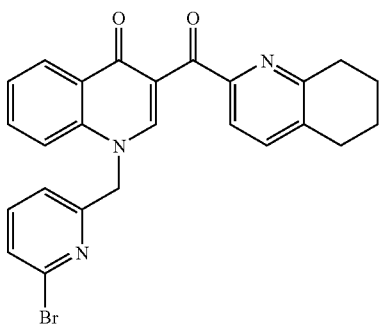 | +++ |
| 90 | 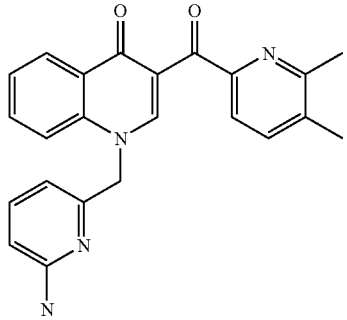 | +++ |
| 91 | 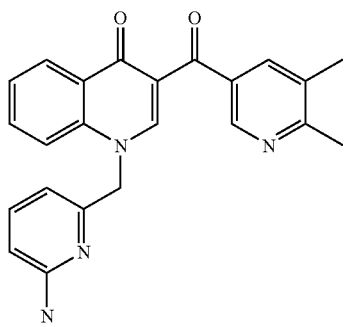 | +++ |
| 92 | 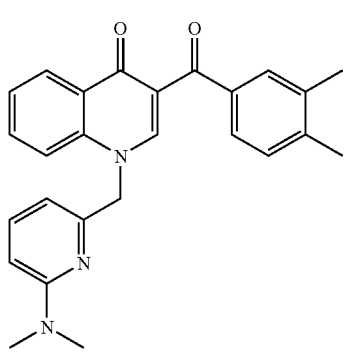 | + |
TABLE 4-continued
| No | Structure | Activity |
|----|-----------|----------|
| 93 | 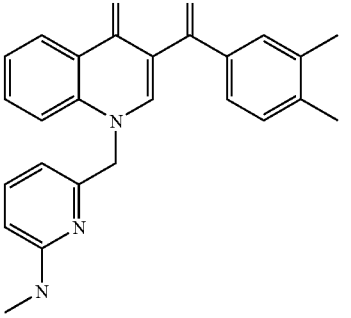 | +++ |
| 94 | 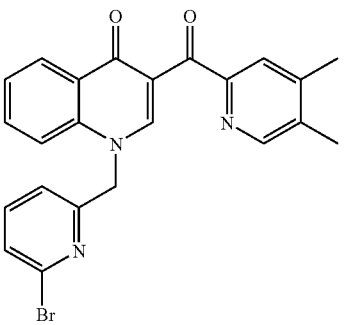 | +++ |
| 95 | 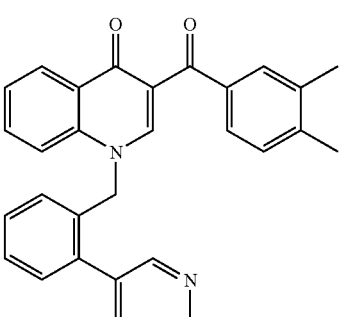 | + |
| 96 | 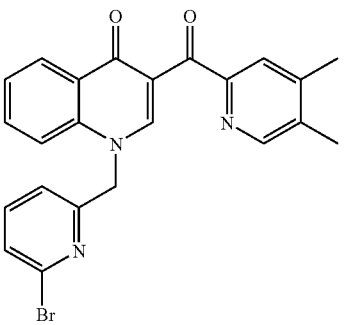 | +++ |

TABLE 4-continued

| No | Structure | Activity |
|---|---|---|
| 97 | 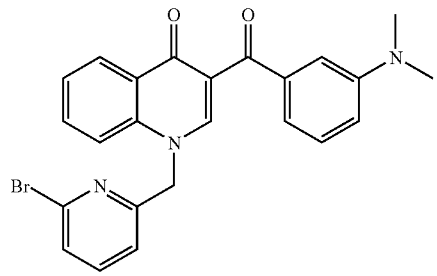 | +++ |
| 98 | 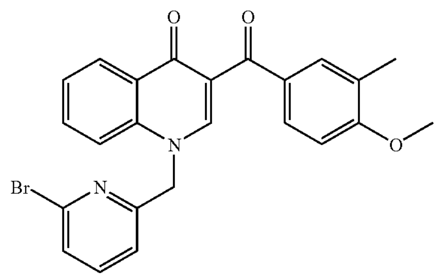 | +++ |
| 99 | 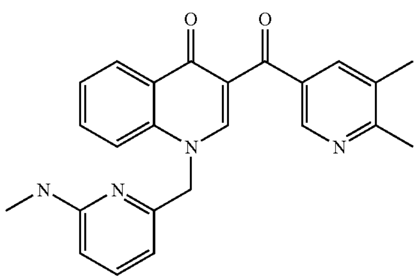 | ++ |
| 100 | 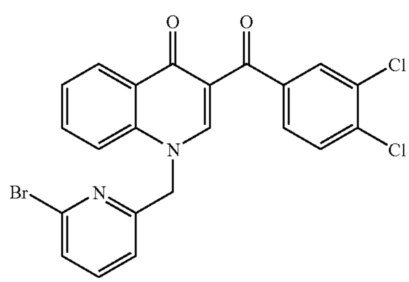 | +++ |
| 101 | 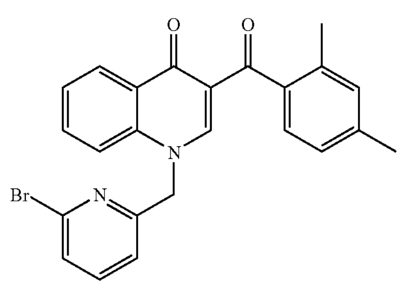 | +++ |
| 102 | 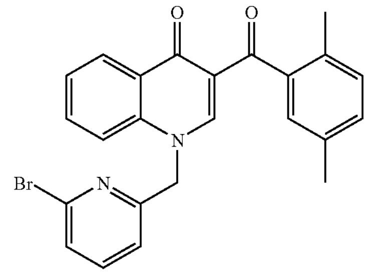 | +++ |
| 103 | 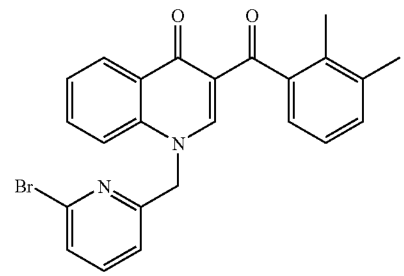 | +++ |
| 104 | 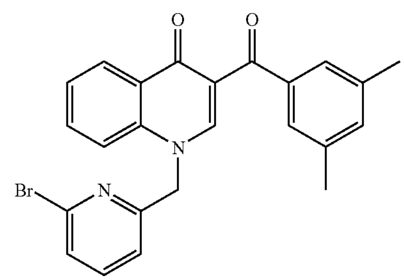 | +++ |
| 105 | 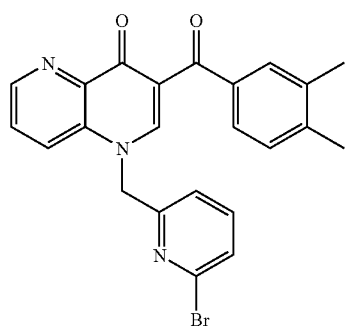 | +++ |
| 106 | 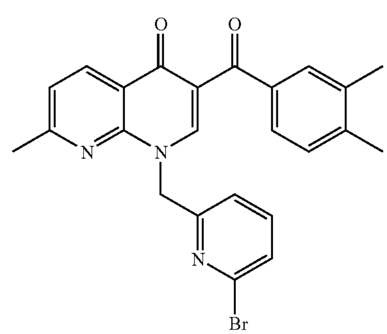 | +++ |

TABLE 4-continued
| No | Structure | Activity |
|----|-----------|----------|
| 107 | 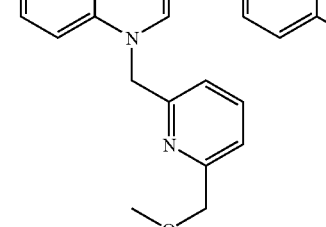 | +++ |
| 108 | | +++ |
| 109 | | + |
| 110 | | + |
| 111 | 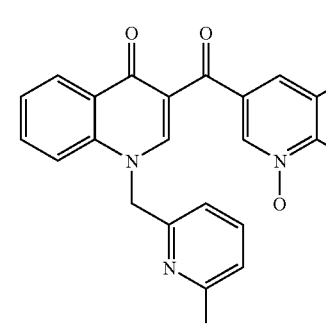 | ++ |
| 112 | 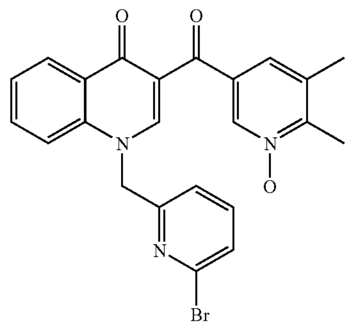 | ++ |
| 113 | 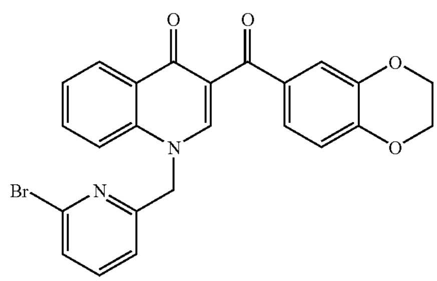 | +++ |
| 114 | 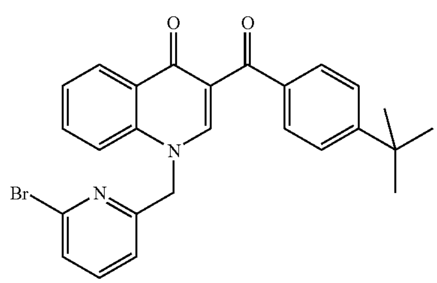 | +++ |
| 115 | 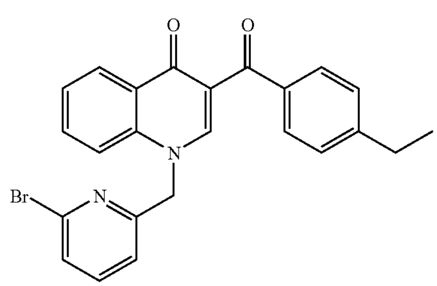 | +++ |

TABLE 4-continued

| No | Structure | Activity |
|---|---|---|
| 116 | | + |
| 117 | | + |
| 118 | | + |
| 119 | | +++ |
| 120 | 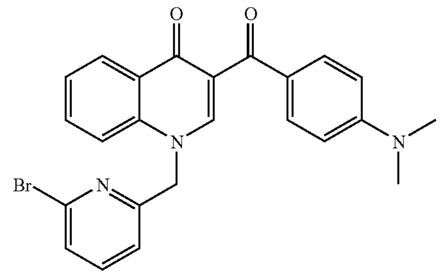 | +++ |
| 121 | 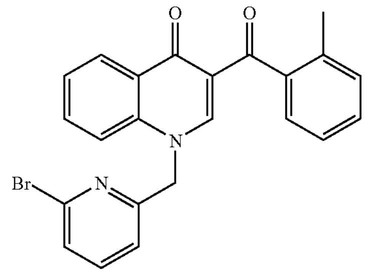 | +++ |
| 122 | 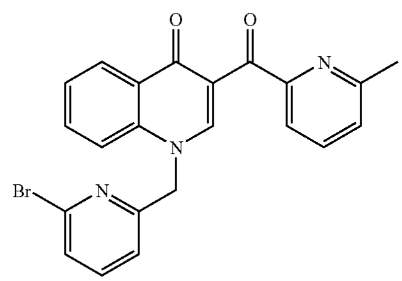 | ++ |
| 123 | 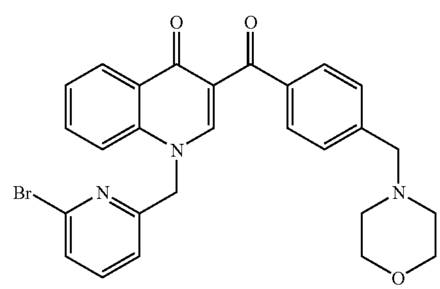 | + |
| 124 | 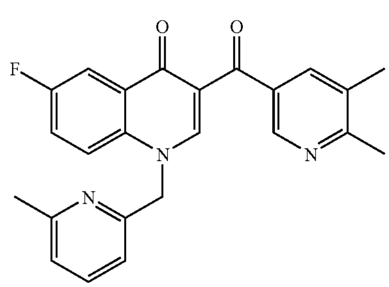 | +++ |

TABLE 4-continued
| No | Structure | Activity |
|----|-----------|----------|
| 125 | 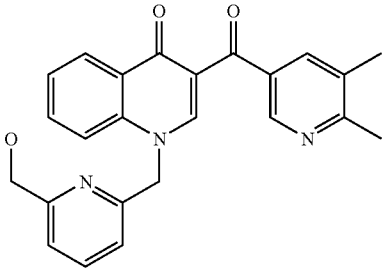 | ++ |
| 126 | 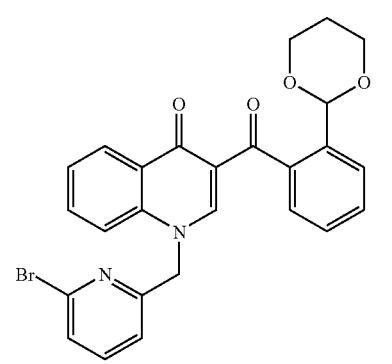 | +++ |
| 127 | 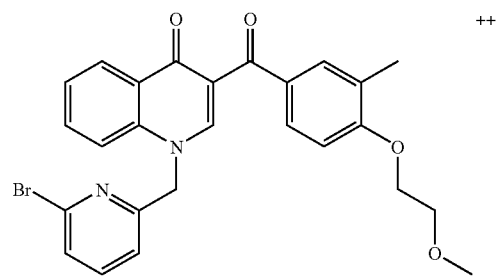 | ++ |
| 128 | 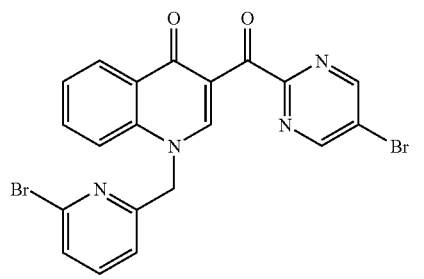 | + |
| 129 | 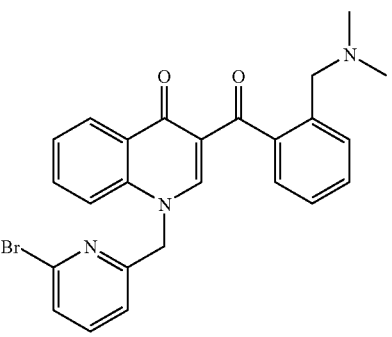 | +++ |
| 130 | 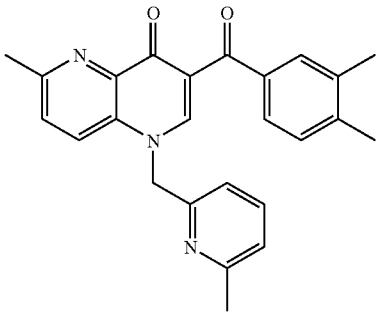 | +++ |
| 131 | 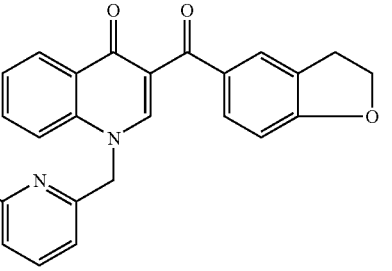 | +++ |
| 132 | 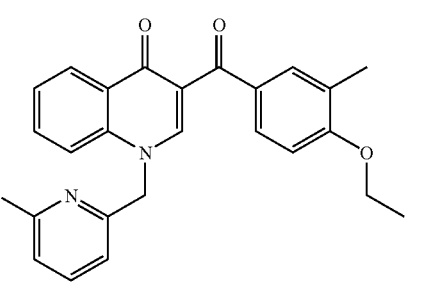 | +++ |
| 133 | 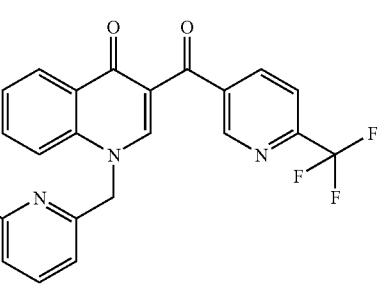 | +++ |
| 134 | 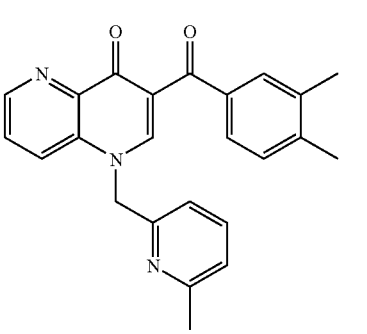 | +++ |

TABLE 4-continued
| No | Structure | Activity |
|---|---|---|
| 135 | 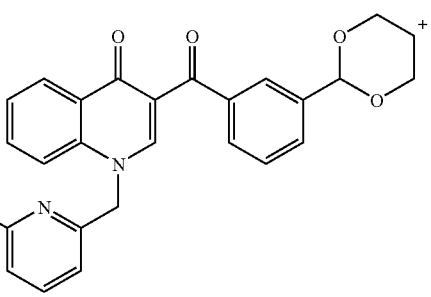 | + |
| 136 | 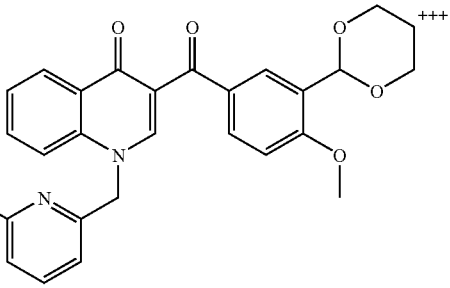 | +++ |
| 137 | 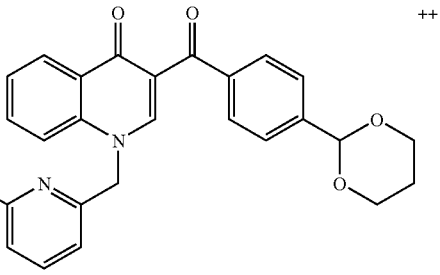 | ++ |
| 138 | 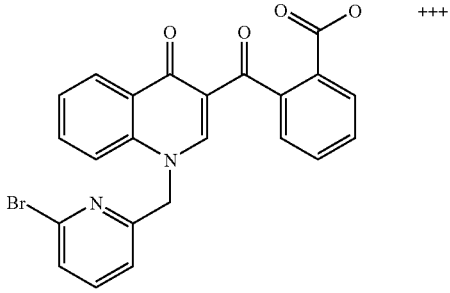 | +++ |
| 139 | 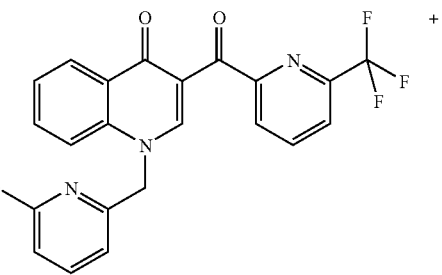 | + |
TABLE 4-continued
| No | Structure | Activity |
|---|---|---|
| 140 | 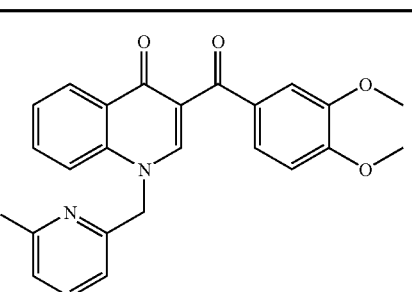 | +++ |
| 141 | 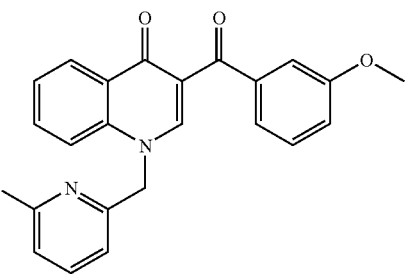 | +++ |
| 142 | 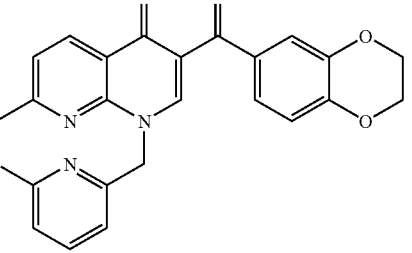 | +++ |
| 143 | 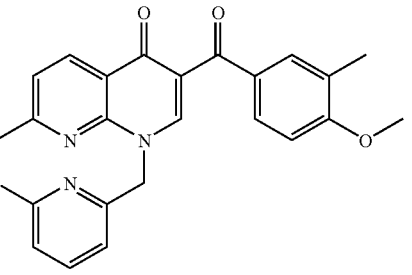 | +++ |
| 144 | 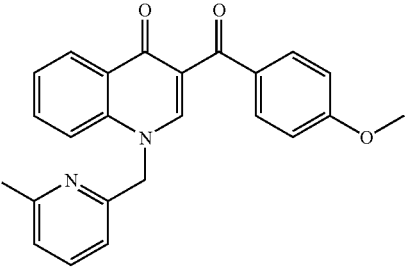 | +++ |

TABLE 4-continued

| No | Structure | Activity |
|---|---|---|
| 145 | 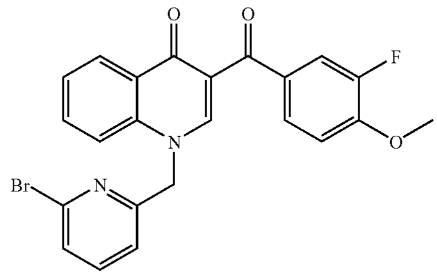 | +++ |
| 146 | 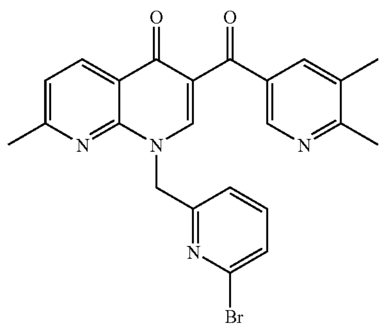 | ++ |
| 147 | 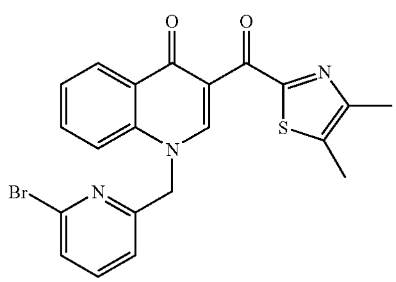 | +++ |
| 148 | 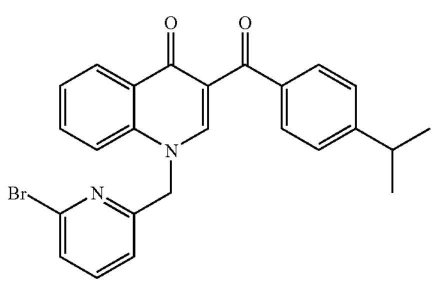 | +++ |
| 149 | 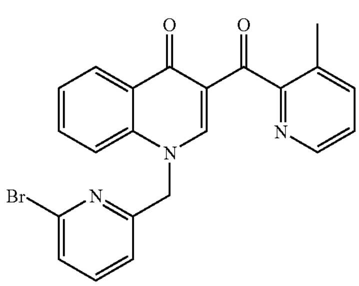 | ++ |
| 150 | | ++ |
| 151 | | +++ |
| 152 | | + |
| 153 | | ++ |
| 154 | | +++ |

TABLE 4-continued
| No | Structure | Activity |
|---|---|---|
| 155 | 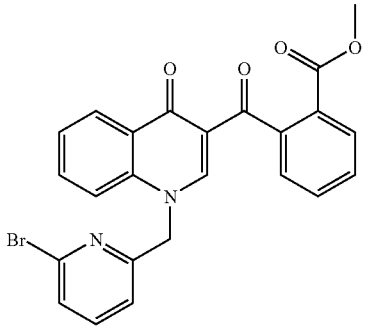 | +++ |
| 156 | 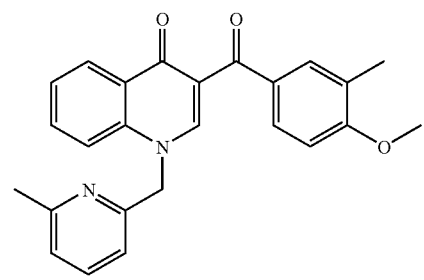 | +++ |
| 157 | 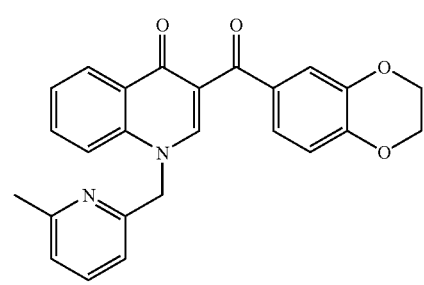 | +++ |
| 158 | 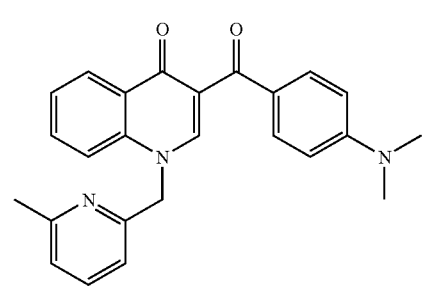 | +++ |
| 159 | 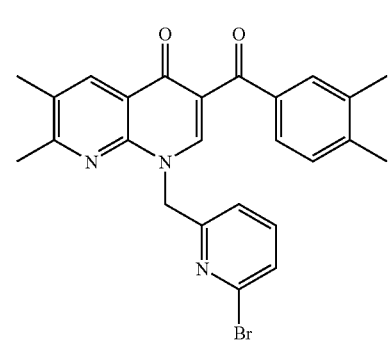 | +++ |
TABLE 4-continued
| No | Structure | Activity |
|---|---|---|
| 160 | 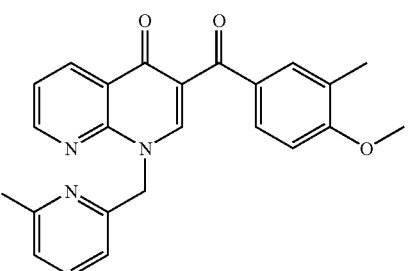 | +++ |
| 161 | 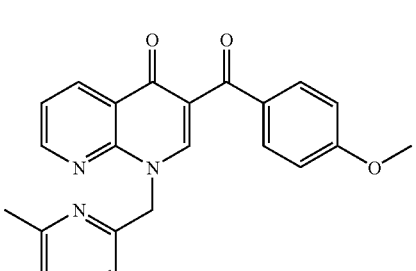 | +++ |
| 162 | 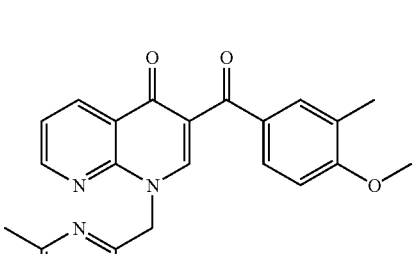 | +++ |
| 163 | 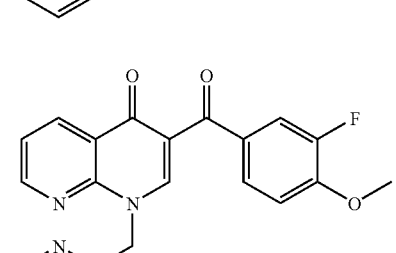 | +++ |
| 164 | 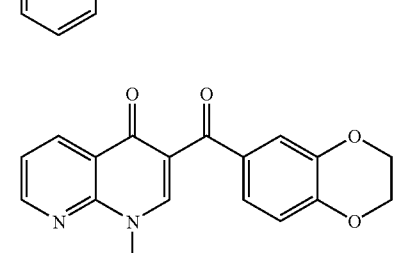 | +++ |

TABLE 4-continued

| No | Structure | Activity |
|---|---|---|
| 165 | 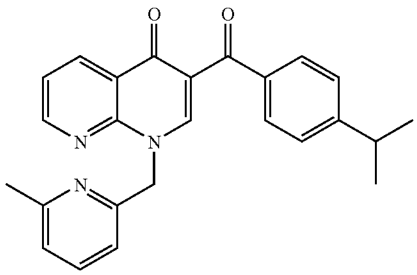 | +++ |
| 166 | 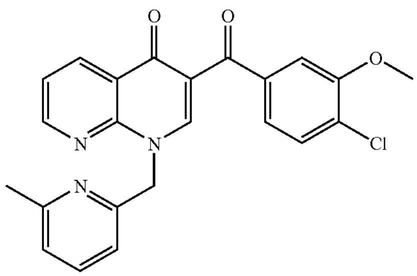 | +++ |
| 167 | 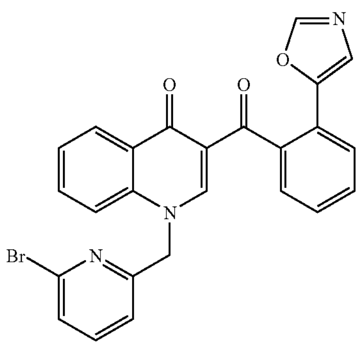 | + |
| 168 | 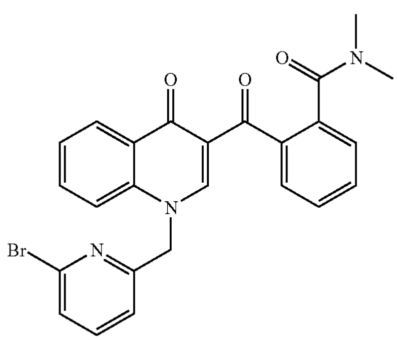 | +++ |
| 169 | 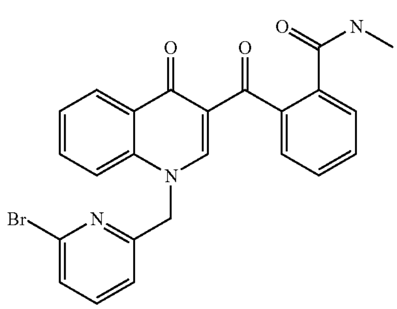 | + |
| 170 | 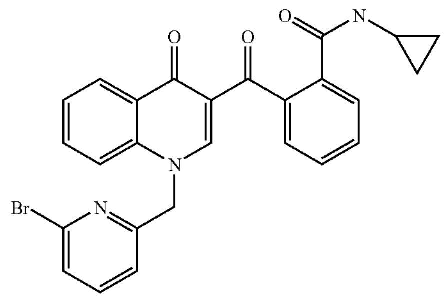 | + |
| 171 | 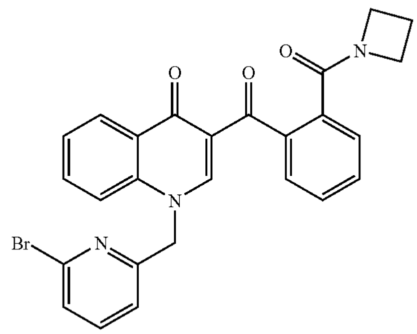 | +++ |
| 172 | 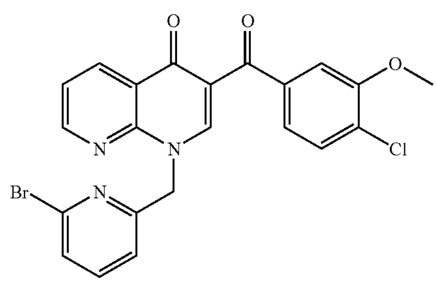 | +++ |
| 173 | 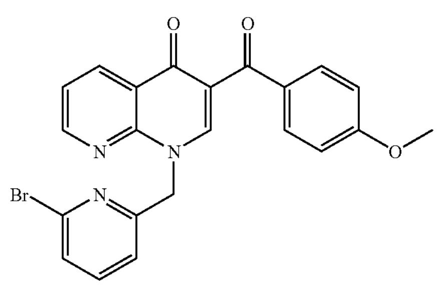 | +++ |
| 174 | 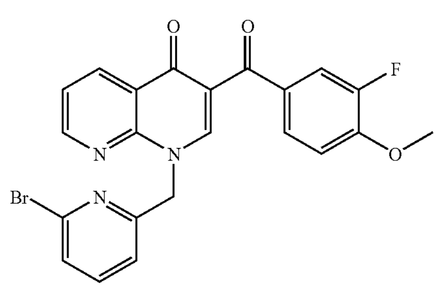 | +++ |

TABLE 4-continued

| No | Structure | Activity |
|----|-----------|----------|
| 175 | 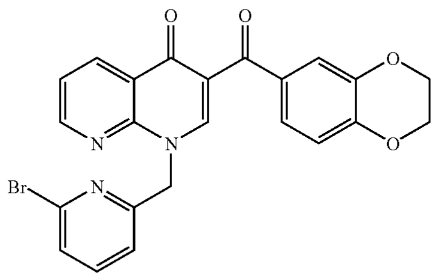 | +++ |
| 176 | 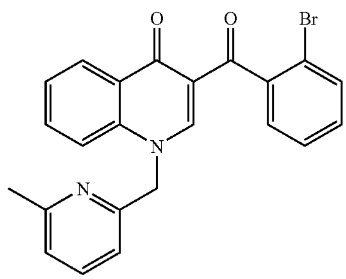 | +++ |
| 177 | 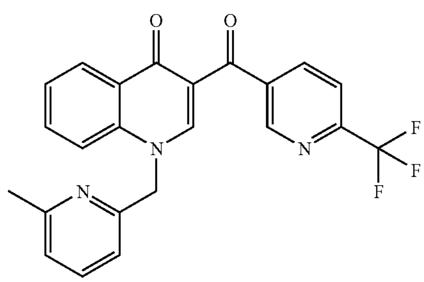 | ++ |
| 178 | 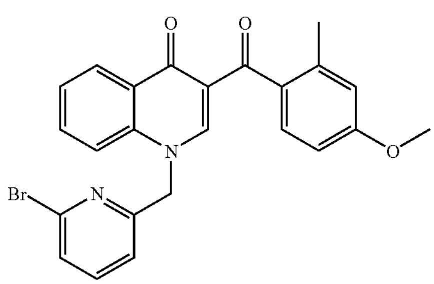 | +++ |
| 179 | 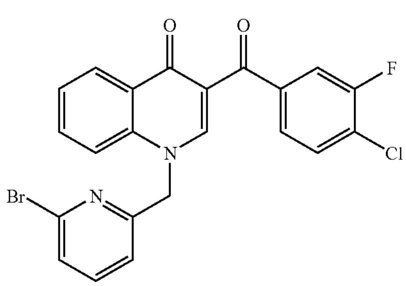 | +++ |
| 180 | | +++ |
| 181 | | + |
| 182 | | +++ |
| 183 | | +++ |
| 184 | | +++ |

TABLE 4-continued

| No | Structure | Activity |
|---|---|---|
| 185 | 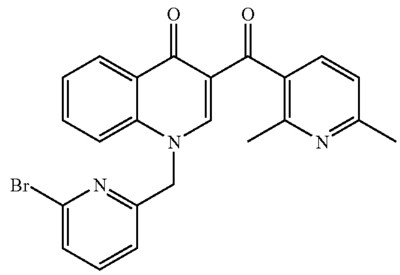 | +++ |
| 186 | 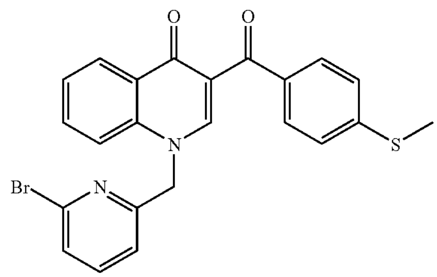 | +++ |
| 187 | 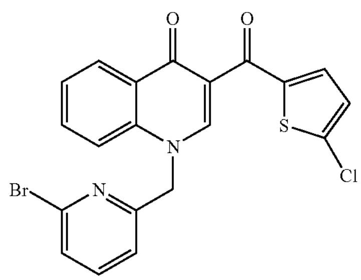 | +++ |
| 188 | 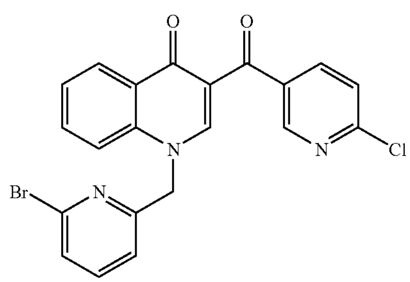 | +++ |
| 189 | 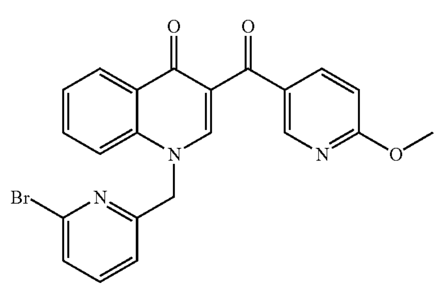 | +++ |
| 190 | | ++ |
| 191 | | ++ |
| 192 | | ++ |
| 193 | | +++ |
| 194 | | +++ |

TABLE 4-continued

| No | Structure | Activity |
|---|---|---|
| 195 | 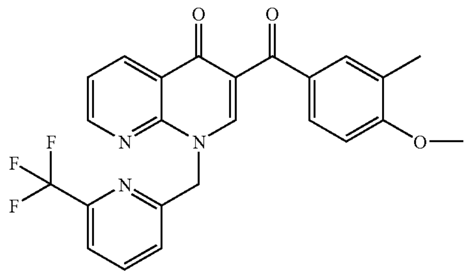 | +++ |
| 196 | 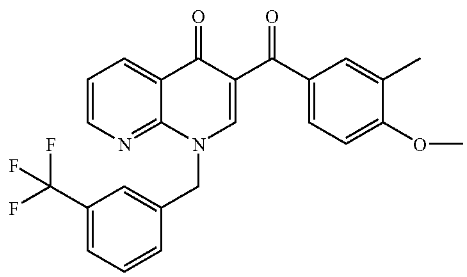 | +++ |
| 197 | 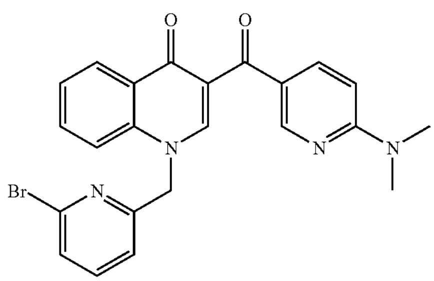 | +++ |
| 198 | 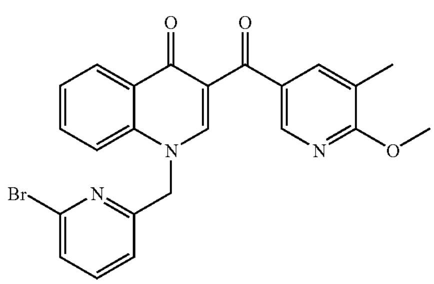 | +++ |
| 199 | 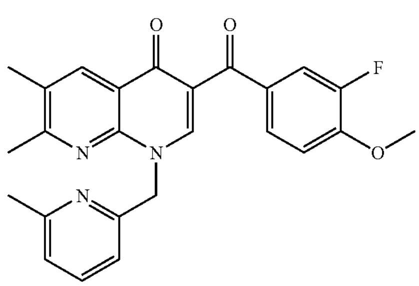 | + |

TABLE 4-continued

| No | Structure | Activity |
|---|---|---|
| 200 | 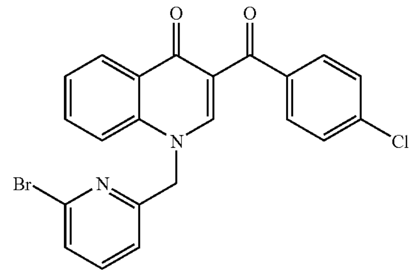 | +++ |
| 201 | 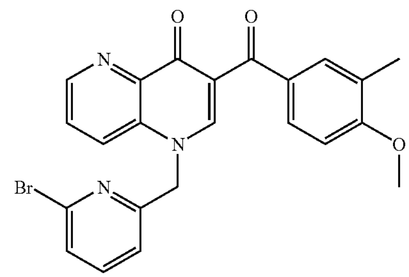 | + |
| 202 | 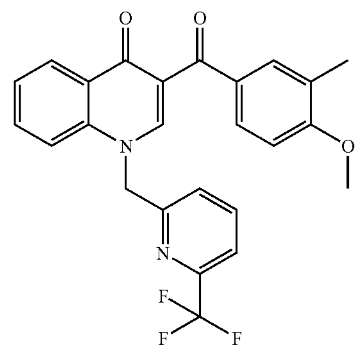 | +++ |
| 203 | 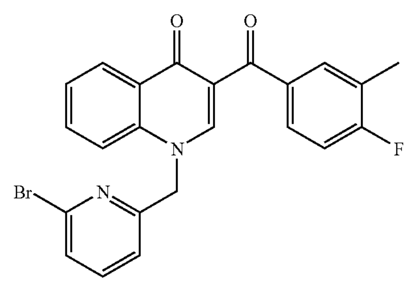 | +++ |
| 204 | 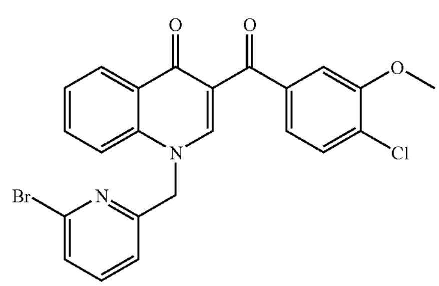 | +++ |

TABLE 4-continued
| No | Structure | Activity |
|----|-----------|----------|
| 205 | 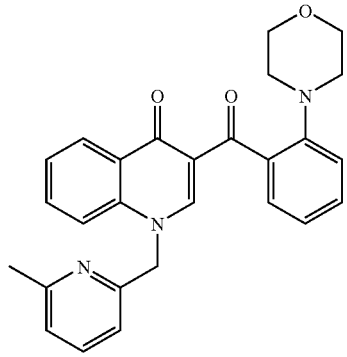 | +++ |
| 206 | 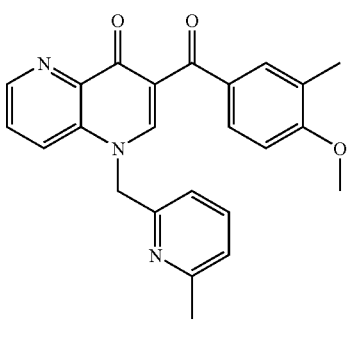 | + |
| 207 | 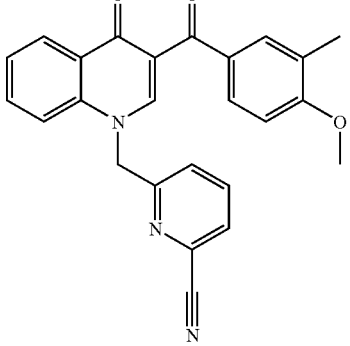 | +++ |
| 208 | 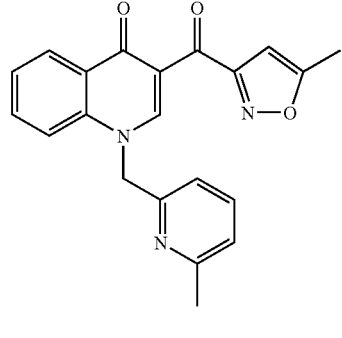 | + |
TABLE 4-continued
| No | Structure | Activity |
|----|-----------|----------|
| 209 | 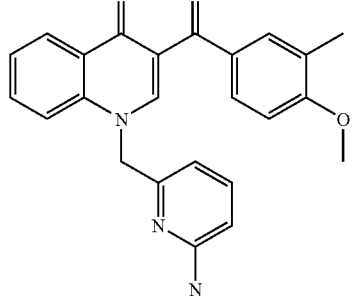 | ++ |
| 210 | 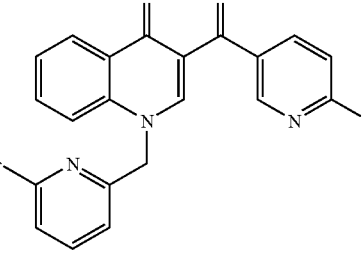 | + |
| 211 | 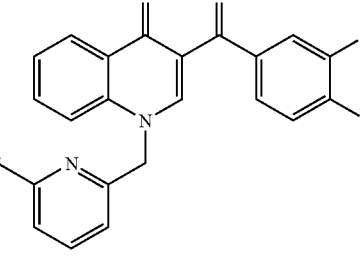 | +++ |
| 212 | 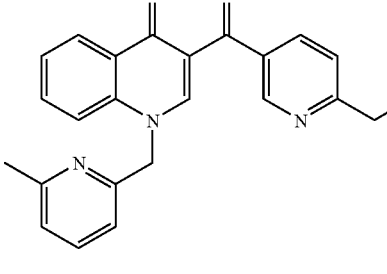 | +++ |
| 213 | 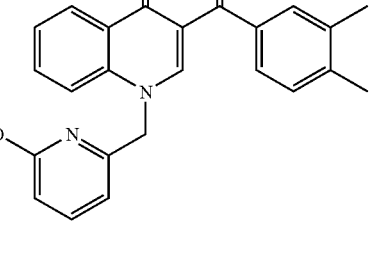 | + |

TABLE 4-continued

| No | Structure | Activity |
|---|---|---|
| 214 | 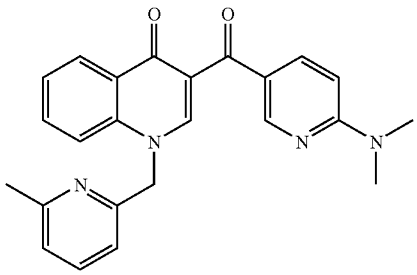 | ++ |
| 215 | 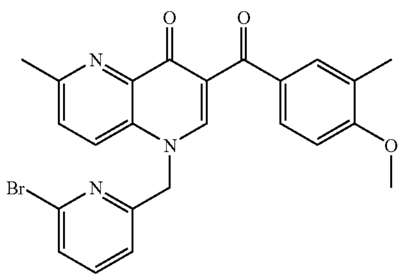 | +++ |
| 216 | 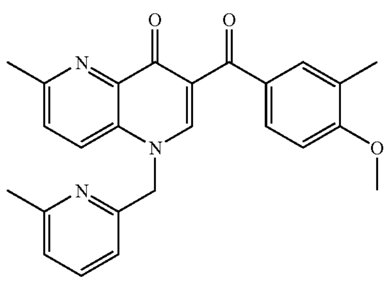 | + |
| 217 | 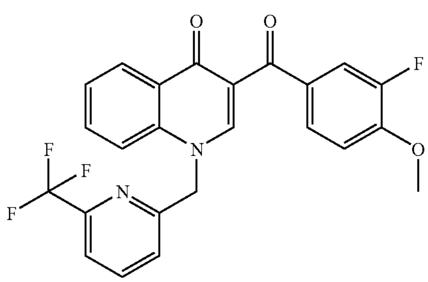 | +++ |
| 218 | 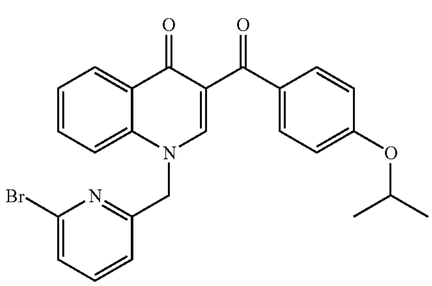 | ++ |
| 219 | | ++ |
| 220 | | +++ |
| 221 | | + |
| 222 | | +++ |
| 223 | | + |

TABLE 4-continued

| No | Structure | Activity |
|---|---|---|
| 224 | 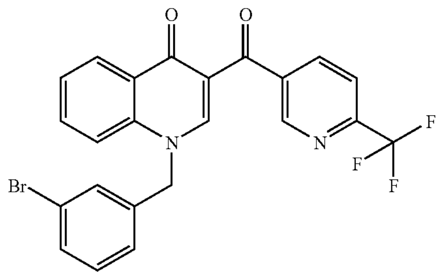 | + |
| 225 | 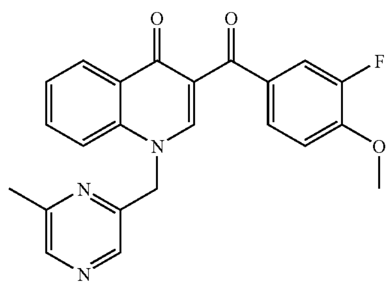 | +++ |
| 226 | 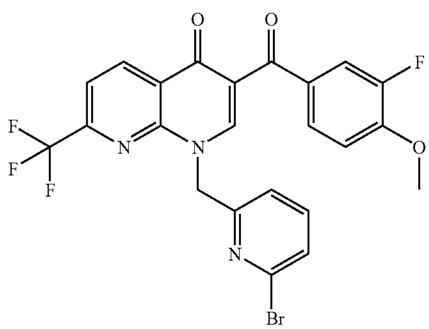 | + |
| 227 | 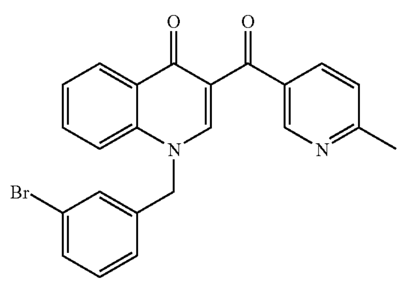 | +++ |
| 228 | 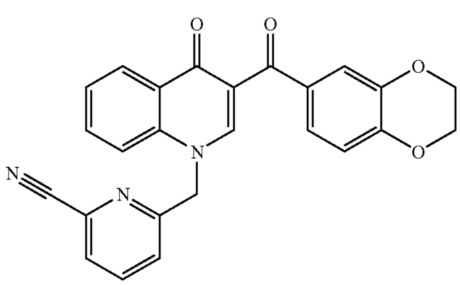 | +++ |
| 229 | | ++ |
| 230 | | ++ |
| 231 | | +++ |
| 232 | | ++ |
| 233 | | +++ |

TABLE 4-continued

| No | Structure | Activity |
|----|-----------|----------|
| 234 | 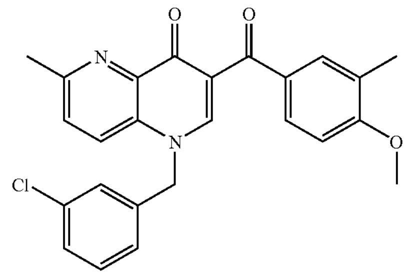 | ++ |
| 235 | 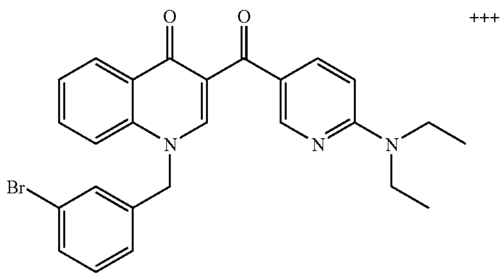 | +++ |
| 236 | 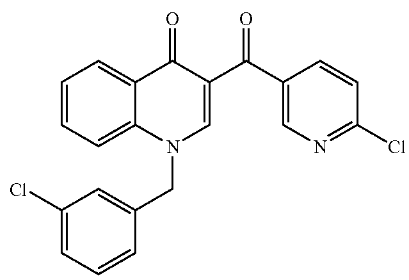 | + |
| 237 | 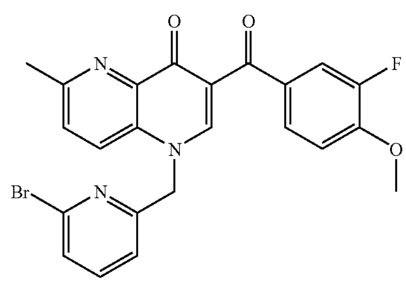 | + |
| 238 | 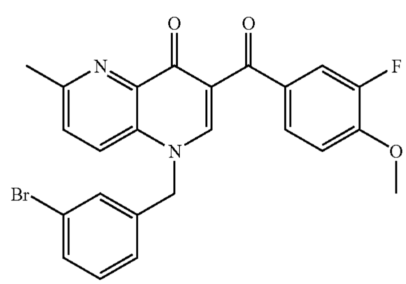 | + |

TABLE 4-continued

| No | Structure | Activity |
|----|-----------|----------|
| 239 | 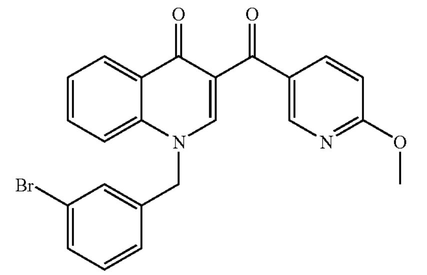 | ++ |
| 240 | 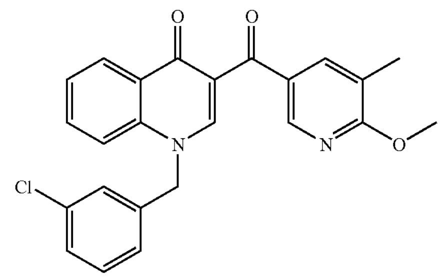 | +++ |
| 241 | 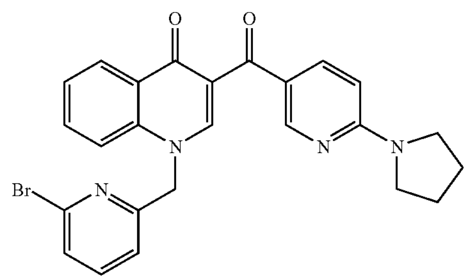 | ++ |
| 242 | 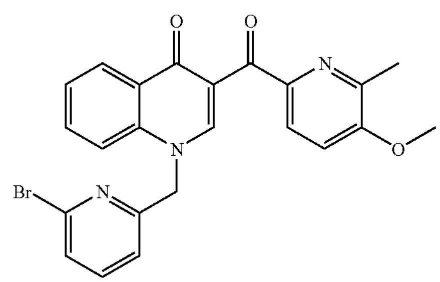 | +++ |
| 243 | 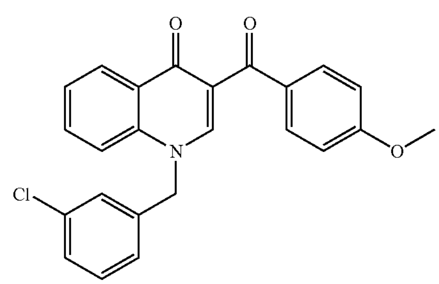 | +++ |

TABLE 4-continued

| No | Structure | Activity |
|---|---|---|
| 244 | 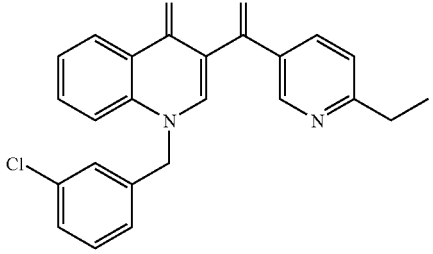 | ++ |
| 245 | 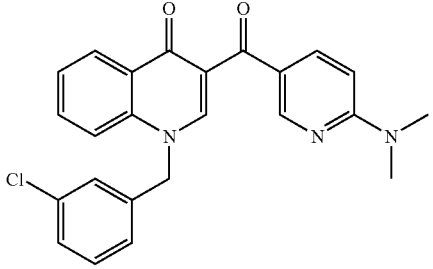 | +++ |
| 246 | 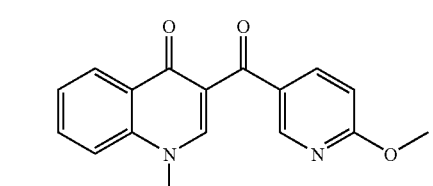 | +++ |

1. Determination of IC$_{50}$ Values.

Reagents and Cells. $^{125}$I-labeled SDF-1 was purchased from Perkin-Elmer Life Sciences, Inc. (Boston, Mass.). The MCF-7 (adenocarcinoma; mammary gland) cell line was obtained from the American Type Culture Collection (Manassas, Va.) or and was cultured in DMEM (Mediatech, Herndon, Va.) supplemented with 10% fetal bovine serum (FBS) (HyClone Logan, Utah) and bovine insulin (0.01 mg/mL) (Sigma, St. Louis, Mo.) at 37° C. in a humidified incubator at a 5% CO$_2$/air mixture. CCXCKR2 transfected MDA-MB-435S were produced as described below. MDA-MB-435S human breast cancer line, was purchased from ATCC, and cultured in DMEM/10% FBS medium. The complete coding sequence of the gene encoding CCXCKR2 (a.k.a. CXCR$^7$, hRDC1), was isolated from MCF-7 cells using μMACs mRNA isolation kit (Miltenyi Biotec, Auburn, Calif.). DNA contamination was removed by DNase digestion via RNeasy columns (Qiagen, Inc., Valencia, Calif.) and cDNA was generated using GeneAmp RNA PCR Core Kit (Applied Biosystems, Foster City, Calif.). PCR of cDNA samples was performed using Taq PCR Master Mix kit (Qiagen, Inc.) and hRDC1 primers harboring 5' and 3' Not I sites (hRDC1F 5'-GAATGCGGCCGCTATGGATCTGCATCTCTTCGACT-3' (SEQ ID NO: 11), hRDC1R 5'-GAATGCGGCCGCT-CATTTGGTGCTCTGCTCCAAG-3' (SEQ ID NO: 12)) Not I digested PCR product was ligated into Not I digested pcDNA3.1(+)(Invitrogen, Carlsbad, Calif.) and screened for orientation and sequence confirmed. Plasmid DNA was then isolated from overnight bacterial cultures by Maxiprep (Qiagen, Inc.). Plasmid DNA (10 μg) was added to MDA-MB-435s cells and cells were electroporated (0.22 kV, 960 uF) via Gene Pulser (Biorad laboratories, Hercules, Calif.). 48 hr post-electroporation, cells were transferred to selection medium (1000 ug/ml G418).

Binding Analysis. Target compounds were tested to determine their ability to bind with CCXCKR2 sites on MCF-7 and/or MDA-MB-435S cells. Efficiency-maximized radioligand binding using filtration protocols as described in Dairaghi D J, et al., *HHV8-encoded vMIP-I selectively engages chemokine receptor CCR5. Agonist and antagonist profiles of viral chemokines.*, J. Biol. Chem. 1999 Jul. 30; 274(31): 21569-74 and Gosling J, et al., *Cutting edge: identification of a novel chemokine receptor that binds dendritic cell- and T cell-active chemokines including ELC, SLC, and TECK.*, J. Immunol. 2000 Mar. 15; 164(6):2851-6 was used.

In these assays, MCF-7 and/or MDA-MB-435S cells were interrogated with the target compounds and the ability of these compounds to displace $^{125}$I radiolabeled SDF-1 was assessed using the protocol described in Dairaghi and Gosling. The target compounds were added to the plate to the indicated concentration and were then incubated with cells followed by the addition of radiolabeled chemokine ($^{125}$I SDF-1) for 3 hr at 4° C. in the following binding medium (25 mM HEPES, 140 mM NaCl, 1 mM CaCl$_2$, 5 mM MgCl$_2$ and 0.2% bovine serum albumin, adjusted to pH 7.1). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM CaCl$_2$, 5 mM MgCl$_2$, adjusted to pH 7.1). Scintillant (MicroScint 10, Packard) was added to the wells, and the filters were counted in a Packard Topcount scintillation counter. Data were analyzed and plotted using Prism (GraphPad Prism version 3.0a for Macintosh, GraphPad Software, www.graphpad.com).

SEQUENCE LISTING

```
SEQ ID NO:1 CCXCKR2 coding sequence
ATGGATCTGCATCTCTTCGACTACTCAGAGCCAGGGAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTTCATT
TACATTTTCATCTTCGTCATCGGCATGATTGCCAACTCCGTGGTGGTCTG
GGTGAATATCCAGGCCAAGACCACAGGCTATGACACGCACTGCTACATCT
TGAACCTGGCCATTGCCGACCTGTGGGTTGTCCTCACCATCCCAGTCTGG
GTGGTCAGTCTCGTGCAGCACAACCAGTGGCCCATGGGCGAGCTCACGTG
CAAAGTCACACACCTCATCTTCTCCATCAACCTCTTCGGCAGCATTTTCT
TCCTCACGTGCATGAGCGTGGACCGCTACCTCTCCATCACCTACTTCACC
AACACCCCCAGCAGCAGGAAGAAGATGGTACGCCGTGTCGTCTGCATCCT
GGTGTGGCTGCTGGCCTTCTGCGTGTCTCTGCCTGACACCTACTACCTGA
AGACCGTCACGTCTGCGTCCAACAATGAGACCTACTGCCGGTCCTTCTAC
CCCGAGCACAGCATCAAGGAGTGGCTGATCGGCATGGAGCTGGTCTCCGT
TGTCTTGGGCTTTGCCGTTCCCTTCTCCATTATCGCTGTCTTCTACTTCC
TGCTGGCCAGAGCCATCTCGGCGTCCAGTGACCAGGAGAAGCACAGCAGC
CGGAAGATCATCTTCTCCTACGTGGTGGTCTTCCTTGTCTGCTGGCTGCC
CTACCACGTGGCGGTGCTGCTGGACATCTTCTCCATCCTGCACTACATCC
CTTTCACCTGCCGGCTGGAGCACGCCCTCTTCACGGCCCTGCATGTCACA
CAGTGCCTGTCGCTGGTGCACTGCTGCGTCAACCCTGTCCTCTACAGCTT
CATCAATCGCAACTACAGGTACGAGCTGATGAAGGCCTTCATCTTCAAGT
ACTCGGCCAAAACAGGGCTCACCAAGCTCATCGATGCCTCCAGAGTCTCA
GAGACGGAGTACTCTGCCTTGGAGCAGAGCACCAAATGA SEQ ID NO:2 CCXCKR2 amino acid sequence
MDLHLFDYSEPGNFSDISWPCNSSDCIVVDTVMCPNMPNKSVLLYTLSFI
YIFIFVIGMIANSVVVWVNIQAKTTGYDTHCYILNLAIADLWVVLTIPVW
VVSLVQHNQWPMGELTCKVTHLIFSINLFGSIFFLTCMSVDRYLSITYFT
NTPSSRKKMVRRVVCILVWLLAFCVSLPDTYYLKTVTSASNNETYCRSFY
PEHSIKEWLIGMELVSVVLGFAVPFSIIAVFYFLLARAISASSDQEKHSS
```

```
-continued
RKIIFSYVVVFLVCWLPYHVAVLLDIFSILHYIPFTCRLEHALFTALHVT
QCLSLVHCCVNPVLYSFINRNYRYELMKAFIFKYSAKTGLTKLIDASRVS
ETEYSALEQSTK SEQ ID NO:3 CCXCKR2.2 coding sequence
ATGGATCTGCACCTCTTCGACTACGCCGAGCCAGGCAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTCATTT
ACATTTTCATCTTCGTCATCGGCATGATTGCCAACTCCGTGGTGGTCTGG
GTGAATATCCAGGCCAAGACCACAGGCTATGACACGCACTGCTACATCTT
GAACCTGGCCATTGCCGACCTGTGGGTTGTCCTCACCATCCCAGTCTGG
TGGTCAGTCTCGTGCAGCACAACCAGTGGCCCATGGGCGAGCTCACGTGC
AAAGTCACACACCTCATCTTCTCCATCAACCTCTTCAGCGGCATTTCTTC
CTCACGTGCATGAGCGTGGACCGCTACCTCTCCATCACCTACTTCACCAA
CACCCCCAGCAGCAGGAAGAAGATGGTACGCCGTGTCGTCTGCATCCTGG
TGTGGCTGCTGGCCTTCTGCGTGTCTCTGCCTGACACCTACTACCTGAAG
ACCGTCACGTCTGCGTCCAACAACAATGAGACCTACTGCCGGTCCTTCTA
CCCCGAGCACAGCATCAAGGAGTGGCTGATCGGCATGGAGCTGGTCTCCG
TTGTCTTGGGCTTTGCCGTTCCCTTCTCCATTATCGCTGTCTTCTACTTC
CTGCTGGCCAGAGCCATCTCGGCGTCCAGTGACCAGGAGAAGCACAGCAG
CCGGAAGATCATCTTCTCCTACGTGGTGGTCTTTCCTTGCTGCTGGCTGC
CCCTACCACGTGGCGGTGCTGCTGGACATCTTCTCCATCCTGCACTACAT
CCCTTTCACCTGCCGGCTGGAGCACGCCCTCTTCACGGCCCTGCATGTCA
CACAGTGCCTGTCGCTGGTGCACTGCTGCGTCAACCCTGTCCTCTACAGC
TTCATCAATCGCAACTACAGGTACGAGCTGATGAAGGCCTTCATCTTCAA
GTACTCGGCCAAAACAGGGCTCACCAAGCTCATCGATGCCTCCAGAGTGT
CGGAGACGGAGTACTCCGCCTTGGAGCAAAACGCCAAGTGA SEQ ID NO:4 CCXCKR2.2 amino acid sequence
MDLHLFDYAEPGNFSDISWPCNSSDCIVVDTVMCPNMPNKSVLLYTLSFI
YIFIFVIGMIANSVVVWVNIQAKTTGYDTHCYILNLAIADLWVVLTIPVW
VVSLVQHNQWPMGELTCKVTHLIFSINLFSGIFFLTCMSVDRYLSITYFT
NTPSSRKKMVRRVVCILVWLLAFCVSLPDTYYLKTVTSASNNETYCRSFY
PEHSIKEWLIGMELVSVVLGFAVPFSIIAVFYFLLARAISASSDQEKHSS
RKIIFSYVVVFLVCWLPYHVAVLLDIFSILHYIPFTCRLEHALFTALHVT
QCLSLVHCCVNPVLYSFINRNYRYELMKAFIFKYSAKTGLTKLIDASRVS
ETEYSALEQNAK SEQ ID NO:5 CCXCKR2.3 coding sequence
ATGGATCTGCATCTCTTCGACTACTCAGAGCCAGGGAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTTCATT
TACATTTTCATCTTCGTCATCGGCATGATTGCCAACTCCGTGGTGGTCT
GGGTGAATATCCAGGCCAAGACCACAGGCTATGACACGCACTGCTACATC
TTGAACCTGGCCATTGCCGACCTGTGGGTTGTCCTCACCATCCCAGTCTG
GGTGGTCAGTCTCGTGCAGCACAACCAGTGGCCCATGGGCGAGCTCACGT
GCAAAGTCACACACCTCATCTTCTCCATCAACCTCTTCGGCAGCATTTTC
TTCCTCACGTGCATGAGCGTGGACCGCTACCTCTCCATCACCTACTTCAC
CAACACCCCCAGCAGCAGGAAGAAGATGGTACGCCGTGTCGTCTGCATCC
TGGTGGCTGCTGGCCTTCTGCGTGTCTCTGCCTGACACCTACTACCTG
AAGACCGTCACGTCTGCGTCCAACAATGAGACCTACTGCCGGTCCTTCTAC
CCCGAGCACAGCATCAAGGAGTGGCTGATCGGCATGGAGCTGGTCTCCGT
TGTCTTGGGCTTTGCCGTTCCCTTCTCCATTGTCGCTGTCTTCTACTTCC
TGCTGGCCAGAGCCATCTCGGCGTCCAGTGACCAGGAGAAGCACAGCAGC
CGGAAGATCATCTTCTCCTACGTGGTGGTCTTTCCTTGCTGCTGGTTGCC
CTACCACGTGGCGGTGCTGCTGGACATCTTCTCCATCCTGCACTACATCC
CTTTCACCTGCCGGCTGGAGCACGCCCTCTTCACGGCCCTGCATGTCACA
CAGTGCCTGTCGCTGGTGCACTGCTGCGTCAACCCTGTCCTCTACAGCTT
CATCAATCGCAACTACAGGTACGAGCTGATGAAGGCCTTCATCTTCAAGT
ACTCGGCCAAAACAGGGCTCACCAAGCTCATCGATGCCTCCAGAGTCTCA
GAGACGGAGTACTCTGCCTTGGAGCAGAGCACCAAATGA SEQ ID NO:6 CCXCKR2.3 amino acid sequence
MDLHLFDYSEPGNFSDISWPCNSSDCIVVDTVMCPNMPNKSVLLYTLSFIY
IFIFVIGMIANSVVVWVNIQAKTTGYDTHCYILNLAIADLWVVLTIPVWV
VSLVQHNQWPMGELTCKVTHLIFSINLFGSIFFLTCMSVDRYLSITYFTN
TPSSRKKMVRRVVCILVWLLAFCVSLPDTYYLKTVTSASNNETYCRSFYP
EHSIKEWLIGMELVSVLGFAVPFSIVAVFYFLLARAISASSDQEKHSSRK
IIFSYVVVFLVCWLPYHVAVLLDIFSILHYIPFTCRLEHALFTALHVTQC
LSLVHCCVNPVLYSFINRNYRYELMKAFIFKYSAKTGLTKLIDASRVSET
EYSALEQSTK SEQ ID NO:7 CCXCKR2.4 coding sequence
ATGGATCTGCATCTCTTCGACTACTCAGAGCCAGGGAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTTCATT
TACATTTTCATCTTCGTCATCGGCATGATTGCCAACTCCGTGGTGGTCTG
GGTGAATATCCAGGCCAAGACCACAGGCTATGACACGCACTGCTACATCT
```
```
-continued
TGAACCTGGCCATTGCCGACCTGTGGGTTGTCCTCACCATCCCAGTCTGG
GTGGTCAGTCTCGTGCAGCACAACCAGTGGCCCATGGGCGAGCTCACGTG
CAAAGTCACACACCTCATCTTCTCCATCAACCTCTTCGGCAGCATTTTCT
TCCTCACGTGCATGAGCGTGGACCGCTACCTCTCCATCACCTACTTCACC
AACACCCCCAGCAGCAGGAAGAAGATGGTACGCCGTGTCGTCTGCATCCT
GGTGTGGCTGCTGGCCTTCTGCGTGTCTCTGCCTGACACCTACTACCTGA
AGACCGTCACGTCTGCGTCCAACAATGAGACCTACTGCCGGTCCTTCTAC
CCCGAGCACAGCATCAAGGAGTGGCTGATCGGCATGGAGCTGGTCTCCGT
TGTCTTGGGCTTTGCCGTTCCCTTCTCCATTATCGCTGTCTTCTACTTCC
TGCTGGCCAGAGCCATCTCGGCGTCCAGTGACCAGGAGAAGCACAGCAGC
CGGAAGATCATCTTCTCCTACGTGGTGGTCTTCCTTGTCTGCTGGCTGCC
TACCACGTGGCGGTGCTGCTGGACATCTTCTCCATCCTGCACTACATCCC
TTTCACCTGCCGGCTGGAGCACGCCCTCTTCACGGCCCTGCATGTCACAC
AGTGCCTGTCGCTGGTGCACTGCTGCGTCAACCCTGTCCTCTACAGCTTC
ATCAATCGCAACTACAGGTACGAGCTGATGAAGGCCTTCATCTTCAAGTA
CTCGGCCAAAACAGGGCTCACCAAGCTCATCGATGCCTCCAGAGTCTCAG
AGACGGAGTACTCTGCCTTGGAGCAGAGCACCAAATGA SEQ ID NO:8 CCXCKR2.4 amino acid sequence
MDLHLFDYSEPGNFSDISWPCNSSDCIVVDTVMCPNMPNKSVLLYTLSFI
YIFIFVIGMIANSVVVWVNIQAKTTGYDTHCYILNLAIADLWVVLTIPVW
VVSLVQHNQWPMGELTCKVTHLIFSINLFGSIFFLTCMSVDRYLSITYFT
NTPSSRKKMVRRVVCILVWLLAFCVSLPDTYYLKTVTSASNNETYCRSFY
PEHSIDEWLIGMELVSVVLGFAVPFSIIAVFYFLLARAISASSDQEKHSS
RKIIFSYVVVFLVCWLPYHVAVLLDIFSILHYIPFTCRLEHALFTALHVT
QCLSLVHCCVNPVLYSFINRNYRYELMKAFIFKYSAKTGLTKLIDASRVS
ETEYSALEQSTK SEQ ID NO:9 CCXCKR2.5 coding sequence
ATGGATCTGCATCTCTTCGACTACTCAGAGCCAGGGAACTTCTCGGACAT
CAGCTGGCCGTGCAACAGCAGCGACTTGCATCGTGGTGGACACGGTGATG
TGTCCCAACATGCCCAACAAAAGCGTCCTGCTCTACACGCTCTCCTTCAT
TTACATTTTCATCTTCGTCATCGGCATGATTGCCAACTCCGTGGTGGTCT
GGGTGAATATCCAGGCCAAGACCACAGGCTATGACACGCACTGCTACATC
TTGAACCTGGCCATTGCCGACCTGTGGGTTGTCCTCACCATCCCAGTCTG
GGTGGTCAGTCTCGTGCAGCACAACCAGTGGCCCATGGGCGAGCTCACGT
GCAAAGTCACACACCTCATCTTCTCCATCAACCTCTTCAGCAGCATTTTC
TTCCTCACGTGCATGAGCGTGGACCGCTACCTCTCCATCACCTACTTCAC
CAACACCCCCAGCAGCAGGAAGAAGATGGTACGCCGTGTCGTCTGCATCC
TGGTGTGGCTGCTGGCCTTCTGCGTGTCTCTGCCTGACACCTACTACCTG
AAGACCGTCACGTCTGCGTCCAACAATGAGACCTACTGCCGGTCCTTCTA
CCCCGAGCACAGCATCAAGGAGTGGCTGATCGGCATGGAGCTGGTCTCC
GTTGTCTTGGGCTTTGCCGTTCCCTTCTCCATTATCGCTGTCTTCTACTT
CCTGCTGGCCAGAGCCATCTCGGCGTCCAGTGACCAGGAGAAGCACAGCA
GCCGGAAGATCATCTTCTCCTACGTGGTGGTCTTCCTTGTCTGCTGGTTG
CCCTACCACGTGGCGGTGCTGCTGGACATCTTCTCCATCCTGCACTACAT
CCCTTTCACCTGCCGGCTGGAGCACGCCCTCTTCACGGCCCTGCATGTCA
CACAGTGCCTGTCGCTGGTGCACTGCTGCGTCAACCCTGTCCTCTACAGC
TTCATCAATCGCAACTACAGGTACGAGCTGATGAAGGCCTTCATCTTCAA
GTACTCGGCCAAAACAGGGCTCACCAAGCTCATCGATGCCTCCAGAGTCT
CAGAGACGGAGTACTCCGCCTTGGAGCAGAGCACCAAATGA SEQ ID NO:10 CCXCKR2.5 amino acid sequence
MDLHLFDYSEPGNFSDISWPCNSSDCIVVDTVMCPNMPNKSVLLYTLSFI
YIFIFVIGMIANSVVVWVNIQAKTTGYDTHCYILNLAIADLWVVLTIPVW
VVSLVQHNQWPMGELTCKVTHLIFSINLFSSIFFLTCMSVDRYLSITYFT
NTPSSRKKMVRRVVCILVWLLAFCVSLPDTYYLKTVTSASNNETYCRSFY
PEHSIKEWLIGMELVSVVLGFAVPFSIIAVFYFLLARAISASSDQEKHSS
RKIIFSYVVVFLVCWLPYHVAVLLDIFSILHYIPFTCRLEHALFTALHVT
QCLSLVHCCVNPVLYSFINRNYRYELMKAFIFKYSAKTGLTKLIDASRVS
ETEYSALEQSTK
```

One of ordinary skill in the art will recognize from the provided description, figures, and examples, that modifications and changes can be made to the various embodiments of the invention without departing from the scope of the invention defined by the following claims and their equivalents.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound having formula I

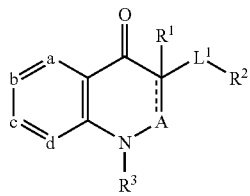

or pharmaceutically acceptable salts and N-oxides thereof; wherein

⚌ is a single or double bond;

A is —CH$_2$—, —CH(R$^a$)—, or —C(R$^a$)$_2$—, wherein each R$^a$ is absent or is C$_{1-4}$ alkyl;

R$^1$ is absent; or is hydrogen;

L$^1$ is —C(O)—;

R$^2$ is a 5-6 membered aryl or heteroaryl group;

R$^3$ —CH$_2$—pyridyl;

wherein R$^2$ and the pyridyl portion of R$^3$ are each optionally substituted with 1-5 substituents selected from the group consisting of halogen, —CN, —NO$_2$, —CO$_2$R$^r$, —OC(O)R$^r$, —C(O)NR$^r$R$^s$, —C(O)R$^r$, —S(O)R$^t$, —S(O)$_2$R$^t$, —R$^t$, —C(NOR$^r$)R$^s$, —NR$^r$—C(O)NR$^r$R$^s$, —NH—C(NH$_2$)=NH, —NR$^t$C(NH$_2$)=NH, —NH—C(NH$_2$)=NR$^t$, —NH—C(NHR$^t$)=NH, —NR$^r$S(O)$_2$R$^t$, —NR$^r$S(O)$_2$R$^t$, —NR$^r$S(O)$_2$NR$^r$R$^s$, —N$_3$, —C(NR$^r$V)=NV, —N(V)C(R$^r$)=NV, —X$^2$C(NOR$^r$)R$^s$, —X$^2$C(NR$^r$V)=NV, —X$^2$N(V)C(R$^r$)=NV, —X$^2$NR$^r$R$^s$, —X$^2$SR$^r$, —X$^2$CN, —X$^2$NO$_2$, —X$^2$CO$_2$R$^r$, —X$^2$OC(O)R$^r$, —X$^2$CONR$^r$R$^s$, —X$^2$C(O)R$^r$, —X$^2$OC(O)NR$^r$R$^s$, —X$^2$NR$^s$C(O)R$^r$, —X$^2$NR$^s$C(O)$_2$R$^t$, —X$^2$NR$^r$C(O)NR$^r$R$^s$, —X$^2$NH—C(NH$_2$)=NH, —X$^2$NR$^t$C(NH$_2$)=NH, —X$^2$NH—C(NH$_2$)=NR$^t$, —X$^2$NH—C(NHR$^t$)=NH, —X$^2$S(O)R$^t$, —X$^2$S(O)$_2$R$^t$, —X$^2$NR$^r$S(O)$_2$R$^t$, —X$^2$S(O)$_2$NR$^r$R$^s$, —X$^2$N$_3$, —OR$^r$, —SR$^r$, —NR$^r$R$^s$, —NR$^s$C(O)R$^r$, —NR$^s$C(O)$_2$ R$^t$, —S(O)$_2$R$^t$, —S(O)$_2$NR$^r$R$^s$, —X$^2$OR$^r$, —O—X$^2$OR$^r$, —X$^2$NR$^r$R$^s$, —O—X$^2$NR$^r$R$^s$ and —NR$^s$—X$^2$CO$_2$R$^r$, X$^2$ is C$_{1-8}$ alkylene, C$_{1-8}$ heteroalkylene, C$_{2-8}$ alkenylene, C$_{2-8}$ alkynylene, arylene or heteroarylene; and each R$^r$ and R$^s$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl, or optionally, R$^r$ and R$^s$ when attached to the same nitrogen atom can be combined with the nitrogen atom to form a five or six-membered ring having from 0 to 2 additional heteroatoms as ring members selected from N, O or S, and wherein each R$^t$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl, V is independently selected from the group consisting of —R$^t$, —CN, —CO$_2$R$^r$ and —NO$_2$, and each of X$^2$, R$^r$, R$^s$ and R$^t$ is optionally further substituted with from one to three members selected from the group consisting of —OH, —OR$^u$, —OC(O)NHR$^u$, —OC(O)N(R$^u$)$_2$, —SH, —SR$^u$, —S(O)R$^u$, —S(O)$_2$R$^u$, —SO$_2$NH$_2$, —S(O)$_2$NHR$^u$, —S(O)$_2$N(R$^u$)$_2$, —NHS(O)$_2$R$^u$, —NR$^u$S(O)$_2$R$^u$, —C(O)NH$_2$, —C(O)NHR$^u$, —C(O)N(R$^u$)$_2$, —C(O)R$^u$, —NHC(O)R$^u$, —NR$^u$C(O)R$^u$, —NHC(O)NH$_2$, —NR$^u$C(O)NH$_2$, —NR$^u$C(O)NHR$^u$, —NHC(O)NHR$^u$, —NR$^u$C(O)N(R$^u$)$_2$, —NHC(O)N(R$^u$)$_2$, —CO$_2$H, —CO$_2$R$^u$, —NHCO$_2$R$^u$, —NR$^u$CO$_2$R$^u$, —CN, —NO$_2$, —NH$_2$, —NHR$^u$, —N(R$^u$)$_2$, —NR$^u$S(O)NH$_2$ and —NR$^u$S(O)$_2$NHR$^u$, wherein each R$^u$ is independently an unsubstituted C$_{1-6}$ alkyl; and each of the ring vertices a, b, c and d in formula I is C(H) or C(R$^4$), wherein R$^4$ at each occurrence is independently is selected from the group consisting of halogen, C$_{1-8}$ alkyl, C$_{1-8}$ haloalkyl, C$_{1-8}$ alkoxy and C$_{1-8}$ haloalkoxy, and optionally any two R$^4$ substituents located on adjacent ring vertices are combined to form a 5- to 6-membered ring having from 0- to 2 heteroatom ring members selected from the group consisting of N, O and S.

2. The compound of claim 1, wherein the compound has formula Ia

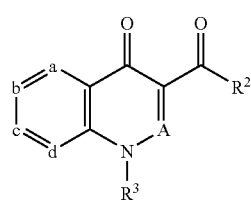

(Ia)

wherein A is CH;

and R$^2$ and the pyridyl portion of R$^3$ are each optionally substituted with 1-5 substituents selected from the group consisting of halogen, —CN, —NO$_2$, —R$^t$, —CO$_2$R$^r$, —CONR$^r$R$^s$, —N$_3$, —X$^2$NR$^r$R$^s$, —X$^2$SR$^r$, —X$^2$CN, —X$^2$NO$_2$, —X$^2$CO$_2$R$^r$, —X$^2$CONR$^r$R$^s$, —X$^2$C(O)R$^r$, —X$^2$NR$^s$C(O)R$^r$, —X$^2$NR$^s$C(O)$_2$R$^t$, —X$^2$N$_3$, —OR$^r$, —SR$^r$, —NR$^r$R$^s$, —NR$^s$C(O)R$^r$, —NR$^s$C(O)$_2$R$^t$, —X$^2$OR$^r$ and —NR$^s$—X$^2$CO$_2$R$^r$, X$^2$ is C$_{1-4}$ alkylene or C$_{1-4}$ heteroalkylene; and each R$^r$ and R$^s$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl, or optionally, R$^r$ and R$^s$ when attached to the same nitrogen atom can be combined with the nitrogen atom to form a five or six-membered ring having from 0 to 2 additional heteroatoms as ring members selected from N, O or S, and wherein each R$^t$ is independently selected from the group consisting of C$_{1-8}$ alkyl, C$_{1-8}$ haloalkyl, aryl and heteroaryl and each of X$^2$, R$^r$, R$^s$ and R$^t$ is optionally further substituted with from one to three members selected from the group consisting of —OH, —OR$^u$, —OC(O)NHR$^u$, —OC(O)N(R$^u$)$_2$, —SH, —SR$^u$, —S(O)R$^u$, —S(O)$_2$R$^u$, —SO$_2$NH$_2$, —S(O)$_2$NHR$^u$, —S(O)$_2$N(R$^u$)$_2$, —NHS(O)$_2$R$^u$, —NR$^u$S(O)$_2$R$^u$, —C(O)NH$_2$, —C(O)NHR$^u$, —C(O)N(R$^u$)$_2$, —C(O)R$^u$, —NHC(O)R$^u$, —NR$^u$C(O)R$^u$, —NHC(O)NH$_2$, —NR$^u$C(O)NH$_2$, —NR$^u$C(O)NHR$^u$, —NHC(O)NHR$^u$, —NR$^u$C(O)N(R$^u$)$_2$, —NHC(O)N(R$^u$)$_2$, —CO$_2$H, —CO$_2$R$^u$, —NHCO$_2$R$^u$, —NR$^u$CO$_2$R$^u$, —CN, —NO$_2$, —NH$_2$, —NHR$^u$, —N(R$^u$)$_2$, —NR$^u$S(O)NH$_2$ and —NR$^u$S(O)$_2$NHR$^u$, wherein each R$^u$ is independently an unsubstituted C$_{1-6}$ alkyl.

3. The compound of claim 1 or 2, wherein R$^2$ is an optionally substituted phenyl ring.

4. The compound of claim 3, wherein R$^2$ is a phenyl ring having the formula

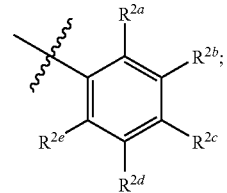

wherein R$^{2a}$, R$^{2b}$, R$^{2c}$, R$^{2d}$ and R$^{2e}$ are each independently selected from the group consisting of hydrogen, halogen, —CN, —NO$_2$, OR$^r$, —SR$^r$, —NR$^r$R$^s$, —CO$_2$R$^r$, C(O)NR$^r$R$^s$, optionally substituted C$_{1-8}$ alkyl, optionally substituted C$_{1-8}$ haloalkyl and optionally substituted C$_{3-6}$ cycloalkyl; and R$^r$ and R$^s$ are each independently selected from the group consisting of hydrogen, C$_{1-8}$ alkyl, C$_{1-8}$ haloalkyl, C$_{3-6}$ cycloalkyl, C$_{2-8}$ alkenyl and C$_{2-8}$ alkynyl.

5. The compound of claim 3, wherein R$^2$ is selected from the group consisting of:

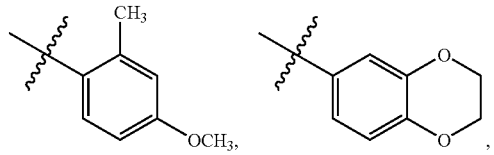

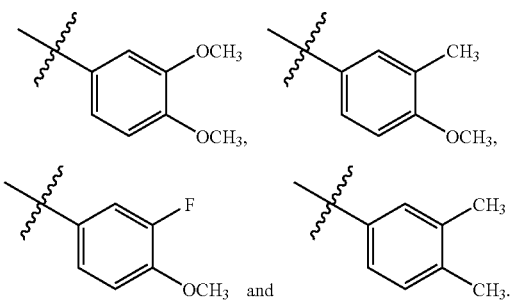

6. The compound of claim 2, wherein the pyridyl group in $R^3$ has the formula

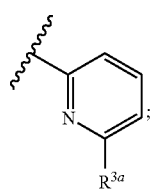

wherein $R^{3a}$ is substituent selected from the group consisting of halogen, —CN, —NO$_2$, —R$^t$, —CO$_2$R$^r$, —CONR$^r$R$^s$, —N$_3$, —X$^2$NR$^r$R$^s$, —X$^2$SR$^r$, —X$^2$CN, —X$^2$NO$_2$, —X$^2$CO$_2$R$^r$, —X$^2$CONR$^r$R$^s$, —X$^2$C(O)R$^r$, —X$^2$NR$^s$C(O)R$^r$, —X$^2$NR$^s$C(O)$_2$R$^t$, —X$^2$N$_3$, —OR$^r$, —SR$^r$, —NR$^r$R$^s$, —NR$^s$C(O)R$^r$, —NR$^s$C(O)$_2$R$^t$, —X$^2$OR$^r$ and —NR$^s$—X$^2$CO$_2$R$^r$.

7. The compound of claim 2, wherein the pyridyl group in $R^3$ is selected from the group consisting of:

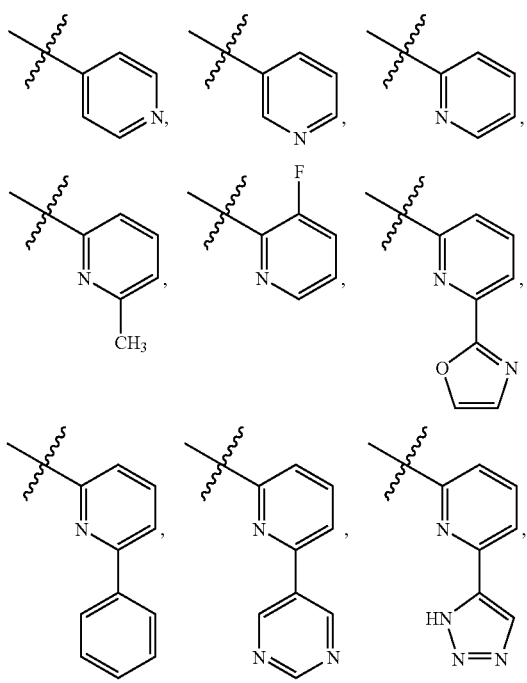

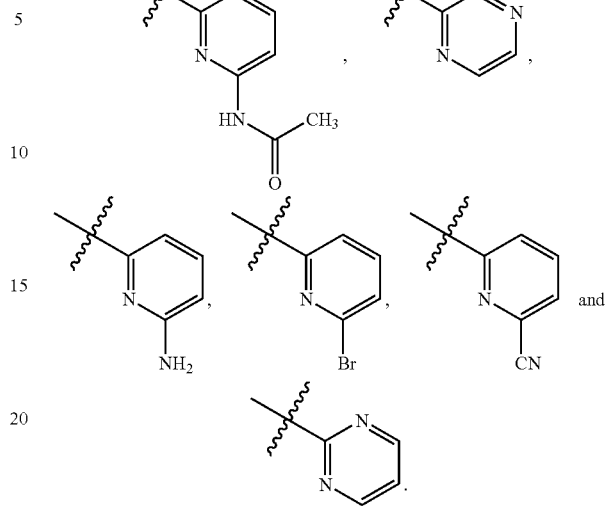

8. The compound of claim 1, wherein the ring vertices a, b, c and d are each CH.

9. The compound of claim 1, wherein the ring vertices a, b, c and d are each independently selected from the group consisting of CH or C(R$^4$), wherein each R$^4$ is independently selected from the group consisting of halogen, C$_{1-8}$ alkyl, C$_{1-8}$ haloalkyl and C$_{1-8}$ alkoxy; or alternatively any two R$^4$ substituents located on adjacent ring vertices are combined to form a 5- to 6-membered ring having 1 to 2 heteroatoms selected from the group consisting of N and O.

10. The compound of claim 9, wherein the ring vertices a, c and d are each CH; and the ring vertex b is CR$^4$, wherein R$^4$ is a C$_{1-4}$ haloalkyl.

11. The compound of claim 9, wherein the ring vertices a and d are each CH and the ring vertices b and c are each C(R$^4$) wherein the R$^4$ substituent are combined to form a 5- or 6-membered ring having two oxygen atoms.

12. The compound of claim 2, wherein a, b, c and d are each CH; R$^2$ is phenyl, substituted with one or two groups selected from the group consisting of halogen, C$_{1-4}$ alkyl, C$_{1-4}$ alkoxy, or are combined to form a fused 6-member ring having two oxygen atom ring members; R$^3$ is a pyridylmethyl group optionally substituted with one or two groups selected from the group consisting of halogen and cyano.

13. The compound of claim 1, wherein said compound is selected from the group consisting of:
   3-(Pyridine-4-carbonyl)-1-pyridin-2-ylmethyl-H-quinolin-4-one;
   3-(3,4-Dimethyl-benzoyl)-1-pyridin-2-ylmethyl-6-trifluoromethyl1H-quinolin-4-one;
   8-(3,4-Dimethyl-benzoyl)-6-pyridin-4-ylmethyl-2,3dihydro-6H-[1,4]dioxino[2,3-g]quinolin-9-one;
   8-(3,4-Dimethyl-benzoyl)-6-pyridin-3-ylmethyl-2,3-dihydro-6H-[1,4]dioxino[2,3-g]quinolin-9-one;
   8-(3,4-Dimethyl-benzoyl)-6-pyridin-2-ylmethyl-2,3-dihydro-6H-[-1,4]dioxino[2,3-g]quinolin-9-one;
   3-(3,4-Dimethyl-benzoyl)-1-pyridin-4-ylmethyl-1H-quinolin-4-one;
   3-(3,4-Dimethyl-benzoyl)-1-pyridin-3-ylmethyl-1H-quinolin-4-one;
   3-(3,4-Dimethyl-benzoyl)-1-pyridin-2-ylmethyl-1H-quinolin-4-one;

7-(3,4-Dimethyl-benzoyl)-5-pyridin-4-ylmethyl-5H-[1,3]dioxolo[4,5-g]quinolin-8-one;
7-(3,4-Dimethyl-benzoyl)-5-pyridin-3-ylmethyl-5H-[1,3]dioxolo[4,5-g]quinolin-8-one;
7-(3,4-Dimethyl-benzoyl)-5-pyridin-2-ylmethyl-5H-[1,3]dioxolo[4,5-g]quinolin-8-one;
3-(3-Methyl-benzoyl)-1-pyridin-2-ylmethyl-1H-quinolin-4-one;
3-(3,4-Dimethyl-benzoyl)-1-(6-methyl-pyridin-2ylmethyl)-1H-quinolin-4-one;
3-(2-Methyl-pyridine-4-carbonyl)-1-(6-methyl-pyridin-2-ylmethyl)-1H-quinolin-4-one;
1-(6-Bromo-pyridin-2-ylmethyl)-3-(3,4-dimethyl-benzoyl)-1H-quinolin-4-one;
1-(6-Methyl-pyridin-2-ylmethyl)-3-(pyridine-3-carbonyl)-1H-quinolin-4-one;
3-(3,4-Dimethyl-benzoyl)-1-(3-fluoro-pyridin-2-ylmethyl)-1H-quinolin-4-one;
3-(5,6-Dimethyl-pyridine-3-carbonyl)-1-(3-fluoro-pyridin-2-ylmethyl)-1H-quinolin-4-one;
3-(5,6-Dimethyl-pyridine-3-carbonyl)-1-(6-oxazol-2-yl-pyridin-2-ylmethyl)-1H-quinolin-4-one;
3-(3,4-Dimethyl-benzoyl)-1-(6-phenyl-pyridin-2-ylmethyl)-1H-quinolin-4-one;
3-(3,4-Dimethyl-benzoyl)-1-(6-methyl-pyridin-2-ylmethyl)-1H-cinnolin-4-one;
3-(5,6-Dimethyl-pyridine-3-carbonyl)-1-(6-methyl-pyridin-2-ylmethyl)-1H-quinolin-4-one;
1-(6-Amino-pyridin-2-ylmethyl)-3-(3,4-dimethyl-benzoyl)-1H-quinolin-4-one;
N-{6-[3-(3,4-Dimethyl-benzoyl)-4-oxo-4H-quinolin-1-ylmethyl]-pyridin-2-yl}-acetamide;
1-(6-Bromo-pyridin-2-ylmethyl)-3-(3,4-dimethyl-benzoyl)-6-fluoro-1H-quinolin-4-one;
1-(6-Bromo-pyridin-2-ylmethyl)-3-(5,6-dimethyl-pyridine-3-carbonyl)-1H-quinolin-4-one;
1-(6-Bromo-pyridin-2-ylmethyl)-3-(3,4-dimethyl-benzoyl)-1H-quinolin-4-one; and
6-[3-(3,4-Dimethyl-benzoyl)-4-oxo-4H-quinolin-1-ylmethyl]-pyridine-2-carbonitrile.

14. A pharmaceutical composition comprising a compound of claim 1, and a pharmaceutically acceptable excipient.

15. The pharmaceutical composition of claim 14, wherein the compound is a compound of claim 2.

* * * * *

UNITED STATES PATENT AND TRADEMARK OFFICE
CERTIFICATE OF CORRECTION

PATENT NO.         : 7,557,213 B2                                    Page 1 of 1
APPLICATION NO. : 11/599183
DATED              : July 7, 2009
INVENTOR(S)        : Anita Melikian et al.

It is certified that error appears in the above-identified patent and that said Letters Patent is hereby corrected as shown below:

Claim 7, Column 284, Line 5: please delete " 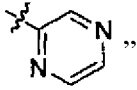 "

Claim 7, Column 284, Line 15: please delete "," after " 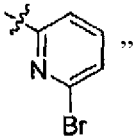 "

Claim 7, Column 284, Line 15: please insert -- and -- after " 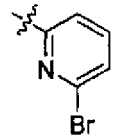 "

Claim 7, Column 284, Lines 15-20: please delete "and 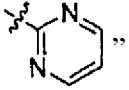 "

Claim 13, Column 284, Line 55: please insert -- - -- between "trifluoromethyl" and "1H"

Signed and Sealed this

Twentieth Day of October, 2009

David J. Kappos
*Director of the United States Patent and Trademark Office*